US009447454B2

(12) United States Patent
Darnell et al.

(10) Patent No.: US 9,447,454 B2
(45) Date of Patent: Sep. 20, 2016

(54) METHOD OF PURIFYING RNA BINDING PROTEIN-RNA COMPLEXES

(71) Applicant: The Rockefeller University, New York, NY (US)

(72) Inventors: Robert Darnell, New York, NY (US); Kirk Jensen, Maryland (AU); Jernej Ule, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 14/104,581

(22) Filed: Dec. 12, 2013

(65) Prior Publication Data

US 2014/0378316 A1    Dec. 25, 2014

Related U.S. Application Data

(63) Continuation of application No. 12/509,856, filed on Jul. 27, 2009, now abandoned, which is a continuation of application No. 10/971,736, filed on Oct. 25, 2004, now abandoned.

(60) Provisional application No. 60/513,183, filed on Oct. 23, 2003.

(51) Int. Cl.
*C12N 15/10* (2006.01)
*C12Q 1/68* (2006.01)

(52) U.S. Cl.
CPC ......... *C12Q 1/6809* (2013.01); *C12N 15/1003* (2013.01); *C12N 15/1006* (2013.01); *C12Q 1/6806* (2013.01)

(58) Field of Classification Search
None
See application file for complete search history.

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,683,195 A | 7/1987 | Mullis et al. |
| 5,143,854 A | 9/1992 | Pirrung et al. |
| 5,242,979 A | 9/1993 | Barnum et al. |
| 5,252,743 A | 10/1993 | Barrett et al. |
| 5,324,663 A | 6/1994 | Lowe |
| 5,384,261 A | 1/1995 | Winkler et al. |
| 5,405,783 A | 4/1995 | Pirrung et al. |
| 5,412,087 A | 5/1995 | McGall et al. |
| 5,424,186 A | 6/1995 | Fodor et al. |
| 5,445,934 A | 8/1995 | Fodor et al. |
| 5,451,683 A | 9/1995 | Barrett et al. |
| 5,482,817 A | 1/1996 | Dichiara et al. |
| 5,482,867 A | 1/1996 | Barrett et al. |
| 5,489,678 A | 2/1996 | Fodor et al. |
| 5,491,074 A | 2/1996 | Aldwin et al. |
| 5,510,270 A | 4/1996 | Fodor et al. |
| 5,523,226 A | 6/1996 | Wheeler |
| 5,527,681 A | 6/1996 | Holmes |
| 5,550,215 A | 8/1996 | Holmes |
| 5,571,639 A | 11/1996 | Hubbell et al. |
| 5,573,933 A | 11/1996 | Seamark et al. |
| 5,593,839 A | 1/1997 | Hubbell et al. |
| 5,599,695 A | 2/1997 | Pease et al. |
| 5,624,711 A | 4/1997 | Sundberg et al. |
| 5,631,734 A | 5/1997 | Stern et al. |
| 5,677,195 A | 10/1997 | Winkler et al. |
| 5,744,101 A | 4/1998 | Fodor et al. |
| 5,744,305 A | 4/1998 | Fodor et al. |
| 5,753,788 A | 5/1998 | Fodor et al. |
| 5,770,456 A | 6/1998 | Holmes |
| 5,800,992 A | 9/1998 | Fodor et al. |
| 5,831,070 A | 11/1998 | Pease et al. |
| 5,837,832 A | 11/1998 | Chee et al. |
| 5,856,011 A | 1/1999 | Sogabe |
| 5,856,092 A | 1/1999 | Dale et al. |
| 5,856,104 A | 1/1999 | Chee et al. |
| 5,858,659 A | 1/1999 | Sapolsky et al. |
| 5,871,928 A | 2/1999 | Fodor et al. |
| 5,925,525 A | 7/1999 | Fodor et al. |
| 6,027,880 A | 2/2000 | Cronin et al. |

(Continued)

FOREIGN PATENT DOCUMENTS

| | | |
|---|---|---|
| WO | WO-92/06180 | 4/1992 |
| WO | WO 92/10588 | 6/1992 |

(Continued)

OTHER PUBLICATIONS

Bertolotti et al. Journal of Cell Science (2001) 114: 3207-3212.*
Niranjanakumari et al. Methods (2002) 26: 182-190.*
Wahls, W.P. PCR Methods and Applications (1994) 3: 272-277.*
Singh et al. Proceedings of the National Academy of Science, USA (1994) 91(26): 12770-12774.*
Jensen et al. Proceedings of the National Academy of Sciences, USA (1995) 92: 12220-12224.*
Pelle et al. Nucleic Acids Research (1993) 21(10): 2453-2458.*
Glickman et al. Journal of Virology (1988) 62(3): 902-911.*

(Continued)

*Primary Examiner* — Angela M Bertagna
(74) *Attorney, Agent, or Firm* — DLA Piper LLP (US)

(57) ABSTRACT

The present invention provides methods for purifying RNA molecules interacting with an RNA binding protein (RBP), and the use of such methods to analyze a gene expression profile of a cell. The invention also provides sequences of RNA molecules that mediate binding to an RBP, proteins encoded by the sequences, a method of identifying the sequences, and the use of the sequences in a screen to identify bioactive molecules. The invention also provides RNA motifs found among the sequences and compounds that bind the RNA motifs. In addition, the invention provides methods of treating diseases associated with a function of an RNA binding protein.

22 Claims, 55 Drawing Sheets

(56) References Cited

U.S. PATENT DOCUMENTS

| | | | |
|---|---|---|---|
| 6,040,138 | A | 3/2000 | Lockhart et al. |
| 6,040,193 | A | 3/2000 | Winkler et al. |
| 6,107,029 | A | 8/2000 | Giordano |
| 6,291,637 | B1 | 9/2001 | Das et al. |
| 6,383,393 | B1 | 5/2002 | Colpan et al. |
| 6,426,183 | B1 | 7/2002 | Beattie |
| 6,586,727 | B2 | 7/2003 | Bateman et al. |
| 6,602,391 | B2 | 8/2003 | Serikov |
| 6,613,516 | B1 | 9/2003 | Christians et al. |
| 6,613,958 | B1 | 9/2003 | Neuhold et al. |
| 6,635,422 | B2 | 10/2003 | Keene et al. |
| 2003/0211466 | A1 | 11/2003 | Keene et al. |
| 2003/0235830 | A1 | 12/2003 | Keene et al. |
| 2004/0096878 | A1 | 5/2004 | Keene et al. |
| 2005/0227251 | A1 | 10/2005 | Darnell et al. |

FOREIGN PATENT DOCUMENTS

| | | | |
|---|---|---|---|
| WO | WO-92/20316 | | 11/1992 |
| WO | WO-92/22635 | | 12/1992 |
| WO | WO-93/14188 | | 7/1993 |
| WO | WO-93/20221 | | 10/1993 |
| WO | WO-93/25071 | | 12/1993 |
| WO | WO-95/04744 | | 2/1995 |
| WO | WO-01/48480 | | 7/2001 |
| WO | WO 0148480 | A1 * | 7/2001 |
| WO | WO-02/060924 | | 8/2002 |
| WO | WO 02060924 | A2 * | 8/2002 |
| WO | WO-02/070746 | | 9/2002 |

OTHER PUBLICATIONS

Aicher, W. K. et al., "Transcription factor early growth response 1 activity up-regulates expression of tissue inhibitor of metalloproteinases 1 in human synovial fibroblasts," Arthritis & Rheumatism, vol. 48, No. 2, pp. 348-359 (Feb. 2003).
Baranov PV, Sergiev PV, Dontsova OA, Bogdanov AA, Brimacombe R. The Database of Ribosomal Cross links (DRC). Nucleic Acids Research, 1998, vol. 26, No. 1 187-189.
Bertolotti A, Ron D. Alterations in an IRE1-RNA complex in the mammalian unfolded protein response. Journal of Cell Science. (2001)114:3207-3212.
Bertrand E, Fromont-Racine M, Pictet R, Grange T. Visualization of the interaction of a regulatory protein with RNA in vivo.: Proc Nail Acad Sci USA. (1993) 90(8): 3496-3500.
Brinster, R. L. et al., "Factors affecting the efficiency of introducing foreign DNA into mice by microinjecting eggs," Proc. Natl. Acad. Sci. USA, vol. 82, pp. 4438-4442 (Jul. 1985).
Brown V, Jin P, Ceman S, Darnell JC, O'Donnell WT, Tenenbaum SA, Jinx, Feng Y, Wilkinson KD. Keene JD, Darnell RB, Warren ST. Microarray identification of FMRP-associated brain mRNAs and altered mRNA translational profiles in fragile X syndrome. Cell. Nov. 16, 2001;107(4):477-87.
Buckanovich RJ, Darnell RB. The neuronal RNA binding protein Nova-1 recognizes specific RNA targets in vitro and in vivo. Mol Cell Bioi. Jun. 1997;17(6):3194-201.
Cardullo, R. A. et al., "Detection of nucleic acid hybridization by nonradiative fluorescence resonance energy transfer," Proc. Natl. Acad. Sci. USA, vol. 85, No. 23, pp. 8790-8794 (Dec. 1988).
Elbashir SM, Lendeckel W, Tuschl T. RNA interference is mediated by 21- and 22-nucleolide RNAs. Genes Dev. Jan. 15, 2001;15(2):188-200.
Fuchs, E. C. et al., "Genetically altered AMPA-type glutamate receptor kinetics in interneurons disrupt long-range synchrony of gamma oscillation," Proc. Natl. Acad. Sci. USA, vol. 98, No. 6, pp. 3571-3576 (Mar. 13, 2001).
Gao FB, Carson CC. Levine T, Keene JD. Selection of a subset of mRNAs from combinatorial 3' untranslaled region libraries using neuronal RNA-binding protein Hei-N1. Proc Nail Acad Sci USA. Nov 8, 1994;91 (23):11207-11.
Glickman JN, Howe JG, Steitz JA. Structural analyses of EBER1 and EBER2 ribonucleoprotein particles present in Epstein-Barr virus-infected cells. Journal of Virology Mar. 1988; 62(3): 902-911.

Hecht A, Strahl-Bolsinger S, Grunstein M. Mapping DNA interaction sites of chromosomal proteins. Crosslinking studies in yeast. Methods Mol Bioi. 1999; 119:469-79.
Hockensmith JW, Kubasek WL, Vorachek WR, von Hippel PH. Laser cross-linking of nucleic acids to proteins. Methodology and first applications to the phage T4 DNA replication system. J Bioi Chem. Mar. 15, 1986;261(8):3512-8.
Jensen KB, Atkinson BL, Willis MC, Koch TH, Gold L. Using in vitro selection to direct the covalent attachment of human immunodeficiency virus type 1 Rev protein to high-affinity NA ligands. Proc Natl Acad Sci USA. Dec. 19, 1995;92(26):12220-4.
Koller, B. H. and Smithies, O., "Inactivating the beta 2-microglobulin locus in mouse embryonic stem cells by homologous recombination," Proc. Natl. Acad. Sci. USA, vol. 86, No. 22, pp. 8932-8935 (Nov. 1989).
Kunz, D. et al., "The Human Leukocyte Platelet-activating Factor Receptor," J. Biol. Chem., vol. 267, No. 13, pp. 9101-9106 (May 5, 1992).
Lagos-Quintana M, Rauhut R, Lendeckel W, Tuschl T. Identification of novel genes coding for small expressed RNAs. Science. Oct. 26, 2001;294(5543):853-8.
Levine TO, Gao F, King PH, Andrews LG, Keene JD. "Hei-N1: an autoimmune RNA-binding protein with specificity for 3' uridylate-rich untranslaled regions of growth factor mRNAs." Malec Cell Bioi13: 3494-3504, 1993.
Meyer, T. F. and Geider, K., "Bacteriophage fd gene II-protein: I. Purification, involvement in RF replication, and the expression of gene II," J. Biol. Chem., vol. 254, No. 24, pp. 12636-12641 (Dec. 25, 1979).
Milt S, Steitz J. Evidence for reassociation of RNA-binding proteins after cell lysis: implications for the interpretation of immunoprecipitation analyses. RNA. Nov. 2004; 10(11 ): 1692-1694.
Miyashiro I, Takach I K, Doki Y, Ishikawa 0, Ohigashi H, Murata K, Sasaki Y, Imaoka S, Nakaizumi A, Takenaka A, Furukawa H, Hiratsuka M. When is curative gastrectomy justified for gastric cancer with positive peritoneal lavage cytology but negative macroscopic peritoneal implant? World J Surg. Sep. 2005;29(9):1131-4.
Montpetit A, Pay Ant C, Nolan JM, Brakier-Gingras L. Analysis of the conformation of the 3' major domain of *Escherichia coli*16S ribosomal RNA using site-directed photoaffinity crosslinking. RNA. Nov. 1998; 4(11 ): 1455-1466.
Niranjanakumari S, Lasda E, Brazas R, Garcia-Blanco MA. Reversible cross-linking combined with immunoprecipitation to study RNA-protein interactions in vivo. Methods (2002) 26: 182-190.
Orlando V. Mapping chromosomal proteins in vivo by formaldehyde-crosslinked-chromatin immunoprecipitation. Trends Biochem Sci. Mar. 2000;25(3):99-104.
Pelle R, Murphy NB. In vivo UV-cross-linking hybridization: a powerful technique for isolating RNA binding proteins. Application to trypanosome mini-exon derived RNA. Nucl. Acids Res. 1993 21 (10): 2453-2458.
Pogue GP, Cao XQ, Singh NK, Nakhasi HL. 5' sequences of rubella virus RNA stimulate translation of chimeric RNAs and specifically interact with two host-encoded proteins. The Journal of Virology (1993) 67 (12): 7106-7117.
Polydorides, A. D. et al., "A brain-enriched polypyrimidine tract-binding protein antagonizes the ability of Nova to regulate neuron-specific alternative splicing," Proc. Natl. Acad. Sci. USA, vol. 97, No. 12, pp. 6350-6355 (Jun. 6, 2000).
Rodriguez-Fonseca, C. et al., "Puromycin-rRNA interaction sites at the peptidyl transferase center," RNA, vol. 6, No. 5, pp. 744-754 (May 2000).
Roy PJ, Stuart JM, Lund J, Kim SK. Chromosomal clustering of muscle-expressed genes in Caenorhabdilis elegans. Nature. Aug. 29, 2002;418(6901 ):975-9.
Singh N, A Trey A CD, Nakhasi HL. Identification of calreticulin as a rubella virus RNA binding protein. Proc Natl Acad Sci US A. vol. 91(26): 12770-12774 (1994).
Stahl, D. A. et al., "Use of phylogenetically based hybridization probes for studies of ruminal microbial ecology," Appl. Environ. Microbiol., vol. 54, No. 5, pp. 1079-1084 (May 1988).

(56) References Cited

OTHER PUBLICATIONS

Struti H, Paro R. Mapping DNA target sites of chromatin proteins in vivo by formaldehyde crosslinking. Methods Mol Biol. 1999;119:455-67.

Teigelkamp S, Whitiaker E, Beggs JD. Interaction of the yeast splicing factor PRP8 with substrate RNA during both steps of splicing. Nucleic Acids Research (1995) 23(3): 320-326.

Tenebaum SA, Lager PJ. Carson CC, Keene JD. Ribonomlcs: identifying mRNA subsets in mRNP complexes using antibodies to RNA-binding proteins and genomic arrays. Methods. Feb. 2002;26(2): 191-8.

Tenenbaum SA, Carson CC, Lager PJ, Keene JD. Identifying mRNA subsets in messenger ribonucleoprotein complexes by using eDNA arrays. Proc Nail Acad Sci U S A. Dec. 19, 2000;97 (26): 4085-90.

Urlaub H, Hartmuth K, Lohrmann R. A two-tracked approach to analyze RNA-protein crosslinking sites in native, nonlabeled small nuclear ribonucleoprotein particles. Methods vol. 26, Issue 2, Feb. 2002, pp. 170-181.

Wahls WP. RNA Associated with a Heterodimeric Protein that Activates a Meiotic Homologous Recombination Hot Spot: RLIRT /PCR Strategy for Cloning any Unknown RNA or DNA. PCR Methods and Applications (1994) 3:272-277.

Zalfa F, Giorgi M, Primerano B, Moro A. Di Penta A. Reiss, Oostra B, Bagni C. The fragile X syndrome protein FMRP associates with BC1 RNA and regulates the translation of specific mRNAs at synapses. Cell. Feb. 7, 2003;112(3):317-27.

\* cited by examiner

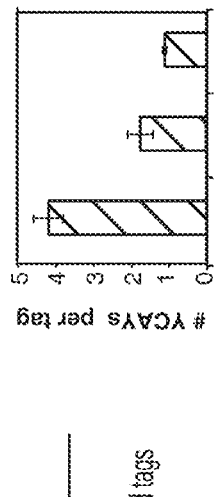

FIG. 3A

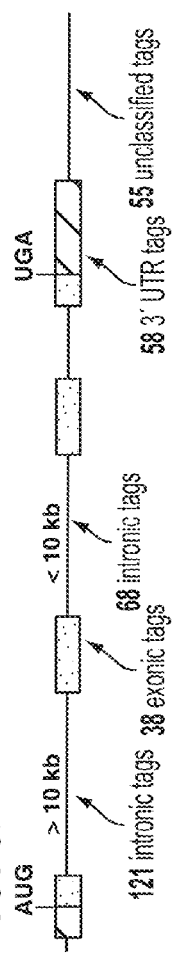

| hexamer | Nova tags obs/exp | control tags obs/exp |
|---|---|---|
| UCCAUC | 30.1 | 1.3 |
| CCAUCC | 27.3 | 1.2 |
| AUCCAU | 25.0 | 0.9 |
| CAUCCA | 23.7 | 1.7 |
| UCAUCC | 14.7 | 0.9 |

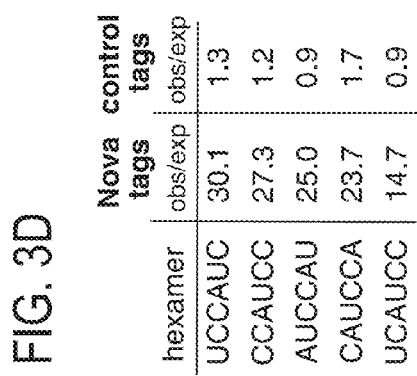

FIG. 3B

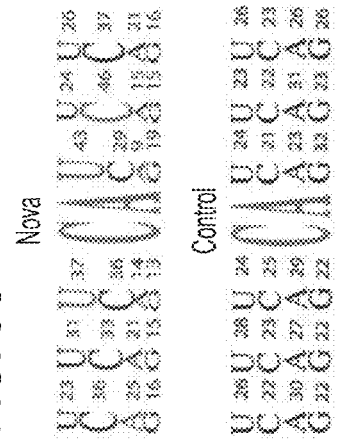

| RNA tag | transcribed sequence | Kd [nM] |
|---|---|---|
| gephyrin1 | GGGCCAGUUCAACCAGGUCCCAGCUUCCAUCCAUGGUUGGGGUGCUAGUAUCUGCAUCUGACUCUUUCAGCU | ~400 |
| control | GGGAGCUGAUGAAACCADAAUGCCUGCCACCUCUUAAUAAACAAUCAGCAUGAGAUCGGUUCCUAAGUCUUCCUCAGAA | >10³ |
| gephyrin2 | GGGCCAACUGACCAGAAUGCCCUGCCACCAGUACAGUGCUUGGAGAAGCAGUGUGGCACUGAAGCCUAGUGUGC | 64 |
| control | GGGAGGAUGCCUGCCAUUUCCAUAUUCUCAGACUAACAUGCGUCUCAUGCU | >10³ |
| JNK2 | GGGGUUUUGUAAAGGAGGCCAUAGGGCAUCCAUCCCCUCGU | 34 |
| control | GGGCUGUAGUUAGUGCCAUUCCCUGGAUAACCDUCCAUCAUUCCAGUCCAG | >10³ |
| neogenin | GGGCUACACUGGCUGGAAGGAGGGGAAUGAGACCAAAAAUGAUGAAUGCCCUUUGACUCUCAG | 23 |
| control | | >10³ |

| sequence | SEQ ID NO | gene name | place on genome |
|---|---|---|---|
| more then 1 tags in the same gene (77 tags / 33 genes) | | | |
| CATCCATCTTGACTCATTGCTGTCACTGCAGAAGGACT AAGTAGCAAAACACTGCTCCAAGGTCTTTGGC | 1 | similar to TULIP-1 | chr2:147362763-147362852 |
| AAACAACATGTCCCTGCAACATAATCCATGTTCTTCC TGTCATTCCACCATCCCTGACCCCACCCCCTCCAC | 2 | similar to TULIP-1 | chr2:147387266-147387363 |
| CATTTCAAATGTTTTCCCCCTTCTAGGCTTCCCCTCTG CAAACCCCTTAAGCCATCCTCTCCCCCTGCTTCTATG | 3 | Rzf (ring zinc finger protein) | chr3:58301266-58301341 |
| ATGTTTTAGTTTTCACAATTACTTTCGCCATCATTTGCT TTTTACTGACAAAATGTCTGTCCATCCTTCTCATTGTCT CCCCCATCCTCAGTT | 4 | Rzf (ring zinc finger protein) | chr3:58363159-58363251 |
| AGCACCAGGGAGCAAATGCCAGCTGATTGTTGTTCCT GCCCAGCTTGCTGGCTAGCTTTGATACATTCCTCA | 5 | BB842374 brain EST | chr3:73864385-73864458 |
| AGCACCAGGGAGCAAATGCCAGCTGATTGTTGTTCCT GCCCAGCTTGCTGGCTAGCTT | 6 | BB842374 brain EST | chr3:73864385-73864442 |
| GGTGGGAAAGTACCTCATGTTCACCATGGTGCTAGTC ACCTTCTCCATCGTCACTAGCGTGTG | 7 | nicotinic acetylcholine receptor beta 2 subunit (Acrb2) | chr3:80601032-80601084 |
| ACACCATCAACCTCATCATCCCCTGCGTACTCATCACC TCGCTGGCCATCCTGGTCTTCTACCTGCC | 8 | neuronal nicotinic acetylcholine receptor beta 2 | chr3:80601205-80601272 |
| AAACCCTTCTGCCAGGTGACCACACGCAGCTTCCCTG CCCGCTCCTTCATCACCTTCCG | 9 | Flamingo 1 | chr3:108897325-108897383 |
| AAAGTGCTTCATTTCTCCTGCCCACCCTTGCAGGTAGG GCCAGTCACTCTTCCATTGCTTCTTTGCTGT | 10 | Flamingo 1 | chr3:108894460-108894528 |
| ACTGTCCCTCCCCATCTACTCACTGTCTTCCCCATCTA CTCACTGTCCTCCCATCTACTCACTGTCCTCTCATCTA CTCACTGTCCTCCCATCT | 11 | GABA-B receptor 2 | chr4:45617592-45617648 |
| AGTCACTGTCCCTCCCCATCTACTCACTGTCCCTCCCC ATCTACTCACTGTCCTCCCATCTACTCACTGTCCTCCCC CATCT | 12 | GABA-B receptor 2 | chr4:45623801-45623941 |
| CCATCAGTTCTCTCTGTGCTCCATCAGTCCTCTCTGTG CTCCATCAGTCCTCTGTGCTCCATCAGTTCTCTCT | 13 | protein kinase C zeta | chr4:150725895-150725948 |
| CTCCATCAGTCCTCTCTGTGCTCCATCAGTCCTCTCTG TGCTCCATCAGTCTCTCTGTGCTCCCTTAGTCCTC | 14 | protein kinase C zeta | chr4:150725897-150725970 |
| TCACCTGTCCATCACCCAGTCATGCATGCATGCACGCA TGCACACACATTCAACCCACCCACTCATCCACCT | 15 | protein kinase C, zeta | chr4:150744198-150744237 |
| TGTTCTGCTCATTTCATTGCCATTGCTATGGGATCACTT TATCATTGCCCCATGATGGCATCATGG | 16 | calneuron 1 (Caln1) | chr5:129016132-129016197 |
| GCCACAGGTCACTTGGCTTTTCTCTCTCCATGGGGAAT TTTCCGTCTGCTCCCTTGTATCTGTCTCCTTTCCTC | 17 | calneuron 1 (Caln1) | chr5:129113412-129113484 |
| ACGTCTCCACCTCACCCTCATTACTAACTTCTACCTGT GTGGTGCCCCAGGAACTGCTCTTGTGCA | 18 | diacylglycerol kinase iota (DGKi) | chr6:37138991-37139058 |
| ATGACGCAGGTGCCACAGCTGCTGTCACCTCCCTCGG CGCCAGCATATGCGCAGGAAGAGCAC | 19 | diacylglycerol kinase iota (DGKi) | chr6:37164474-37164538 |

FIG. 3H

| place on pre-mRNA | comments | blast search |
|---|---|---|
| intron 19 (5 kb) | 1 kb 5' to exon 20 | |
| intron 11 (8kb) | 1.5 kb 3' to exon 11 | |
| intron 3 | 500 bp 5' to (alternative) exon 4 (cDNA data) | (part of Lx2, L1, LINE repeat), (recloned in XNS18) |
| intron 9 | 2.2 kb 5' to (alternative) exon 9 (contains internal cryptic splice site, used only in brain) | highest expression in brain |
| intron (170 kb) | 5 kb 3' to exon | |
| intron (170 kb) | 5 kb 3' to exon | |
| exon 5 | (edited in Drosophila) | |
| exon 5 | | |
| exon 3 | | AB028499.1 Flamingo 1 |
| 3' UTR | | |
| intron 7 (38 kb) | 19 kb 3' of exon 7 (homologous exon 7 in GABAB1 is alternatively spliced) | |
| intron 7 (38 kb) | 19 kb 3' of exon 7, part of 161, with some mismatch (gap in BLAT sequence) | part of (TGGG)n Simple_repeat |
| intron 10 (12 kb) | 1 kb 5' to exon 11 (misalignment) | |
| intron 10 (12 kb) | 1 kb 5' to exon 11 (repetitive seq., some mismatch) | |
| intron 7 | 1.5 kb 5' to exon 8 | (part of (TGGG)n Simple_repeat |
| intron 3 (100 kb) | 30 kb 5' to exon 4 (alternative promoters) | |
| intron 6 (200 kb) | 10 kb 3' to exon 6 | |
| intron 23 (23 kb) | 7 kb 3' of exon 23 | |
| intron 21 (25 kb) | 1 kb 3' to exon 21 (alternative exon 15a?) | |

FIG. 3H CONT.

| Sequence | # | Gene | Location |
|---|---|---|---|
| ACTCCATCCTTCACTCTCTCCCTCCTCACAATCGCTCC TCCTCGCTCTCAGCCTGGCCCCCCAGCCCTCCTC | 20 | plasma membrane Ca2+-ATPase 2 (Pmca2) | chr6:114656968-114659066 |
| AACTCCATCCTTCTCTCTCCGTCCTCACAATCGCTCCT CCTCGCTCTTC | 21 | ATPase, Ca++ transporting, plasma membrane 2 | chr6:114659009-114659059 |
| GCTCATCTCGAGGACCATGATGAAGAACATCCTGGGC CACGCCGTCTACCAGCTCACCCTCATCTTCACCCT | 22 | plasma membrane Ca2+-ATPase 2 (Pmca2) | chr6:114673868-114673939 |
| AGAGTACCGGGATGTCTCTGTTACCTGGTAGAGGTTC CCGATGTCATTCATCTGTCTGTCTCTGCATCAGCTGAC CA | 23 | KIAA1110 brain protein | chr6:122181056-122181132 |
| GTCATTCATCTGTCTGTCTCTGCATCAGCTGACCATCT TCCAGTGGTACCTCTCCTCCCCTGCTCACCCCTCAC | 24 | KIAA1110 brain protein | chr6:122181017-122181090 |
| CCACCGGTCCAGCTCCTGACCCGCCTCATCTGAGCTC CCCAGCCAGCCCTCACTTGCCCT | 25 | parathymosin (11.5 kDa Zn-binding protein) | chr6:125801027-125801088 |
| CCTTCACCCTCACTGCCACCGGTCCAGCTCCTGACCG GCCTCATCTGAGCTCCCCAGCCAGCCCTCACT | 26 | 11.5 kDa Zn-binding protein (parathymosin) | chr6:125801033-125801101 |
| ACAAATCCAGCCCCGTTTCTCCTGGCTCCCTGCTCTG GCCCTGCCCCAGAGCTGTGACCCTTGTCCTTTGACCC AGCCTCTCATTTCCATCTCTC | 27 | 11.5 kDa Zn-binding protein (parathymosin) | chr6:125801113-125801207 |
| TCATTTACCATTTCATCCATCTATCCATTCACCTATCTA CTATCCACTCATGTATCCATCCATCTACCCATTCATTCA TCCACTCGTCCACCCACTTATCCATTCATCCACCCACC CACTCATTATTCACCCCTACCCATCCATCCAC | 28 | Shank1 | chr7:33866843-33886870 |
| CCTGGTCCCATGCTGCAGACACACATGGGACTTTCCT TCCCTCTCCTGCTCC | 29 | Shank1 | chr7:33924680-33924731 |
| GATGAGCAACACTCACCATCTTTCGTTTGAGTCTCACG ACTGTGAGATCAACCCATGCACCGCTCTGAGA | 30 | ribosomal protein L13a | chr7:34694154-34694223 |
| TCCATGATGAGCAACAGTCACCATCTTTCGTTTGAGTC TCACGACTGTGAGATCAACCCATGCACCGCTCTGA | 31 | ribosomal protein L13a | chr7:34694156-34694228 |
| CTTGTCCCGACAGCTCTACCCACGGTCATCTGCCACC TCCACCATCTATCTCG | 32 | KIAA1923 WD repeat protein | chr8:111377449-111377501 |
| CTGGCTTGTCCTCCCCAGTTCCTTCCTGTTCATCCTTC GCACAACTCTGACTGCCCACAGCCCATGCTCCATGT GGCTAAGTCCCATGGTGCCAGATGCTGACC | 33 | KIAA1923 WD repeat protein | chr8:111415997-111416102 |
| CAGGTTTAGGCCTGACTGTCTGTCTGTCCATCTACCCA TTTGTCCTCAATTCACCATCCTTCCATCCATCATCTC | 34 | H/T-cadherin | chr8:116530091-116530165 |
| AGCTCACCATCCTCCCAGCTCACCATCCTCCCAGCTC ACCATCCTCCCAGCTCACCATCCTCCCAGCTCACCAT | 35 | H/T-cadherin | chr8:118886807-118886880 |
| ACATCTGGATCCTCCTCACACCCACATCTGCATGCTCC TCACACCCACATCTGCATGCTCCTCACACCCACA | 36 | ARPP21/TARPP | chr9:113217776-113217847 |
| AATTCCTCATCCTCATTGCTTCCTCCTCACACCTACATC TGCATC | 37 | ARPP21/TARPP | chr9:113217929-113217973 |
| AATTCCACACTCCTGTCCATTCCAGGGAGTGACCACTA TCAGGAATCTACCTCCATTCCTATAGGCACTTTACCT GGATTTTC | 38 | Teneurin 2 (Neurestin alpha) | chr11:37118813-37118897 |
| AGGCCACATTCATTGCATATACTTTCAGCAGAAGCTGA AACCACAGGTGAACTCGCAATGCCCGGT | 39 | Teneurin 2 (Neurestin alpha) | chr11:37233999-37234064 |
| GTGGCAAGGATATATATGTCTGTGCCTGTGCAGATGC ATTTGTGTGTGTGTGTGTGTGTGTGTGTGTGTGTGT | 40 | rabaptin-5 | chr11:71461782-71461854 |

FIG. 3H CONT.

| | | |
|---|---|---|
| 3' UTR | | |
| 3' UTR | | RATATPIF2 Rat plasma membrane Ca2+ ATPase-isoform 2 mRNA |
| exon 14 | (alternative exons 17b, 18a - no difference in N2 KO) | |
| last intron | 50 b 5' to terminal exon | |
| Intron/terminal exon junction | | |
| 3' UTR | 220 b 3' to stop codon | cytoplasmic protein in brain, nuclear in intestine) |
| 3' UTR | 200 b 3' to stop codon | |
| 3' UTR | 100 b 3' to stop codon | X16481 zinc(2+) binding protein |
| intron 8 | 300 b 3' of exon 8 | (part of (TCCA)n Simple_repeat) |
| exon 27 = 3' UTR | exon 26 is alternatively spliced | AF158046 Rattus norvegicus SPANK-1 mRNA; see XN358 |
| intron 2 (200 b) | 30 b 3' to exon 2 | |
| intron 2 (200 b) | 30 b 3' to exon 2 | same as 428a |
| intron 26 | 200 b 3' to (alternative) exon 26 | (close to SINE repeat) |
| intron 7 | 300 b 3' of exon 7 | |
| intron 2 (160 kb) | 25 kb 3' of exon 2 | (expressed in cancers, methylated!) |
| intron 5 (160kb) | 30 kb 3' to exon 5 | part of (CACCT)n Simple_repeat |
| intron 17 (52kb) | 11.3 kb 3' to exon 17 | |
| intron 17 (52kb) | 11.4 kb 3' to exon 17 | |
| intron 3 (470 kb) | 60.5 kb 3' to exon 2 (two alternative promoters 120 kb and 300 kb downstream) | |
| intron 1 (60 kb) | 20 kb 3' of exon 1 (alternative promoters downstream) | |
| intron 2 (27 kb) | 12 kb 3' of alternative exon 2 | |

FIG. 3H CONT.

| Sequence | # | Gene | Location |
|---|---|---|---|
| TCCATGACCATTTCATTCCCTCTTCTAAGTGAGGCTCA AGCATTTTTGCTTGTACCCTCCTTCCTG | 41 | rabaptin-5 | chr11:71493024-71493089 |
| TCATTCATTCATTCATTCATTCATTCATTCATTCATCTTT TTCTGT | 42 | rabaptin 5 | chr11:71535098-71535144 |
| AACCTCATGGTCCACCATCGACCCATCCATCAGTTCAC CCATCCATCCATTCACCTAAGCACCCACCATCAA | 43 | brain sodium channel 1 alpha subunit (Accn1) | chr11:61574052-61574123 |
| ACCTCCTCACCCTCTCACCTCCTCACCCACTCACCCCC TCACCCACTCACCC | 44 | brain sodium channel 1 alpha subunit (Accn1) | chr11:61595014-61595065 |
| CCAGTTCAACCACAGGTCCCCAGCTTCCATCCATTGG TTGGGTGCTAGTATCTGCATCTGACTCTTTCAGCT | 45 | gephyrin | chr12:73163177-73163245 |
| CCAACCACAAATGCCAGCACCTCTTAATAACAATCAGC ATGACCTCTGCCTAAGTCTTGGCTTCTTCCTCAGAA | 46 | gephyrin | chr12:73256858-73256931 |
| TGACCCTTGGCACAATGCCAGCTCTGGCTGGACACAA GGACACACGCATCTCCTCCATTCCTGCTGCTCCATTG | 47 | GI2 | chr12:103805757-103805830 |
| ACTCAGAGCAGGGGGAAGAAACACACCCTCAACTCTG CTTCCCCGTGCTCCATCTTCCTTTCTGCCTTCCA | 48 | GI2 | chr12:103824824-103824894 |
| GCCTGTGTTCAGCCCTCTCACCCCATGCTTATCTGGAC ATTGAAGCTTGGAAAGCCAGTGGTGACTTC | 49 | GI2 | chr12:103826302-103826369 |
| TGTGTTCAGCCCTCTCACCCCATGCTTATCTGGACATT GAAGCTTGGAAAGCCAGTGGTGACTTCAACT | 50 | GI2 | chr12:103826305-103826373 |
| TCCACCCATCCATCTGGCTATCCATCCATCCATCTGTC AGTCAATCCATCCATCCATCCATCCATCCATTCATCCA | 51 | GI2 | chr12:103826387-103826462 |
| AGCCATCTGTCAGTCAATCCATCCATCCATCCATCCAT TCATCCATCC | 52 | GI2 | chr12:103826414-103826455 |
| AGCCATCTGTCAGTCAATCCATCCATCCATCCATCCAT TCATCCATCCATCCATGCAT | 53 | GI2 | chr12:103826414-103826465 |
| CCATCTCAGTCAATCCATCCATCCATCCATCCATTCAT CCATCCATCCATGCATACACACATTGGGCCTCCATCAC TTGACCTGGTGCT | 54 | GI2 | chr12:103826416-103826510 |
| TCATGAAGCAAGGCCCCCATTCACAGCCTCCTCCTCC TCCTCCTAGGTCACGGCTCTGAGCACGTCCCAGCTGG ACCCCTATCACC | 55 | GI2 | chr12:103826583-103826688 |
| GGCTTCCCACACCCCACACCCTCCTCCTGTGATCCAG GAGGGCCAGATTCCCAGAGTGCCCTGGGGCTGGCCC TTCCCAC | 56 | GI2 | chr12:103826687-103826766 |
| GCGGAGCTGCCTCCCCAGGCTTCACACTGCCTGGTGC ATGGTCCCTCATGAGCTTGGCCTTC | 57 | GI2 | chr12:103826772-103826835 |
| GGATTCTCACCTTTCCCCCTGTATGTTCTATACCTTCTC TTCTTCTTTCCTCTCTCTCATCCTCCTCTTCCCTT | 58 | FLJ31787 brain protein | chr13:10283608-10283679 |
| GAATAGAGGCATCAAGTCACGATGTTGTCAGTGGGAA GCAGCTAGGTCTGCCCTGAGGGTGGTTTCCAGCTTTG | 59 | FLJ31787 brain protein | chr13:10133232-10133305 |
| AAGTGGCAGATTCACGTCCCAGGGTTCAGAGGTGGCA AACTTCTCAGTGGCAGCTGTGCTCGGTCATGC | 60 | MAP1b | chr13:96780336-96780404 |
| AGATTTCGAGTTAGTCGAAAATTGCCTACCCCCGTTCA TCTCTGCTGAACATTCGG | 61 | MAP1b | chr13:96782250-96782305 |
| TACATAGTCAGGGGAGGGCCCCTGTCAACGTGCGCAC AAGGTTCCTTTATCCTTTGTCATTACGTCATTGTCCAAG GTGACAGGAGGAACTCAGTCGTTAAAATGACGAGCCT TATTTTCATGA | 62 | MAP1b | chr13:96859716-96859839 |
| CCTCCCTCATCCTCCCTCATCCTCCTCATCTACAGCAG ATCCCCATCCTCCTCTCCTGCGGCAGTGTCCTCCCCG | 63 | no gene prediciton | chr14:58110355-58110429 |

FIG. 3H CONT.

| | | |
|---|---|---|
| intron 4 (6.4 kb) | 3.4 kb 5' to alternative exon 5 | |
| intron 13 | 2.2 kb 5' of exon 14 | |
| intron 3 (60 kb) | 30 kb 3' to exon 3 (misalignment) | |
| intron 3 (60 kb) | 7 kb 3' of exon 3 (alternative promoter in intron 1) | (includes (TGGG)n Simple_repeat) |
| intron 6 (10 kb) | 2.5 kb 3' to exon 6 (exons 4 and 7 are alternatively spliced) | |
| intron 9 (27 kb) | 14 kb 3' to exon 14 | |
| intron 4 (2.6 kb) | 20 b 3' to exon 4 | |
| intron 8 (14 kb) | 7 kb 5' to exon 9 (alternative poly-A, splicing) | |
| intron 8 (14 kb) | 5 kb 5' to exon 9 | BM116899.1 |
| intron 8 (14 kb) | 4.99 kb 5' to exon 9 | (same as 322a) BM116899.1 |
| intron 8 (14 kb) | 4.85 kb 5' to exon 9 | BM116899.1 |
| intron 8 (14 kb) | 4.8 kb 5' to exon 9 | (part of (TGGA)n Simple_repeat) BM116899.1 |
| intron 8 (14 kb) | 4.78 kb 5' to exon 9 | (part of (TGGA)n Simple_repeat) BM116899.1 |
| intron 8 (14 kb) | 4.76 kb 5' to exon 9 | BM116899.1 |
| intron 8 (14 kb) | 4.6 kb 5' to exon 9 | BM116899.1 |
| intron 8 (14 kb) | 4.5 kb 5' to exon 9 | BM116899.1 Mouse Newborn Brain cDNA |
| intron 8 (14 kb) | 4.4 kb 5' to exon 9 | BM116899.1 Mouse Newborn Brain cDNA |
| intron 1 (130 kb) | 20 kb 5' to exon 1 | |
| intron 2 (100 kb) | 8 kb 3' of exon 2 | |
| 3' UTR | | |
| 3' UTR | 133 b 3' to stop codon | NM_008634.1| Mus musculus Mtap1b |
| intron 2 (64 kb) | 5 kb 3' to exon 2 (exon 3 is alternatively spliced, alternative promoter starts with exon 3) | |
| | | |

FIG. 3H CONT.

| Sequence | # | Gene | Location |
|---|---|---|---|
| TCCCTCATCCTCCCTCATCCTCCCCATCCTCCCTCATC CTCCCCATCCTCCGTCATCCTCCCTCATCCTCCCTCAT CCTCCCCATCCTCCCTCATCCTCCCTCATCCTCCCTCA TCCTCCCCATCCTCCCTCATCCICCCCATCCTCCCTCA | 64 | no good gene prediction | chr14:58110469-58110640 |
| ACCAAGTGGAAATCAGGAGAGGCAGAGGCATTATCTC GACATCTCCGTGGGTTCACTTTTCAATTTGTCCATCATT GCCATCATCATTGTT | 65 | Ataxin 2-binding protein (RNA binding) | chr16:6366304-6366394 |
| TCCTCACTGTGTGTCAATCAGGCACTGGAAGAATCTGC CACGGCTTTTCTCTGCCTGCCCTGCTCCCTCTCAC | 66 | ataxin 2-binding protein | chr16:6435218-6435292 |
| CAAAGCTCTGCAGAGATGCCTTCATCCCCTCCATCCAT CACAGCACAATTGCACTGGTGTGGACTCC | 67 | ataxin 2-binding protein | chr16:6658766-6658832 |
| GCAAGACATGCTGCCATCACATCCCTCAGCCACTGTCA TGATAATCATCCATTCTTATCCCTGCTTGGACACCA | 68 | G-protein coupled inwardly rectifying K+ channel (Girk2A-2) | chr16:95855648-95855721 |
| AGTGTCTGCATTTGGTGGCTGATTACGGGATGGATCC CTGGGTGTGGTTGTCTCTGCATGGTCCATCCTTATCA GTT | 69 | G-protein coupled inwardly rectifying K+ channel (Girk2A-1) | chr16:95888242-95888318 |
| ATCAGCAGTTCCGTTTACAGCTCACTCCATGTTCACAC TTTCTGGCTGTGTGTTG | 70 | ribosomal protein S6 kinase, 90kD, polypeptide 2, mouse (RSK3) | chr17:7030714-7030788 |
| CCACCCTGAGCCCTGGCTACTCTCTCTCCTTCCCCCT CCCTCCTCTCCATGTGTTCCCTGCTAGCCTTTTCCT GTCT | 71 | pp90 ribosomal protein S6 kinase 3 (pp90RSK3) | chr17:7108440-7108518 |
| GTGCTCACACTGTACTCACGCTCACGCTCTGTGCTCAC GCTCATGCTCTGTGCTCACATTGTACTCACGCTCACGC TCATGCTCTGTGCTCACGCTCTGCTCTGTGCTCACGCT CTGTGCTCACACTTACTTATTTGGTCAGTTAGTGCACT CACC | 72 | SET-binding protein (SEB) | chr18:79533137-79533292 |
| CACGCTCTGTGCTCACACTCTGTACTCACGCTCTGCTC TGTGCTCACACTGTACTCACGCTCACGCTCT | 73 | SET-binding protein (SEB) | chr18:79533263-79533331 |
| TTTCAGACCGTCCCTCACCTTCCCTGCTCAGCCCCATT GCTGTTCCTCCATCACTGTCTACAAC | 74 | neurexin II | chr19:4322569-4322632 |
| AGCTCCCATCATGCCAGCCCGACCCTCACCTCCATCT CTCCATTCCTCCTGCTCACCCT | 75 | neurexin II | chr19:4323747-4323805 |
| CCACGAGTGGGGTCAGGCATGTGGGTTTAAAGAGTTT TCCTTTGCAGAGCCTCATTTCATCGTTCATGGAGCTGC TCA | 76 | no gene prediction | chr19:5025277-5025354 |
| TGGGGTCAGGCATGTGGGTTTAAAGAGTTTTCCTTTG CAGAGCCTCATTTCATCCTTCATGGAGCTGCTCAGGAC TT | 77 | no gene prediction | chr19:5025284-5025360 |
| AGTGATTTCTCTGCCACATCGCCACCATGGGCCTTTG GCCTAATCA | 78 | no gene prediction | chr19:5026709-5026754 |
| related genes | | | |
| TCACACAGTCCCCAAGCAGGTCCAGCGTGGCATCACC CCGACGACCAGCAACGTCTCATCTTCTGGAAGCA | 79 | microtubule-associated protein 2 (MAP2) | chr1:67069834-67069905 |
| ACGCACATCACTGTTGTGATGCAGTGAGCTGCTCCTTT CCTTTATCTGCCTCTCGTTCCAGTCATCCC | 80 | neurexin III-alpha | chr12:83814745-83814813 |
| TCCCATGCATTCCATCATCTCCATCTTCTGCCATGACT TGCTTTTAATTTTATCCTTTTTTGTCTCAACTTGAC | 81 | hrb (ataxin-2 binding protein homologue) | chr15:77596576-77596691 |
| ACCAGTCCTAGCCCCGTCCCCAACCGGCTTTCGCTTGG GGAGTTGGGGGAATTCCTGCCAA | 82 | ataxin-2 related protein | chr7:116347188-116347247 |

FIG. 3H CONT.

| | | (part of (GGGA)n Simple_repeat) |
|---|---|---|
| Intron 4 (424 kb) | 93 kb 3' of exon 4 | alternatively spliced |
| Intron 4 (424 kb) | 80 kb 5' of alternative promoter | |
| Intron 4 (424 kb) | 30 kb 5' to exon 5 (3' to alternative promoters) | |
| Intron 2 (105 kb) | 50 kb 5' to exon 3 | |
| Intron 2 (105 kb) | 10 kb 3' to exon 2, 65 kb 5' of alternative promoter for Kir3.2d | |
| 3'UTR | (aligns also to another genomic locus) | 6755373 ribosomal protein S6 kinase, 90kD |
| Intron 1 (60 kb) | 1 kb 5' of exon 2 | antibodies available |
| Intron 1 (163 kb) | 40 kb 5' of exon 2 | |
| Intron 1 (163 kb) | 40 kb 5' of exon 2 | |
| Intron 17 (11 kb) | 1.4 kb 3' to exon 1 of neurexin II-beta | |
| Intron 17 (11 kb) | 150 b 3' to exon 1 of neurexin II-beta (misalignment) | |
| - | | |
| - | | |
| | | |
| exon 19 | right before stop codon (alternative exon 16) | |
| Intron 12 | 6365 b 5' to exon 13b (alternative exon 12) | |
| Intron 8 (4 kb) | 1.5 kb 3' to exon 8 (exon 8 alternatively spliced) | |
| 3' UTR | | |

FIG. 3H CONT.

| Sequence | # | Gene | Location |
|---|---|---|---|
| TCCATCCATCCATCATCCACCCATCCATCTATCCATCC ATCCTCCCATCCATCCATCCATCCATCC | 83 | ataxin-1 (sca1) | chr13:45282390-45282456 |
| AAGTCTGTCTAAACACCAGATCGCATTTGTGACTCATT AGCATTTCTCATCCCACCAACGCCTGCCTTTCCCACTC ACTTTCCCC | 84 | no gene | chr12:103926771-103926855 |
| AACCAACCACCTGTTCTTCTTTCTCCTCCTGTCCCACA TCATCGTCATGGAAAGCCTTGCCTGGTTCATCCTCTCG TACTTCGGCACTGGCTGGA | 85 | delta-6 desaturase | chr19:9426989-9427078 |
| CTGACCTCTGGTCTTCACATGTGTGGGCAAGTACAGC TGCACACATGCGTACCCCTCTCTCCCTCATCCCCA | 86 | delta-5 desaturase | chr19:9527077-9527142 |
| TCAATGTAGACCACCGCTCACCACGCACACACACCAT GCCCGCCTGGGTGCGCAGAGTCTTCCTGGACATTGTG CCCCGTC | 87 | nicotinic acetylcholine receptor alpha 4 subunit (Acra4) | chr2:179350862-179351042 |
| GCACCTCCTTCCTCTTCATCACATCTCACTTCACCTCTG GAGATGGGAAGGTAGCAGAGCGGCTACTGG | 88 | inositol polyphosphate 5-phosphatase pharbin | chr2:26985975-26986275 |
| ACTGTAGCACTGTGAGCTTGTATGTGTAACCGTCCTGT GGTGTCCAGAAGTCACTGTCTTGTTGCATTCGTCT | 89 | inositol polyphosphate 4-phosphatase | chr6:81165453-81165525 |
| CACCTCTCATCCCGCTGCTCTCCCTCACATCATCAAAC TGTAAGTCCACCTCTCATCCCGCTGCTCTCCCTCACAT CATC | 90 | 5'-AMP-activated protein kinase (AMPK) alpha-1 | chr15:4980558-4980547 |
| GATCACCGCCATCACTGTTATCAGCACCGTTATCACCA CCATCACTGTTATCAGCACCGTGATCACCACC | 91 | AMP-activated protein kinase (AMPK) gamma2 subunit | chr5:23553306-23553375 |
| TACTAGTCATCTTGCAGATGTCTACCCATCTGTCCCTC CTCACCTGCTTCCGCTCAGGTGGGTCCATTCATGCAC ATACTCATCCATTTATCATCCACTCAT | 92 | voltage dependent Ca++ channel beta 4 | chr2:53125938-53126038 |
| GCCAGTGGCTGAGGACATGACAGTCCACTTCACCTCC ACACTTATGGCTCTGATCCGGACAGCTCTGGAC | 93 | voltage-dependent alpha-1 E calcium channel | chr1:155359770-155359839 |
| TCTCCAAGCGTCAGTTTCTCCAGGCCACCTCCTGTCC CTCCACCCCTTGTTGGTTGAAC | 94 | voltage-gated calcium channel, alpha-1-G | chr11:95210325-95210384 |
| GATTTATTCCTCTCTCCCAGTCCACCCTCCAACTGTT CCACATCCCATACCTCCTCCCTACGCCATGTTTTCATG AGGATGTCCTTCCCCTCCACCCACTCCAC | 95 | K+ voltage-gated channel Q 3 | chr15:68444691-68444795 |
| GCTATGGCCACACGGTGCCCCTGTCAGATGGGGGCA AAGCCTCTGCCATCATCTACTCTGTC | 96 | TWIK-1 K+ channel | chr8:128032561-128032622 |
| ccatccttttctcattgacacccgtttgcGTTTTCCGAAATCATAT ACCTTATACTCCACCATTCCCATTCCTTGCTCCCC | 97 | similar to potassium channel Kv4.2 | chr8:21218017-21216068 |
| ATCTTTGCCTCCTCACTCATCAAAACTCATCTGTAGCAT GGCTTTCATCCATAGATTCTCAGGGGAATCACTTAACA TCCATAGTCTCA | 98 | erg3 (the ether-a-go-go-related K+ channel) | chr2:63642506-63642588 |
| 3' UTR targets (47) | | | |
| ATCTTCATGCCCGTTAGTCATCGTTTGCCTAGCATGTC CCTGTGGCGTCTCAAAAACAGTTTCATCGTCCCGTC | 99 | apoptosis-related RNA binding protein (Napor-1) | chr2:6553077-6553150 |
| CAACTGCAGCCCTCGGCTCCTTCCTTCCCACCTCCGA GACATCTCCTCTCTTCTCGCATCCCTCCTCAG | 100 | KIAA0515 brain protein | chr2:32585588-32585668 |
| CTGCAGAGCTCACTGCATTCACCCCTCCTCATCCTTTG CTTCCTTCCCCTTGCCTAGTCAGTAG | 101 | apoptosis inhibitory protein 5 = FGF-2- interacting factor | chr2:85389483-85389556 |

FIG. 3H CONT.

| | | |
|---|---|---|
| intron 7 (130 kb) | 14 kb 3' to alternative exon 7 (5' UTR) | |
| | same methylation region as G9f | |
| exon 3 | | NM_019699.1 Mus musculus fatty acid desaturase 2 (Fads2), highest expression in brain |
| intron 5 | 2 kb 3' from exon 6 | high expression in brain |
| exon 5 | a4b2 is the most abundant nAChR subtype in brain | (part of LINE repeat) |
| exon 5-6 junction | (converts fibroblasts to dendritic forms) | |
| intron 1 (300kb) | 80kb 3' to exon 2 | |
| intron 2 (4kb) | 1 kb 3' to exon 2 | |
| intron 1 (70kb) | 20 kb 3' to exon 1 | |
| intron 1 (189 kb) | 75 kb 3' to exon 1 | alternative promoter (beta 4a) ~100 kb 3' to Nova binding site |
| intron 39/exon 39 junction | alternative exons 39a, 39b (also in other CAC alpha-1 genes) | |
| intron 10 (14 kb) | 6 kb 5' to exon 11 (alternative exon 15) | |
| intron 15 | 70 bp downstream of exon 15 | |
| exon 2 | | |
| intron 1 (503 kb) | 63 kb 3' to exon 1 | |
| intron 1 (309 kb) | 57 kb 3' to exon 1 | |
| | | |
| 3' UTR | | |
| 3' UTR | | |
| 3' UTR | 1.9 kb 3' to stop codon | BC007133 Mus musculus, apoptosis inhibitory protein 5 |

FIG. 3H CONT.

| Sequence | # | Name | Location |
|---|---|---|---|
| GGCTTGCTCTCAATGTCTCTCCCTTTCTGAGTGAAAGT ATCCCACGGCAGTCCCATCTCACTTCCTGTCCTGCTAA GGC | 102 | neuronal protein 4.1 | chr2:157392230-157392308 |
| GATGTCTACTTCATTGCCACCCTGTCATTCCTCTGGAA GGTGTCCGTCATCACCTTGGTCA | 103 | putative E1-E2 ATPase (class II, type 9A) | chr2:169635729-169635799 |
| CCCTACCCCAGGGACCATGGTTCCTAGGATCTCACTG CCTCCCTCTCTGGCCTTCCTGTCCCCTCCC | 104 | TRH3 | chr3:95610938-95611004 |
| AGGTGCAGAGCTCGGAAGGGGGCTAGGCAGTCCTCA TCGTCACACCAGTAGTGCCTCATCCTCATCCCAATGGT | 105 | BMP/retinoic acid-inducible neural-specific protein (BRINP) | chr4:66089771-66089844 |
| GATGCACCACCTTCACGCAGTGCTCAGCCATCCTGAT GCTTCTGCTACATCGTAGGCCACTGTCATTG | 106 | neuroglycan | chr4:128360081-128360148 |
| ACCCACCTCACTGAATCTGATGGACACTGTACAGTCG CAGTCTCTTTGTGCAGAATTGGCAGCGATGCCTGTGC TT | 107 | KIAA0231 | chr5:103117854-103117929 |
| TTACAGATTTCTTTGTTCCTTCTCCGCTCCCACTGCTTC ACTTGACCAGCCT | 108 | Y3 scRNA | chr6:48109705-48109758 |
| TGACTGGGAACCCATGTGATCAGGCACAGACTTTCCT CATCTTTCTACCAACCACTCCAAGTCAGTC | 109 | RIKEN cDNA | chr6:83532629-83532695 |
| CAAGCGAACCCAGGTCAACTCATCACAGGTCACCGGC TGGGTCTTGGGGTCGCTGGCACAGCTGATGGCCTGC TT | 110 | (STAR) steroidogenic acute regulatory protein | chr6:84658969-84659063 |
| ATCATCCAGGCTCCTCTTCCTGTCTGTACTCACCCCA ATTTGCCTAAACCCCCCCCCCAAAT | 111 | mouse contactin 3 | chr6:103365191-103365255 |
| TAGACCTGGCTTCGGTTTCTACCTCCCCAGTGCTGTCA TGTTCATGTTTGTTTT | 112 | homolog to ETHANOLAMINE KINASE | chr6:143792762-143792815 |
| TCCATTTGTGCATCAGACCCATTACCCACGGCCCTTCT CACCCCTTGCTCATCAGCATCACTTGATGTCCCTT | 113 | Na-Ca exchanger NCX2 isoform | chr7:11282341-11282414 |
| CTTCTGTCCCTCCATCTGCGTCTGGCCCCCCCCTCTG CCGCTGCTATCATCACCAGAAAT | 114 | synaptotagmin 3 | chr7:33956803-33956965 |
| GGACGGAGTCAGCGGATGCTCTGTACACCTCTGGCTC ATCTGTTTCTCCTCATTTCTCCCAC | 115 | chapsyn-110 (channel associated protein of synapse) | chr7:82183504-82183567 |
| AGCATATCTGGCTGTCTGTCCCTTCACCCATGCACCCA GACCTCACATGTGTGCCAGCCTTCATCCTGT | 116 | TRF1-interacting ankyrin-related ADP-ribose | chr8:33751977-33752045 |
| ATGCAGCTGCCTACATCCAAACACAGTTTGAAAGCAAA AACCGCTCACCCAACAAAGAAATTTACTGTCACATGAC TTGTGCCA | 117 | guanine nucleotide binding protein, alpha o (Gnao) | chr8:93751770-93751853 |
| AGACTGGGTTACATGGAAGCTGGGCTCTCCTCCATCT CCCTCCCTCCCCCTCTCTTCCCCTGTCTGAAACA | 118 | BC021949 | chr8:94628079-94628149 |
| AAGGTGTGTCATCACATGCAGCACTCATGCTTCTGTCT CCAGTGATGCCCGTCCGGCTGAAGT | 119 | cytochrome b5 | chr8:107024663-107024725 |
| CAGCAGTGCCCCGGCTCTCACACGCACAGCACTCCCC GCCCTGCCCCACCTCTCTTAGAAC | 120 | solute carrier family 7 (cationic amino acid transporter, y+ system), member 5 | chr8:121953545-121953559 |
| TAAATATATTATTCTCATTTAGTGCCCCTGTAGCCAGAA CCTCATTACTGCTTCATTTTTGTAATAACATTTAATTTAG ATATTTTCCATATATTGGCCCTGCTA | 121 | CDC10 | chr8:25388787-25398891 |
| TCCTCTTCCATTCACGAGAACGACAGGATTCGATTCCA GGCCTTTCCTTAGTTCTCTTAGAACCCTCATCTCTCTC TA | 122 | secretory carrier membrane protein 5 | chr9:57977035-57977112 |
| AAAGCGTCTGTGTTATTAGCCTTGTGTGTCACTCATG | 123 | DDM36 | chr9:85715954-85715991 |
| TTCACCATTTCACATGTTTGTACTTCTTTGTCTTCCCAT TAACCTTTGCCAGTGTTATGATTGTATACATTTTTAAAA ATGCTGGTTA | 124 | CLASP2 | chr9:115040743-115040830 |

FIG. 3H CONT.

| | | |
|---|---|---|
| 3' UTR | | |
| 3' UTR | | |
| 3' UTR | | |
| 3' UTR? | | |
| 3' UTR | 700 b 3' to stop codon | |
| 3' UTR? | | |
| | | (part of HY3, scRNA repeat element) |
| 3' UTR | | |
| 3' UTR | | |
| 3' UTR | | |
| 3' UTR | 1.5 kb 3' to stop codon | XM_132935.1 RIKEN cDNA |
| 3' UTR | | |
| 3' UTR | 415 b 3' to stop codon (3 b misalignment of CLIP tag) | D45888 Mus musculus mRNA for synaptotagmin III |
| 3' UTR | | |
| 3' UTR | | |
| 3' UTR | same as Kirk's | M_010308.1 (Gnao) |
| 3' UTR | | |
| 3' UTR? | (prediction on basis of m-h homology) | |
| 3' UTR | 805 b 3' to stop codon | BC026131.1 |
| 3' UTR | 600 b 3' to stop codon | 20864205 similar to CDC10 |
| 3' UTR | 1374 b 3' to stop codon | BC018813 Mus musculus, secretory carrier membrane protein 5 |
| 3' UTR | | NM_020043.1 Mus musculus neighbor of Punc E11 (Nope) |
| 3' UTR (exon 16) | 250 b 3' of stop codon | AJ276961.1 Mus musculus CLIP-associating protein CLASP2 |

FIG. 3H CONT.

| Sequence | # | Name | Location |
|---|---|---|---|
| TCAGCATCCAGCTGCTTGNTGTGTGTTAGTTGTCTCAC AGCTGAGGGCTCTGCCTCGGCTACTTCAGGCTC | 125 | FLJ20396 - chemokine-like factor super family 6 | chr9:115941885-115941954 |
| CATTCCACGACACAGTTCTGACTCTCCGGGTGACTGT CACCTGCTCCATCCTCTTCTTCCTCCCTCCCTTCCTC A | 126 | KIAA0275 brain protein | chr10:80118459-80118544 |
| TGGGATACCTGCCGTGCTGTACACATTCATCAAACTGT TTGCCCAGAGGAAGGAAGGGGTGAGCAGGTCA | 127 | uridindiphosphoglucosepyrophosphorylase 2 (Ugp2) | chr11:21339071-21339141 |
| AACTCTGAGGCCATGGCCCATCCACAGCCTCCTGGTC CCTGCACTACCCAGTGTCTCACTGGCTGTGTTGGAA ACGGAGTTGCATAAGCTCACCGTCCACAAGCA | 128 | SPARC-like 1 (mast9, hevin) | chr11:55880407-55880512 |
| ACTGAGACCCCGGCGTTGAGCTGCCATTGTGGCATCA TGTCACATCATATTGTCATCTTTTCACCA | 129 | brain protein | chr11:59945359-59945407 |
| ACTCACAGAATTCCGNCTGCTTCTGCCTCCGGTCCCAT TTCTGGGATCGACGTGTGCTACTACGCCTG | 130 | PHD zinc finger transcription factor | chr11:78617928-78617985 |
| TCTGTGTCCATTGCCCATGTCTGTCTGTCTGCTGCTG AGGCAGTCATCCATCTCGTGTCCCCNTCTGTGTCGTG CTAGCACTTAAGTGGGAACAAA | 131 | WD-repeat protein | chr11:106839035-106839131 |
| GTGTCTGTCCACATCATTGAGGGTGACCACCGCACAC TGCTGGAGGGCAGTGGCCTGGAATCCATCATCAACAT CATCC | 132 | fatty acid synthase | chr11:121745148-121745227 |
| TCAGCATACACAGAGACACGCAACATCCAGTGCAAGC TGGATTTCCCACCAGGTTCTCTAGCCACAACTCCTGAA AC | 133 | calmodulin 1 (phosphorylase kinase, delta) | chr12:94384120-94384196 |
| TGGGGCTGCCCCTGCCGTAGCCCAGCTCAACCCTCA GCCGGCTGCCAGGATTCTTCCTCAGTCTCACCTCACC C | 134 | zinc finger protein alphaA-CRYBP1 | chr13:41780053-41780128 |
| CCCGAGGCACTGAGCACCCACAGCACCTCCCTGCCC GGTTGTTGCCCCTCCCTCATGGCATGTCTCACCACGAT CCTGTTGCTACATcagggtgtttttgtaattctcaagctaacattttaalg gcccccatcttctcactcactctt | 135 | Nocicepin precursor (Orphanin FQ) (PPNOC) (N23K/N27K) | chr14:96508153-96508239 |
| GAGCGATGCTTCACCTTCTGATGGCTGGACGCTGGCC AAGCCTGTGCCTGCTGCTCACGCACTCACGA | 136 | NADH-cytochrome b5 reductase (b5R) | chr15:83947075-83947142 |
| TTCTTCCCCGTCCCTTTTCTGTCAGCCCATCACAGCCA CCTGCTCTGCTCAGACAGCCAGGCACCAGAAGTGAGA GCAGAAGTCTGCATCCTGCCCGAGCTGCCG | 137 | probable Bax inhibitor-1 | chr15:100324227-100324330 |
| TTGTAATGCCAGCATTCCTCTTCCCCATTTCCAGCTGT CACTCCTTCATTAAACTGCTGAGTCATTCAAA | 138 | afadin - AF-6 (trithorax (Drosophila) homolog) | chr17:12927724-12927780 |
| TTCCAGGAGGAGCTCAGGTCACCCCCACCACCGCCG CCACTGCGTCTGCCGCCCTAGGCTTTCAGACATCATT AGTTCC | 139 | pacsin 1 (protein kinase C and casein kinase substrate 1) / syndapin 1 | chr17:26910448-26910525 |
| CTATGACACCACCTTCACCTTCATCCTGTCATTGGAGG TTGCTGTTAGACTCTTGCTAGTCCAGGGACACATG | 140 | cyclin-box carrying protein | chr18:9172990-9173062 |
| CATCATTGACCGTGGCGTCCTGGTACTGCTGGTACTC GGACACCAGGTCATTCATGTTACTCTCGGCCTC | 141 | beta-6 tubulin | chr18:87741552-87741621 |
| GTTAACTTCATCCTTCCTTACTGCTCCCATGCTTCACAC TACATACACATACAACA | 142 | VPS10 domain receptor | chr19:46737530-46737635 |
| GGATCGTCCAGCCCTTTCTCTGTGTGGCTTAAACCTA GGTTGCCATTGCTTTATACATTTTCACTTAGCA | 143 | AK025562 | chrX:3324707-3324778 |
| GACTGCAAGCTTCTGCCCATAAGGCCTGTGCTGACGC TGCCATTTCAAGCCCGTGCACAACCCATCTGT | 144 | RIKEN cDNA 1110012O05 (leucine zipper) | chrUn:63072951-63073019 |
| exonic targets (30) | | | |

FIG. 3H CONT.

| | | |
|---|---|---|
| 3' UTR | | |
| 3' UTR | | |
| 3' UTR | | |
| 3' UTR | 200 b 3' to stop codon | NM_009242.1| Mus musculus secreted acidic cysteine rich glycoprotein (Sparc) |
| 3' UTR | | |
| 3' UTR? | (no gene prediction) | part of SINE repeat |
| 3' UTR | | XM_181295 RIKEN cDNA |
| 3' UTR | | |
| 3' UTR of longer isoform | 70 bp downstream of shorter isoform | NM_031969.1| Rattus norvegicus Calmodulin 1 (phosphorylase kinase, delta) |
| 3' UTR | | |
| 3' UTR | at the beginning of exon 3 | MUSNOP Mouse mRNA for nociceptin/orphanin FQ |
| 3' UTR | | |
| 3' UTR | only longer poly-adenylation site includes this 3' UTR; shorter expressed in testis | BC005566 Mus musculus, RIKEN cDNA |
| 3' UTR | to last 10 b of 3' UTR of longest mRNA | BC028648.1| clone IMAGE:4987654 |
| 3' UTR | (endocytosis regulator) | |
| 3' UTR? | | |
| 3' UTR | in minus III (micro RNA?) | same as 251a |
| 3' UTR | only in longer isoform | AK020713 Mus musculus adult male hypothalamus cDNA |
| 3' UTR | | |
| 3' UTR | | |

FIG. 3H CONT.

| Sequence | # | Gene | Location |
|---|---|---|---|
| ATGCCTCGGCACTCCCTCTACATCATCATCGGAGCCC TCTGCGTCGCCCTTCATCCTCATGCTCATCATCCTGAT | 145 | transmembrane protein Bet (with EGF-like repeats) | chr1:85272953-85273028 |
| TCAGTTCATCCCTATCCATCACCCTGGAGCCTTCCCTC CTCTTCC | 146 | KIAA0250 gene product | ~chr1:153760180 |
| ACAGGGCGACGTTCCAGGCCAAGTGATGTGATTGTGA AGACCCATGTCCTGTGGTGGATGA | 147 | astrolactin | chr1:159800711-159800772 |
| CAGAGCCACCTGGAGGATGACCAGCCAGGATTGTTCA GGGCTTCATTGTCTTGGTCACATTGCTTCATTGTCT | 148 | hypothetical protein XP_149237 | chr2:158258103-158258173 |
| ACCACACCTGTCTCCTCCTTCACATCAGGTTCCATGTT GGGCCGAACAGACACCGCCCTCACCAACACGTACAGT GC | 149 | Pax6 | chr2:106811345-106811537 |
| ACCTCACGTGGTCAGCCATGACCAATGAACCTGAGCG GTCCTGCAATCCCTCCCTTATGAGCATCATC | 150 | membrane protein TMS-1 | chr2:164560001-164561142 |
| ACCTCATCCCTGGCAGCCCCTTGCCTCACGTGGGTGC TGCTCTCACAGTCACTACCCACCCCCACATCAGCA | 151 | myocyte-specific enhancer-binding factor 2 (Mef2d) | chr3:86955291-86955355 |
| CCGCAGGGAAGTGACTTTCACAGCTTCCGGCCTGCCT GTCCGTCTGTGTCTGTCTGTCCATTCAGTGG | 152 | polyadenylate binding protein | chr4:11597662-11597729 |
| ACCAACAGTGGGAGCAGCAGCTCTCTGTTTGGCAGCT CTGCTCCATCCCCATTCACATTCGGTGGCTC | 153 | integral membrane glycoprotein | chr5:133984033-133984100 |
| TCTACACCTCCAACATCCCCATCATCTTGCAGTCTGCT CTGGTGTCCAAC | 154 | Sec61 alpha subunit 2 | chr6:89376214-89376283 |
| TTGCCACCTTATCATCCTCATTTCCATCCTTGTCGGCT GCCAACCTGCTCATCGTCACCGGGACCTTCG | 155 | solute carrier family 25 (mitochondrial carrier) | chr7:131744322-131744390 |
| CCATAGACGGGCCCATACTGCCAACCCATTGCACCGC TGTCGCTGTGGCAAGACCTTCAGCAACATGAC | 156 | (XM_057401) similar to Zinc finger protein 84 | chr7:17468841-17468909 |
| CCCTCATTGCTTTCCTCATCGGCCACCTGCAGTTGCAG GTTTCCTCCCACTGTTCTGGCCTCACCACTCCTG | 157 | KIAA1832 brain protein | chr7:3475872-3475943 |
| CATCAGTCAGCCAGCTTATTTTGAGGAGGTTTTTGGAT TTGAAATCAGCAAGGTTGGCATGTTGTCTGCAGTCCCT CACCTTG | 158 | vesicular glutamate transporter 2 | chr7:41262607-41287435 |
| TTCTACCATCCCCTCCCGTCGGCAGCCCATCCA | 159 | translation repressor NAT1 | chr7:100874353-100874385 |
| CAGGGGCTCTAAACCTATCATGGCAGAACAGCAGCCCATTC ATGGTGGTGGAAGCTGTCACATCATAGCTACCCAGGC AGTGGCAAGGCA | 160 | zinc finger, DHHC domain containing 1 (ZDHHC1) | chr8:105330401-105330487 |
| CTGTGATTAGTGCCCATCCCATCCATTCCCTCGATAAC CCTCACCATCATTTCCACTCCAG | 161 | neogenin (DCC-like protein) | chr9:59424988-59425048 |
| CAAACCATCATCATCCTAAACAACCGCAAATTTGCTAA TTCACTGGTTGGGGTCCAGCAGCAGCTCCAGGCA | 162 | brain beta spectrin (Spnb-2) | chr11:30111273-30111344 |
| TGTGGCAGCCCACCGCTCACTCACTGCCACAGCAGCA GGGAGAAGATCGTCATCCCCTTCTTCAGTCTGCTCATC A | 163 | AB060888 brain protein | chr11:50381111-50382254 |
| CATCTTCATCTACGCGGCCATCGCCTCTCCATCACCTC CTGCATCTTCACCTATATCCATTTGGA | 164 | UGS148 | chr11:71635810-71635876 |
| GTCACCATCTTCATCTTCATCATCATCATCTACTGGGGA AACTCAGACCCAGTCTTCAAGTCGGTTATCCCAGGTC CCGATGTCAGGTCTGAAATCTGTTACTTCTGCCAGTTT TTCTAATGGGC | 165 | KIAA1321 protein | chr11:78326338-78326460 |
| AATCCAGCCCATTCCAAACAGCCCCACCCTGGTCCCTG ATCATCAC | 166 | SARM | chr11:79111832-79111876 |
| ACCCAGCAGGGGCAGTGTGATGCCGGCCACGTCAT CCCTCCCGCTGTCCTTGTCTCCATTCAT | 167 | ADAM11 (disintegrin) | chr11:103583305-103583365 |
| AACAAGCAGCTGGCTCGTTCTGCGCAATCTCACACCC CAGATCGATGGTTCTACACTTCGGACGCTGTGTCTGA AGCATG | 168 | KIAA1582 protein | chr11:118668079-118668807 |
| GAGACCTACCGGTTAGGCGTGCAAATGCATCCCGGCC AAGAAATCCATAACTCACCCTGACTGGTCGCA | 169 | D-factor/LIF receptor/MDR/MSDR2 | chr15:6999514-6999583 |

FIG. 3H CONT.

| | | |
|---|---|---|
| exon 12 | 240 b 5' to stop codon (in exon 13) | |
| exon 10 | | XM_002201.3] Homo sapiens KIAA0250 gene product |
| exon 16 | | |
| exon 1 | | same as 352c, 356a |
| exon 10-11 junction | alternative exons 5a, 12 | |
| exon 7-8 junction | | |
| exon 11 | (misalignment) | |
| exon 1 | same as 319... (contamination?) | |
| exon 11 (1.5 kb) | | |
| exon 9 | 881-930 (stop codon 1461) | AF222743 Mus musculus Sec61 alpha-1 mRNA |
| exon 3 | | |
| exon 3 | | |
| exon | alternatively spliced part | |
| exon 8-9 junction | | |
| exon 2 | | |
| exon 3/intron 3 junction | exon 3 & 4 alternatively spliced | BE885257 retina cDNA |
| alternative exon 23 | (misalignment) | |
| exon 7 | | |
| exon 9-10 junction | | |
| exon 1 | 344-409, stop codon: 419 | |
| exon 2 (1713 b) | | XM_137740.1 Mus musculus similar to KIAA1321 protein |
| exon/intron junction | | cloned from brain |
| exon 25/intron 26 junction | alternative exon 26 | |
| exon 16/17 junction | | |
| exon 6 | | |

FIG. 3H CONT.

| Sequence | # | Gene/Description | Location |
|---|---|---|---|
| AACATCCATCCCCACTTCCATTCTTCATTCTTTCCAAGT CTGTGACTGGTGAGTTATCTCCATCTTTGAAAATAGCT TTA | 170 | FLJ23082 (neural retina cDNA) | chr15:8076457-8076535 |
| AACCCCAGCCATTCTCATCAGCCTTACCATCAACCAGG TCTCCTGGGTCTACCTCTGAGACAACCACATCCTCACC ATCA | 171 | KIAA1237 brain protein | chr18:33521853-33521942 |
| ACAGCAACAAGCAGCAACGGTTAGCATGATGCCTGTG GCCCCTCATTCATCTCTCTACCCTCCTTC | 172 | UREB1 (tyrosine phosphorylated nuclear protein) | chrX:128930351-128930416 |
| CACATATTCATCATCATATCCATCTTCATCTGGAACTCC AGTATTAGGGTCACAATCCCGGACTGTGAAC | 173 | coatomer protein gamma 2-subunit (COPG2) | chrUn:127872042-127872111 |
| intronic targets (48) | | | |
| TCACGCTTCCTCTGAAAACACATTGCACCCTCCACCCG CCACCCCTTCACCCTCCACCCGCC | 174 | Rab23 | chr1:34189409-34189470 |
| TGAATTCCAGGACACCTGAGGACATAAAGGAGATTTTA AGAAAACAACCATCATCATTATCTTGTCGTCATCATCAT CTGCATCTGC | 175 | clone C40 unknown mRNA | chr1:40049118-40049204 |
| CACTCCAGCCATCACTGCCTGTGCTTGCTGCAGATGTT CCTGCTACCTGCTTTGCTGAGTCTGTA | 176 | cytochrome P450 monooxygenase | chr1:60972292-60972358 |
| TCGAACTCAGAAATCCACCTGCCTCTGCCTCCCAAGTT CTGGGATTAAAGGCATGCAGCCCCATTACCA | 177 | ribulose-5-phosphate-epimerase | chr1:87340700-87340766 |
| GTGTTTGATCATGTCTTCCACACTGCTCCCTGCCCCCAGCC TCCTCCCAGAGCCTCCCACTTGGCTTCCAGCCC | 178 | GAP2 | chr1:132126421-132126491 |
| GGAGGCGTGCGAAGGTAGGCTCAGAAATGGCCCTAC CTCACCTTCACCTCTCACTCTGCTTCATGCTT | 179 | KIAA0969 brain protein | chr1:134134914-134134955 |
| GAGGGCCCACCCCATTCCCATTCTACATGTACCAACTT CATGGCAAATCATTACAATAGTCTCTGCATTTCCAGT | 180 | N2,N2-dimethylguanosine tRNA methyltransferase-like | chr1:162370269-162370356 |
| GCTTCCCTAGCGCAGGCAGGAACTGATGACAGGCCAT GGAGGAGTGCTGTCTATCTCCACCCTGCCTCCCCTCA | 181 | HSPC163 brain protein | chr1:182547933-182547985 |
| CGTTCTCTTGCTCATCTCCGAGTTCTGCCTTGCCCCTC TCAGATG | 182 | G protein-coupled receptor msr/APJ | chr2:86042431-86042475 |
| CCATCCCCCCATACCATCTCTGAATCTCCTTCCCGTCC TCATCTCAG | 183 | TALE homeobox protein Meis2b | chr2:116786603-116795650 |
| CCATCTCACCCCTGCCTTGCCCTCCATCTCACCCTGCC TTCTCTCTCCATCATCTTACTCCTGCCTTCCCATCCATC TCACCCCTGCCTTCCCATCCATCTCACCCCTGCCTTCT CCTCCATCCCATCCCTGCCTTCCCCTCTATCTGACCGC TGCCTTCCCCCTCCATCTCACCCCTGCCTTGCCCTCTA CCATCTCATCCCTGCCTTCCCCCTCTACCATCTCACCCC TGCCTTCTCTCTCCAT | 184 | similar to erythrocyte protein band 4.1-like 4 | chr2:122564425-122564474 |
| ACTTCTGGGGTCTCATGATTTCCCCATCTAAGACCTTA GTCCACCTGAACCAGCGTTTCTGTCTGTGTCCAAATGT CCATCTGTTTGTCTTTTCTTCATTTC | 185 | similar to Xenopus laevis putative Zic3 | chr2:156738596-156738682 |
| AGCTCTTTGAGCATCTACATCATCTTAGTATTTCCTCCA GAGAGGAAGTCTGGTCATGTTCCCCTTAGGTC | 186 | Trp4 Ca++ channel | chr3:54781947-54782017 |
| TCACCCTTCTCACACTCTTCATCATAATCCCAGGGGTA TCTGATATAGAACATGTCTTCCAAGTGTGTTGAGTGTCA GGAACAACTACAGTATTGAGATCTGTAAAGAGAGAGG AGTTTTTTTCAACC | 187 | guanosine 5'-monophosphate synthetase | chr3:64548922-64549049 |
| AGTGTGAAGTCTGAAATGTTCTCAGCATCCTCGTCCTC CCTGGGCCCAGAGAGTCTCATTCTCCATAGGT | 188 | AK055665 (brain protein) | chr3:117673991-117674060 |

FIG. 3H CONT.

| | | |
|---|---|---|
| exon 2 | 200 bp 3' from alternative cryptic exonal splice site in exon 2 | BB638404.1 thymus Mus musculus cDNA clone |
| exon 1 | (5' UTR?) | |
| exon 18 | (of the longer isoform) within alternative part of exon 18 | |
| exon (1) | | |
| intron 2 | 200 b 5' to exon 3 | |
| intron 3 | 400 b 5' of exon 4 (part of B1_MM, Alu, SINE repeat element) | |
| intron 4 (8kb) | 1.5 kb 3' to exon 4 | |
| intron 2 (8kb) | 3 kb 3' to alternative exon 2 | |
| intron 17 (3 kb) | 500 b 5' to exon 18 | |
| intron 10 (2 kb) | 1.5 kb 3' to alternative exon 10 (5' part of sequence bacterial) | |
| intron 7 | 1500 b 5' to exon 8 | (close to B1_MM, Alu, SINE repeat element) |
| intron 3 (6 kb) | 3 kb 3' to alternative exon 4 (misalignment) | |
| intron 1 | 100 b 3' to exon 1 | |
| intron 10 | 200 bp upstream from alternatively spliced exon 11 | no |
| intron 6 | 2 kb 3' to exon 6 (part of (GGATG)n repeat element) | |
| intron 4 | (2.3 kb 3' of alternatively spliced exon 4) | |
| intron 6 | 1.2 kb 5' of exon 7 (exon 8 alternatively spliced?) | |
| intron 2 | 200 b 5' of exon 3 | (the CLIP sequence is in italic - interestingly, there is TCAY rich region 5') |
| intron 3 (4 kb) | 1.5 kb 3' to exon 3 | |

FIG. 3H CONT.

| Sequence | # | Name | Location |
|---|---|---|---|
| CCATAAATTCATCCTTTGCTTCTTTCCTCAGGCTATCTT AGTAGAAATGGCATAATTGTCTTATCTACTTTGACTTAT TTTTCCATTCTGA | 189 | brain polypyrimidine-tract binding protein | chr3:120099830-120099920 |
| AACACTCTGCAGGGCTGCTTGGTCTGCTGGTATCTTTT CAGTTACCACTCATGTCTCACCCCATTGTTCACATC | 190 | junctate / Asph | chr4:9085576-9086651 |
| CCCACACCACCCCTCCACTGCTACATATTTCTAATCAT TCTCTTAGCCCTCTACTTCTCTCTTGTCTCANCCCATA CCTGACCC | 191 | matrix metalloproteinase 18 | chr4:17623741-17623824 |
| CCTAACAGTGATGTCACTTCACCTCAGCCCCCGCCCA CTCTGAAACCACTTTTCCATTACCTTCAGTGACTCTTTC TT | 192 | LOC230541 (genescan prediction) | chr4:101409808-101409854 |
| CACCACCACGACTACCGCCACCAGCAGCACCAAACGT AATGTCTTTTCATTTCATTGACT | 193 | patched-related protein | chr4:143630924-143630983 |
| TCCATCCTCACCCTCCACCCCCAACCCTGCTCACACAG | 194 | Ubiquitination factor E4B / Ufd2 | chr4:144725827-144725864 |
| AACCTCCATCACCACACCCCTTCCCTGATCCTAACCTC CATCACCACACCCCTTCCCCTGCCTAACCTCCATCACC | 195 | reelin | chr5:20352203-20352260 |
| TGCTTCTGCCTGCTTGTGCTCTGCTCCCTGTGAGCGC ACGCTAATGGTCTCTCTGGGTCTGCTCTGCTTC | 196 | FLJ14028 brain protein | chr5:21852685-21832755 |
| TTGTCTATTCCTTAAGAGAGCCAAGAGTCCATTTTTCAT CACTGGTGAATGTGTTCATCTTGGGAATCCAGGGTTCC TGGATCCTTATGAACGTCACAGTCC | 197 | protein kinase related to Raf | chr5:115696483-115696584 |
| TTCCTGTCTCATCCCTGTGCACTCCTGCACACTGTGGC CTTCCCGTCTCATCCCTGTGCACTCCTGTACACTGTGG CCTTCCCGTCTCATCCC | 198 | PALS2-alpha splice variant | chr6:50574032-50574124 |
| TCTAGAATGTTCATTGCTCATTGGTTTTCTTGCTGTGTA GTCCAGGCTGGCTGAAACCTGAGGCCTTTCCTCCT | 199 | Hrlp5 | chr6:87876871-87876944 |
| AGCGGCTGGGTTGCTTCTGTTTTTGTCATCGTCATCAT CATCACCACCATCACCATCACCATCATCATTG | 200 | SGP prediction | chr7:38817115-38817184 |
| TTCATTCCAGAGGGGAAACATCACCCTGCTGGCCTCT GCTCCCCATGACCCC | 201 | epidermal growth factor receptor pathway substrate 18, related sequence | chr8:71770514-71770565 |
| AAACAACATGTCCCCTGCAACATAATCCATGTTCTTCC TGTCATTCCACCATCCCTGACCCCAGCCCCTCCAC | 202 | similar to TULIP-1 | chr2:147387286-147387363 |
| AACCTCATCCATGCTAACCTCATCCATGCTAACCTCAT CCATGCTAACCTCATCCATGCTAACCTCACCCATGCC | 203 | 5-azacytidine induced gene 2 | chr9:118292708-118292685 |
| GGAACTGATCCCCCTCTTCTGGCCTCTACAGGAACCA TACATGCTCATGGTGTG | 204 | genescan prediction (homolofous to synaptic nuclei expressed gene 2) | chr10:5176401-5176454 |
| ATTGGCCAGCCCTCATGGCCATATTTTCAAGCTCACCT ACCCCATGGCATCTCTCCTCTCTCCACCTTCTTCCTTC | 205 | bcr (breakpoint cluster region) | chr10:76532521-76532588 |
| TTTATCCATACAAATCCCTCCTGCTGCTCGTCATGGTT GCTG | 206 | SWI/SNF related, matrix associated, actin dependent regulator of chromatin, subfamily c, member 2 | chr10:129153669-129153730 |
| GTGTTCTTCCATTTTCCACATTCTTCACGCTAACATGC GTCTTCATGCT | 207 | JNK/SAPK alpha (JNK2) | chr11:50285204-50285252 |
| TCATTTTTAAACTCATTTCTGTTTTCTGACTTGTGTGAA AGTCATGTTCACGCTGTGCCAGCACTGGGCTCCTGCC TCTGCTCAGCCC | 208 | KIAA1817 protein | chr11:117233622-117233674 |

FIG. 3H CONT.

| | | |
|---|---|---|
| intron 8 | 2 kb 3' of exon 8 (internal SS in exon 9, 34 nt exon 10 is spliced out in non-neuronal tissues, producing a dominant-negative product) | |
| intron 4 | 65 b 3' to exon 4 (alternative exons 4a, 5) | |
| intron 5 | 2 kb 5' of exon 6 | (predominantly expressed in brain) |
| intron 2 | 30 b 3' to exon 2 | |
| intron 2 (8 kb) | 4 kb 3' to exon 2 | (part of Lx8, L1, LINE repeat) |
| intron 23 | 2.5 kb 3' from exon 23 | |
| intron 55 (1 kb) | 300 b 3' to (alternative?) exon 56 (misalignment) | |
| intron 22 (100b) | 5b 3' to exon 23 | |
| intron 3 | 1.5 kb 5' to exon 4 | |
| intron 11 | 200 bp downstream exon 11 | |
| intron 4 | 100 b 3' of exon 4 | |
| intron 4 | 700 b 5' of exon 5 | |
| intron 3 | 200 bp from exon 3 | |
| intron 8 (8kb) | 1.5 kb 3' to exon 8 | |
| intron 4 (1.4 kb) | 500 b 3' to alternative exon 5 | |
| intron 15 | 1.9 kb 5' to exon 16 | (part of B3, B2, SINE repeat element) |
| intron 4 (4kb) | 2 kb (3' of exon 4) | |
| intron 27 | 300 bp downstream of exon 27 | AK013190 Mus musculus 10, 11 days embryo cDNA |
| intron 8 | 700 bp downstream of alternatively spliced exon 6 | |
| intron | 1.3 kb 3' to exon | cloned from brain |

FIG. 3H CONT.

| Sequence | # | Name | Location |
|---|---|---|---|
| AGTCTCACGCCAGGCTGTTAGTATTCCATCAGTCTGTC CTAAGGGAGTATGTCTCATGTGCTCCTGACCCATCCC ATCTACATCC | 228 | SPAF homologue | chr3:37444852-37444931 |
| ACCCCCTCTTCAGCCTCATGTCTGACCTCCTCACCCGC CCACCATTGTTC | 229 | similar to embryonic blastocoelar extracellular matrix protein precursor (SGP gene prediction) | chr3:54038643-54038582 |
| CCCTGAAGAGCCATCCCACTGCCTGGCCGCCTACCTG CTGACACCACCCAGCATGGCTTGTGAACGTCACGTCA GTTCACTGCCGCA | 230 | tetraspanin Tspan-5 | chr3:139299425-139289911 |
| ACTCCATCATCTCCTCAAAAGCTAGACCAGCCCACTGC ATCCGCATTGGCTCCATTCCGTCATTGCC | 231 | RAP1 | chr3:139518271-139518337 |
| AGAAGTGCAGCTTGGTCTTCATGTGGGTCTCCCAACA ATTGGAGCAGGGGCTATCCCTGACTCTGTTGCCTGCC TGTGGATCCTGTTCTCCTCACTGGGCT | 232 | dimethylarginine dimethylaminohydrolase 2 | chr2:145370425-145370525 |
| TCAGCAGGGAAACTGGTTATCCACACAGTTCTTCACCC TCATCCTCACGTCTGTCAGCCATTCACCCGCA | 233 | A8058417 brain protein | chr4:41306575-41306644 |
| CAACCTCAGACTCCTCATCTCTCACCCTGCTCTGAAGT GATACCCGCAGCGCAGTCCTGCCTGGCCTGTGCAG | 234 | nuclear factor I (NfB) | chr4:78723374-78723449 |
| AATCCCATTCCCATTGCTCATGAGTCTTTCTCTCCTTTT CAGTACAA | 235 | Similar to hypothetical protein DKFZp761D221 | chr4:100508893-100508748 |
| AGTGCGTGCTGTGGCGATCAGAGGAGGGGGATGGCT TCTCTGGAACCAGTTACAGATGCTTGTTAGCCT | 236 | actin-related protein 3-beta (ARP3b) | chr5:24244880-24244927 |
| AGAGAGAGACGTCATCATCATCATCATTGTCATCATCG TCGTCATCGTTGTCATCATCATCATCGT | 237 | dipeptidyl aminopeptidase-like protein 6 (Dpp6) | chr5:28179962-28180028 |
| TATCCATCCATCCATCCATCCATCCATCCATCCATCCA TCCACCCAG | 238 | KIAA0366 | chr5:89463627-89463673 |
| GAACAAGACCTCATAGCTCATGAATGTCAGTGTCCTTC AGCCCACAAGCTACACAAACCTCTTACTCTGTCTCTGG GAGATATAA | 239 | autism-related protein 1 | chr5:130701387-130701471 |
| AAGTGTATGGCAGTCCCATTTTTCGTCATGCCCATCCC ATTTCTGAGCTGTGCTTGCGCACTGGGTCTTT | 240 | N-methyl-D-aspartate (NMDA) receptor subunit NR3 | chr6:136477292-136477361 |
| TTCTTTCCTTCCATGGTGCTTCATCATCTCTTCTTCAGA ATCATTTGTCTGACATCCTTGGCAATGTAGGAAAGGCT TTACCAAGTACCCTGTGAGTTCCCATCA | 241 | BF181819 cDNA | chr6:36617813-36617889 |
| CAATCCGTCTTACCTGTGTTCACAGGCGTTGTCAGGACT CCTGGGAGACCCACTCTCTCCCGTAG | 242 | cDNA clone | chr6:38084282-38084348 |
| AGCTGACCACCACCCACCATCCATCTCCATCCCTCAC CACCGCC | 243 | N-acetylgalactosamine-4-O-sulfotransferase | chr7:25184837-25184879 |
| ACCACCACCAAGCCTGCTGCTGTCAAGCCAAGGACTA TCGCTGCTGGGACTCATTGGAGCTCCGCTTCCC | 244 | ? | chr7:51295705-51295775 |
| TCTCCACATTATCCCTCTGGAGCTCGGGTGACAGGCC TCATCAGGTTCACCTTCTGCGGCTTGTGGTCACA | 245 | FLJ10010 (brain protein) | chr7:59844258-85844329 |
| TAATGTCCTCTTTCTAGGCTCCACCCCAGCCATGGCTG CTACTTCCTATTAGAGCCACAGCCCATGCCTTTGGCAT ATTGTCTTTAGGGACTTTGGGATCTACATCATAATGTT GTCATGGAAAGGGTTTCCTTGTCTTGTGTTTTCCCTCTT CTTTCTTTTCTTGACGCATGAGTCTTTCTGGACTCCTTT TAATGTCCTTTT | 246 | neurotrophin-3 receptor non-catalytic isoform 2 (trkC) | chr7:67823824-67824025 |
| AACTCCAGCCTCATCGATCCAGCGCACTCTGCTGGAC CCTGTGGGCACACATTCTCATATACA | 247 | melfin alpha | chr7:124083249-124083311 |
| TACAAAGCTAGATGTCCTTACCACATCCGGGTCCTTCC GACCCACCTCGAGATGAACATCAT | 248 | Camd1 / hypothetical protein XP_163818 (genacan) | chr8:17437171-17437233 |
| CAGGGCCTTCTTCCCGTGTCAGCACTTGGATGCCAG ATTTCCCAGCCTC | 249 | glutathione reductase | chr8:32575577-32575628 |

FIG. 3H CONT.

| | | |
|---|---|---|
| intron 15 (50 kb) | 20 kb 5' to exon 17 alternatively spliced exon 16 | |
| intron (11 kb) | 2 kb 5' to exon | 1. 3' gene is trp4 (500 kb 3') |
| intron 1 (123 kb) | 55 kb 3' from exon 1 (or 20 kb 3', or 12 kb 5'); alternative promoters! | expressed mostly in brain |
| intron 3 (30 kb) | 300 b 3' to exon 3 (alternative exon 4) | |
| intron 1 (57 kb) | 10 kb 5' to exon 2 | (part of Lx5, L1, LINE repeat) |
| intron 1 (85 kb) | 15 kb 5' to exon 2 | |
| intron 2 (120 kb) | 20 kb 2' to alternative promoter | |
| intron 1 (92 kb) | 40 kb 3' of exon 1 | |
| intron 1 (40kb) | 2.5 kb 3' to exon 1 | (alternative exon 2) |
| intron 11 (12 kb) | 5 kb 5' to exon 10 | |
| intron 3 (80 kb) | 30 kb 3' to exon 3 (mismatch) | |
| intron 2 (213 kb) | 55 kb 3' to exon 2 | many cDNAs align closeby |
| intron 1 (190 kb) | 50 kb 5' to exon 1 | |
| intron 2 (129 kb) | 37 kb 3' to exon 2 | |
| intron | 12 kb 5' to intron? | |
| intron 2 (53 kb) | 28 kb from exon 3 | |
| intron (15 kb) | 5 kb 5' to exon ? | (RMER13B, LTR repeat) |
| intron 17 (40 kb) | 5 kb 5' to exon 2 | |
| intron 11 (94 kb) | 3 kb 3' to exon 11 | |
| intron 3 (124 kb) | 52 kb 3' to exon 3 | |
| intron 2 (1288 kb) | 143 kb 3' to exon 2 | |
| intron 1 (15 kb) | 5.5 kb 3' to exon 1 | |

FIG. 3H CONT.

| Sequence | # | Gene | Location |
|---|---|---|---|
| CCACCTCCACCTCCTCCTCCCCTCCCCGGAGGGCTTG CCTTCTATGGAACAGATATGCGACCCATCAGTG | 209 | KIAA0386 brain protein | chr13:24113964-24114034 |
| ACTGCCTCCATGCATCCATCCATGATCCATCTGTCTTT CCATCCATCCATCCATCCATCCATCCATCCATCCATGC ATACAC | 210 | cardiac ryanodine receptor 2 | chr13:11711606-11711875 |
| GTCTGTCTGNCTGNCTATCTATCTGNCCATCCATCTAT CATCCTTCCCTGCCTCCTTCCCGTTAACCCGCCCCCCCT CCATCAGCC | 211 | cDNA AW456878 / Genie Gene Prediction | chr13:98063469-98063944 |
| GAATCTGTCTCCCCATCATCTATCACATGAATCACAGA ATCTGTCTCCCCATCATCTATCACATGAATCACAGAATC TGTCTCCCCATCATCTATCACATGAATCACAGAATCTGT CTCCCCATCATCTATCAC | 212 | actin-binding protein homolog ABP-278 | chr14:3154788-3154801 |
| TCATAGCTCCTGTGAGTACCTGACTGTACACTGGTACC ATTTTccctccatsacigccctigcggogtggotgtzaccatcac | 213 | retinoic acid induced 17 (RAI17) | chr14:20580072-20550114 |
| CTCAAGTCAAGGACAGTGTAGGTGGTACTTGCCTGGG AATAGCTTTTCGCTCCTGCCTCCCTCCCTCCC | 214 | tumor protein | chr14:55922328-55922397 |
| AAACCCTATAAGCCCCTGCCCTCTTCCATCTCTTCTGT CTCTTTCT | 215 | myosin X (myo 10 gene) | chr15:25745138-25745183 |
| CCATTCACCCATTCATCTACCTACTCACCCATCTACCC ACCCATTGTCCTGTCTCATCCGCCTACTCATTCATCTT CTTAGCCACTCATCTGTCCAGGTACCCATCTCATCATC TATCCACCTATCCATTCATCTATTCATCT | 216 | guanine nucleotide exchange factor cytohesin-4p | chr15:79341644-79341690 |
| TGTAGCATGACTGTGGCATGATTGTAACATGTCTTCAC CCCAGCTGCATGTGCTCACTTTGCATCTTCACTGCA | 217 | activin type IB receptor | chr15:102163785-102163836 |
| ATTTCATTCCCCTCCCAGTNGGCCCTCCAACTGTTCCA CATTCCATACCTCCTCCCCACTGGACTGTCTCCACAAG GATGTCCCCACCTCCCAGTCCAC | 218 | frabin alpha, beta | chr16:15920017-15920115 |
| CACTCATTGTGTTTTCCCAGTGAACTTCAATCTGCTG GTATTCATTTTCTATTTTTTTTACATTAA | 219 | CTCL tumor antigen L14-2 (myosin heavy chain homologue) | chr19:56846085-56846131 |
| AGGACTTGGTGGTGGGAGCTAGTTTTCAAATGTACTG AGGTGAGACAGCCCCAGTGCCCCCAACTTCATATG | 220 | FLJ30437 (brain protein) | chrX:128321608-128321878 |
| GTCCACGTGCAATTTGCACACACACTTGGCTCGCATTC ATCCCCTTTCCCACCGCCCCCTCACTCACCT | 221 | KIAA1423 | chrUn:94487868-94487838 |
| Intronic targets, that are far from exon-intron junction, in introns longer than 10 kb (71) | | | |
| ACCCAACTGCTTAGCAGTGTGGAGCAGACTGGAGGAA TCACTTTTCTTGCTTGCATCACATGTGCCGCCTGT | 222 | BAI 3 | chr1:25714835-25714907 |
| TTCAGCTTGCAGCTGTCATCTCTCTGCTGTTCCCAGCT GTC | 223 | BARD1 (BRCA1 associated RING domain) | chr1:71775451-71775491 |
| TGTTATTAGTTTCCATCCATTCATCCATCAATCCATTCA TCCATTTACCTATGCATTACCTAACCACCCTTCTCCATC CCTCC | 224 | KIAA1486, similar to Myosin heavy chain Myr 8b | chr1:81995681-81995783 |
| TCCGTCCATCCATCCGTCCATCCTTCTATCCATTCATC TATCCATCCCATGACCAGGATGAAGGTGCGGTA | 225 | KIAA1415 brain protein | chr2:187629873-187629919 |
| TTCATTCATTCATTCATTCATTCGTTCATTTATGGTTTTC GAGACAGGGTTTCTCTGTGTAGCCCTGGCTGTCCTGG AACTCACTCTGTACACCAGGCTGGCCTCGAACTCAGA A | 226 | Nuclear receptor co-repressor/HDAC3 complex subunit TBLR1 | chr3:21815734-21915849 |
| AAATTATTCATCGCCATCCACCATCCACCAGTCCCTCC TGCTCCACATGCTCCATTTCC | 227 | Traf2 and NCK Interacting kinase (TNIK) | ~chr3 28344045 |

FIG. 3H CONT.

| | | |
|---|---|---|
| Intron 11 | 400 b 5' to exon 12 (alternative exon 11) | |
| Intron (1.5 kb) | 480 b 3' to exon | |
| Intron | 1.5 kb 3' to exon | |
| Intron 4 | 1.8 kb 5' to exon 5 | |
| Intron 3 | 380 b 3' of exon 3 | |
| Intron 8 (4 kb) | 380 b 3' to exon 8 | |
| Intron 2 | 2.6 kb 3' to exon 2 | alternative splice variant expressed in brain |
| Intron 9 | 700 b 3' to exon 9 (possible alternatively spliced 3 bp long exon 10) | |
| Intron 7 (5kb) | 2.5 kb 3' to exon 7 | |
| Intron 5 | 2.5 kb downstream of exon 5 | |
| Intron 2 | 500 b 3' of exon 2 (part of AT_rich, Low_complexity repeat) | |
| Intron 2 ? (200 b) | 50 b 5' to exon 3 | |
| Intron (3) | 50 b 3' to exon (3) | |
| | | |
| Intron 11 (200 kb) | 80 kb 5' to exon 12 | |
| Intron 1 (13 kb) | ~ 2 kb from exon 1 | |
| Intron 2 (104 kb) | 37 kb 3' of exon 2 (both exon 2 and 3 are alternatively spliced/alt. Promoter?) | (part of (TCCA)n Simple_repeat) |
| Intron 1 (60 kb) | 12kb 5' to exon 2 (3' 18 bases of the original sequence are bacterial) | |
| Intron 1 (30 kb) | 10kb 5' from exon 1 (part of B1_MM, Alu, SINE repeat element) | inhibits JNK pathway |
| Intron 2 (18 kb) | 6 kb from nearest exon | (brain specific splice variants, activates c-jun) |

FIG. 3H CONT.

| Sequence | # | Description | Location |
|---|---|---|---|
| CATCATCTCCTGCCCAGACCCCAGCATCATCAGCATCA GCATCATCTCCTGCCCAGACCCCAGCAGTGTCTTCCC TTGTCAATGTCTTCTTTCTT | 250 | BB529891 cDNA = hypothetical protein XP_150135 | chr8:105474366-105474418 |
| CCAGCCCTCAGTCGTTCTGTCGGGTCCTGTACACTGC TGTGGTTTCTCACTTCCCAGCCCTCAGTCATTCTG | 251 | BCNT | chr8:111741691-111741722 |
| ATGCACTTTCCCATCATCTGTCCACTCACCTCCCCAG CCATCCATTCACCCATCCATCCATCCACCCACCCACCC ATCCATCTACCCACCCATCTATCTACTCACCCATTCA | 252 | KIAA1694 | chr8:117328345-117328457 |
| ATGGGAAGGGGGCCCTTCCTCCTTTTCCTCTTCCTCC TCCTCTTCCTCCTCCTCCTGTCACTCATCCCC | 253 | neural cell adhesion molecule (NCAM) | chr9:48898505-48898573 |
| TCAACACCACAGGCTGACCCCTGTCCCTTCTATATTTG CTGCATATGTTCA | 254 | ubiquitin specific protease 3 (USP3) | chr9:67172147-67172197 |
| CCACCCCTCCCCTTCACCTCTGAGAAGGGGGAGGTCC CCCTCTGTATCACCCACCCTGGCACCTCA | 255 | KIAA1164 brain protein | chr9:71237075-71237141 |
| CCTGACTAAGACAGTCACCCAAGCTTGTATGACGTGG AGTTGAAGTTCATGCTCACTTTTGTCTT | 256 | protein tyrosine kinase (NET PTK) | chr9:103020454-103020510 |
| AATTCCATTTCATTGTTCATCCTCAAAAGTCAGGGCAAT CAAAGCAGAAA | 257 | clone MGC:3040 (brain neuroblastoma protein) | chr9:104465369-104465408 |
| CCACATTTCAGTTCGTCTCCATTCACTGCCTTGCTCAT CCATCACGCATGCTTCAGTGTGGCGGTGGCACCCT | 258 | phospholipase C delta-1 | chr9:120330255-120330327 |
| TGACAAGCTGCTATTCTCTAAAACTCTTGAAATTCATAG TTTCTGAATAGAAGCAGGCCTGGTGTCCTGCTGTGTG | 259 | AV244488 head EST | chr10:32737611-32737682 |
| AAAGCCATTACCTCCCCTCTTCAGCTCACTGCACCCTC TGTTTCTGGGCGTCCAGAGCAGTCTGTTCTCTTC | 260 | DNA binding protein DESRT (Desrt) / MRF 2 | chr10:68169667-68169738 |
| TCTGAGAGGGGGCTTCATTCACCCAGCCCCACACCTC ATCCATCTAGCATGCATCCTCCTTCCCTGGGGCATC | 261 | E2a-Pbx1-associated protein (EB-1) | chr10:80482197-80482288 |
| CAATCTCTGCATGGACTTTCCTTCAGTCTCTGCTCCAC ACTTTGTCTATGCATTTCCTCCCTTGAGTA | 262 | KIAA1912 brain protein | chr11:28503585-28803632 |
| TTCTCGCTCGCCCATTTGATCGGAGCTTCAGGCTGCA CATACCCTGCATTCTCCTGCGCAC | 263 | BB653452 brain EST | chr11:29935096-29935158 |
| GAGTGGCTAATCATCTCTGCGGGCAAACTGACAGTAC ATCCTCTAGAATTCCTTCCTTCTCATTTC | 264 | early B-cell transcription factor | chr11:45203604-45203670 |
| CCAAACATTCAAACACATGAGTCTATGGGGGTCATTTC TATTCAAACCACCAACACGGCTGCTTCTCCACCTAC | 265 | axonemal dynein heavy chain 9 | chr11:68538213-68538287 |
| CATCATGCCATTCCTCTCAGTGACACAGGTCAGGGTG TCATCCCACTCTTCTTAATGATTTGGTCAGGTCATCA | 266 | Carbonic anhydrase-related protein 10 | chr11:93890855-93880928 |
| TCAGACTCAAAGATTCATCTGCCTGCTTCTGCCTCCCA ATTGCTGGGACTAGAGGTGTGCAGCTCCACCACCTG | 267 | hypothetical protein XP_109700 | chr11:105177642-105177705 |
| TGCACCCATGTCAGGCATTTCACAACCACCTGTAATTC CAGCTTCCTTGCCTCTGTGAGCATCTGCACTC | 268 | E3 ubiquitin ligase Smurf2 | chr11:107674857-107674927 |
| AACTCATCGTTTCTGTGGCTTGGCTTGTGCCGGCTCACT CTGTCTAGACTTCATCTCATTTCCTCTGTGTTCAG | 269 | B-cell receptor-associated protein 29 | chr12:25732178-25732249 |
| GTTGGTCACAAGCCATTGGGATGTGCCTGTCTCTGCC TACTCCAGTTCTGGATTACTGGCTCACACTGCCACACT | 270 | BC005675 | chr12:76112833-76112907 |
| TCTTCTTGCTTGATGCCTACGTGTCTATCACCTGTTTAT TCTCCATCCATCTAGCTACCATCTGTCTGTATCTCTGT CTTCTCCATCTGTCATTTAGCCACCAATCCATCTTT | 271 | RIKEN cDNA | chr13:28954184-28854233 |
| GCTTAAGTCATTAGCGGGGTCATCGTCATCATCACCAT CATCACCATCGCCATCATCACCTTCTTCATCATCG | 272 | KIAA1733 protein | chr13:42526025-42526098 |

FIG. 3H CONT.

| | | |
|---|---|---|
| Intron (12 kb) | 5.5 kb 5' to exon | |
| Intron 5 (51 kb) | 9 kb 3' to exon 5 | |
| Intron 1 (119 kb) | 47 kb 5' to exon 2 | cloned from brain (part of (TCCA)n Simple_repeat) |
| Intron 1 (230 kb) | 30 kb 5' to exon 2 | (edited Intron?) |
| Intron 1 (26 kb) | 12kb 5' to exon 2 (misalignment) | |
| Intron 5 (10 kb) | 4 kb 5' to exon 6 | |
| Intron 1 (120 kb) | 60 kb 3' to exon 1 | |
| Intron 1 (142 kb) | 49 kb 3' to exon 1 | (part of MTC, MaLR, LTR repeat) |
| Intron 1 (40 kb) | 10 kb 5' to alternative promoter | |
| Intron (250 kb) | 120 kb 3' of exon | |
| Intron 3 (60 kb) | 25 kb 5' to exon 4 | |
| Intron 3 (50 kb) | 20 kb 3' to exon 3 | |
| Intron 2 (150 kb) | 70 kb 5' to exon 3 | |
| Intron (120 kb) | 30 kb 5' to exon | |
| Intron 4 (230 kb) | 25 kb 5' of exon 5 | |
| Intron 40 (30 kb) | 10 kb 5' to exon 41 | |
| Intron 1 (395 kb) | 36.5 kb 3' to exon 1 | |
| Intron 3 (47 kb) | 20 kb 5' to exon 4 | (part of B1_MM, Alu, SINE repeat) same as 254 |
| Intron 1 (45 kb) | 10 kb 5' to exon 2 | |
| Intron 1 (3.3 kb) | 1.3 kb 5' to exon 2 | |
| Intron 3 (120 kb) | 60 kb 5' to exon 4 | |
| Intron 3 (31 kb) | 800 b 3' of exon 3 | |
| Intron 3 (253kb) | 10 kb 5' to exon 3 (alternative exon 2?) | |

FIG. 3H CONT.

| Sequence | # | Gene | Location |
|---|---|---|---|
| TTGTCATCCTCAATATCACCTGCACTACGCTTCTTAAGT TTACTATTGTCATCC | 273 | cyclic AMP specific phosphodiesterase PDE4D5A | chr13:107219572-107219624 |
| GTCTACAATGCATCCCTACCCACTCCTATCCCATCTCT Gctgtgctgcttgtgctatcacctcat tct | 274 | small GTP-binding protein Rab3C | chr13:107624228-107624288 |
| TCGTTCAACTCTTCTCATTCAAGTTAGCAGTCATTTCAA TCAGTTCAATAAGCATATTAGGCAAGCA | 275 | neuregulin-3 (NRG3) | chr14:34400062-34400128 |
| AGGCGTGGGGGATCAGGGTGTTAGACTCTGCCCCCC CTCACCCCACTCTCTTCCCATGTTCGTTGAT | 276 | KIAA0323 brain protein (HCDI) | chr14:46995006-46995061 |
| tcttcctctcccdgatggccatggtcgtcatcccccaagagaggatgtgagtgg actgtggCACCCCAAGNTCAGCACATGCCTCCCTCACCCT TGACTCTG | 277 | PIN2/TRF1-interacting protein (Pinx1) (SGP prediction) | chr14:54938405-54938445 |
| GAGGGGTGCTTGGACTAGAGCCAGAAAGGGAGAGCA GACTCCGAGGGAACATGGGGAACTAAAGGACAC | 278 | heparan sulfate 6-sulfotransferase 3 | chr14:110389949-110390014 |
| CAGCCTCATCCATCTCTTGCCCACCAGCCCACCGACC CCTCCATCTCTCG | 279 | similar to KIAA0767 protein | chr15:85903217-85903262 |
| GACAGACCATAAATCCATGTGGGGACTGTGCCCCATT TGCATCTCATTTGTCCCATCTGCCCCGGTTTCACGCG | 280 | BG807701 brain EST (BC036194 unknown protein) | chr16:28656085-28856160 |
| TTTTATCTCCGCTGTGCTTGTGTTGTCTGTAGCCCTGG GCGTCCTGGGCTGACCTTGGGGTCCCTTCC | 281 | KIAA0349 brain protein | chr17:46919864-46919931 |
| GTGTGGCCTGTTTCCCACTCCGCATCCTACTCTTTCCT TCAGCACTCCTCACTCTCAAATCCTGCTCCAT | 282 | F-box protein FBX13 | chr17:62226653-62226722 |
| ACAACACTCTAGTGCTCTTTCTTTACTAGAGTTCGTTCA TCATCCCCTGTGCTTCCCGATCCTTTGCTCATCCTTTC TTCAT | 283 | alpha-mannosidase II | chr17:63746985-63747046 |
| ATGCATCATCTATTTGTCTGTCTTCATGTCCATACATTT ACTAATCATCTGTCTGTTTGTCATCCATTCATTCATCT ATCTCCATCCATCCATCCATATGGCTA | 284 | similar to early B-cell factor associated zinc finger protein | chr18:13950520-13950817 |
| AAATCCATCACATTACGAAGCATTCAAATCATTTGTAAA CACTCTTGGTTTCACTAG | 285 | basic transcription factor MITF-2B | chr18:69883232-69883289 |
| TAAACCCCCACTATGGGGTCTCAACCCACAGCTCGAG AAACACTGTTGTAGATGCGTGCACTACTACT | 286 | GTP-binding protein alpha q subunit | chr19:15892681-15892828 |
| CGCTTCTGGATTGCAAATAAACAGTAGGCTTGGACCA CTGCCGAGCATAGGGCTGGGAAGTCTTGGCTCA | 287 | glypican-3 (Gpc3) | chrX:38162860-38162838 |
| GTGGGTGAAACAGGCCTCCTGGCCCATGTACGCCTGC CATGTCACTATAAAGCCAAATCAACAGGGTCAGGAC | 288 | many ESTs | chrX:87923897-87923958 |
| ACATTTCCATATCATGCCTCACTACCACTGTGCTCCAT GCTTCTGCCGACAATGGCCCATTAAAGCCCCACTTAAA GTGTTCAG | 289 | hippocampal cDNA (Per1 interacting protein PIPS?) | chrX:115155741-115155822 |
| GATCCATTCTGTCACCACGGTGCCCCTCACCCATCCAG GTTCCATACTATCCAAAAGTTTGGGCT | 290 | midline 2 protein (mid 2/Fxy2) | chrX:120063482-120063548 |
| TCATCCCCTGCCTCAGAAACTCACTCACAGTTAAATC CCTGCTTCATACAGTTCACTCAGCTTCATCTCCTGCCTC ATTTCACCCCTGCCTCACACATTCAATCAGCACAAA TCACTTACAGTCATCCCCTGCCTTAGAAAATCACTCACA GTCATCCCCCTGCTTCAC | 291 | ring finger protein Fxy | chrUn:118210332-118210374 |
| no gene prediction (42) | | | |
| AATTCATTCATTCATTCACTCTCTCTGTGTGTCTCTCCC TGTCTCTCTGTCTCTGTCTCTCAGGAGTTTCTCTGTAT AGCTCTGGCTGCCCTGGAACTCACTCTGTAGACCAGG CTGGCCTCAAACTCAT | 292 | | chr1:133828098-133829148 |
| TGCCTCCTCATGTCAGCCTCACCATCTTCAGCTGCTTC ATCTCAGCA | 293 | no gene | chr12:103051773-103051819 |
| CTCTGTGTAAGTTGTCAGGGTTCCACCTTTGCTGTCATC TCCTGGTAACGCCTCAGGTGGACCAGGGAGCAAACCT GACTCCTGATCAGCCTCTGAAGCCTACTTGGTTGCCA TCTTCCGAG | 294 | | chr3:91344105-91344226 |

FIG. 3H CONT.

| | | |
|---|---|---|
| intron 4 (138 kb) | 4 kb 3' to exon 4 | alt. spliced |
| intron 3 (96 kb) | 4 kb 3' to exon 3 | |
| intron 1 (100 kb) | 40 kb 3' of exon 1 | |
| intron 6 | 100 kb 3' to exon 6 (ESTs show a lot of alternative splicing | |
| intron 1 (10 kb) | 4.5 kb 5' to exon 2 | |
| intron 1 (780 kb) | 1 kb 3' to exon 1 | |
| intron 6 (17 kb) | 3kb 3' to exon 6 | |
| intron (100 kb) | 40 kb 3' to exon | |
| intron 2 (20 kb) | 8 kb 3' of exon 2 | same as 368 |
| intron 7 (160 kb) | 60 kb 5' to exon 6 | |
| intron 3 (14 kb) | 3 kb 3' to exon 3 | (close to RSINE1, B4 repeat) |
| intron 1 (102 kb) | 3.5 kb 3' to exon 1 | |
| intron 3 (45 kb) | | |
| intron 2 (100 kb) | 40 kb 5' to exon 3 | |
| intron 2 (160 kb) | 25 kb 5' to exon 3 | |
| intron (20 kb) | 1.5 kb 3' of exon (next exon is alternatively spliced) | |
| intron 5 (45 kb) | 10 kb 5' to exon 6 | (part of ORR18-int, MaLR, LTR repeat element) |
| intron 3 (42 kb) | 20 kb 3' to exon 3 | |
| intron | 3 kb 5' to exon (10) | |
| | | |
| | | repeat element included |
| | | |
| | | |

FIG. 3H CONT.

| Sequence | # | Note | Location |
|---|---|---|---|
| CCATTTCTGCCATTGCTCTAAAATGACTTCACTCCTTCT CCAACTCTGCTTTTGTTTACACTCCTGTGCTTCAGTAA CACCTTG | 295 | | chr9:81924785-81924869 |
| TTCTTCTTTTGGTCATCTTGGAGCCAAGACTAGAAAGA GCTATTTACATTTCAAAGTTATTCCCTCTTCCTGGTTTC CCCTCTGCAAACCCCCATCCCATTGCCTGCTTCTATGA CAGTGCTCCCTCACCCACTCCCATATCCCCACCCTATC ATTCCCAT | 296 | | chr12:39922265-39922321 |
| GATTGTCTCTCCCCATCCATTTCTAACTCCATGAAATCA AACGTGTCTGAAGGTTCTCTTTGATTTGTTTGTTTTGTT GACCTTAAGG | 297 | | chr19:40795884-40795971 |
| GATAGTCACTGCATCCTAAAGTCACTGCAAGTCACTGC ATCCATCAATCACTGCATCTGACAGTC | 298 | ESTs, but no good gene prediction | chr4:82968597-82968645 |
| ACCATCCCTGCACCCATCTGTCCATCTGTCTGTCTTTT CACCTCTCTGTCCATCCACAGACAGGTGTTCATCT | 299 | no gene prediction | chr5:111213802-111213954 |
| GCTGTGCCTAGGCCTGTCTGTGGCAAGCTCCTCCATC TCTCTCCCTCTGTGTGTGTCTTTGTCTCTGCATCAT | 300 | no gene prediction | chr4:139614748-139614818 |
| AAACATCAAAACTCCTATCCTCGCGCCAGGGCTGACC TCATCTTGTTCCACCCCATCTCATCCAATCAG | 301 | no gene prediction | chr12:50016438-50016506 |
| CATCTGCCACTAATCCATCCATCCATCCATCCATCCAT CCATCCATCCATCCGTCTGTCCATCTGTCCATTCATCC TTA | 302 | no gene prediction | chr7:113863080-113883138 |
| TTTCACTCCACCTGCTATCTTGACTTGACTC | 303 | no gene prediction | chr2:150411042-150411072 |
| ACACTTCTCCCAGTGGTCACTCTGGCTTTGATCACACC TCATTGGGTGGCTCCTTAGCAGTGTTGGACA | 304 | no gene prediction | chr1:196518134-196518202 |
| GGCCCACCTCTCACCTTCTGGCTGAAGTCCCATTTTCA GACCAAAACCTGTGGCCTTGTTGGTAGGAA | 305 | no gene prediction | chr7:105854520-105854588 |
| ACCAGGAAGCGGGACCCGCCTGACCCGACCCGAGGCC CTCTCCACCCTCACTCACACTTCAGCCCCG | 306 | no hit | |
| GTTATCCTGCTGCCATTTCCCTTCCCCCCCCCTCTCCCA CAAAGATCCCTCCCTCCTTCTGCCTCCCATGAT | 307 | no gene prediction | chr12:81523705-81523777 |
| TGCCTCCTGCCATTGATGATCGTTCTTCCCTCCTTTGG GAGGGTGAGAGGGAGGGAACGCAGTCTGAGTGGA | 308 | no gene prediction | chr11:88107430-88107501 |
| AGACCTTGGGGGTCCAGGTTAGTTGAGACTGCTGGTC TATGGGGTCACTCTCCTCCTCACCTTC | 309 | no gene prediction | chr5:48425248-48425311 |
| GCTTCCCATCCGAGTTTCCATCCTCACACCTGCCCACT CACCTTCCATGTCGCTATCTGTGTCCCTC | 310 | no gene prediction | chr8:32309238-32309305 |
| CATCCATCCATCTACCCATCCATCCTGTTACCCATCCA CCCATCCATCCATCCA | 311 | no gene prediction | chr1:119720535-119720588 |
| CAGCTCTCAACATTCAGTAGGCATGCTAGGTGTGCTC TCTCATTGGCTTTCGAAGTAAGCTCAGCC | 312 | no gene prediction | chr6:97180376-97180442 |
| GCCAAGCTCACATCAGCAGCACCCTGTAGCACATGGA GTTGGGCCAGTTCATGCTGTTACCCCTGCGTCACACA | 313 | unknown protein | Celera: 78944-79017 no BLAT match |
| GATAGTCACTGCATCCTAAAGTCACTGCAAGTCACTGC ATCCATCAATCACTGCATCTGACAGTC | 314 | ESTs, but no good gene prediction | chr4:82968597-82968645 |
| ATGCGTTTGGACAGTTGTCTACATTTATCAAACGACCA GCTCTGGACTCACTGCTGTTCCAGCTTCTGCA | 315 | many brain ESTs, but no good prediction | chr5:106051907-106051977 |
| TGGGGTCAGGCATGTGGGTTTAAAGAGTTTTCCTTTG CAGAGCCTCATCCTTCATGGAGCTGCTCAGGACTT | 316 | no good gene prediction | chr19:5025284-5025360 |
| CATGGAATCCTCTGCCATCAGGTTCCCATCATCATTGC TTGGG | 317 | no gene prediction | chr3:157938432-157938474 |
| ACCACCCATGCCAGTCACCCACCCCCACCCATAGTCCC AGTCACTCACCTGTATCCATGGTCGCAAGTCAC | 318 | no gene prediction | chr4:139842257-139842328 |
| AGTACTGGTTCCAGGCAGATCTATCTGTCTGTCTGTCT GTCTGTCTCTGTCTGTCTGTCTATCTGTCTATCT | 319 | no hit | |

FIG. 3H CONT.

| | | |
|---|---|---|
| | | (part of Lx2, L1, LINE repeat element) |
| | | |
| | (misalignment) | |
| | | |
| | | |
| | (misalignment) | part of (TCCA)n simple repeat |
| | | |
| | | |
| | | |
| | part of LINE repeat | |
| | | |
| | | |
| 3' UTR of AB0808327 | | |
| | | |
| | | RP24-372J5 |
| | (misalignment) | |
| | | |
| | | |
| | | |
| | | |

FIG. 3H CONT.

| Sequence | # | Annotation | Location |
|---|---|---|---|
| GGCAGTTGCAGATTTCCATTCATTTTCATGGCCATCTG GCCAACCCGCCTGCCCTTCTCCACACCTGATC | 320 | no mRNA | chr4:109092192-109092261 |
| CTAACATAAGAGGCCCCAAGCTTCATTCACTGTTTGGG TGCGGGTGTTTGGATCCCTCTGAGTCACCTGCTTGGT | 321 | no mRNA | chr5:51080989-51081083 |
| CCTCATCCTGCCTCCCTGCATCCCAGCTCCTGTGGCC TCATCCTGCATCCCAGCTCCTGTGGCCTCATC | 322 | no gene | chr1:138304233-138304301 |
| ACTTCATTCCATGATCACAGTTACCATACTGTCACTGTC ACACTCACCGTCACACTC | 323 | no gene | chr13:23529738-23529791 |
| GAGATCGTTAGGACCTCTCGAGGTCTTCACCAAGCCC TGCATCTCCCATCCATCTATCTTCTCCATCC | 324 | no gene prediction | chr2:20620819-20620887 |
| CTCATTACTGTGCTGTTCTGGTGAGCAGAGTCCTGGC ATTATGTAGCCAGCGCCTTTCTT | 325 | no mRNA | chr3:29401302-29401361 |
| CCACCATCACCACCACTACCACCACCACCACCATCATC ATCATCATATTTCTGAGACAGGATCTCAGCA | 326 | no gene prediction | chr10:110230382-110230450 |
| TCCATCTATGGGTGCTGTGAAGCCATTTTTACAGAAGC CATTTCATGTCCCGATGGCAGCATTTGTGAGCGC | 327 | no gene prediction | chr7:49342267-49342336 |
| GGTCTCATTCCTCTTCCCTTGGCATCAAGTCTCTACAG GATTAGGCGCATCTTCTCCCGCTGAGGTCAGAC | 328 | no gene prediction | chr15:83662612-83662682 |
| TCTGTCCATGCATCCATCCATCCATCTATCCATCCGTA CATCTGTCTATCTGTCCATCTGTCCATCCATCCACTG | 329 | no gene prediction | chr18:77945443-77945517 |
| AATGGCTGCATCATGTCAGAAGGCACTGTTTCACAGCA GGCCTCCCTAGCTGCTGTCTCTATGACGTTCC | 330 | no gene | chr7:100183344-100183413 |
| ACATCTCCATGTTTGCAAAGCAAGCCCTCTAACTCACC GATCCATCTCCCACAGCCCCTTTGCTCA | 331 | no gene prediction | chr6:37422342-37422407 |
| CATCTGCCACTAATCCATCCATCCATCCATCCATCCAT CCATCCATCCATCCGTCTGTCCATCTGTCCATTCATCC TTA | 332 | no gene prediction | chr7:113883060-113883138 |
| GACAGTAACCCGTCACCCCCGTGACAGTTAGCTGGTT GTGGGCCAGCATGGTGGGAGGAAGTGTCCCTGTGCA GTGGC | 333 | no gene prediction | chr15:85779704-85779781 |
| CCAGCTTGCAATCCCACCAGCAATGGAGGAGTGTTCC TCTTTCTCCACATCCTCACCAACATCTGCTGTCA | 334 | no gene | chr13:72590456-72590526 |
| GACCTGGGCTAGAGTCCCCCTCCCCTCATCCTCTTCT GCGTACATTCTGAACAGTCTTCTCACGGGTGT | 335 | no gene prediction | chr5:114427985-114428033 |

FIG. 3H CONT.

| | | |
|---|---|---|
| | | part of Lx4, L1 LINE repeat |
| | | part of Lx4, L1 LINE repeat |
| | | duplicated sequence |
| | | part of (ATGGTG)n simple repeat |
| | | |
| | | |
| | | part of (TGG)n repeat |
| | | |
| | | part of Lx4, L1 LINE repeat |
| | | part of (TGGA)n simple repeat |
| | | part of Lx8, L1 LINE repeat |
| | | part of B4A SINE repeat |
| | | part of (TCCA)n repeat |
| | | |
| | (misalignment) | |
| | | |

FIG. 3H CONT.

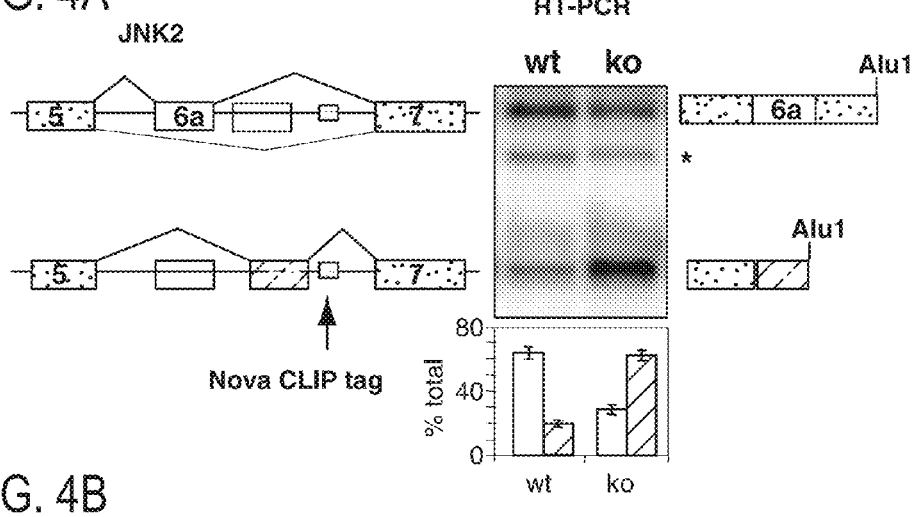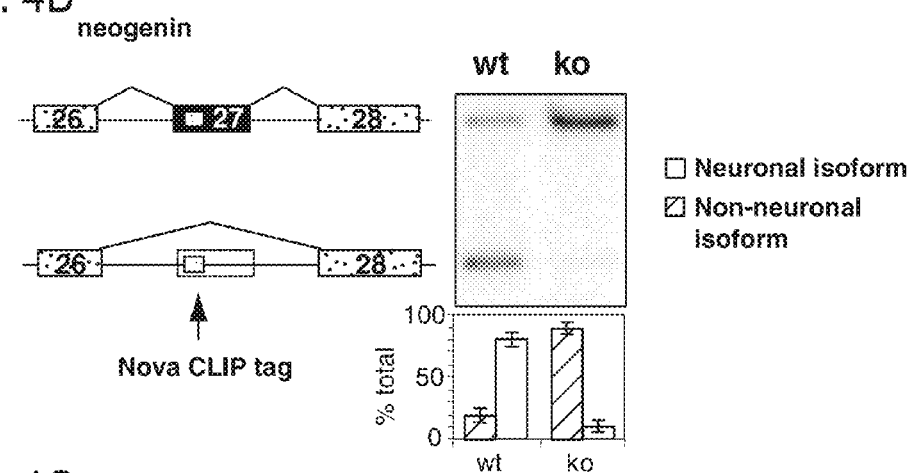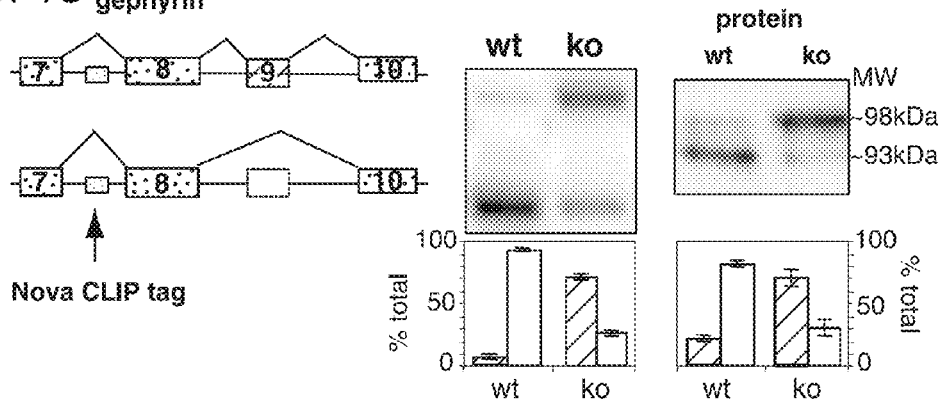

Figure 5A: 21 multiple hit Nova CLIP-tags organized by primary encoded function

| Inhibitory | Gephyrin, MAP1b, GABA-B receptor 2, G-protein coupled inwardly rectifying K+ channel, nicotinic acetylcholine receptor beta 2 subunit (Acrb2) |
|---|---|
| Postsynaptic | Flamingo 1, plasma membrane Ca2+ATPase 2, Shank1, brain sodium channel 1 alpha subunit, protein kinase C zeta, calneuron 1 |
| Presynaptic | Neurexin II, H/T-cadherin, Teneurin 2, rabaptin-5 |
| Signaling, Protein synthesis, other | Ataxin 2-binding protein, ribosomal S6 kinase 3, ribosomal protein L13a, parathymosin, diacylglycerol kinase iota, TARPP |

Figure 5B Nova targets with a role in inhibitory control

| CLIP RNA Target | CLIP tag | CLIP tag position | Change in N2 KO cortex | Reference | Function |
|---|---|---|---|---|---|
| GABA(B) 2 receptor | ACUGUCCCUCCCAUCUACUCACUGUCUCCCAUCUACUAGUCACUGUCUCCCAUC UACUCACUGUCUCCUCCCAUCUACUGACUGUCUCCUCCCAUCU ACUCACUGUCUCCUCCCAUCUACUGACUGUCUCCUCCCAUCUCCC CAUCUACUCACUGUCUCCCCAUCU | Intron 7 Intron 7 | none | Science 283:74-7 | Stimulation of GIRK channels. |
| GIRK2 channel | GCAAGACAUGGCUGCCAUCACAUCCCUCACCACCUGUCAUGAUAAUCAUCCAUUCU UAUCCCUGCUUGGACACCA AGUGUCUGCAUUGGUUGCUGAUUACGGAUGGAUCCUGGGUGUGGUCUC UGCAUGGUCCAUCCUUAUCAGUU | Intron 2 Intron 2 | none | Neuron 19:687-95 | Generation of slow inhibitory postsynaptic potential. |
| Gephyrin | CCAGUUCAACCACAAGGUCCCCAGCUUCCAUCCAUUGGUUGGGUGCUAGUAUCUGC AUCGACUCUUCAGCU CCAACCACAAAUGCCAGCACUCUUUAAUAACAAUCAGCAUGACCUCUGCCUAAGU CCUGGCCUCUUCCUCAGAA | Intron 7 Intron 15 | 60X increase in exon 9 inclusion | Nat Rev Neurosci 4:251-65 | Scaffold of inhibitory synapse. |
| MAP1b | AAGUGGCAGAUUCACGUCCCAGGGUUCAGAGGUGGCAAACUUCUCAGGGCAGCU GUGCUCGGUCAUGC AGAUUUCGAGUUACUGCAAAAAUUGCCUACCCCGUUCUACUCUGCUGAACAUUCGA G UACAUAGUCAGUCAGGGGAGGGCCCCUGUCAACGUGCCCACAAGGUUCCUUUAUCCUUU GUCAUUACUUCAUUGUCCAAGGUUAAGGAGGAACUCAGUCGGUUAAAAUGACGA GCCUAUUUUCAUGA | Intron 2 3' UTR 3' UTR | none | J Neurosci 20:8643-50 | Modulation of GABA(C) receptor current |
| KCNQ3 | CCUGACGGAUCCGUGACGCCCACGUAUCCCUGUAGCAGAGACUGCCAUGCUUUG CCUGUGA GAUUGUAUUCUGCUCCCCAGUCCACCCUCCAACGUUCCACAUAGCCAUAGCUCCU CCCUACCGCAUGUUUUCAUGAGGAUGUCCCCACCCUCCACCACUGCAC | Intron 1 3' UTR | none | Am J Med Genet; 106:146-59. | Inhibition of repetitive action potentials by mediating M-current. |
| Nicotinic AChR β2 | CGUGCGAAAGUACCUCAUGUUCACCAUGGUGCUAGUCACGUGCCAUGGUCACU AGCGUGUG AGACCAUCCAACCUCAUCAUUCCCGGCGUACUCAUCAUCCUCGCCCAUCCUCGGUC UUCUACUUGCC | Exon 5 Exon 5 | none | Neuron 31:131-41; J Neurophys 87:3117-25 | Activation of GABAergic interneurons, part of Acrb2/Acra4 receptor |
| Nicotinic AChR α4 | UCAAUGUACACCACCGGCUCACACCACACAACCACCAUGCCCGCCUGGGUCCGCAGA GUCUUCCUGGGACAUUGUGCCCCGUC | Exon 5 | none | ibid | Part of Acrb2/Acra4 receptor |
| Jnk2 | CUGUCUUCCAUUUUCCCACAUUCUUCCACAUUCACGUAAACGUCCCUCGUCAUGCU | Intron 6 | 6X increase in exon 6a vs 6b inclusion | EMBO J 20:5114-28. | Regulates GABA action in C. elegans |

| Other RNA targets | Functional Nova-binding site (defined by mutagenesis) | Position | Change in Nova1 KO spinal cord | Reference | Function |
|---|---|---|---|---|---|
| GABA$_A$ γ2 | CUCAUUUUCAGAUCAUCAUCUCA | Intron 9 | decrease in exon 9 inclusion | MCB 23:4687-4700 | Inhibitory receptor |
| GlyRα2 | UCUCUCUCAUUUCAUGUU | Intron 2 | decrease in exon 3a inclusion | Neuron 25: 359-71 | Inhibitory receptor |

Figure 7
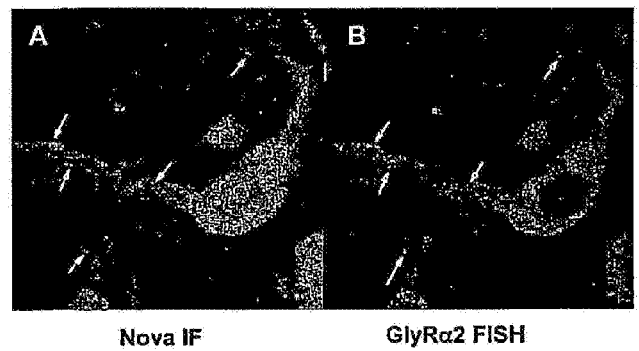
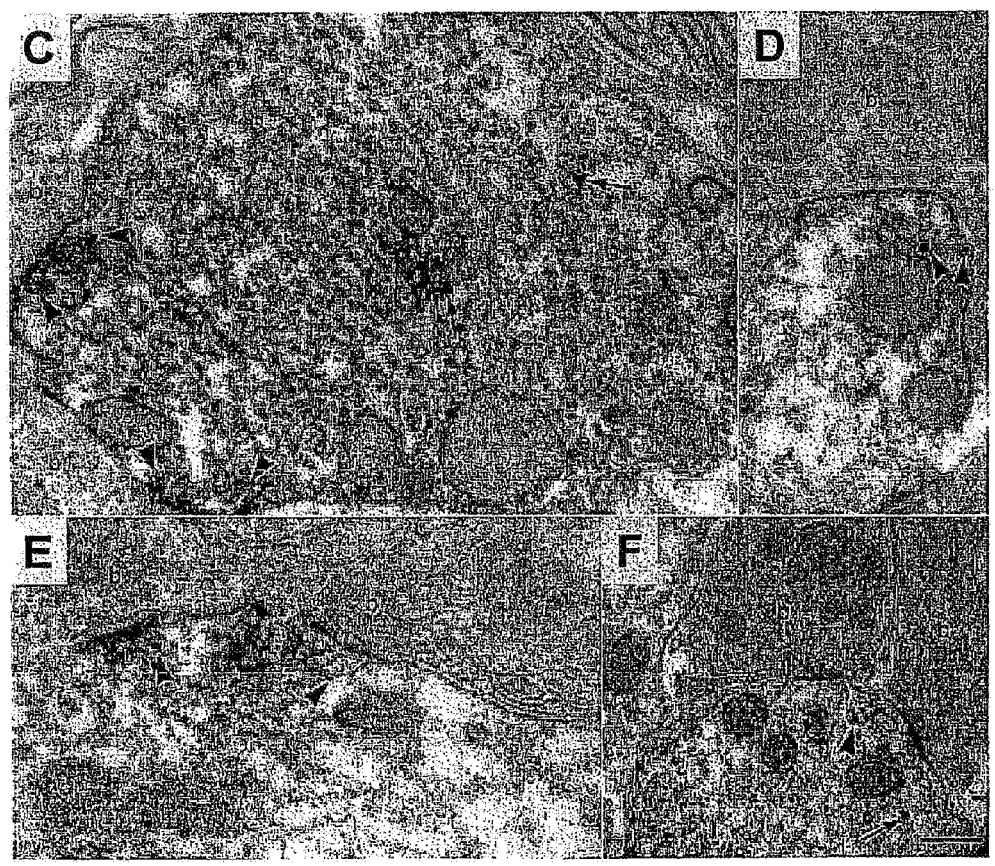

| Sequence | Nt | Match description | Site in RNA | Function | SEQ ID NO |
|---|---|---|---|---|---|
| 3' UTR CLIP tags | | | | | |
| AACCAGTCCTTCCTCCCAGCATTCAGAGTTGCACC GGTAAG | 46 | 3' UTR Rho GEF 12 (LARG) nt 37135 - 37183 Interacts with plexin B1, B2 | 3' UTR | RhoGEF | 336 |
| CCAACCGACTGACCTGCCTTCCTTCTTTTGTCC TCCTTCG | 45 | 3' UTR; Slit-Robo GAP2 RhoGAPfamily member nt 86964 - 87009 | 3' UTR | RhoGAP | 337 |
| ATGAGAGAGGAGGGACCCACACTTTGCAACA | 30 | 3' UTR DIP1/2 Ras GAP | 3' UTR | RasGAP | 338 |
| CTGCAGGAGAGCTCTCTTGGCCCATCCAGACTTGGC GTCTCTC | 47 | 3' UTR of mouse Rab11b nt 1494-1540 | 3' UTR | Rab | 339 |
| ATGCCCCTTGCTGAGAGATTACTACTCTGTCGCTC ACTATAGTTTT | 52 | 3' UTR Rab24 nt 14850 - 14914 | 3' UTR | Rab | 340 |
| GCGAGTGTGCTGCGTGACCGTCAAGGCTTGC AGGGGCATG | 49 | 3' UTR of SNIP (SNAP-25 interacting protein) nt 33705 - 33754 SEE CODING CLIP TAG | 3' UTR | neurotransmitter vesicle transport | 341 |
| CCAGCTCGGTCCAGCATGCTACCAGACGAGGACTTC CTCCCCCTCTCTGCTCCCAGACCC | 64 | 3' UTR of Shank14Spank1 nt 7269 - 7337 | 3' UTR | PSD/neuron molecular scaffold protein | 342 |
| CGGGCAACCCTCCTCTGTGAGCTGCTGGCAAGCT TCTGCCGTGCCCCTGC | 57 | 3' UTR of Calmodulin III nt 922-979 | 3' UTR | calmodulin | 343 |
| CCCAGGCAGGACCCCAACTAAGCATGGTCCTGGATGG NTGA | 48 | 3' UTR nuclear factor I/C nt 38440 -38494; likely 3' UTR | 3' UTR | NF-I/C transcription factor | 344 |
| CCCCAGGTCCTGCGTTCTGTTAAACAGCATCTTTGCCTTGA CTCTCTTCGCCTTCT | 54 | 3' UTR nuclear factor I/X nt 72823 - 72876; likely 3' UTR | 3' UTR | NF-I/X transcription factor | 345 |
| CCTCTTCCTATTGCTTGCCCCCCCCCACCCTCCCCTCCAG | 39 | 3' UTR of Segm10 like-protein (Sellp) nt 700 - 738 | 3' UTR | neuron specific signalling protein | 346 |
| GTGGCAGCCCAGTCTTTTCTTTGTTAGAGCCTGTGCA GCAG | 44 | 3' UTR neuronal kinesin KIF3C2 nt 2912-2955 | 3' UTR | kinesin | 347 |
| CTCTTGCGTAGTCTTCTCCCCCCCCTCAGAGCCCTGTGA | 34 | 3' UTR of adducin 1 (alpha) nt 67823 - 67851 | 3' UTR | alpha adducin | 348 |
| CTTCGACGACTGCCCCGTCCCCCGTCCCCAAACCC | 35 | 3' UTR transcript similar to ref|NP_080269.1| RIKEN cDNA 2010110M21 gene nt 502 - 536 | 3' UTR | | 349 |
| GGCAACGTGCTGGCGCAGCCCTCATCCCCGAG ACAACTGTCTCCAGCTGAACC | 63 | 3' UTR of KIAA0427 mRNA, similar to polyA binding protein interacting protein and eIF4G | 3' UTR | | 350 |
| NACATACTACAGCCCATATTTGCCCTTCATGGGTTG GCCATGACAC | 50 | 3' UTR of quaking | 3' UTR | | 351 |
| CAGCCCAGCAGGCCCTTGCTCCCCCCCCACTCCTCAC CCG | 62 | 3' UTR EST match nt 254 - 255; gp EST matches protocadherin 1 | 3' UTR | protocadherin | 352 |
| ACCTCGACAGAGCAGCCCTTGCTGCCCACACTCTCAC CCCACCCCACAC | 50 | 3' UTR endophilin B1a | 3' UTR | | 353 |
| TGAGAGTAGAGACAAGCATGGTTTGGGTAATGTCANCATCCCACC CCTAAGTTCATCTTGCTTGGACAATG | 65 | 3' UTR dynein light chain 2 | 3' UTR | | 354 |
| NATCTGTTGTTNATTTGAACTACTGCAGCTACACATTC AAGGTAGTACTAGCTACCAGTGAGAGAATGTCTTCTT GA | 80 | 3' UTR nuclear poly A binding protein (pabpn1) | 3' UTR | | 355 |
| AAAGCCCTTCAACTGATTTTGTTTCTTGCTTTGACC AACCCG | 46 | 3' UTR Nova-2 | 3' UTR | | 356 |
| CAAGAGTATGAAACATGTGTGTGACAGACACCTC TACATGTAGCAGAAGACAATGCAGCGGGCGCCTTTC TGGCAGTA | 67 | 3' UTR Trek-2 K+ channel | 3' UTR | | 357 |
| ACCCAGAGAGAGCAGCCCTGCGCTGAGCCGCTGGT GGCCCTTTTTGGC | 54 | 3' UTR phosphatidylinositol transfer protein, beta | 3' UTR | | 358 |

FIG. 8A

| Sequence | Nt | Match description | Site in RNA | Function | |
|---|---|---|---|---|---|
| TTGGTCTGGGCTACTGCTGCCAAGCAAACCCTGTGCT GTGCCTGG | 48 | 3' UTR, CPSF 30K | 3' UTR | | 359 |
| GGGGCTGTGTGGCGCTGCTGCCCCCCACGCGGCCACT CACAGTCATCCCGTGCCT | 58 | 3' UTR midline 1 | 3' UTR | | 360 |
| ACAGCCCCCCATTCCCCTATCCCCCACCCCATACTGGCA ACT | 42 | 3' UTR of cofilin | 3' UTR | | 361 |
| AGGCCCCCCCCTCCTGTCGCAGCGCCTCCCTCTCTGTC CAGTGAGCTGCGCTTCCTGCTCTCAT | 65 | Gs alpha subunit 3' utr of UTR-A form SEE ALSO CODING CLIP TAG | 3' UTR | | 362 |
| 1st intron CLIP tags | | | | | |
| GGCGCTGTGTGCTCTTCCTGGCTGCTTGGAAGCAAGTGTC GTCTCATTCTGCA | 54 | 1st intron, unc5 homolog (C. elegans) unc5h3 nt 46031 - 46134 | Intron, b/w coding exons 1 and 2–b/g distance, about 100 b/p | netrin receptor, unc-5 | 363 |
| AGTGCGCAGCCTCTTCTTGTTGTCAGGGCGCGCCCACAGT CAAATACAGACCTGTACC | 59 | 1st intron, sema domain, transmembrane domain (TM), and cytoplasmic domain, (semaphorin) 6A nt 27140 - 27198 | Intron, b/w 1 and 2nd exon; intron is around 100 kb | sema 6a (transmembrane) | 364 |
| GCTGTTCACGTCTTCTTGCCTCAGAATCTGAATTCCCGACC GGGCCATTTCCTGAZ | 53 | 1st intron, SER/THR FAMILY OF PROTEIN KINASES-RELATED KIAA0537 | Intron b/w exons 1 and 2 of predicted mRNA | ser/thr kinase | 365 |
| AGTACCTGTTATCTGCTCCTGTTTCATGTGGGATGCTTGCTT G | 40 | 1st intron KIAA1048 protein [Homo sapiens] ser/thre KINASE-RELATED nt 59538 - 59637 | b/w exons 1 & 2–about at about distance | ser/thr kinase | 366 |
| ATCGACTGGCTGCTTGCCTGGGTTCCACAGCCCTGTGGTT TTTCTTG | 46 | 1st intron U2AF65 nt 13316-43361 | Intron, 3.2 kb 3'- of exon 1, 1,775 nt 5' of exon 2 | splicing factor | 367 |
| GCTGTTTGCTGCATTTTCCTCAGGATGCCCCCAACCACTG CTTTCTG | 46 | 1st intron, voltage dependent calcium channel beta 4 subunit (CACNB4) mRNA | Intron b/w exons 1 and 2, intron is about 100kb | K channel | 368 |
| ATAPATCAGGAATCAGGATGCTTTCAATTAAGTTAAAA GTGTCGTCCCA | 51 | 1st intron, anterin3 (ank3) SEE ALSO 2ND CLIP TAG IN DOWNSTREAM INTRON | Intron b/w exons 1 and 2; there are at two upstream "1" exons, the closer to the CLIP tag is the brain specific form, intron is about 100kb | link b/w spectrin and membrane proteins, many ultimately spliced forms of ankyrin3 (ank3), some w/o first exon | 369 |
| AAATCTTCGTGTACTTCAGCATTCTGGTTTCTCATCTG | 37 | 1st intron, potassium voltage-gated channel, Shal-related family, member 2 (Kcnd2), mRNA | Intron b/w exons 1 and 2; intron is about 500kb | K+ channel | 370 |
| CAACCTCCCTGCATTTCTCTGTGTGCTGTAGCTC | 35 | 1st intron, zinc finger protein RIZ mRNA, complete cds | Intron b/w exons 1 and 2; intron is about 17kb; first exons is not always present. | Rb interacting zinc finger protein | 371 |
| ACACCCAGAGAGAGCAGCACCATGATTGCAGTGCTGTGT CCC | 42 | 1st intron, dihydropin-1 related protein (VAPB) mRNA | intron b/w exons 1 and 2; intron is greater than 100 kb | | 372 |
| GGAGGCGAGCCAAGCTTTCCAGCACTTTCGGCACCCC CATCTGCAGTGTTTGGTTTGTTTTA | 57 | 1st intron of EBF1GR-1 | Intron b/w exons 1 and 2; 200 nt 3' of exon 1 | neuronal, (and B cell?) transcription factor | 373 |
| GACACCTTGGAGATGAGATGGCTGCACCCAGTTTCAC CA | 41 | 1st intron, uncharacterized gene | | | 374 |
| TGACTCTTTTACCCACTTTCTTTTGAGGCAGGATT GGTGCACTGAACCAGGGTTGG | 61 | 1st intron, autism-related protein 1 (AUTS2) SEE ALSO 2ND CLIP TAG INDOWNSTREAM INTRON | | | 375 |
| ACTGTCATTACCCTTTGTCATCTGACCAAATCATGGA CTTCTCCAGCTG | 54 | 1st intron astrotactin 1 | | | 376 |
| CCTGCCCCTGTGGCCCTCTGCCTCTGGATATTGGATG AGATGCACGCCGGGCCTCTGCTGACCCCTGACTCTT GTGGGGCTATG | 95 | 1st intron, unknown gene (alternative promoters) | | | 377 |
| AGCGGCAAGAATGGCCTGCCATGGGCCGGGGCCTCTGCT GCGTCATGGAAGG | 50 | 1st intron, hypothetical N-6 adenine DNA methylase | | | 378 |
| GAGAATGCAGGAGACAATGCCTGCAGGAGCTCTGCT CTGATTTTACTACTTTTCTCCCTCTCTG | 70 | 1st intron retinonin 1 | | | 379 |

FIG. 8A CONT.

| Sequence | Nt | Match description | Site in RNA | Function | |
|---|---|---|---|---|---|
| AANTCAATCAACTCCGTTGGTGTGTG | 30 | 1st intron novel protein | | | 380 |
| ATGCCATTGCATTGGGATGCAGCGCTAGGTGACGGCAGG AGG | 44 | 1st intron 7afin36 | | | 381 |
| TCCCTCTGTGATCAGCGGCTCTGTCTCTTTTTCTAGTTACGACACAT | 39 | 1st intron twr-3 alternative upstream strand of uncharacterized helicase | | | 382 |
| ACTGGCGGCTACTACTTGCCTTTTCTTTTTTCTGAATTAC TTATCCTTGCATTCCACGTGCCTCT | 60 | 1st intron neurofimin | | | 383 |
| GCAGGGTGCCGCAATGCTAAGCGATTAATTGGGAACGA AACTGAATCACTGTCTTTTGCTCCATCATCCCTTCAG CTCTC | 84 | 1st intron uncharacterized gene | | | 384 |
| AGTGTGGCCTACTACTGTCGTTTTCAGATGTCTTCTGTAC CACAGATCCCACCAG | 54 | 1st intron Kcnq5 potassium channel | | | 385 |
| ANTCTACAAGACTGTGTGTGTGTAACTTTGTCAGTGC AACTAGAACCTGTCTACACAGTCAGGGA | 69 | 1st intron alpha 2f subunit of guanylyl cyclase | | | 386 |

Other intron CLIP tags

| Sequence | Nt | Match description | Site in RNA | Function | |
|---|---|---|---|---|---|
| TCGGCTGATAAGATGGCTTTTCTTGAACGCCAGTTTG ATTGCACC | 40 | Intron, uncharacterized protein | | | 387 |
| AAATTGTCGTGACGACGACAGAGTTTGTGTGTGTGTGC TCTCCACGTGCCTGGTTAGGTTTTACTGATG | 74 | Intron synaptotagmin 1 | | | 388 |
| ATGGCTACCACTCTCTGATTCCCTTCAGTAGATCTGATC TACGGCT | 47 | Intron HiRA protein | | | 389 |
| AAATCCTAACCATGGCATGTGGTACCCAATGATATTCCAGCTCA ACCTATCCATGAGCGGGACGGACGCCTTGATCCAAAGAGTT CAAG | 82 | Intron grip1 | | | 390 |
| CCCAAGTAACTGGTCTCTGCCTCCAGCTCTGAAGTA CTCAGGTAAAGACAGGTACGACGAACACCCTCTGGGCTC TTGCTTATG | 89 | Intron Trolb binding protein | | | 391 |
| CATGGCCAGTCTCTTTTAAACTCTCTATTCCTCTCTGAT CCAGACTTTAATTACTCCTAATCCACTCGTTATTTTAGAT CGTAG | 84 | Intron dihydropyrimidino dehydrogenase | | | 392 |
| TACTTGGCTCCTGCATTGTCTCATGGCTGTTCCTTTTAAG GTGCATTTGTGGTCACCAGCTCTTCTGTCTTTGAAG | 76 | Intron/3' UTR neurexin alpha 1 | | | 393 |
| AAGGCTGCTAACTGCCTGGTGATGCGTTTCGAGCACC TGCTTAACTCGAATTTGTTTGTCAAGCCCCCTGTG TAATGTT | 86 | Intron, uncharacterized gene | | | 394 |
| ATCAGGCTGGCTGCCTTGTGTGACCTCTGTCTTCCA | 37 | Intron, uncharacterized gene | | | 395 |
| TCTAGGTGGATCAACAATGAACTAGCCAGTGCCCCA GAACTCAGGTCTCTAGCTG | 58 | Intron/e uncharacterized gene | | | 396 |
| CATGTGAACCAACTGTCAGCATTTATTTTCATTTT AGCCATTATTACAC | 51 | Intron SET binding protein | | | 397 |
| CCCATCAATCCTGATAGCTGGACTGCCTCCACTAT GTTAAGAAACAACCACAC | 53 | 2nd in last intron, Cngho2 (Mapor) | | | 398 |
| ATTCAACCATTTTTAATAAATAACATTTTCTGATAGT CTTGCTTGCCAGGTGAACGTGGTATCATCATGACTACAT AAT | 73 | Intron, autism-related protein 1 (AUTS2) SEE ALSO 2ND CLIP TAG IN 1st INTRON | | | 399 |
| GAGATTCTGACTTAATCAGCCTGGTCTTCTTCTACA CATGCCACACACAGAC | 55 | gene kalirin (RhoGEF) nt 18469 - 16723; unc-73 | intron: 1560 nt 3' of 1st "branching" exon; experimental evidence of alternative splicing at tag site | RhoGEF; unc-73 | 400 |
| ACACACAGCAGCCACAGCAATCACGAGCACATACTCGCCGCA GACTCGTAG | 49 | gene munc13 nt 16026 -16075 | intron: 38 4 nt 3' of upstream exon 3; 437 nt 5' of downstream exon 4 | neurotransmitter vesicle transport; unc-13 | 401 |

FIG. 8A CONT.

| Sequence | Nt | Match description | Site in RNA | Function | |
|---|---|---|---|---|---|
| CACACCGCATCCCTGCCGTCCCCTCTCCACTCTGTGTCTCTGGCGCACTCA TGCAGTT | 47 | gene plexin A1 nt 28441 - 28487 | Intron; lies in 127 nt 3' of exon for 2nd cys-rich domain; 195 nt 5' of next exon | plexin 1 | 402 |
| AGAATCCCTCTCGCCACTCCTTGCTTTTCATT | 32 | Intron, ankyrin3 (ank3) SEE ALSO 2ND CLIP TAG IN 1st INTRON | | | 403 |
| CAGGTCTCCAGTAGGTACCTGCCAGCTTAGAACTTG CTATATGACAATCCAGTT | 50 | mouse core myeloid/lymphoid or mixed lineage-leukemia translocation to 10 homolog (mAF10) nt 111979 - 112028 | Intron; 1,743nt 3' of exon 9; 5.5kb 5' of exon 10 | mAF10 | 404 |
| CCAGGAGGCCGGTCTCTCCTTTTTAAAGACAGGTT CTTGCTATGTATGCTCTATCAAG | 61 | Intron; topoisomerase I gene | Intron b/w exons 2 and 3; | | 405 |
| TATTCTAAGAAAGTAGATTTGAAGGCTTTGTCTGGC AGTC | 40 | Intron, glutamate receptor, ionotropic, delta 2 (GluD2), mRNA | Intron b/w penultimate and last exon | glutamate receptor; Lurcher | 406 |
| TATCACACCAAGCTACCCTAAACTAAACAGCTA | 33 | Intron; membrane-associated guanylate kinase 1 (Magi-1) mRNA | Intron b/w exons 5 and 6 | PDZ domains, guanylate kinase | 407 |
| CTTAGCTCTCATGCTCACTCACTTC | 25 | Intron Zic binding protein nt 96393 - 96962 | | Zic binding protein; zinc finger protein; transcription factor | 408 |
| ACACCTCGTCGCTCTGCCCCTCTGCAGCACTTTTA TAA | 42 | Intron, c-Abl | | | 409 |
| CTCCCTGTTGCCCCAAATGTCTGTCATCTTTTTCTTC TCCCCGTCTCAGTCTAGTGTCCTATCTTTTTTTTCTCC | 76 | Intron, or 3' UTR, and maybe even exon 9- GlcNAc transferase (OGT) | | | 410 |
| TAAGTTAACTTTTCACTTCAGTGACTACAGCTGCAT | 35 | Intron sortcoin/ 4 receptor "Tex compl" | | | 411 |
| CTTGGCTTGGCCTGAAATTCTGCTATGTATGAGGTTG CTTTGACTCAAGAGAGCCCACCTGTTCTCGCCTCGTGA CATTCTCAG | 57 | Intron, associated with Myc protein | | | 412 |
| CATCTCCTAACAATGTCAGCTCTGCTAAGCTAGCA GGAGTGGTCGTCAATGATAATTAATGCC | 72 | Intron phospholipase C beta 1a mRNA | | | 413 |

5' UTR and coding CLIP tags

| | | | | | |
|---|---|---|---|---|---|
| GGTCCATGGAGCGGGAGGAGGAGAGTCAGTCA GGAGCAAGAGAG | 52 | 5' UTR of EphA7 receptor tyrosine kinase family protein nt 10013 - 10054 | 5' UTR | EphA receptor/tyrosine kinase; alt. Splicing at 3' end | 414 |
| AACAACGAATGGACCTCAAAAAACAACATAGATGCTTTA GTAAGTATGTCCCCACACACTTTCAAGTCACACTG | 75 | 5' UTR, unknown protein | | | 415 |
| TCATCCTTGGCCAGCAAGGGCTGAGTATTATTCTTCTTCCGAA GGAAGC | 45 | 5' UTR of zinc finger protein; sits over intron/exon boundary w/ alternative 3' splice site | | | 416 |
| TGTCAAGATCCCAGTGATGACCCCCAAGATCTTGGCCTTTGGC ACTGCCCACGCCTCTG | 50 | coding (and possibly an alternative 5' UTR) plexin B2 | | plexin | 417 |
| AATGAAAGCATCGGAGGACAATATATAAACCTGCAGGG TGCAGATTTCTAAGAAGATGTGTGAGCCTAATGCGGC AG | 80 | coding, rab2 (rundabout) | | | 418 |
| GTCGCTCAACAGTACGCAGGACGTGCACGCAGGAGGACCCT CCAGTCATCCCCAGCAGCACTCGTCTCCCCAGGC | 70 | coding; mouse homologue of rat SNIP (interacts with SNAP-25) coding; there are alternative 3' ends SEE 5' UTR CLIP TAG | | | 419 |
| ATGCAGCTGGCTACCACCAGCAAGGTTGAAGAACAAT AGCCGCCACCAACAAGAATTACTGTCTGCAGCTACT TGTCGCA | 85 | mouse Go alpha subunit; 3' end of coding region (exon tie in humans) SEE ALSO CLIP TAG IN 3' UTR | | | 420 |
| CAGAGAAGAACAGACTACCAACAATGGACCCCTAACC AATGAAGCACTAATCCAACTGATGAGCCCACCACTGG | 76 | coding, uncharacterized RING finger protein | | | 421 |
| TGGAGCCACCAGAATCAACTCTCCTACCCTCGCTCTCAC | 38 | 3' UTR or coding (alternative transcripts share) Latrophilin-3 | transcript | G-coupled receptor | 422 |
| AGATCTACAGCCAATCAGGCACTCCACCCCTCGTTACA CAGTCTCACTCAT | 51 | transcript of human KIAA1267 protein nt 583 - 634 | transcript | | 423 |

| Sequence | Nt | Match description | Site in RNA | Function | |
|---|---|---|---|---|---|
| CCGCCCCACATTCGCCGTCGCAAGATGGGCGCTGACATC CTGTGTTCTAAGTTGG | 53 | many BLAT hits; repetitive element | | | 447 |
| ATCCATCAAGGCCACAATTCCTAATAGTGTCATTTCCTG TTCCAAGCATAACAAACAATCACAAATGAGTCTGTTGGT TTATTCTG | 87 | many BLAT hits; repetitive element | | | 448 |
| TCCACTGGATGGTTTTAGCTCCCTTGTCAAAGATCAAGT GACCATAGGTGTGTGGGTTCATCTCTGGGTCTTCAATTC | 78 | many BLAT hits; repetitive element | | | 449 |

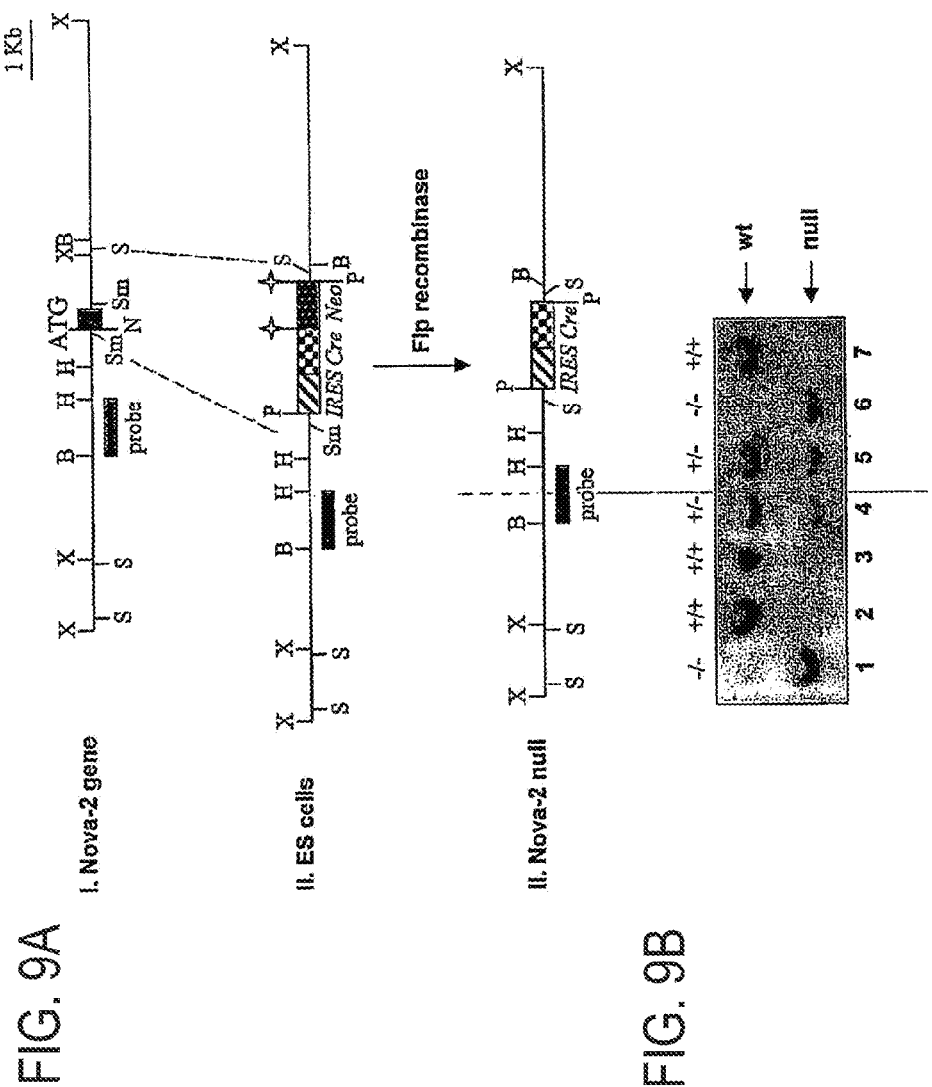

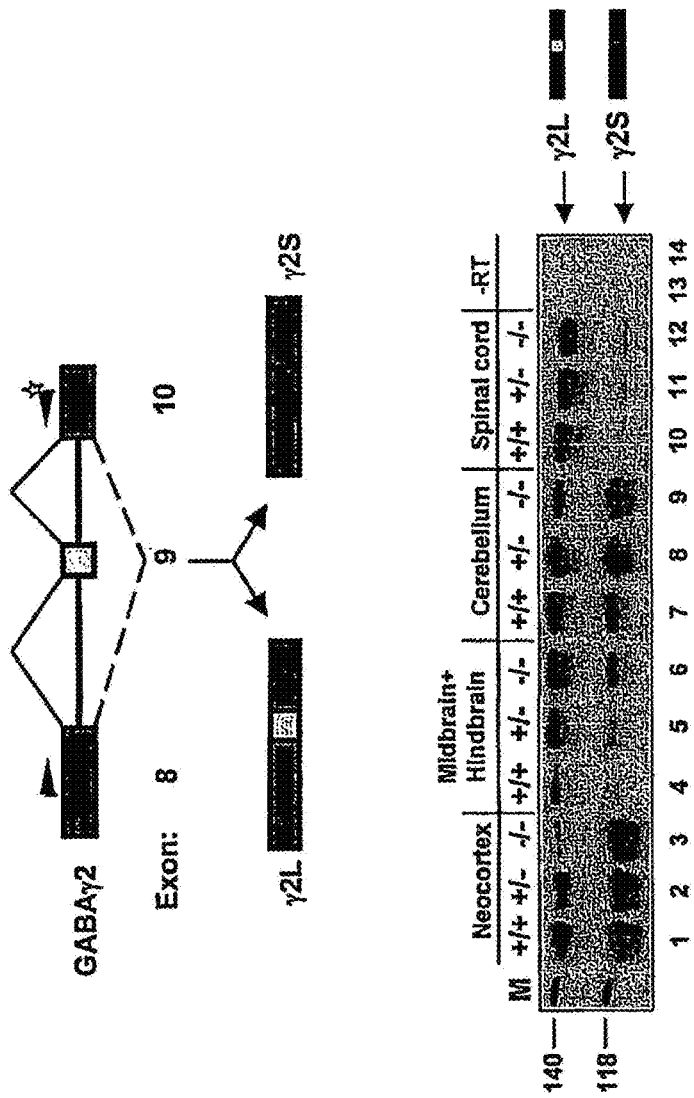

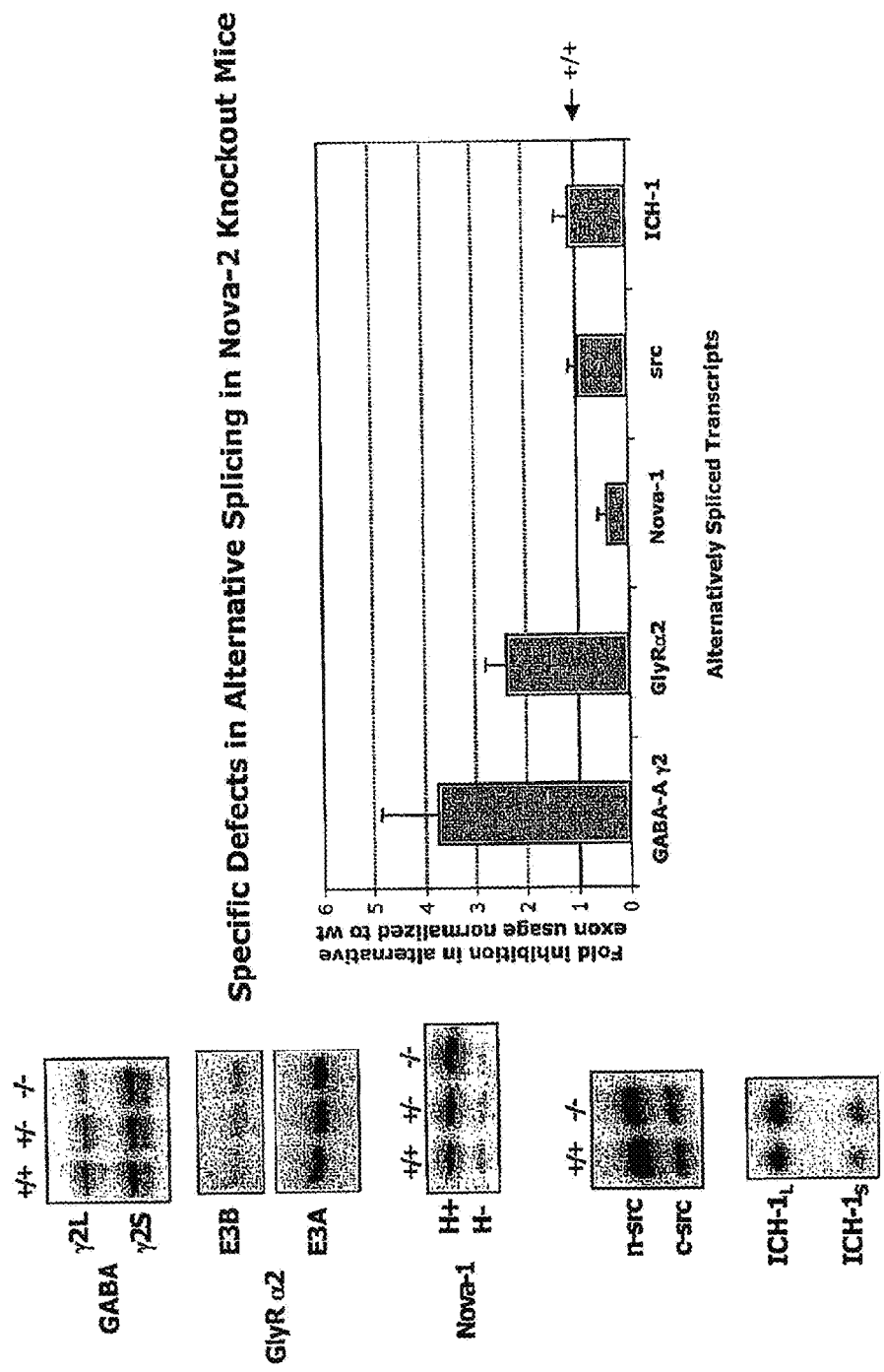

SEQUENCE LISTING

```
<160> NUMBER OF SEQ ID NOS: 522

<210> SEQ ID NO 1
<211> LENGTH: 70
<212> TYPE: DNA
<213> ORGANISM: Mus musculus

<400> SEQUENCE: 1
catccatctt gactcattgc tgtcactgca gaaggactaa gtagcaaaac actgctccaa      60
ggtctttggc                                                            70

<210> SEQ ID NO 2
<211> LENGTH: 73
<212> TYPE: DNA
<213> ORGANISM: Mus musculus

<400> SEQUENCE: 2
aaacaacatg tccctgcaa cataatccat gttcttcctg tcattccacc atccctgacc      60
``` ccacccctc cac                                                73

<210> SEQ ID NO 3
<211> LENGTH: 76
<212> TYPE: DNA
<213> ORGANISM: Mus musculus

<400> SEQUENCE: 3
catttcaaat gttttccccc ttctaggctt ccctctgca aacccttaa gccatcctct    60 cccccctgct tctatg                                            76

<210> SEQ ID NO 4
<211> LENGTH: 93
<212> TYPE: DNA
<213> ORGANISM: Mus musculus

<400> SEQUENCE: 4
atgttttagt tttcacaatt actttcgcca tcatttgctt tttactgaca aaatgtctgt    60
ccatccttct cattgtctcc cccatcctca gtt                         93

<210> SEQ ID NO 5
<211> LENGTH: 72
<212> TYPE: DNA
<213> ORGANISM: Mus musculus

<400> SEQUENCE: 5
agcaccaggg agcaaatgcc agctgattgt tgttcctgcc cagcttgctg gctagctttg    60
atacattcct ca                                                72

<210> SEQ ID NO 6
<211> LENGTH: 58
<212> TYPE: DNA
<213> ORGANISM: Mus musculus

<400> SEQUENCE: 6
agcaccaggg agcaaatgcc agctgattgt tgttcctgcc cagcttgctg gctagctt     58

<210> SEQ ID NO 7
<211> LENGTH: 63
<212> TYPE: DNA
<213> ORGANISM: Mus musculus

<400> SEQUENCE: 7
ggtgggaaag tacctcatgt tcaccatggt gctagtcacc ttctccatcg tcactagcgt    60
gtg                                                          63

<210> SEQ ID NO 8
<211> LENGTH: 67
<212> TYPE: DNA
<213> ORGANISM: Mus musculus

<400> SEQUENCE: 8
acaccatcaa cctcatcatc ccctgcgtac tcatcacctc gctggccatc ctggtcttct    60
acctgcc                                                      67

<210> SEQ ID NO 9
<211> LENGTH: 59
<212> TYPE: DNA
<213> ORGANISM: Mus musculus

```
<400> SEQUENCE: 9
aaacccttct gccaggtgac cacacgcagc ttccctgccc gctccttcat caccttccg      59

<210> SEQ ID NO 10
<211> LENGTH: 69
<212> TYPE: DNA
<213> ORGANISM: Mus musculus

<400> SEQUENCE: 10
aaagtgcttc atttctcctg cccacccttg caggtagggc cagtcactct tccattgctt    60
ctttgctgt                                                            69

<210> SEQ ID NO 11
<211> LENGTH: 95
<212> TYPE: DNA
<213> ORGANISM: Mus musculus

<400> SEQUENCE: 11
actgtccctc cccatctact cactgtcttc cccatctact cactgtcctc cccatctact    60
cactgtcctc tcatctactc actgtcctcc catct                               95

<210> SEQ ID NO 12
<211> LENGTH: 81
<212> TYPE: DNA
<213> ORGANISM: Mus musculus

<400> SEQUENCE: 12
actcactgtc cctccccatc tactcactgt ccctccccat ctactcactg tcctccccatc   60 tactcactgt cctccccatc t                                              81

<210> SEQ ID NO 13
<211> LENGTH: 73
<212> TYPE: DNA
<213> ORGANISM: Mus musculus

<400> SEQUENCE: 13
ccatcagttc tctctgtgct ccatcagtcc tctctgtgct ccatcagtcc tctgtgctcc    60
atcagttctc tct                                                       73

<210> SEQ ID NO 14
<211> LENGTH: 73
<212> TYPE: DNA
<213> ORGANISM: Mus musculus

<400> SEQUENCE: 14
ctccatcagt cctctctgtg ctccatcagt cctctctgtg ctccatcagt ctctctgtgc    60
tcccttagtc ctc                                                       73

<210> SEQ ID NO 15
<211> LENGTH: 72
<212> TYPE: DNA
<213> ORGANISM: Mus musculus

<400> SEQUENCE: 15
tcacctgtcc atcacccagt catgcatgca tgcacgcatg cacacacatt caacccaccc    60
actcatccac ct                                                        72

<210> SEQ ID NO 16
<211> LENGTH: 66
```

```
<212> TYPE: DNA
<213> ORGANISM: Mus musculus

<400> SEQUENCE: 16
tgttctgctc atttcattgc cattgctatg ggatcacttt atcattgccc catgatggca      60
tcatgg                                                                 66

<210> SEQ ID NO 17
<211> LENGTH: 73
<212> TYPE: DNA
<213> ORGANISM: Mus musculus

<400> SEQUENCE: 17
gccacaggtc acttggcttt tctctctcca tggggaattt tcctctcctc ccttgtatct      60
gtctcctttc ctc                                                         73

<210> SEQ ID NO 18
<211> LENGTH: 66
<212> TYPE: DNA
<213> ORGANISM: Mus musculus

<400> SEQUENCE: 18
acgtctccac ctcaccctca ttactaactt ctacctgtgt ggtgcccag gaactgctct       60 tgtgca                                                                 66

<210> SEQ ID NO 19
<211> LENGTH: 63
<212> TYPE: DNA
<213> ORGANISM: Mus musculus

<400> SEQUENCE: 19
atgacgcagg tgccacagct cctgtcacct ccctcggcgc cagcatatgc gcaggaagag      60
cac                                                                    63

<210> SEQ ID NO 20
<211> LENGTH: 72
<212> TYPE: DNA
<213> ORGANISM: Mus musculus

<400> SEQUENCE: 20
actccatcct tcactctctc cctcctcaca atcgctcctc ctcgctctca gcctggcccc      60
ccagccctcc tc                                                          72

<210> SEQ ID NO 21
<211> LENGTH: 49
<212> TYPE: DNA
<213> ORGANISM: Mus musculus

<400> SEQUENCE: 21
aactccatcc ttctctctcc ctcctcacaa tcgctcctcc tcgctcttc                  49

<210> SEQ ID NO 22
<211> LENGTH: 72
<212> TYPE: DNA
<213> ORGANISM: Mus musculus

<400> SEQUENCE: 22
gctcatctcg aggaccatga tgaagaacat cctgggccac gccgtctacc agctcaccct      60
catcttcacc ct                                                          72
```

<210> SEQ ID NO 23
<211> LENGTH: 77
<212> TYPE: DNA
<213> ORGANISM: Mus musculus

<400> SEQUENCE: 23
agagtaccgg gatgtctctg ttacctggta gaggttcccg atgtcattca tctgtctgtc    60
tctgcatcag ctgacca    77

<210> SEQ ID NO 24
<211> LENGTH: 74
<212> TYPE: DNA
<213> ORGANISM: Mus musculus

<400> SEQUENCE: 24
gtcattcatc tgtctgtctc tgcatcagct gaccatcttc cagtggtacc tctcctcccc    60
tgctcacccc tcac    74

<210> SEQ ID NO 25
<211> LENGTH: 60
<212> TYPE: DNA
<213> ORGANISM: Mus musculus

<400> SEQUENCE: 25
ccaccggtcc agctcctgac ccgcctcatc tgagctcccc agccagccct cacttgccct    60

<210> SEQ ID NO 26
<211> LENGTH: 69
<212> TYPE: DNA
<213> ORGANISM: Mus musculus

<400> SEQUENCE: 26
ccttcaccct cactgccacc ggtccagctc ctgacccgcc tcatctgagc tccccagcca    60
gccctcact    69

<210> SEQ ID NO 27
<211> LENGTH: 95
<212> TYPE: DNA
<213> ORGANISM: Mus musculus

<400> SEQUENCE: 27
acaaatccag cccccttct cctggctccc tgctctggcc ctgccccaga gctgtgaccc    60
ttgtcctttg acccagcctc tcatttccat ctctc    95

<210> SEQ ID NO 28
<211> LENGTH: 148
<212> TYPE: DNA
<213> ORGANISM: Mus musculus

<400> SEQUENCE: 28
tcatttacca tttcatccat ctatccattc acctatctac tatccactca tgtatccatc    60
catctaccca ttcattcatc cactcgtcca cccacttatc cattcatcca cccacccact    120
cattattcac ccctacccat ccatccac    148

<210> SEQ ID NO 29
<211> LENGTH: 52
<212> TYPE: DNA
<213> ORGANISM: Mus musculus

<400> SEQUENCE: 29
cctggtccca tgctgcagac acacatggga cttccttcc ctctcctgct cc            52

<210> SEQ ID NO 30
<211> LENGTH: 70
<212> TYPE: DNA
<213> ORGANISM: Mus musculus

<400> SEQUENCE: 30
gatgagcaac actcaccatc tttcgtttga gtctcacgac tgtgagatca acccatgcac    60
cgctctgaga                                                          70

<210> SEQ ID NO 31
<211> LENGTH: 73
<212> TYPE: DNA
<213> ORGANISM: Mus musculus

<400> SEQUENCE: 31
tccatgatga gcaacactca ccatctttcg tttgagtctc acgactgtga gatcaaccca    60
tgcaccgctc tga                                                      73

<210> SEQ ID NO 32
<211> LENGTH: 53
<212> TYPE: DNA
<213> ORGANISM: Mus musculus

<400> SEQUENCE: 32
cttgtcccca cacctctacc cacggtcatc tgccacctcc accatctatc tcg           53

<210> SEQ ID NO 33
<211> LENGTH: 105
<212> TYPE: DNA
<213> ORGANISM: Mus musculus

<400> SEQUENCE: 33
ctggcttgtc ctccccagtt ccttcctgtt catccttcgc acaactctga ctgcccacag    60
cccatgctcc atggtggcta agtcccatgg tgccagatgc tgacc                   105

<210> SEQ ID NO 34
<211> LENGTH: 75
<212> TYPE: DNA
<213> ORGANISM: Mus musculus

<400> SEQUENCE: 34
caggtttagg cctgactgtc tgtctgtcca tctacccatt tgtcctcaat tcaccatcct    60
tccatccatc atctc                                                    75

<210> SEQ ID NO 35
<211> LENGTH: 74
<212> TYPE: DNA
<213> ORGANISM: Mus musculus

<400> SEQUENCE: 35
agctcaccat cctcccagct caccatcctc ccagctcacc atcctcccag ctcaccatcc    60
tcccagctca ccat                                                     74

<210> SEQ ID NO 36
<211> LENGTH: 72
<212> TYPE: DNA
<213> ORGANISM: Mus musculus

```
<400> SEQUENCE: 36
acatctggat cctcctcaca cccacatctg catgctcctc acacccacat ctgcatgctc      60
ctcacaccca ca                                                         72

<210> SEQ ID NO 37
<211> LENGTH: 45
<212> TYPE: DNA
<213> ORGANISM: Mus musculus

<400> SEQUENCE: 37
aattcctcat cctcattgct tcctcctcac acctacatct gcatc                     45

<210> SEQ ID NO 38
<211> LENGTH: 84
<212> TYPE: DNA
<213> ORGANISM: Mus musculus

<400> SEQUENCE: 38
aattccacac tcctgtccat tccagggagt gaccactatc aggaatctac ctccatttcc     60
tataggcact ttacctggat tttc                                            84

<210> SEQ ID NO 39
<211> LENGTH: 66
<212> TYPE: DNA
<213> ORGANISM: Mus musculus

<400> SEQUENCE: 39
aggccacatt cattgcatat actttcagca gaagctgaaa ccacaggtga actcgcaatg     60
cccggt                                                                66

<210> SEQ ID NO 40
<211> LENGTH: 73
<212> TYPE: DNA
<213> ORGANISM: Mus musculus

<400> SEQUENCE: 40
gtggcaagga tatatatgtc tgtgcctgtg cacatgcatt tgtgtgtgtg tgtgtgtgtg     60
tgtgtgtgtg tgt                                                        73

<210> SEQ ID NO 41
<211> LENGTH: 66
<212> TYPE: DNA
<213> ORGANISM: Mus musculus

<400> SEQUENCE: 41
tccatgacca tttcattccc tcttctaagt gaggctcaag cattttttgct tgtaccctcc    60 ttcctg                                                                66

<210> SEQ ID NO 42
<211> LENGTH: 46
<212> TYPE: DNA
<213> ORGANISM: Mus musculus

<400> SEQUENCE: 42
tcattcattc attcattcat tcattcattc attcatcttt ttctgt                    46

<210> SEQ ID NO 43
<211> LENGTH: 72
<212> TYPE: DNA
<213> ORGANISM: Mus musculus
```

<400> SEQUENCE: 43
aacctcatgg tccaccatcc acccatccat cagttcaccc atccatccat tcacctaagc    60
acccaccatc aa    72

<210> SEQ ID NO 44
<211> LENGTH: 52
<212> TYPE: DNA
<213> ORGANISM: Mus musculus

<400> SEQUENCE: 44
acctcctcac cctctcacct cctcacccac tcacccctc acccactcac cc    52

<210> SEQ ID NO 45
<211> LENGTH: 72
<212> TYPE: DNA
<213> ORGANISM: Mus musculus

<400> SEQUENCE: 45
ccagttcaac cacaggtccc cagcttccat ccattggttg ggtgctagta tctgcatctg    60
actctttcag ct    72

<210> SEQ ID NO 46
<211> LENGTH: 74
<212> TYPE: DNA
<213> ORGANISM: Mus musculus

<400> SEQUENCE: 46
ccaaccacaa atgccagcac ctcttaataa caatcagcat gacctctgcc taagtcttgg    60
cttcttcctc agaa    74

<210> SEQ ID NO 47
<211> LENGTH: 74
<212> TYPE: DNA
<213> ORGANISM: Mus musculus

<400> SEQUENCE: 47
tgacccttgg cacaatgcca gctctggctg gacacaagga cacacgcatc tcctccattc    60
ctgctgctcc attg    74

<210> SEQ ID NO 48
<211> LENGTH: 71
<212> TYPE: DNA
<213> ORGANISM: Mus musculus

<400> SEQUENCE: 48
actcagagca gggggaagaa acacaccctc aactctgctt cccgtgctc catcttcctt    60 tctgccttcc a    71

<210> SEQ ID NO 49
<211> LENGTH: 68
<212> TYPE: DNA
<213> ORGANISM: Mus musculus

<400> SEQUENCE: 49
gcctgtgttc agccctctca ccccatgctt atctggacat tgaagcttgg aaagccagtg    60
gtgacttc    68

<210> SEQ ID NO 50

```
<211> LENGTH: 69
<212> TYPE: DNA
<213> ORGANISM: Mus musculus

<400> SEQUENCE: 50
tgtgttcagc cctctcaccc catgcttatc tggacattga agcttggaaa gccagtggtg    60
acttcaact                                                             69

<210> SEQ ID NO 51
<211> LENGTH: 76
<212> TYPE: DNA
<213> ORGANISM: Mus musculus

<400> SEQUENCE: 51
tccacccatc catctggcta tccatctagc catctgtcag tcaatccatc catccatcca    60
tccatccatt catcca                                                     76

<210> SEQ ID NO 52
<211> LENGTH: 48
<212> TYPE: DNA
<213> ORGANISM: Mus musculus

<400> SEQUENCE: 52
agccatctgt cagtcaatcc atccatccat ccatccattc atccatcc                  48

<210> SEQ ID NO 53
<211> LENGTH: 58
<212> TYPE: DNA
<213> ORGANISM: Mus musculus

<400> SEQUENCE: 53
agccatctgt cagtcaatcc atccatccat ccatccattc atccatccat ccatgcat      58

<210> SEQ ID NO 54
<211> LENGTH: 89
<212> TYPE: DNA
<213> ORGANISM: Mus musculus

<400> SEQUENCE: 54
ccatctcagt caatccatcc atccatccat ccattcatcc atccatccat gcatacacac    60
attgggcctc catcacttga cctggtgct                                       89

<210> SEQ ID NO 55
<211> LENGTH: 86
<212> TYPE: DNA
<213> ORGANISM: Mus musculus

<400> SEQUENCE: 55
tcatgaagca aggcccccat tcacagcctc ctcctcctcc tcctaggtca cggctctgag    60
cacgtcccag ctggacccct atcacc                                          86

<210> SEQ ID NO 56
<211> LENGTH: 80
<212> TYPE: DNA
<213> ORGANISM: Mus musculus

<400> SEQUENCE: 56
ggcttcccac accccacacc ctcctcctgt gatccaggag ggccagattc ccagagtgcc    60
ctggggctgg cccttcccac                                                 80
```

<210> SEQ ID NO 57
<211> LENGTH: 62
<212> TYPE: DNA
<213> ORGANISM: Mus musculus

<400> SEQUENCE: 57
gcggagctgc tcccccaggc ttcacactgc ctggtgcatg gtccctcatg agcttggcct    60
tc                                                                  62

<210> SEQ ID NO 58
<211> LENGTH: 74
<212> TYPE: DNA
<213> ORGANISM: Mus musculus

<400> SEQUENCE: 58
ggattctcac ctttccccct gtatgttcta taccttctct tcttctttcc tctctctcat    60
cctctccttc cctt                                                     74

<210> SEQ ID NO 59
<211> LENGTH: 74
<212> TYPE: DNA
<213> ORGANISM: Mus musculus

<400> SEQUENCE: 59
gaatagaggc atcaagtcac gatgttgtca gtgggaagca gctaggtctg ccctgagggt    60
ggtttccagc tttg                                                     74

<210> SEQ ID NO 60
<211> LENGTH: 69
<212> TYPE: DNA
<213> ORGANISM: Mus musculus

<400> SEQUENCE: 60
aagtggcaga ttcacgtccc agggttcaga ggtggcaaac ttctcagtgg cagctgtgct    60
cggtcatgc                                                           69

<210> SEQ ID NO 61
<211> LENGTH: 56
<212> TYPE: DNA
<213> ORGANISM: Mus musculus

<400> SEQUENCE: 61
agatttcgag ttactgcaaa attgcctacc cccgttcatc tctgctgaac attcgg        56

<210> SEQ ID NO 62
<211> LENGTH: 124
<212> TYPE: DNA
<213> ORGANISM: Mus musculus

<400> SEQUENCE: 62
tacatagtca ggggagggcc cctgtcaacg tgcccacaag gttcctttat cctttgtcat    60
tacgtcattg tccaaggtga caggaggaac tcagtcgtta aaatgacgag ccttatttc    120 atga                                                                124

<210> SEQ ID NO 63
<211> LENGTH: 75
<212> TYPE: DNA
<213> ORGANISM: Mus musculus

<400> SEQUENCE: 63

```
cctccctcat cctccctcat cctcctcatc tacagcagat ccccatcctc ctctcctgcg    60
gcagtgtcct ccccg                                                     75

<210> SEQ ID NO 64
<211> LENGTH: 152
<212> TYPE: DNA
<213> ORGANISM: Mus musculus

<400> SEQUENCE: 64
tccctcatcc tccctcatcc tcccatcct ccctcatcct ccccatcctc cctcatcctc    60
cctcatcctc cctcatcctc cccatcctcc ctcatcctcc ctcatcctcc ctcatcctcc   120
ccatcctccc tcatcctccc catcctccct ca                                  152

<210> SEQ ID NO 65
<211> LENGTH: 91
<212> TYPE: DNA
<213> ORGANISM: Mus musculus

<400> SEQUENCE: 65
accaagtgga aatcaggaga ggcagaggca ttatctcgac atctccgtgg gttcactttt    60
caatttgtcc atcattgcca tcatcattgt t                                   91

<210> SEQ ID NO 66
<211> LENGTH: 75
<212> TYPE: DNA
<213> ORGANISM: Mus musculus

<400> SEQUENCE: 66
tcctcactgt gtgtcaatca ggcactggaa gaatctgcca cggcttttct ctctgcctgc    60
cctgctccct ctcac                                                     75

<210> SEQ ID NO 67
<211> LENGTH: 67
<212> TYPE: DNA
<213> ORGANISM: Mus musculus

<400> SEQUENCE: 67
caaagctctg cagagatgcc ttcatcccct ccatccatca cagcacaatt gcactggtgt    60
ggactcc                                                              67

<210> SEQ ID NO 68
<211> LENGTH: 74
<212> TYPE: DNA
<213> ORGANISM: Mus musculus

<400> SEQUENCE: 68
gcaagacatg gctgccatca catccctcac cactgtcatg ataatcatcc attcttatcc    60
ctgcttggac acca                                                      74

<210> SEQ ID NO 69
<211> LENGTH: 77
<212> TYPE: DNA
<213> ORGANISM: Mus musculus

<400> SEQUENCE: 69
agtgtctgca tttggtggct gattacggga tggatccctg ggtgtggttg tctctgcatg    60
gtccatcctt atcagtt                                                   77
```

```
<210> SEQ ID NO 70
<211> LENGTH: 55
<212> TYPE: DNA
<213> ORGANISM: Mus musculus

<400> SEQUENCE: 70
atcagcagtt ccgtttacag ctcactccat gttcacactt tctggctgtg tgttg      55

<210> SEQ ID NO 71
<211> LENGTH: 79
<212> TYPE: DNA
<213> ORGANISM: Mus musculus

<400> SEQUENCE: 71
ccaccctgag ccctggctac tctctctcct tcccctccc tcctctctcc atgtgttccc   60
tgctagcctt ttcctgtct                                               79

<210> SEQ ID NO 72
<211> LENGTH: 156
<212> TYPE: DNA
<213> ORGANISM: Mus musculus

<400> SEQUENCE: 72
gtgctcacac tgtactcacg ctcacgctct gtgctcacgc tcatgctctg tgctcacatt   60
gtactcacgc tcacgctcat gctctgtgct cacgctctgc tctgtgctca cgctctgtgc  120
tcacacttac ttatttggtc agttagtgca ctcacc                            156

<210> SEQ ID NO 73
<211> LENGTH: 69
<212> TYPE: DNA
<213> ORGANISM: Mus musculus

<400> SEQUENCE: 73
cacgctctgt gctcacactc tgtactcacg ctctgctctg tgctcacact gtactcacgc   60
tcacgctct                                                          69

<210> SEQ ID NO 74
<211> LENGTH: 64
<212> TYPE: DNA
<213> ORGANISM: Mus musculus

<400> SEQUENCE: 74
tttcagaccg tccctcacct tccctgctca gccccattgc tgttcctcca tcactgtcta   60
caac                                                               64

<210> SEQ ID NO 75
<211> LENGTH: 59
<212> TYPE: DNA
<213> ORGANISM: Mus musculus

<400> SEQUENCE: 75
agctcccatc atgccagccc caccctcacc tccatctctc cattcctcct gctcaccct    59

<210> SEQ ID NO 76
<211> LENGTH: 78
<212> TYPE: DNA
<213> ORGANISM: Mus musculus

<400> SEQUENCE: 76
ccacgagtgg ggtcaggcat gtgggtttaa agagttttcc tttgcagagc ctcatttcat   60
```

| | |
|---|---|
| ccttcatgga gctgctca | 78 |

<210> SEQ ID NO 77
<211> LENGTH: 77
<212> TYPE: DNA
<213> ORGANISM: Mus musculus

<400> SEQUENCE: 77

| | |
|---|---|
| tggggtcagg catgtgggtt taaagagttt tcctttgcag agcctcattt catccttcat | 60 |
| ggagctgctc aggactt | 77 |

<210> SEQ ID NO 78
<211> LENGTH: 46
<212> TYPE: DNA
<213> ORGANISM: Mus musculus

<400> SEQUENCE: 78

| | |
|---|---|
| agtgatttct ctgccacatc gccaccatgg gcctttggcc taatca | 46 |

<210> SEQ ID NO 79
<211> LENGTH: 71
<212> TYPE: DNA
<213> ORGANISM: Mus musculus

<400> SEQUENCE: 79

| | |
|---|---|
| tcacacagtc cccaagcagg tccagcgtgg catcaccccg acgaccagca acgtctcatc | 60 |
| ttctggaagc a | 71 |

<210> SEQ ID NO 80
<211> LENGTH: 69
<212> TYPE: DNA
<213> ORGANISM: Mus musculus

<400> SEQUENCE: 80

| | |
|---|---|
| acgcacatca ctgttgtgat gcagtgagct gctcctttcc tttatctgcc tctcgtttcc | 60 |
| agtcatccc | 69 |

<210> SEQ ID NO 81
<211> LENGTH: 75
<212> TYPE: DNA
<213> ORGANISM: Mus musculus

<400> SEQUENCE: 81

| | |
|---|---|
| tcccatgcat tccatcatct ccatcttctg ccatgacttg cttttaattt tatccttttt | 60 |
| ttgtctcaac ttgac | 75 |

<210> SEQ ID NO 82
<211> LENGTH: 60
<212> TYPE: DNA
<213> ORGANISM: Mus musculus

<400> SEQUENCE: 82

| | |
|---|---|
| accagtccta gccccgtccc caacccctttc ccttgggga gttgggggaa ttcctgccaa | 60 |

<210> SEQ ID NO 83
<211> LENGTH: 66
<212> TYPE: DNA
<213> ORGANISM: Mus musculus

<400> SEQUENCE: 83

| | |
|---|---|
| tccatccatc catcatccac ccatccatct atccatccat cctcccatcc atccatccat | 60 |

```
ccatcc                                                              66

<210> SEQ ID NO 84
<211> LENGTH: 85
<212> TYPE: DNA
<213> ORGANISM: Mus musculus

<400> SEQUENCE: 84
aagtctgtct aaacaccaga tcgcatttgt gactcattag catttctcat cccaccaacg    60
cctgcctttc ccactcactt tcccc                                         85

<210> SEQ ID NO 85
<211> LENGTH: 95
<212> TYPE: DNA
<213> ORGANISM: Mus musculus

<400> SEQUENCE: 85
aaccaaccac ctgttcttct ttctcctcct gtcccacatc atcgtcatgg aaagccttgc    60
ctggttcatc ctctcgtact tcggcactgg ctgga                              95

<210> SEQ ID NO 86
<211> LENGTH: 72
<212> TYPE: DNA
<213> ORGANISM: Mus musculus

<400> SEQUENCE: 86
ctgacctctg gtcttcacat gtgtgggcaa gtacagctgc acacatgcgt accctctct    60 ccctcatccc ca                                                       72

<210> SEQ ID NO 87
<211> LENGTH: 81
<212> TYPE: DNA
<213> ORGANISM: Mus musculus

<400> SEQUENCE: 87
tcaatgtaca ccaccgctca ccacgcacac acaccatgcc cgcctgggtg cgcagagtct    60
tcctggacat tgtgccccgt c                                             81

<210> SEQ ID NO 88
<211> LENGTH: 69
<212> TYPE: DNA
<213> ORGANISM: Mus musculus

<400> SEQUENCE: 88
gcacctcctt cctcttcatc acatctcact tcacctctgg agatgggaag gtagcagagc    60
ggctactgg                                                           69

<210> SEQ ID NO 89
<211> LENGTH: 73
<212> TYPE: DNA
<213> ORGANISM: Mus musculus

<400> SEQUENCE: 89
actgtagcac tgtgagcttg tatgtgtaac cgtcctgtgg tgtccagaag tcactgtctt    60
gttgcattcg tct                                                      73

<210> SEQ ID NO 90
<211> LENGTH: 80
<212> TYPE: DNA
```

```
<213> ORGANISM: Mus musculus

<400> SEQUENCE: 90
cacctctcat cccgctgctc tccctcacat catcaaactg taagtccacc tctcatcccg    60
ctgctctccc tcacatcatc                                                 80

<210> SEQ ID NO 91
<211> LENGTH: 70
<212> TYPE: DNA
<213> ORGANISM: Mus musculus

<400> SEQUENCE: 91
gatcaccgcc atcactgtta tcagcaccgt tatcaccacc atcactgtta tcagcaccgt    60
gatcaccacc                                                            70

<210> SEQ ID NO 92
<211> LENGTH: 102
<212> TYPE: DNA
<213> ORGANISM: Mus musculus

<400> SEQUENCE: 92
tactactcat cttgcagatg tctacccatc tgtccctcct cacctgcttc cgctcaggtg    60
ggtccattca tgcacatact catccattta tcatccactc at                      102

<210> SEQ ID NO 93
<211> LENGTH: 70
<212> TYPE: DNA
<213> ORGANISM: Mus musculus

<400> SEQUENCE: 93
gccagtggct gaggacatga cagtccactt cacctccaca cttatggctc tgatccggac    60
agctctggac                                                            70

<210> SEQ ID NO 94
<211> LENGTH: 60
<212> TYPE: DNA
<213> ORGANISM: Mus musculus

<400> SEQUENCE: 94
tctccaagcc tcagtttctc caggccacct cctgtccctc caccccttgt ttggttgaac    60

<210> SEQ ID NO 95
<211> LENGTH: 105
<212> TYPE: DNA
<213> ORGANISM: Mus musculus

<400> SEQUENCE: 95
gattttattc ctctctccca gtccaccctc caactgttcc acatcccata cctcctccct    60
acgccatgtt ttcatgagga tgtccttccc ctccacccac tccac                   105

<210> SEQ ID NO 96
<211> LENGTH: 61
<212> TYPE: DNA
<213> ORGANISM: Mus musculus

<400> SEQUENCE: 96
gctatggcca cacggtgccc ctgtcagatg ggggcaaagc ctctgcatca tctactctgt    60
c                                                                     61
```

<210> SEQ ID NO 97
<211> LENGTH: 87
<212> TYPE: DNA
<213> ORGANISM: Mus musculus

<400> SEQUENCE: 97
ccatcctttt tttctcatta gacacccgtt ttgcgttttc ccaaatcata taccttatac       60
tccaccattc ccattccttg ctccccc                                          87

<210> SEQ ID NO 98
<211> LENGTH: 89
<212> TYPE: DNA
<213> ORGANISM: Mus musculus

<400> SEQUENCE: 98
atctttgcct cctcactcat caaaactcat ctgtagcatg gctttcatcc atagattctc       60 agggaatca cttaacatcc atagtctca                                          89

<210> SEQ ID NO 99
<211> LENGTH: 74
<212> TYPE: DNA
<213> ORGANISM: Mus musculus

<400> SEQUENCE: 99
atcttcatgc ccgttagtca tcgtttgcct agcatgtccc tgtggcgtct caaaaacagt       60
ttcatcgtcc cgtc                                                         74

<210> SEQ ID NO 100
<211> LENGTH: 69
<212> TYPE: DNA
<213> ORGANISM: Mus musculus

<400> SEQUENCE: 100
caactgcagc cctcggctcc ttccttccca cctccgacac atctcctctc ttctcgcatc       60
cctcctcag                                                              69

<210> SEQ ID NO 101
<211> LENGTH: 64
<212> TYPE: DNA
<213> ORGANISM: Mus musculus

<400> SEQUENCE: 101
ctgcagagct cactgcattc accctcctc atcctttgct tccttcccct tgcctagtca       60
gtag                                                                   64

<210> SEQ ID NO 102
<211> LENGTH: 79
<212> TYPE: DNA
<213> ORGANISM: Mus musculus

<400> SEQUENCE: 102
ggcttgctct caatgtctct ccctttctga gtgaaagtat cccacggcag tcccatctca       60
cttcctgtcc tgctaaggc                                                   79

<210> SEQ ID NO 103
<211> LENGTH: 61
<212> TYPE: DNA
<213> ORGANISM: Mus musculus

<400> SEQUENCE: 103

```
gatgtctact tcattgccac cctgtcattc ctctggaagg tgtccgtcat caccttggtc        60
a                                                                        61

<210> SEQ ID NO 104
<211> LENGTH: 67
<212> TYPE: DNA
<213> ORGANISM: Mus musculus

<400> SEQUENCE: 104
ccctacccca gggaccatgg ttcctaggat ctcactgcct ccctctctgg ccttcctgtc        60
ccctccc                                                                  67

<210> SEQ ID NO 105
<211> LENGTH: 74
<212> TYPE: DNA
<213> ORGANISM: Mus musculus

<400> SEQUENCE: 105
aggtgcagag ctcggaaggg ggctaggcag tcctcatcgt cacaccagta gtgcctcatc        60
ctcatcccaa tggt                                                          74

<210> SEQ ID NO 106
<211> LENGTH: 68
<212> TYPE: DNA
<213> ORGANISM: Mus musculus

<400> SEQUENCE: 106
gatgcaccac cttcacgcag tgctcagcca tcctgatgct tctgctacat cgtaggccac        60
tgtcattg                                                                 68

<210> SEQ ID NO 107
<211> LENGTH: 76
<212> TYPE: DNA
<213> ORGANISM: Mus musculus

<400> SEQUENCE: 107
acccacctca ctgaatctga tggacactgt acagtcgcag tctctttgtg cagaattggc       60
agcgatgcct gtgctt                                                        76

<210> SEQ ID NO 108
<211> LENGTH: 52
<212> TYPE: DNA
<213> ORGANISM: Mus musculus

<400> SEQUENCE: 108
ttacagattt ctttgttcct tctccgctcc cactgcttca cttgaccagc ct                52

<210> SEQ ID NO 109
<211> LENGTH: 67
<212> TYPE: DNA
<213> ORGANISM: Mus musculus

<400> SEQUENCE: 109
tgactgggaa cccatgtgat caggcacaga ctttcctcat ctttctacca accactccaa       60
gtcagtc                                                                  67

<210> SEQ ID NO 110
<211> LENGTH: 75
<212> TYPE: DNA
<213> ORGANISM: Mus musculus
```

<400> SEQUENCE: 110
caagcgaacc caggtcaact catcacaggt caccggctgg gtcttggggt cgctggcaca    60
gctgatggcc tgctt                                                    75

<210> SEQ ID NO 111
<211> LENGTH: 64
<212> TYPE: DNA
<213> ORGANISM: Mus musculus

<400> SEQUENCE: 111
atcatccagg ctcctgttcc tgtctgtact caccccaat ttgcctaaac ccccccccc    60 aaat                                                                64

<210> SEQ ID NO 112
<211> LENGTH: 54
<212> TYPE: DNA
<213> ORGANISM: Mus musculus

<400> SEQUENCE: 112
tagacctggc ttcggtttct acctccccag tgctgtcatg ttcatgtttg tttt          54

<210> SEQ ID NO 113
<211> LENGTH: 73
<212> TYPE: DNA
<213> ORGANISM: Mus musculus

<400> SEQUENCE: 113
tccatttgtg catcagaccc attacccacg gcccttctca ccccttgctc atcagcatca    60
cttgatgtcc ctt                                                      73

<210> SEQ ID NO 114
<211> LENGTH: 60
<212> TYPE: DNA
<213> ORGANISM: Mus musculus

<400> SEQUENCE: 114
cttctgtccc tccatctgcg tctggccccc ccctctgccg ctgctatcat caccagaaat    60

<210> SEQ ID NO 115
<211> LENGTH: 62
<212> TYPE: DNA
<213> ORGANISM: Mus musculus

<400> SEQUENCE: 115
ggacggagtc agcggatgct ctgtacacct ctggctcatc tgtttctcct catttctccc    60
ac                                                                  62

<210> SEQ ID NO 116
<211> LENGTH: 69
<212> TYPE: DNA
<213> ORGANISM: Mus musculus

<400> SEQUENCE: 116
agcatatctg gctgtctgtc ccttcaccca tgcacccaga cctcacatgt gtgccagcct    60
tcatcctgt                                                           69

<210> SEQ ID NO 117
<211> LENGTH: 84
<212> TYPE: DNA

<213> ORGANISM: Mus musculus

<400> SEQUENCE: 117

```
atgcagctgc ctacatccaa acacagtttg aaagcaaaaa ccgctcaccc aacaaagaaa      60
tttactgtca catgacttgt gcca                                             84
```

<210> SEQ ID NO 118
<211> LENGTH: 71
<212> TYPE: DNA
<213> ORGANISM: Mus musculus

<400> SEQUENCE: 118

```
agactgggtt acatggaagc tgggctctcc tccatctccc tccctccccc tctcttcccc      60
tgtctgaaac a                                                           71
```

<210> SEQ ID NO 119
<211> LENGTH: 63
<212> TYPE: DNA
<213> ORGANISM: Mus musculus

<400> SEQUENCE: 119

```
aaggtgtgtc atcacatgca gcactcatgc ttctgtctcc agtgatgccc gtccggctga      60
agt                                                                    63
```

<210> SEQ ID NO 120
<211> LENGTH: 61
<212> TYPE: DNA
<213> ORGANISM: Mus musculus

<400> SEQUENCE: 120

```
cagcagtgcc ccggctctca cacgcacagc actccccgcc ctgccccacc tctcttagaa      60
c                                                                      61
```

<210> SEQ ID NO 121
<211> LENGTH: 105
<212> TYPE: DNA
<213> ORGANISM: Mus musculus

<400> SEQUENCE: 121

```
taaatatatt attctcattt agtgcccctg tagccagaac ctcattactg cttcattttt      60
gtaataacat ttaatttaga tattttccat atattggccc tgcta                     105
```

<210> SEQ ID NO 122
<211> LENGTH: 78
<212> TYPE: DNA
<213> ORGANISM: Mus musculus

<400> SEQUENCE: 122

```
tcctcttcca ttcacgagaa cgacaggatt cgattccagg cctttcctta gttctcttag      60
aaccctcatc tctctcta                                                    78
```

<210> SEQ ID NO 123
<211> LENGTH: 38
<212> TYPE: DNA
<213> ORGANISM: Mus musculus

<400> SEQUENCE: 123

```
aaagcgtctg tgtttattag ccttgtgtgt cactcatg                              38
```

```
<210> SEQ ID NO 124
<211> LENGTH: 88
<212> TYPE: DNA
<213> ORGANISM: Mus musculus

<400> SEQUENCE: 124
ttcaccattt cacatgtttg tacttctttg tcttcccatt aacctttgcc agtgttatga      60
ttgtatacat ttttaaaaat gctggtta                                        88

<210> SEQ ID NO 125
<211> LENGTH: 71
<212> TYPE: DNA
<213> ORGANISM: Mus musculus
<220> FEATURE:
<221> NAME/KEY: misc_feature
<222> LOCATION: (19)..(19)
<223> OTHER INFORMATION: n is a, c, g, t or u

<400> SEQUENCE: 125
tcagcatcca gctgcttgnt gtgtgttagt tgtctcacag ctgagggctc tgcctcggct      60
acttcaggct c                                                          71

<210> SEQ ID NO 126
<211> LENGTH: 76
<212> TYPE: DNA
<213> ORGANISM: Mus musculus

<400> SEQUENCE: 126
cattccacga cacagttctg actctccggg tgactgtcac ctgctcccat cctcttcttc      60
ctccctccct tcctca                                                     76

<210> SEQ ID NO 127
<211> LENGTH: 70
<212> TYPE: DNA
<213> ORGANISM: Mus musculus

<400> SEQUENCE: 127
tgggatacct gccgtgctgt acacattcat caaactgttt gcccagagga aggaaggggt      60
gagcaggtca                                                            70

<210> SEQ ID NO 128
<211> LENGTH: 106
<212> TYPE: DNA
<213> ORGANISM: Mus musculus

<400> SEQUENCE: 128
aactctgagg ccatggccca tccacagcct cctggtcccc tgcactaccc agtgtctcac      60
tggctgtgtt ggaaacggag ttgcataagc tcaccgtcca caagca                    106

<210> SEQ ID NO 129
<211> LENGTH: 66
<212> TYPE: DNA
<213> ORGANISM: Mus musculus

<400> SEQUENCE: 129
actgagaccc cggcgttgag ctgccattgt ggcatcatgt cacatcatat tgtcatcttt      60
tcacca                                                                66

<210> SEQ ID NO 130
<211> LENGTH: 68
<212> TYPE: DNA
```

```
<213> ORGANISM: Mus musculus
<220> FEATURE:
<221> NAME/KEY: misc_feature
<222> LOCATION: (16)..(16)
<223> OTHER INFORMATION: n is a, c, g, t or u

<400> SEQUENCE: 130
actcacagaa ttccgnctgc ttctgcctcc ggtcccattt ctgggatcga cgtgtgctac      60
tacgcctg                                                              68

<210> SEQ ID NO 131
<211> LENGTH: 97
<212> TYPE: DNA
<213> ORGANISM: Mus musculus
<220> FEATURE:
<221> NAME/KEY: misc_feature
<222> LOCATION: (64)..(64)
<223> OTHER INFORMATION: n is a, c, g, t or u

<400> SEQUENCE: 131
tctgtgtcca tttgcccatg tctgtctgtc tgctgctgag gcagtcatcc atctcgtgtc      60
cccntctgtg tcgtgctagc acttaagtgg gaacaaa                              97

<210> SEQ ID NO 132
<211> LENGTH: 79
<212> TYPE: DNA
<213> ORGANISM: Mus musculus

<400> SEQUENCE: 132
gtgtctgtgc acatcattga gggtgaccac cgcacactgc tggagggcag tggcctggaa      60
tccatcatca acatcatcc                                                  79

<210> SEQ ID NO 133
<211> LENGTH: 77
<212> TYPE: DNA
<213> ORGANISM: Mus musculus

<400> SEQUENCE: 133
tcagcataca cagagacacg caacatccag tgcaagctgg atttcccacc aggttctcta      60
gccacaactc ctgaaac                                                    77

<210> SEQ ID NO 134
<211> LENGTH: 75
<212> TYPE: DNA
<213> ORGANISM: Mus musculus

<400> SEQUENCE: 134
tggggctgcc cctgccgtag cccagctcaa ccctcagccg gctgccagga tttcttcctc      60
agtctcacct caccc                                                      75

<210> SEQ ID NO 135
<211> LENGTH: 150
<212> TYPE: DNA
<213> ORGANISM: Mus musculus

<400> SEQUENCE: 135
cccgaggcac tgagcaccca cagcacctcc ctgcccggtt gttgcccctc cctcatggca      60
tgtctcacca cgatcctgtt gctacatcag agtgtatttt tgtaatttct ccagctaaca     120
ttttaatggc cccatcttct cactcatctt                                     150
```

```
<210> SEQ ID NO 136
<211> LENGTH: 68
<212> TYPE: DNA
<213> ORGANISM: Mus musculus

<400> SEQUENCE: 136
gagcgatgct tcaccttctg atggctggac gctggccaag cctgtgcctg ctgctcacgc    60
actcacca                                                            68

<210> SEQ ID NO 137
<211> LENGTH: 104
<212> TYPE: DNA
<213> ORGANISM: Mus musculus

<400> SEQUENCE: 137
ttcttccccg tcccttttct gtcagcccat cacagccacc tgctctgctc agacagccag    60
gcaccagaag tgagagcaga agtctgcatc ctgccgagct gccg                    104

<210> SEQ ID NO 138
<211> LENGTH: 70
<212> TYPE: DNA
<213> ORGANISM: Mus musculus

<400> SEQUENCE: 138
ttgtaatgcc agcattcctc ttccccattt ccagctgtca ctccttcatt aaactgctga    60
gtcattcaaa                                                          70

<210> SEQ ID NO 139
<211> LENGTH: 79
<212> TYPE: DNA
<213> ORGANISM: Mus musculus

<400> SEQUENCE: 139
ttccaggagg agctcaggtc accccacca ccgccgccac tgcgtctgcc gccctaggct     60
ttcagacatc attagttcc                                                79

<210> SEQ ID NO 140
<211> LENGTH: 73
<212> TYPE: DNA
<213> ORGANISM: Mus musculus

<400> SEQUENCE: 140
ctatgacacc accttcacct tcatcctctc attggaggtt gctgttagac tcttgctagt    60
ccagggacac atg                                                      73

<210> SEQ ID NO 141
<211> LENGTH: 70
<212> TYPE: DNA
<213> ORGANISM: Mus musculus

<400> SEQUENCE: 141
catcattgac cgtggcgtcc tggtactgct ggtactcgga caccaggtca ttcatgttac    60
tctcggcctc                                                          70

<210> SEQ ID NO 142
<211> LENGTH: 56
<212> TYPE: DNA
<213> ORGANISM: Mus musculus

<400> SEQUENCE: 142
```
gttaacttca tccttcctta ctcctcccat gcttcacact acatacacat acaaca       56

<210> SEQ ID NO 143
<211> LENGTH: 70
<212> TYPE: DNA
<213> ORGANISM: Mus musculus

<400> SEQUENCE: 143
ggatcgtcca gcccttctc tgtgtggctt aaacctaggt tgccattgct ttatacattt    60
tcacttagca                                                          70

<210> SEQ ID NO 144
<211> LENGTH: 69
<212> TYPE: DNA
<213> ORGANISM: Mus musculus

<400> SEQUENCE: 144
gactgcaagc ttctgcccat aaggcctgtg ctgacgctgc catttcaagc cctgcacaa    60 cccatctgt                                                           69

<210> SEQ ID NO 145
<211> LENGTH: 74
<212> TYPE: DNA
<213> ORGANISM: Mus musculus

<400> SEQUENCE: 145
atgcctcggc actccctcta catcatcatc ggagccctct gcgtcgcctt catcctcatg   60
ctcatcatcc tgat                                                     74

<210> SEQ ID NO 146
<211> LENGTH: 45
<212> TYPE: DNA
<213> ORGANISM: Mus musculus

<400> SEQUENCE: 146
tcagttcatc cctatccatc accctggagc cttccctcct cttcc                   45

<210> SEQ ID NO 147
<211> LENGTH: 62
<212> TYPE: DNA
<213> ORGANISM: Mus musculus

<400> SEQUENCE: 147
acagggcgac gttccaggcc aagtgatgtg attgtgaaga ccccatgtcc tgtggtggat   60
ga                                                                  62

<210> SEQ ID NO 148
<211> LENGTH: 73
<212> TYPE: DNA
<213> ORGANISM: Mus musculus

<400> SEQUENCE: 148
cagagccacc tggaggatga ccagccagga ttgttcaggg cttcattgtc ttggtcacat   60
tgcttcattg tct                                                      73

<210> SEQ ID NO 149
<211> LENGTH: 77
<212> TYPE: DNA
<213> ORGANISM: Mus musculus

<400> SEQUENCE: 149
accacacctg tctcctcctt cacatcaggt tccatgttgg gccgaacaga caccgccctc    60
accaacacgt acagtgc                                                  77

<210> SEQ ID NO 150
<211> LENGTH: 68
<212> TYPE: DNA
<213> ORGANISM: Mus musculus

<400> SEQUENCE: 150
acctcacgtg gtcagccatg accaatgaac ctgagcggtc ctgcaatccc tcccttatga   60
gcatcatc                                                           68

<210> SEQ ID NO 151
<211> LENGTH: 72
<212> TYPE: DNA
<213> ORGANISM: Mus musculus

<400> SEQUENCE: 151
acctcatccc tggcagcccc ttgcctcacg tgggtgctgc tctcacagtc actacccacc   60
cccacatcag ca                                                      72

<210> SEQ ID NO 152
<211> LENGTH: 68
<212> TYPE: DNA
<213> ORGANISM: Mus musculus

<400> SEQUENCE: 152
ccgcagggaa gtgactttca cagcttccgg cctgcctgtc cgtctgtgtc tgtctgtcca   60
ttcagtgg                                                           68

<210> SEQ ID NO 153
<211> LENGTH: 68
<212> TYPE: DNA
<213> ORGANISM: Mus musculus

<400> SEQUENCE: 153
accaacagtg ggagcagcag ctctctgttt ggcagctctg ctccatcccc attcacattc   60
ggtggctc                                                           68

<210> SEQ ID NO 154
<211> LENGTH: 50
<212> TYPE: DNA
<213> ORGANISM: Mus musculus

<400> SEQUENCE: 154
tctacacctc caacatcccc atcatcttgc agtctgctct ggtgtccaac              50

<210> SEQ ID NO 155
<211> LENGTH: 69
<212> TYPE: DNA
<213> ORGANISM: Mus musculus

<400> SEQUENCE: 155
ttgccacctt atcatcctca tttccatcct tgtcggctgc caacctgctc atcgtcaccg   60
ggaccttcg                                                          69

<210> SEQ ID NO 156
<211> LENGTH: 69
<212> TYPE: DNA

<213> ORGANISM: Mus musculus

<400> SEQUENCE: 156
ccatagacgg gcccatactg ccaacccatt gcaccgctgt cgctgtggca agaccttcag    60
caacatgac    69

<210> SEQ ID NO 157
<211> LENGTH: 72
<212> TYPE: DNA
<213> ORGANISM: Mus musculus

<400> SEQUENCE: 157
ccctcattgc tttcctcatc ggccacctgc agttgcaggt ttcctcccac tgttctggcc    60
tcaccactcc tg    72

<210> SEQ ID NO 158
<211> LENGTH: 83
<212> TYPE: DNA
<213> ORGANISM: Mus musculus

<400> SEQUENCE: 158
catcagtcag ccagcttatt ttgaggaggt ttttggattt gaaatcagca aggttggcat    60
gttgtctgca gtccctcacc ttg    83

<210> SEQ ID NO 159
<211> LENGTH: 33
<212> TYPE: DNA
<213> ORGANISM: Mus musculus

<400> SEQUENCE: 159
ttctaccatc ccctcccctc cccaccccat cca    33

<210> SEQ ID NO 160
<211> LENGTH: 86
<212> TYPE: DNA
<213> ORGANISM: Mus musculus

<400> SEQUENCE: 160
caggggctct aacctatcat ggcagaacag cccattcatg gtggtggaag ctgtcacatc    60
atagctaccc aggcagtggc aaggca    86

<210> SEQ ID NO 161
<211> LENGTH: 61
<212> TYPE: DNA
<213> ORGANISM: Mus musculus

<400> SEQUENCE: 161
ctgtgattag tgcccatccc atccattccc tcgataaccc tcaccatcat ttccactcca    60
g    61

<210> SEQ ID NO 162
<211> LENGTH: 72
<212> TYPE: DNA
<213> ORGANISM: Mus musculus

<400> SEQUENCE: 162
caaaccatca tcatcctaaa caaccgcaaa tttgctaatt cactggttgg ggtccagcag    60
cagctccagg ca    72

```
<210> SEQ ID NO 163
<211> LENGTH: 76
<212> TYPE: DNA
<213> ORGANISM: Mus musculus

<400> SEQUENCE: 163
tgtggcagcc caccgctcac tcactgccac agcagcaggg agaagatcgt catcccttc    60 ttcagtctgc tcatca                                                    76

<210> SEQ ID NO 164
<211> LENGTH: 65
<212> TYPE: DNA
<213> ORGANISM: Mus musculus

<400> SEQUENCE: 164
catcttcatc tacgcggcca tcgcctctcc atcacctcct gcatcttcac ctatatccat    60
ttgca                                                                65

<210> SEQ ID NO 165
<211> LENGTH: 125
<212> TYPE: DNA
<213> ORGANISM: Mus musculus

<400> SEQUENCE: 165
gtcaccatct tcatcttcat catcatcatc tactggggaa actcagaccc agtcttcaag    60
tcggttatcc caggtcccga tgtcagctct gaaatctgtt acttctgcca gttttctaa    120 tgggc                                                                125

<210> SEQ ID NO 166
<211> LENGTH: 45
<212> TYPE: DNA
<213> ORGANISM: Mus musculus

<400> SEQUENCE: 166
aatccagcca ttccaaacac ccccaccctg gtccctgatc atcac                    45

<210> SEQ ID NO 167
<211> LENGTH: 64
<212> TYPE: DNA
<213> ORGANISM: Mus musculus

<400> SEQUENCE: 167
acccagcagg gggcagtgtg atgccggcca cgtcatccct cccgctgtcc ttgtctccat    60
tcat                                                                 64

<210> SEQ ID NO 168
<211> LENGTH: 80
<212> TYPE: DNA
<213> ORGANISM: Mus musculus

<400> SEQUENCE: 168
aacaagcagc tggctcgttc tgcgcaatct cacacccag atcgatggtt ctacacttcg     60
gacgctgtgt ctgcagcatg                                                80

<210> SEQ ID NO 169
<211> LENGTH: 69
<212> TYPE: DNA
<213> ORGANISM: Mus musculus

<400> SEQUENCE: 169
```

```
gagacctacc ggttaggcgt gcaaatgcat cccggccaag aaatccataa ctcaccctga      60
ctggtcgca                                                              69

<210> SEQ ID NO 170
<211> LENGTH: 80
<212> TYPE: DNA
<213> ORGANISM: Mus musculus

<400> SEQUENCE: 170
aacatccatc cccacttcca ttcttcattc tttccaagtc tgtgactggt gagttatctc      60
catctttgaa aatagcttta                                                  80

<210> SEQ ID NO 171
<211> LENGTH: 80
<212> TYPE: DNA
<213> ORGANISM: Mus musculus

<400> SEQUENCE: 171
aaccccagcc attctcatca gccttaccat caaccaggtc tcctgggtct acctctgaga      60
caaccacatc ctcaccatca                                                  80

<210> SEQ ID NO 172
<211> LENGTH: 66
<212> TYPE: DNA
<213> ORGANISM: Mus musculus

<400> SEQUENCE: 172
acagcaacaa gcagcaacgg ttagcatgat gcctgtggcc cctcattcat ctctctaccc      60
tccttc                                                                 66

<210> SEQ ID NO 173
<211> LENGTH: 70
<212> TYPE: DNA
<213> ORGANISM: Mus musculus

<400> SEQUENCE: 173
cacatattca tcatcatatc catcttcatc tggaactcca gtattagggt cacaatcccg      60
gactgtgaac                                                             70

<210> SEQ ID NO 174
<211> LENGTH: 62
<212> TYPE: DNA
<213> ORGANISM: Mus musculus

<400> SEQUENCE: 174
tcacgcttcc tctgaaaaca cattgcaccc tccacccgcc acccttcac cctccacccg       60 cc                                                                     62

<210> SEQ ID NO 175
<211> LENGTH: 87
<212> TYPE: DNA
<213> ORGANISM: Mus musculus

<400> SEQUENCE: 175
tgaattccag gacacctgag gacataaagg agattttaag aaaacaacca tcatcattat      60
cttgtcgtca tcatcatctg catctgc                                          87

<210> SEQ ID NO 176
<211> LENGTH: 65
```

<212> TYPE: DNA
<213> ORGANISM: Mus musculus

<400> SEQUENCE: 176
cactccagcc atcactgcct gtgcttgctg cagatgttcc tgctacctgc tttgctgagt    60
ctgta    65

<210> SEQ ID NO 177
<211> LENGTH: 69
<212> TYPE: DNA
<213> ORGANISM: Mus musculus

<400> SEQUENCE: 177
tcgaactcag aaatccacct gcctctgcct cccaagttct gggattaaag gcatgcagcc    60
ccattacca    69

<210> SEQ ID NO 178
<211> LENGTH: 71
<212> TYPE: DNA
<213> ORGANISM: Mus musculus

<400> SEQUENCE: 178
gtgtttgatc atgtcttcca ctgctccctg cccccagctc ctcccagagc ctcccacttg    60
gcttccagcc c    71

<210> SEQ ID NO 179
<211> LENGTH: 68
<212> TYPE: DNA
<213> ORGANISM: Mus musculus

<400> SEQUENCE: 179
ggaggcgtgc gaaggtaggc tcagaaatgg ccctacctca ccttcacctc tcactctgct    60
tcatgctt    68

<210> SEQ ID NO 180
<211> LENGTH: 75
<212> TYPE: DNA
<213> ORGANISM: Mus musculus

<400> SEQUENCE: 180
gagggcccac cccattccca ttctacatct accaacttca tggcaaatca ttacaatagt    60
ctctgcattt ccagt    75

<210> SEQ ID NO 181
<211> LENGTH: 74
<212> TYPE: DNA
<213> ORGANISM: Mus musculus

<400> SEQUENCE: 181
gcttccctag cgcaggcagg aactgatgac aggccatgga ggagtgctgt ctatctccac    60
cctgcctccc ctca    74

<210> SEQ ID NO 182
<211> LENGTH: 45
<212> TYPE: DNA
<213> ORGANISM: Mus musculus

<400> SEQUENCE: 182
cgttctcttg ctcatctccg agttctgcct tgcccctctc agatg    45

<210> SEQ ID NO 183
<211> LENGTH: 47
<212> TYPE: DNA
<213> ORGANISM: Mus musculus

<400> SEQUENCE: 183 ccatccccc ataccatctc tgaatctcct tcccctcctc atctcag                47

<210> SEQ ID NO 184
<211> LENGTH: 245
<212> TYPE: DNA
<213> ORGANISM: Mus musculus

<400> SEQUENCE: 184
ccatctcacc cctgccttcc cctccatctc accctgcctt ctctctccat catcttactc      60
ctgccttccc atccatctca ccctgcctt cccatccatc tcaccctgc cttctcctcc      120 atcccatccc tgccttcccc tctatctgac ccctgccttc ccctccatc tcaccctgc      180 cttgccctct accatctcat ccctgccttc ccctctacca tctcaccct gccttctctc      240 tccat                                                                245

<210> SEQ ID NO 185
<211> LENGTH: 102
<212> TYPE: DNA
<213> ORGANISM: Mus musculus

<400> SEQUENCE: 185
acttctgggg tctcatgatt tccccatcta agaccttagt ccacctgaac cagcgtttct     60
gtctgtgtcc aaatgtccat ctgtttgtct tttcttcatt tc                       102

<210> SEQ ID NO 186
<211> LENGTH: 71
<212> TYPE: DNA
<213> ORGANISM: Mus musculus

<400> SEQUENCE: 186
agctctttga gcatctacat catcttagta tttcctccag agaggaagtc tggtcatgtt     60
ccccttaggt c                                                         71

<210> SEQ ID NO 187
<211> LENGTH: 127
<212> TYPE: DNA
<213> ORGANISM: Mus musculus

<400> SEQUENCE: 187
tcacccttct cacactcttc atcataatcc cagggtatc tgatatagaa ctgtcttcca     60
agtgtgttga gtgtcaggaa caactacagt attgagatct gtaaagagag aggactttt     120 ttcaacc                                                              127

<210> SEQ ID NO 188
<211> LENGTH: 70
<212> TYPE: DNA
<213> ORGANISM: Mus musculus

<400> SEQUENCE: 188
agtgtgaact ctgaaatgtt ctcagcatcc tcgtcctccc tgggcccaga gagtctcatt     60
ctccataggt                                                           70

```
<210> SEQ ID NO 189
<211> LENGTH: 91
<212> TYPE: DNA
<213> ORGANISM: Mus musculus

<400> SEQUENCE: 189
ccataaattc atcctttgct tctttcctca ggctatctta gtagaaatgg cataattgtc    60
ttatctactt tgacttattt ttccattctg a                                   91

<210> SEQ ID NO 190
<211> LENGTH: 74
<212> TYPE: DNA
<213> ORGANISM: Mus musculus

<400> SEQUENCE: 190
aacactctgc agggctgctt ggtctgctgg tatcttttca gttaccactc atgtctcacc    60
ccattgttca catc                                                      74

<210> SEQ ID NO 191
<211> LENGTH: 84
<212> TYPE: DNA
<213> ORGANISM: Mus musculus
<220> FEATURE:
<221> NAME/KEY: misc_feature
<222> LOCATION: (70)..(70)
<223> OTHER INFORMATION: n is a, c, g, t or u

<400> SEQUENCE: 191
cccacaccac ccctccactg ctacatattt ctaatcattc tcttagccct ctacttctct    60
cttgtctcan cccatacctg accc                                           84

<210> SEQ ID NO 192
<211> LENGTH: 78
<212> TYPE: DNA
<213> ORGANISM: Mus musculus

<400> SEQUENCE: 192
cctaacagtg atgtcacttc acctcagccc ccgcccactc tgaaaccact tttccattac    60
cttcagtgac tctttctt                                                  78

<210> SEQ ID NO 193
<211> LENGTH: 61
<212> TYPE: DNA
<213> ORGANISM: Mus musculus

<400> SEQUENCE: 193
caccaccacc actaccgcca ccagcagcac caaacgtaat gtctttttca tttcattgac    60
t                                                                    61

<210> SEQ ID NO 194
<211> LENGTH: 38
<212> TYPE: DNA
<213> ORGANISM: Mus musculus

<400> SEQUENCE: 194
tccatcctca ccctccaccc ccaaccctgc tcacacag                            38

<210> SEQ ID NO 195
<211> LENGTH: 76
<212> TYPE: DNA
<213> ORGANISM: Mus musculus
```

-continued

<400> SEQUENCE: 195
aacctccatc accacacccc ttccctgatc ctaacctcca tcaccacacc ccttcccctg     60
cctaacctcc atcacc                                                    76

<210> SEQ ID NO 196
<211> LENGTH: 70
<212> TYPE: DNA
<213> ORGANISM: Mus musculus

<400> SEQUENCE: 196
tgcttctgcc tgcttgtgct ctgctccctg tgagcgcacg ctaatggtct ctctgggtct     60
gctctgcttc                                                           70

<210> SEQ ID NO 197
<211> LENGTH: 102
<212> TYPE: DNA
<213> ORGANISM: Mus musculus

<400> SEQUENCE: 197
ttgtctattc cttaagagag ccaagagtcc attttcatc actggtgaat gtgttcatct      60
tgggaatcca gggttcctgg atccttatga acgtcacagt cc                       102

<210> SEQ ID NO 198
<211> LENGTH: 93
<212> TYPE: DNA
<213> ORGANISM: Mus musculus

<400> SEQUENCE: 198
ttcctgtctc atccctgtgc actcctgcac actgtggcct tcccgtctca tccctgtgca     60
ctcctgtaca ctgtggcctt cccgtctcat ccc                                 93

<210> SEQ ID NO 199
<211> LENGTH: 74
<212> TYPE: DNA
<213> ORGANISM: Mus musculus

<400> SEQUENCE: 199
tctagaatgt tcattgctca ttggttttct tgctgtgtag tccaggctgg ctgaaacctg     60
aggcctttcc tcct                                                      74

<210> SEQ ID NO 200
<211> LENGTH: 70
<212> TYPE: DNA
<213> ORGANISM: Mus musculus

<400> SEQUENCE: 200
agcggctggg ttgcttctgt ttttgtcatc gtcatcatca tcaccaccat caccatcacc     60
atcatcattg                                                           70

<210> SEQ ID NO 201
<211> LENGTH: 52
<212> TYPE: DNA
<213> ORGANISM: Mus musculus

<400> SEQUENCE: 201
ttcattccag aggggaaaca tcaccctgct ggcctctgct ccccatgacc cc             52

<210> SEQ ID NO 202
<211> LENGTH: 73

```
<212> TYPE: DNA
<213> ORGANISM: Mus musculus

<400> SEQUENCE: 202
aaacaacatg tcccctgcaa cataatccat gttcttcctg tcattccacc atccctgacc    60
ccaccccctc cac                                                      73

<210> SEQ ID NO 203
<211> LENGTH: 75
<212> TYPE: DNA
<213> ORGANISM: Mus musculus

<400> SEQUENCE: 203
aacctcatcc atgctaacct catccatgct aacctcatcc atgctaacct catccatgct    60
aacctcaccc atgcc                                                    75

<210> SEQ ID NO 204
<211> LENGTH: 54
<212> TYPE: DNA
<213> ORGANISM: Mus musculus

<400> SEQUENCE: 204
ggaactgatc cccctcttct ggcctctaca ggaaccatac atgctcatgg tgtg          54

<210> SEQ ID NO 205
<211> LENGTH: 76
<212> TYPE: DNA
<213> ORGANISM: Mus musculus

<400> SEQUENCE: 205
attggccagc cctcatggcc atattttcaa gctcacctac cccatggcat ctctcctctc    60
tccaccttct ccttc                                                    76

<210> SEQ ID NO 206
<211> LENGTH: 42
<212> TYPE: DNA
<213> ORGANISM: Mus musculus

<400> SEQUENCE: 206
tttatccata caaatccctc ctgctgctcg tcatggttgc tg                      42

<210> SEQ ID NO 207
<211> LENGTH: 49
<212> TYPE: DNA
<213> ORGANISM: Mus musculus

<400> SEQUENCE: 207
gtgttcttcc attttccaca ttcttcacgc taacatgcgt cttcatgct               49

<210> SEQ ID NO 208
<211> LENGTH: 88
<212> TYPE: DNA
<213> ORGANISM: Mus musculus

<400> SEQUENCE: 208 tcattttaa actcatttct gttttctgac ttgtgtgaaa gtcatgttca cgctgtgcca    60
gcactggcct cctgcctctg ctcagccc                                      88

<210> SEQ ID NO 209
<211> LENGTH: 70
<212> TYPE: DNA
```

<213> ORGANISM: Mus musculus

<400> SEQUENCE: 209

```
ccacctccac ctcctcctcc cctccccca gggcttgcct tctatggaac agatatccca    60
cccatcagtg                                                          70
```

<210> SEQ ID NO 210
<211> LENGTH: 82
<212> TYPE: DNA
<213> ORGANISM: Mus musculus

<400> SEQUENCE: 210

```
actgcctcca tgcatccatc catgatccat ctgtctttcc atccatccat ccatccatcc    60
atccatccat ccatgcatac ac                                             82
```

<210> SEQ ID NO 211
<211> LENGTH: 85
<212> TYPE: DNA
<213> ORGANISM: Mus musculus
<220> FEATURE:
<221> NAME/KEY: misc_feature
<222> LOCATION: (10)..(10)
<223> OTHER INFORMATION: n is a, c, g, t or u
<220> FEATURE:
<221> NAME/KEY: misc_feature
<222> LOCATION: (14)..(14)
<223> OTHER INFORMATION: n is a, c, g, t or u
<220> FEATURE:
<221> NAME/KEY: misc_feature
<222> LOCATION: (26)..(26)
<223> OTHER INFORMATION: n is a, c, g, t or u

<400> SEQUENCE: 211

```
gtctgtctgn ctgnctatct atctgnccat ccatctatca tccttccctg cctccttccc    60
ttaacccgcc cccctccat cagcc                                           85
```

<210> SEQ ID NO 212
<211> LENGTH: 134
<212> TYPE: DNA
<213> ORGANISM: Mus musculus

<400> SEQUENCE: 212

```
gaatctgtct ccccatcatc tatcacatga atcacagaat ctgtctcccc atcatctatc    60
acatgaatca cagaatctgt ctccccatca tctatcacat gaatcacaga atctgtctcc   120
ccatcatcta tcac                                                    134
```

<210> SEQ ID NO 213
<211> LENGTH: 83
<212> TYPE: DNA
<213> ORGANISM: Mus musculus

<400> SEQUENCE: 213

```
tcatagctcc tgtgagtacc tgactgtaca ctggtaccat tttccctcca taactgccct    60
tgagggtgg ctgtcaccat cac                                             83
```

<210> SEQ ID NO 214
<211> LENGTH: 70
<212> TYPE: DNA
<213> ORGANISM: Mus musculus

<400> SEQUENCE: 214

```
ctcaagtcaa ggacagtgta ggtggtactt gcctgggaat agcttttccc tccctccctc    60
```

```
cctccctccc                                                              70

<210> SEQ ID NO 215
<211> LENGTH: 46
<212> TYPE: DNA
<213> ORGANISM: Mus musculus

<400> SEQUENCE: 215
aaaccctata agcccctgcc ctcttccatc tcttctgtct ctttct                      46

<210> SEQ ID NO 216
<211> LENGTH: 144
<212> TYPE: DNA
<213> ORGANISM: Mus musculus

<400> SEQUENCE: 216
ccattcaccc attcatctac ctactcaccc atctacccac ccattgtcct gtctcatccg       60
cctactcatt catcttctta gccactcatc tgtccagcta cccatctcat catctatcca      120
cctatcccat tcatctattc atct                                             144

<210> SEQ ID NO 217
<211> LENGTH: 74
<212> TYPE: DNA
<213> ORGANISM: Mus musculus

<400> SEQUENCE: 217
tgtagcatga ctgtggcatg attgtaacat gtcttcaccc cagctgcatg tgctcacttt       60
gcatcttcac tgca                                                         74

<210> SEQ ID NO 218
<211> LENGTH: 100
<212> TYPE: DNA
<213> ORGANISM: Mus musculus
<220> FEATURE:
<221> NAME/KEY: misc_feature
<222> LOCATION: (20)..(20)
<223> OTHER INFORMATION: n is a, c, g, t or u

<400> SEQUENCE: 218
atttcattcc cctcccagtn ggccctccaa ctgttccaca ttccatacct cctccccact       60
ggactgtctc cacaaggatg tcccccacct cccactccac                            100

<210> SEQ ID NO 219
<211> LENGTH: 67
<212> TYPE: DNA
<213> ORGANISM: Mus musculus

<400> SEQUENCE: 219
cactcattgt gttttcccca gtgaacttca atctgctggt attcattttc tattttttt        60 acattaa                                                                 67

<210> SEQ ID NO 220
<211> LENGTH: 72
<212> TYPE: DNA
<213> ORGANISM: Mus musculus

<400> SEQUENCE: 220
aggacttggt ggtgggagct agttttcaaa tgtactgagg tgagacagcc ccagtgcccc       60
caacttcata tg                                                           72
```

<210> SEQ ID NO 221
<211> LENGTH: 69
<212> TYPE: DNA
<213> ORGANISM: Mus musculus

<400> SEQUENCE: 221
gtccacgtgc aatttgcaca cacacttggc tcgcattcat cccctttccc accgcccct    60 cactcacct                                                           69

<210> SEQ ID NO 222
<211> LENGTH: 73
<212> TYPE: DNA
<213> ORGANISM: Mus musculus

<400> SEQUENCE: 222
acccaactgc ttagcagtgt ggagcagact ggaggaatca cttttcttgc ttgcatcaca    60
tgctgccccc tgt                                                      73

<210> SEQ ID NO 223
<211> LENGTH: 41
<212> TYPE: DNA
<213> ORGANISM: Mus musculus

<400> SEQUENCE: 223
ttcagcttgc agctgtcatc tctctgctgt tcccagctgt c                       41

<210> SEQ ID NO 224
<211> LENGTH: 83
<212> TYPE: DNA
<213> ORGANISM: Mus musculus

<400> SEQUENCE: 224
tgttattagt ttccatccat tcatccatca atccattcat ccatttacct atgcattacc    60
taaccaccct tctccatccc tcc                                           83

<210> SEQ ID NO 225
<211> LENGTH: 71
<212> TYPE: DNA
<213> ORGANISM: Mus musculus

<400> SEQUENCE: 225
tccgtccatc catccgtcca tccttctatc cattcatcta tccatcccat gaccaggatg    60
aaggtgcggt a                                                        71

<210> SEQ ID NO 226
<211> LENGTH: 115
<212> TYPE: DNA
<213> ORGANISM: Mus musculus

<400> SEQUENCE: 226
ttcattcatt cattcattca ttcgttcatt tatggttttc gagacagggt ttctctgtgt    60
agccctggct gtcctggaac tcactctgta caccaggctg gcctcgaact cagaa        115

<210> SEQ ID NO 227
<211> LENGTH: 59
<212> TYPE: DNA
<213> ORGANISM: Mus musculus

<400> SEQUENCE: 227
aaattattca tcgccatcca ccatccacca ctccctcctg ctccacatgc tccatttcc    59

<210> SEQ ID NO 228
<211> LENGTH: 85
<212> TYPE: DNA
<213> ORGANISM: Mus musculus

<400> SEQUENCE: 228
agtctcaccc caggctgtta gtattccatc agtctgtcct aagggagtat gtctcatgtg     60
ctcctgaccc atcccatcta catcc                                          85

<210> SEQ ID NO 229
<211> LENGTH: 50
<212> TYPE: DNA
<213> ORGANISM: Mus musculus

<400> SEQUENCE: 229
accccctctt cagcctcatg tctgacctcc tcacccgccc accattgttc                50

<210> SEQ ID NO 230
<211> LENGTH: 87
<212> TYPE: DNA
<213> ORGANISM: Mus musculus

<400> SEQUENCE: 230
ccctgaagag ccatcccact gcctggccgc ctacctgctg acaccaccca gcatggcttg     60
tgaacgtcac gtcagttcac tgccgca                                        87

<210> SEQ ID NO 231
<211> LENGTH: 67
<212> TYPE: DNA
<213> ORGANISM: Mus musculus

<400> SEQUENCE: 231
actccatcat ctcctcaaaa gctagaccag cccactgcat ccgcattggc tccattccgt     60
cattgcc                                                              67

<210> SEQ ID NO 232
<211> LENGTH: 101
<212> TYPE: DNA
<213> ORGANISM: Mus musculus

<400> SEQUENCE: 232
agaagtgcag cttggtcttc atgtgggtct cccaacaatt ggagcagggg ctatccctga     60
ctctgttgcc tgcctgtgga tcctgttctc ctcactgggc t                        101

<210> SEQ ID NO 233
<211> LENGTH: 70
<212> TYPE: DNA
<213> ORGANISM: Mus musculus

<400> SEQUENCE: 233
tcagcaggga aactggttat ccacacagtt cttcaccctc atcctcacgt ctgtcagcca     60
ttcacccgca                                                           70

<210> SEQ ID NO 234
<211> LENGTH: 73
<212> TYPE: DNA
<213> ORGANISM: Mus musculus

<400> SEQUENCE: 234

```
caacctcaga ctcctcatct ctcaccctgc tctgaagtga tacccgcagc gcagtcctgc    60
ctggcctgtg cag                                                      73

<210> SEQ ID NO 235
<211> LENGTH: 47
<212> TYPE: DNA
<213> ORGANISM: Mus musculus

<400> SEQUENCE: 235
aatcccattc ccattgctca tgagtctttc tctccttttc agtacaa                 47

<210> SEQ ID NO 236
<211> LENGTH: 69
<212> TYPE: DNA
<213> ORGANISM: Mus musculus

<400> SEQUENCE: 236
agtgcgtgct gtggcgatca gaggagggggg atggcttctc tggaaccagt tacagatgct   60
tgttagcct                                                           69

<210> SEQ ID NO 237
<211> LENGTH: 66
<212> TYPE: DNA
<213> ORGANISM: Mus musculus

<400> SEQUENCE: 237
agagagagac gtcatcatca tcatcattgt catcatcgtc gtcatcgttg tcatcatcat    60
catcgt                                                              66

<210> SEQ ID NO 238
<211> LENGTH: 47
<212> TYPE: DNA
<213> ORGANISM: Mus musculus

<400> SEQUENCE: 238
tatccatcca tccatccatc catccatcca tccatccatc cacccac                 47

<210> SEQ ID NO 239
<211> LENGTH: 85
<212> TYPE: DNA
<213> ORGANISM: Mus musculus

<400> SEQUENCE: 239
gaacaagacc tcatagctca tgaatgtcag tgtccttcag cccacaagct acacaaacct    60
cttactctgt ctctgggaga tataa                                         85

<210> SEQ ID NO 240
<211> LENGTH: 70
<212> TYPE: DNA
<213> ORGANISM: Mus musculus

<400> SEQUENCE: 240
aagtgtatgg cagtcccatt tttcgtcatc cccatcccat ttctgagctg tgcttgcgca    60
ctgggtcttt                                                          70

<210> SEQ ID NO 241
<211> LENGTH: 105
<212> TYPE: DNA
<213> ORGANISM: Mus musculus

<400> SEQUENCE: 241
```

```
ttctttcctt ccatggtgct tcatcatctc ttcttcagaa tcatttgtct gacatccttg    60
gcaatgtagg aaaggcttta ccaagtaccc tgtgagttcc catca                   105

<210> SEQ ID NO 242
<211> LENGTH: 65
<212> TYPE: DNA
<213> ORGANISM: Mus musculus

<400> SEQUENCE: 242
caatccgtct tacctgtgtt cacaggcttg tcagcactcc tgggagaccc actctctccc    60
tgtag                                                                65

<210> SEQ ID NO 243
<211> LENGTH: 44
<212> TYPE: DNA
<213> ORGANISM: Mus musculus

<400> SEQUENCE: 243
agctgaccac cacccaccat ccatctccat ccctcaccac cgcc                     44

<210> SEQ ID NO 244
<211> LENGTH: 71
<212> TYPE: DNA
<213> ORGANISM: Mus musculus

<400> SEQUENCE: 244
accaccacca agcctgctgc tgtcaagcca aggactatcg ctgctgggac tcattggagc    60 tcccctccc c                                                          71

<210> SEQ ID NO 245
<211> LENGTH: 71
<212> TYPE: DNA
<213> ORGANISM: Mus musculus

<400> SEQUENCE: 245
tctccacatt atccctctgg agctcgggtg acaggcctca tcaggttcac cttctgcggc    60
ttgtggtcac a                                                         71

<210> SEQ ID NO 246
<211> LENGTH: 202
<212> TYPE: DNA
<213> ORGANISM: Mus musculus

<400> SEQUENCE: 246
taatgtcctc tttctaggct ccacccagcc atggctgcta cttcctatta gagccacagc    60
ccatgccttt ggcatattgt ctttagggac tttgggatct acatcataat gttgtcatgg   120
aaagggtttc cttgtcttgt gtttccctct tctttctttt cttgacgcat gagtctttct   180
ggactccttt taatgtcctt tt                                            202

<210> SEQ ID NO 247
<211> LENGTH: 63
<212> TYPE: DNA
<213> ORGANISM: Mus musculus

<400> SEQUENCE: 247
aactccagcc tcatcgatcc agcgcactct gctggaccct gtgggcacac attctcatat    60
aca                                                                  63
```

```
<210> SEQ ID NO 248
<211> LENGTH: 62
<212> TYPE: DNA
<213> ORGANISM: Mus musculus

<400> SEQUENCE: 248
tacaaaccta gatgtcctta ccacatccgg gtccttccga cccacctcga gatgaacatc      60
at                                                                    62

<210> SEQ ID NO 249
<211> LENGTH: 50
<212> TYPE: DNA
<213> ORGANISM: Mus musculus

<400> SEQUENCE: 249
cagggccttc tttcccgtgt cagcacttgg atgccagatt tcccagcctc                50

<210> SEQ ID NO 250
<211> LENGTH: 95
<212> TYPE: DNA
<213> ORGANISM: Mus musculus

<400> SEQUENCE: 250
catcatctcc tgcccagacc ccagcatcat cagcatcagc atcatctcct gcccagaccc      60
cagcagtgtc ttcccttgtc aatgtcttct ttctt                                95

<210> SEQ ID NO 251
<211> LENGTH: 72
<212> TYPE: DNA
<213> ORGANISM: Mus musculus

<400> SEQUENCE: 251
ccagccctca gtcgttctgt cgggtcctgt acactgctgt ggtttctcac ttcccagccc      60
tcagtcattc tg                                                         72

<210> SEQ ID NO 252
<211> LENGTH: 113
<212> TYPE: DNA
<213> ORGANISM: Mus musculus

<400> SEQUENCE: 252
atgcactttc ccatcatctg tccactcacc tcccccaccc atccattcac ccatccatcc      60
atccacccac ccaccatcc atctacccac ccatctatct actcacccat tca             113

<210> SEQ ID NO 253
<211> LENGTH: 69
<212> TYPE: DNA
<213> ORGANISM: Mus musculus

<400> SEQUENCE: 253
atgggaaggg ggcccttcct cctttcctc ttcctcctcc tcttcctcct cctcctgtca      60
ctcatcccc                                                             69

<210> SEQ ID NO 254
<211> LENGTH: 51
<212> TYPE: DNA
<213> ORGANISM: Mus musculus

<400> SEQUENCE: 254
tcaacaccac aggctgaccc ctgtcccttc tatatttgct gcatatgttc a               51
```

<210> SEQ ID NO 255
<211> LENGTH: 67
<212> TYPE: DNA
<213> ORGANISM: Mus musculus

<400> SEQUENCE: 255
ccacccctcc ccttcacctc tgagaagggg gaggtccccc tctgtatcac cccaccctgg    60
cacctca                                                              67

<210> SEQ ID NO 256
<211> LENGTH: 65
<212> TYPE: DNA
<213> ORGANISM: Mus musculus

<400> SEQUENCE: 256
cctgactaag acagtcaccc aagcttgtat gacgtggagt tgaagttcat gctcactttt    60
gtctt                                                                65

<210> SEQ ID NO 257
<211> LENGTH: 50
<212> TYPE: DNA
<213> ORGANISM: Mus musculus

<400> SEQUENCE: 257
aattccattt cattgttcat cctcaaaagt cagggcaatc aaagcagaaa                50

<210> SEQ ID NO 258
<211> LENGTH: 73
<212> TYPE: DNA
<213> ORGANISM: Mus musculus

<400> SEQUENCE: 258
ccacatttca gttcgtctcc attcactgcc ttgctcatcc atcacgcatg cttcagtgtg    60
gcggtggcac cct                                                       73

<210> SEQ ID NO 259
<211> LENGTH: 76
<212> TYPE: DNA
<213> ORGANISM: Mus musculus

<400> SEQUENCE: 259
tgacaagctg ctattctcta aaactcttga aattcatagt ttctgaatag aagcaggcct    60
ggtgtcctgc tgtgtg                                                    76

<210> SEQ ID NO 260
<211> LENGTH: 72
<212> TYPE: DNA
<213> ORGANISM: Mus musculus

<400> SEQUENCE: 260
aaagccatta cctcccctct tcagctcact gcaccctctg tttctgggcg tccagagcag    60
tctgttctct tc                                                        72

<210> SEQ ID NO 261
<211> LENGTH: 73
<212> TYPE: DNA
<213> ORGANISM: Mus musculus

<400> SEQUENCE: 261

```
tctgagaggg ggcttcattc acccagcccc acacctcatc catctagcat gcatcctcct    60
tccctggggc atc                                                       73

<210> SEQ ID NO 262
<211> LENGTH: 68
<212> TYPE: DNA
<213> ORGANISM: Mus musculus

<400> SEQUENCE: 262
caatctctgc atggactttc cttcagtctc tgctccacac tttgtctatg catttcctcc    60
cttgagta                                                             68

<210> SEQ ID NO 263
<211> LENGTH: 61
<212> TYPE: DNA
<213> ORGANISM: Mus musculus

<400> SEQUENCE: 263
ttctcgctcg cccatttgat cgcagcttga ggctgcacat accctgcatt ctcctgcgca    60
c                                                                    61

<210> SEQ ID NO 264
<211> LENGTH: 66
<212> TYPE: DNA
<213> ORGANISM: Mus musculus

<400> SEQUENCE: 264
gagtggctaa tcatctctgc gggcaaactg acagtacatc ctctagaatt ccttccttct    60
catttc                                                               66

<210> SEQ ID NO 265
<211> LENGTH: 75
<212> TYPE: DNA
<213> ORGANISM: Mus musculus

<400> SEQUENCE: 265
ccaaacattc aaacacatga gtctatgggg gtcatttcta ttcaaaccac caacaccctg    60
cttctctcca cctac                                                     75

<210> SEQ ID NO 266
<211> LENGTH: 74
<212> TYPE: DNA
<213> ORGANISM: Mus musculus

<400> SEQUENCE: 266
catcatgcca ttcctctcag tgacacaggt cagggtgtca tcccactctt cttaatgatt    60
tggtcaggtc atca                                                      74

<210> SEQ ID NO 267
<211> LENGTH: 74
<212> TYPE: DNA
<213> ORGANISM: Mus musculus

<400> SEQUENCE: 267
tcagactcaa agattcatct gcctgcttct gcctcccaat tgctgggact agaggtgtgc    60
agctccacca cctg                                                      74

<210> SEQ ID NO 268
<211> LENGTH: 71
```

```
<212> TYPE: DNA
<213> ORGANISM: Mus musculus

<400> SEQUENCE: 268
tgcacccatg tcaggcattt cacaaccacc tgtaattcca gctttccttg cctctgtgag    60
catctgcact c                                                        71

<210> SEQ ID NO 269
<211> LENGTH: 73
<212> TYPE: DNA
<213> ORGANISM: Mus musculus

<400> SEQUENCE: 269
aactcatcgt ttctgtggct tggcttgtgc cgctcactct gtctagactt catctcattt    60
cctctgtgtt cag                                                      73

<210> SEQ ID NO 270
<211> LENGTH: 75
<212> TYPE: DNA
<213> ORGANISM: Mus musculus

<400> SEQUENCE: 270
gttggtcaca agccattggg atgtgcctgt ctctgcctac tccagttctg gattactggc    60
tcacactgcc acact                                                    75

<210> SEQ ID NO 271
<211> LENGTH: 113
<212> TYPE: DNA
<213> ORGANISM: Mus musculus

<400> SEQUENCE: 271
tcttcttgct tgatgcctac gtgtctatca cctgtttatt ctccatccat ctagctacca    60
tctgtctgta tctctgtctt ctccatctgt catttagcca ccaatccatc ttt          113

<210> SEQ ID NO 272
<211> LENGTH: 73
<212> TYPE: DNA
<213> ORGANISM: Mus musculus

<400> SEQUENCE: 272
gcttaagtca ttagcggggt catcgtcatc atcaccatca tcaccatcgc catcatcacc    60
ttcttcatca tcg                                                      73

<210> SEQ ID NO 273
<211> LENGTH: 54
<212> TYPE: DNA
<213> ORGANISM: Mus musculus

<400> SEQUENCE: 273
ttgtcatcct caatatcacc tgcactacgc ttcttaagtt tactattgtc atcc          54

<210> SEQ ID NO 274
<211> LENGTH: 74
<212> TYPE: DNA
<213> ORGANISM: Mus musculus

<400> SEQUENCE: 274
gtctacaatg catccctacc cactcctatc ccatctctgc ttgtggtagt tagtgtacta    60
tcaccctcat ttct                                                     74
```

<210> SEQ ID NO 275
<211> LENGTH: 67
<212> TYPE: DNA
<213> ORGANISM: Mus musculus

<400> SEQUENCE: 275
tcgttcaact cttctcattc aagttagcag tcatttcaat cagttcaata agcatattag    60
gcaagca    67

<210> SEQ ID NO 276
<211> LENGTH: 67
<212> TYPE: DNA
<213> ORGANISM: Mus musculus

<400> SEQUENCE: 276
aggcgtgggg gatcagggtc ttagactctg ccccccctca ccccactctc ttcccatgtt    60
cgttgat    67

<210> SEQ ID NO 277
<211> LENGTH: 105
<212> TYPE: DNA
<213> ORGANISM: Mus musculus
<220> FEATURE:
<221> NAME/KEY: misc_feature
<222> LOCATION: (74)..(74)
<223> OTHER INFORMATION: n is a, c, g, t or u

<400> SEQUENCE: 277
ttctttcctc tccctgatgg ccatggtcag ttcttcccca agagaggatg tgagtggact    60
gtggcacccc aagntcagca catgcctccc tcacccttga ctctg    105

<210> SEQ ID NO 278
<211> LENGTH: 69
<212> TYPE: DNA
<213> ORGANISM: Mus musculus

<400> SEQUENCE: 278
gaggggtgct tggactagag ccagaaaggg agagcagact ccgagggaac atggggaact    60
aaaggacac    69

<210> SEQ ID NO 279
<211> LENGTH: 50
<212> TYPE: DNA
<213> ORGANISM: Mus musculus

<400> SEQUENCE: 279
cagcctcatc catctcttgc ccaccagccc acccacccct ccatctctcg    50

<210> SEQ ID NO 280
<211> LENGTH: 75
<212> TYPE: DNA
<213> ORGANISM: Mus musculus

<400> SEQUENCE: 280
gacagaccat aaatccatgt ggggactgtg ccccatttgc atctcatttg gtcccatctg    60
ccccggtttc acgcg    75

<210> SEQ ID NO 281
<211> LENGTH: 68
<212> TYPE: DNA
<213> ORGANISM: Mus musculus

<400> SEQUENCE: 281
ttttatctcc gctgtgcttg tgttgtctgt agccctgggc gtcctgggct gaccttgggg    60
tcccttcc                                                             68

<210> SEQ ID NO 282
<211> LENGTH: 70
<212> TYPE: DNA
<213> ORGANISM: Mus musculus

<400> SEQUENCE: 282
gtgtggcctg tttcccactc cgcatcctac tctttccttc agcactcctc actctcaaat    60
cctgctccat                                                           70

<210> SEQ ID NO 283
<211> LENGTH: 82
<212> TYPE: DNA
<213> ORGANISM: Mus musculus

<400> SEQUENCE: 283
acaacactct agtgctcttt ctttactaga gttcgttcat catcccctgt gcttcccgat    60
cctttgctca tcctttcttc at                                             82

<210> SEQ ID NO 284
<211> LENGTH: 105
<212> TYPE: DNA
<213> ORGANISM: Mus musculus

<400> SEQUENCE: 284
atgcatcatc tatttgtctg tcttcatgtc catacattta ctaatcatct gtctgtttgt    60
ccatccattc atccatctat ctccatccat ccatccatat ggcta                   105

<210> SEQ ID NO 285
<211> LENGTH: 57
<212> TYPE: DNA
<213> ORGANISM: Mus musculus

<400> SEQUENCE: 285
aaatccatca cattacgaag cattcaaatc atttgtaaac actcttggtt tcactag       57

<210> SEQ ID NO 286
<211> LENGTH: 68
<212> TYPE: DNA
<213> ORGANISM: Mus musculus

<400> SEQUENCE: 286
taaaccccca ctatggggtc tcaacccaca gctcgagaaa cactgttgta gatgcgtgca    60
ctactact                                                             68

<210> SEQ ID NO 287
<211> LENGTH: 70
<212> TYPE: DNA
<213> ORGANISM: Mus musculus

<400> SEQUENCE: 287
cgcttctgca ttgcaaataa acagtaggct tggaccactg ccgagcatag ggctgggaag    60
tcttggctca                                                           70

<210> SEQ ID NO 288

```
<211> LENGTH: 72
<212> TYPE: DNA
<213> ORGANISM: Mus musculus

<400> SEQUENCE: 288
gtgggtgaaa caggcctcct ggccatgtac gcctgccatg tcactataaa gccaaatcaa    60
cagggtcagg ac                                                        72

<210> SEQ ID NO 289
<211> LENGTH: 83
<212> TYPE: DNA
<213> ORGANISM: Mus musculus

<400> SEQUENCE: 289
acatttccat atcatgcctc actaccactg tgctccatgc ttctgcgaca atgcccatt     60 aaagccccac ttaaagtgtt cag                                            83

<210> SEQ ID NO 290
<211> LENGTH: 64
<212> TYPE: DNA
<213> ORGANISM: Mus musculus

<400> SEQUENCE: 290
gatccattct gtcaccaccc tgcccctcac catccaggtt ccatactatc caaaagtttg    60
ggct                                                                 64

<210> SEQ ID NO 291
<211> LENGTH: 171
<212> TYPE: DNA
<213> ORGANISM: Mus musculus

<400> SEQUENCE: 291 tcatcccct gcctcagaaa ctcactcaca gttaaatccc tgcttcatac attcactcag     60
cttcatctcc tgcctcattt catgcccctg cctcacacat tcaatcagca caaatcactt   120
acagtcatcc cctgccttag aaaatcactc acagtcatcc ccctgcttca c            171

<210> SEQ ID NO 292
<211> LENGTH: 130
<212> TYPE: DNA
<213> ORGANISM: Mus musculus

<400> SEQUENCE: 292
aattcattca ttcattcact ctctctgtgt gtctctccct gtctctctgt ctctgtctct    60
caggagtttc tctgtatagc tctggctgcc ctggaactca ctctgtagac caggctggcc   120
tcaaactcat                                                           130

<210> SEQ ID NO 293
<211> LENGTH: 47
<212> TYPE: DNA
<213> ORGANISM: Mus musculus

<400> SEQUENCE: 293
tgcctcctca tctcagcctc accatcttca cctgcttcat ctcagca                  47

<210> SEQ ID NO 294
<211> LENGTH: 121
<212> TYPE: DNA
<213> ORGANISM: Mus musculus

<400> SEQUENCE: 294
```

```
ctctgtgtag ttgtcagggt tccacctttg ctgtcatctc ctggtaacgc ctcaggtgga    60
ccagggagca aacctgactc ctgatcagcc tctgaagcct acttggttgc catcttccga   120
g                                                                  121
```

<210> SEQ ID NO 295
<211> LENGTH: 84
<212> TYPE: DNA
<213> ORGANISM: Mus musculus

<400> SEQUENCE: 295

```
ccatttctgc cattgctcta aaatgacttc actccttctc caactctgct tttgtttaca    60
ctcctgtgct tcagtaacac cttg                                           84
```

<210> SEQ ID NO 296
<211> LENGTH: 161
<212> TYPE: DNA
<213> ORGANISM: Mus musculus

<400> SEQUENCE: 296

```
ttcttctttt ggtcatcttg gagccaagac tagaaagagc tatttacatt tcaaagttat    60
tccctcttcc tggtttcccc tctgcaaacc cccatcccat tgcctgcttc tatgacagtg   120
ctccctcacc cactcccata tccccaccct atcattccca t                       161
```

<210> SEQ ID NO 297
<211> LENGTH: 88
<212> TYPE: DNA
<213> ORGANISM: Mus musculus

<400> SEQUENCE: 297

```
cattgtctct ccccatccat ttctaactcc atgaaatcaa acgtgtctga aggttctctt    60
tgatttgttt gttttgttga ccttaagg                                       88
```

<210> SEQ ID NO 298
<211> LENGTH: 65
<212> TYPE: DNA
<213> ORGANISM: Mus musculus

<400> SEQUENCE: 298

```
gatagtcact gcatcctaaa gtcactgcaa gtcactgcat ccatcaatca ctgcatctga    60
cagtc                                                                65
```

<210> SEQ ID NO 299
<211> LENGTH: 73
<212> TYPE: DNA
<213> ORGANISM: Mus musculus

<400> SEQUENCE: 299

```
accatccctg cacccatctg tccatctgtc tgtcttttca cctctctgtc catccacaga    60
caggtgttca tct                                                       73
```

<210> SEQ ID NO 300
<211> LENGTH: 73
<212> TYPE: DNA
<213> ORGANISM: Mus musculus

<400> SEQUENCE: 300

```
gctgtgccta ggcctgtctg tggcaagctc ctccatctct ctccctctgt gtgtgtcttt    60
```
gtctctgcat cat                                                          73

<210> SEQ ID NO 301
<211> LENGTH: 69
<212> TYPE: DNA
<213> ORGANISM: Mus musculus

<400> SEQUENCE: 301
aaacatcaaa actcctatcc tcgcgccagg gctgacctca tcttgttcca ccccatctca      60
tccaatcag                                                              69

<210> SEQ ID NO 302
<211> LENGTH: 79
<212> TYPE: DNA
<213> ORGANISM: Mus musculus

<400> SEQUENCE: 302
catctgccac taatccatcc atccatccat ccatccatcc atccatccat ccgtctgtcc      60
atctgtccat tcatcctta                                                   79

<210> SEQ ID NO 303
<211> LENGTH: 31
<212> TYPE: DNA
<213> ORGANISM: Mus musculus

<400> SEQUENCE: 303
tttcactcca cctgctatct tgacttgact c                                     31

<210> SEQ ID NO 304
<211> LENGTH: 69
<212> TYPE: DNA
<213> ORGANISM: Mus musculus

<400> SEQUENCE: 304
acacttctcc cagtggtcac tctggctttg atcacacctc attgggtggc tccttagcag      60
tgttggaca                                                              69

<210> SEQ ID NO 305
<211> LENGTH: 68
<212> TYPE: DNA
<213> ORGANISM: Mus musculus

<400> SEQUENCE: 305
ggcccacctc tcaccttctg gctgaagtcc cattttcaga ccaaaacctg tggccttgtt      60
ggtaggaa                                                               68

<210> SEQ ID NO 306
<211> LENGTH: 65
<212> TYPE: DNA
<213> ORGANISM: Mus musculus

<400> SEQUENCE: 306
accaggaagc gggacccgcc tgacccaccc gaggccctct ccaccctcac tcacacttca      60
gcccc                                                                  65

<210> SEQ ID NO 307
<211> LENGTH: 71
<212> TYPE: DNA
<213> ORGANISM: Mus musculus

<400> SEQUENCE: 307

```
gttatcctgc tgccatttcc cttcccccc ctctcccaca aagatccctc cctccttctg    60
cctcccatga t                                                        71
```

<210> SEQ ID NO 308
<211> LENGTH: 72
<212> TYPE: DNA
<213> ORGANISM: Mus musculus

<400> SEQUENCE: 308

```
tgcctcctgc cattgatgat cgttcttccc tcctttggga gggtgagagg gagggaacgc   60
agtctgagtg ga                                                       72
```

<210> SEQ ID NO 309
<211> LENGTH: 64
<212> TYPE: DNA
<213> ORGANISM: Mus musculus

<400> SEQUENCE: 309

```
agaccttggg ggtccaggtt agttgagact gctggtctat ggggtcactc tcctcctcac   60
cttc                                                                64
```

<210> SEQ ID NO 310
<211> LENGTH: 67
<212> TYPE: DNA
<213> ORGANISM: Mus musculus

<400> SEQUENCE: 310

```
gcttcccatc cgagtttcca tcctcacacc tgcccactca ccttccatgt cgctatctgt   60
gtccctc                                                             67
```

<210> SEQ ID NO 311
<211> LENGTH: 54
<212> TYPE: DNA
<213> ORGANISM: Mus musculus

<400> SEQUENCE: 311

```
catccatcca tctacccatc catcctctta cccatccacc catccatcca tcca         54
```

<210> SEQ ID NO 312
<211> LENGTH: 66
<212> TYPE: DNA
<213> ORGANISM: Mus musculus

<400> SEQUENCE: 312

```
cagctctcaa cattcagtag gcatgctagg tgtgctctct cattggcttt cgaagtaagc   60
tcagcc                                                              66
```

<210> SEQ ID NO 313
<211> LENGTH: 74
<212> TYPE: DNA
<213> ORGANISM: Mus musculus

<400> SEQUENCE: 313

```
gccaagctca catcagcagc accctgtagc acatggagtt gggccagttc atgctgttac   60
ccctgcgtca caca                                                     74
```

<210> SEQ ID NO 314
<211> LENGTH: 65
<212> TYPE: DNA

```
<213> ORGANISM: Mus musculus

<400> SEQUENCE: 314
gatagtcact gcatcctaaa gtcactgcaa gtcactgcat ccatcaatca ctgcatctga      60
cagtc                                                                  65

<210> SEQ ID NO 315
<211> LENGTH: 70
<212> TYPE: DNA
<213> ORGANISM: Mus musculus

<400> SEQUENCE: 315
atgcgtttgg acagttgtct acatttatca aacgaccacc tctggactca ctgctgttcc      60
agcttctgca                                                             70

<210> SEQ ID NO 316
<211> LENGTH: 72
<212> TYPE: DNA
<213> ORGANISM: Mus musculus

<400> SEQUENCE: 316
tggggtcagg catgtgggtt taaagagttt tcctttgcag agcctcatcc ttcatggagc      60
tgctcaggac tt                                                          72

<210> SEQ ID NO 317
<211> LENGTH: 43
<212> TYPE: DNA
<213> ORGANISM: Mus musculus

<400> SEQUENCE: 317
catggaatcc tctgccatca ggttcccatc atcattgctt ggg                        43

<210> SEQ ID NO 318
<211> LENGTH: 70
<212> TYPE: DNA
<213> ORGANISM: Mus musculus

<400> SEQUENCE: 318
accacccatg ccagtcaccc accccaccca tagtcccagt cactcacctg tatccatggt      60
cgcaagtcac                                                             70

<210> SEQ ID NO 319
<211> LENGTH: 70
<212> TYPE: DNA
<213> ORGANISM: Mus musculus

<400> SEQUENCE: 319
agtactggtt ccaggcagat ctatctgtct gtctgtctgt ctgtctgtct gtctgtctat      60
ctgtctatct                                                             70

<210> SEQ ID NO 320
<211> LENGTH: 70
<212> TYPE: DNA
<213> ORGANISM: Mus musculus

<400> SEQUENCE: 320
ggcagttgca gatttccatt catttcatg gccatctggc caacccgcct gcccttctcc       60
acacctgatc                                                             70
```

```
<210> SEQ ID NO 321
<211> LENGTH: 75
<212> TYPE: DNA
<213> ORGANISM: Mus musculus

<400> SEQUENCE: 321
ctaacataag aggccccaag cttcattcac tgtttgggtg cgggtgtttg gatccctctg      60
agtcacctgc ttggt                                                      75

<210> SEQ ID NO 322
<211> LENGTH: 69
<212> TYPE: DNA
<213> ORGANISM: Mus musculus

<400> SEQUENCE: 322
cctcatcctg cctccctgca tcccagctcc tgtggcctca tcctgcatcc cagctcctgt      60
ggcctcatc                                                             69

<210> SEQ ID NO 323
<211> LENGTH: 57
<212> TYPE: DNA
<213> ORGANISM: Mus musculus

<400> SEQUENCE: 323
acttcattcc atgatcacag ttaccatact gtcactgtca cactcaccgt cacactc         57

<210> SEQ ID NO 324
<211> LENGTH: 69
<212> TYPE: DNA
<213> ORGANISM: Mus musculus

<400> SEQUENCE: 324
gagatcctta ggacctctcg aggtcttcac caagccctgc atctcccatc ccatctatct      60
tctccatcc                                                             69

<210> SEQ ID NO 325
<211> LENGTH: 60
<212> TYPE: DNA
<213> ORGANISM: Mus musculus

<400> SEQUENCE: 325
ctcattactg tgctgttctg gtgagcagag tcctggcatt atgtagccag cgcctttctt      60

<210> SEQ ID NO 326
<211> LENGTH: 69
<212> TYPE: DNA
<213> ORGANISM: Mus musculus

<400> SEQUENCE: 326
ccaccatcac caccactacc accaccacca ccatcatcat catcatattt ctgagacagg      60
atctcagca                                                             69

<210> SEQ ID NO 327
<211> LENGTH: 72
<212> TYPE: DNA
<213> ORGANISM: Mus musculus

<400> SEQUENCE: 327
tccatctatg ggtgctgtga agccattttt acagaagcca tttcatgtcc cgatggcagc      60
atttgtgagc gc                                                         72
```

<210> SEQ ID NO 328
<211> LENGTH: 71
<212> TYPE: DNA
<213> ORGANISM: Mus musculus

<400> SEQUENCE: 328
ggtctcattc ctcttccctt ggcatcaagt ctctacagga ttaggcgcat cttctcccgc    60
tgaggtcaga c                                                        71

<210> SEQ ID NO 329
<211> LENGTH: 75
<212> TYPE: DNA
<213> ORGANISM: Mus musculus

<400> SEQUENCE: 329
tctgtccatg catccatcca tcatctatc catccgtaca tctgtctatc tgtccatctg     60
tccatccatc cactg                                                    75

<210> SEQ ID NO 330
<211> LENGTH: 70
<212> TYPE: DNA
<213> ORGANISM: Mus musculus

<400> SEQUENCE: 330
aatggctgca tcatgtcaga aggcactgtt tcacagcagg cctccctagc tgctgtctct    60
atgacgttcc                                                          70

<210> SEQ ID NO 331
<211> LENGTH: 66
<212> TYPE: DNA
<213> ORGANISM: Mus musculus

<400> SEQUENCE: 331
acatctccat gtttgcaaag caagccctct aactcaccga tccatctccc acagccctt     60 tgctca                                                              66

<210> SEQ ID NO 332
<211> LENGTH: 79
<212> TYPE: DNA
<213> ORGANISM: Mus musculus

<400> SEQUENCE: 332
catctgccac taatccatcc atccatccat ccatccatcc atccatccat ccgtctgtcc    60
atctgtccat tcatcctta                                                79

<210> SEQ ID NO 333
<211> LENGTH: 78
<212> TYPE: DNA
<213> ORGANISM: Mus musculus

<400> SEQUENCE: 333
gacagtaacc cgtcaccccc gtgacagtta gctggttgtg ggccagcatg gtgggaggaa    60
gtgtccctgt gcagtggc                                                 78

<210> SEQ ID NO 334
<211> LENGTH: 71
<212> TYPE: DNA
<213> ORGANISM: Mus musculus

<400> SEQUENCE: 334

```
ccagcttgca atcccaccag caatggagga gtgttcctct ttctccacat cctcaccaac     60
atctgctgtc a                                                          71

<210> SEQ ID NO 335
<211> LENGTH: 69
<212> TYPE: DNA
<213> ORGANISM: Mus musculus

<400> SEQUENCE: 335
gacctgggct agagtccccc tccctcatc ctcttctgcg tacattctga acagtcttct      60
cacgggtgt                                                             69

<210> SEQ ID NO 336
<211> LENGTH: 46
<212> TYPE: DNA
<213> ORGANISM: Mus musculus

<400> SEQUENCE: 336
aaaccagtcc ttccctccca gccattgcca ggtgccaccc gctaag                    46

<210> SEQ ID NO 337
<211> LENGTH: 45
<212> TYPE: DNA
<213> ORGANISM: Mus musculus

<400> SEQUENCE: 337
ccaacccgac tcaccctccc tgccctcctt ttcttgtcct cgtcg                     45

<210> SEQ ID NO 338
<211> LENGTH: 30
<212> TYPE: DNA
<213> ORGANISM: Mus musculus

<400> SEQUENCE: 338
atggagagag cggccccacc cttgccaaca                                      30

<210> SEQ ID NO 339
<211> LENGTH: 47
<212> TYPE: DNA
<213> ORGANISM: Mus musculus

<400> SEQUENCE: 339
ctgcacgcag cgctctcctc tgcccatccc cacttctctg tctcgtc                   47

<210> SEQ ID NO 340
<211> LENGTH: 51
<212> TYPE: DNA
<213> ORGANISM: Mus musculus

<400> SEQUENCE: 340
atggcgccct ctgctggaga attactgctc tgtggactca ctctagtttt t              51

<210> SEQ ID NO 341
<211> LENGTH: 49
<212> TYPE: DNA
<213> ORGANISM: Mus musculus

<400> SEQUENCE: 341
cccgctctac cctgcccact ctcacgcctg aagggttgca gggggcatg                 49

<210> SEQ ID NO 342
```

```
<211> LENGTH: 64
<212> TYPE: DNA
<213> ORGANISM: Mus musculus

<400> SEQUENCE: 342
ccaccctggt cccatgctgc agacacacat gggactttcc tccccccctc ctgctcccag    60
accc                                                                 64

<210> SEQ ID NO 343
<211> LENGTH: 57
<212> TYPE: DNA
<213> ORGANISM: Mus musculus

<400> SEQUENCE: 343
cgggcacctc ctgcccctcc gtggtgactt ggcatcgctt tctgccctcg ccctgcc       57

<210> SEQ ID NO 344
<211> LENGTH: 43
<212> TYPE: DNA
<213> ORGANISM: Mus musculus

<400> SEQUENCE: 344
cccacccagg gaccccaccc tggcccagtc ctcaggtgga tga                      43

<210> SEQ ID NO 345
<211> LENGTH: 54
<212> TYPE: DNA
<213> ORGANISM: Mus musculus

<400> SEQUENCE: 345
ccccagtcac tgcgcttctg ttataccatc tttgcctgac tctcttcggc ttct          54

<210> SEQ ID NO 346
<211> LENGTH: 39
<212> TYPE: DNA
<213> ORGANISM: Mus musculus

<400> SEQUENCE: 346
cctgttccta tctgctcccc tgtacccctc agcttcctg                           39

<210> SEQ ID NO 347
<211> LENGTH: 44
<212> TYPE: DNA
<213> ORGANISM: Mus musculus

<400> SEQUENCE: 347
gatcggaccc actttggctc tccctccccc cagcctggag ccag                     44

<210> SEQ ID NO 348
<211> LENGTH: 34
<212> TYPE: DNA
<213> ORGANISM: Mus musculus

<400> SEQUENCE: 348
ctctttgcgt tagtttttgt tgtagagcct gtga                                34

<210> SEQ ID NO 349
<211> LENGTH: 35
<212> TYPE: DNA
<213> ORGANISM: Mus musculus

<400> SEQUENCE: 349
cttccaccgc tgcccctcc cgctcccaaa atccc                                35
```

<210> SEQ ID NO 350
<211> LENGTH: 63
<212> TYPE: DNA
<213> ORGANISM: Mus musculus

<400> SEQUENCE: 350
ggccaaccct gctcgcgcca accccttcca tctacccgta tatcctgctt cccagctgaa    60
ccc                                                                 63

<210> SEQ ID NO 351
<211> LENGTH: 50
<212> TYPE: DNA
<213> ORGANISM: Mus musculus

<400> SEQUENCE: 351
aacatagtac aacccatatt tgtgcccttc ctggggttgg cccatgacac                50

<210> SEQ ID NO 352
<211> LENGTH: 42
<212> TYPE: DNA
<213> ORGANISM: Mus musculus

<400> SEQUENCE: 352
caggcaccgc ccctaccccc cctccggttc ggttcgtttc cg                       42

<210> SEQ ID NO 353
<211> LENGTH: 50
<212> TYPE: DNA
<213> ORGANISM: Mus musculus

<400> SEQUENCE: 353
acccgagcag agcctcctca ccccgcccac actcctcacc ccgcccacac                50

<210> SEQ ID NO 354
<211> LENGTH: 65
<212> TYPE: DNA
<213> ORGANISM: Mus musculus

<400> SEQUENCE: 354
tgagggtgag aacaggttgg tatcaaacca tcccctccc cttagttcat cttgcttgga     60
cactg                                                                65

<210> SEQ ID NO 355
<211> LENGTH: 80
<212> TYPE: DNA
<213> ORGANISM: Mus musculus
<220> FEATURE:
<221> NAME/KEY: misc_feature
<222> LOCATION: (11)..(11)
<223> OTHER INFORMATION: n is a, c, g, t or u

<400> SEQUENCE: 355
aatctgtcct nctttgaacc tactgattgg ccacgtttca aggtatgtac taccactccc    60
agaacaaatt agtcttgtga                                                80

<210> SEQ ID NO 356
<211> LENGTH: 46
<212> TYPE: DNA
<213> ORGANISM: Mus musculus

<400> SEQUENCE: 356

```
aaacccctct caactgattt ccttccatcc tctttgacca gcgccg          46
```

<210> SEQ ID NO 357
<211> LENGTH: 87
<212> TYPE: DNA
<213> ORGANISM: Mus musculus

<400> SEQUENCE: 357

```
caaacagtat gcagaacatg tgtgtgataa cacagctgct acatgttacg tacaaacatc   60
agcccagcct acccttctc ctcagta                                        87
```

<210> SEQ ID NO 358
<211> LENGTH: 54
<212> TYPE: DNA
<213> ORGANISM: Mus musculus

<400> SEQUENCE: 358

```
aacccagagc acagcaccct gccatcagag cacccgagtg accccttgt tggc           54
```

<210> SEQ ID NO 359
<211> LENGTH: 48
<212> TYPE: DNA
<213> ORGANISM: Mus musculus

<400> SEQUENCE: 359

```
ttggtctgcg cctacctcct gccaagcaag ctctgtgctg tcactcag                 48
```

<210> SEQ ID NO 360
<211> LENGTH: 58
<212> TYPE: DNA
<213> ORGANISM: Mus musculus

<400> SEQUENCE: 360

```
gcgggtgtgc ggacctgacc ctcccccaca gcagccactc acagtcatcc ccctgcct     58
```

<210> SEQ ID NO 361
<211> LENGTH: 42
<212> TYPE: DNA
<213> ORGANISM: Mus musculus

<400> SEQUENCE: 361

```
acaccctac tccgtatccc tccccatccc atgctgccaa ct                        42
```

<210> SEQ ID NO 362
<211> LENGTH: 66
<212> TYPE: DNA
<213> ORGANISM: Mus musculus

<400> SEQUENCE: 362

```
aagccctccc ctgtgtgtgg cccctctcc tctctgttcc agtgacctgt gttccctcgc    60
tctcat                                                               66
```

<210> SEQ ID NO 363
<211> LENGTH: 54
<212> TYPE: DNA
<213> ORGANISM: Mus musculus

<400> SEQUENCE: 363

```
ggccactgtg ctcttcctca gcgctcacaa gcaagtgtcc acctcattgc tgcg           54
```

<210> SEQ ID NO 364
<211> LENGTH: 59

<212> TYPE: DNA
<213> ORGANISM: Mus musculus

<400> SEQUENCE: 364
accccacacc ctcttctgct ccccaccggc acccacactc aaatacacaa acctgtacc    59

<210> SEQ ID NO 365
<211> LENGTH: 53
<212> TYPE: DNA
<213> ORGANISM: Mus musculus
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (25)..(25)
<223> OTHER INFORMATION: n is a, c, g, t or u

<400> SEQUENCE: 365
gtggtctcct ggtctttcgt ntctnctgta ttcccacccg ggccatttgc aat    53

<210> SEQ ID NO 366
<211> LENGTH: 40
<212> TYPE: DNA
<213> ORGANISM: Mus musculus
<220> FEATURE:
<221> NAME/KEY: misc_feature
<222> LOCATION: (8)..(8)
<223> OTHER INFORMATION: n is a, c, g, t or u
<220> FEATURE:
<221> NAME/KEY: misc_feature
<222> LOCATION: (11)..(11)
<223> OTHER INFORMATION: n is a, c, g, t or u

<400> SEQUENCE: 366
atacctgnta nctcccttc ctgttgggcc tgcttgcttg    40

<210> SEQ ID NO 367
<211> LENGTH: 46
<212> TYPE: DNA
<213> ORGANISM: Mus musculus

<400> SEQUENCE: 367
atccacctgc ctgcctttgc cctctgaggc tttgtagttt ttcttg    46

<210> SEQ ID NO 368
<211> LENGTH: 46
<212> TYPE: DNA
<213> ORGANISM: Mus musculus

<400> SEQUENCE: 368
gctgtttgct ggatttcctg cagctccccc accccgtgtc tttgag    46

<210> SEQ ID NO 369
<211> LENGTH: 51
<212> TYPE: DNA
<213> ORGANISM: Mus musculus

<400> SEQUENCE: 369
atattatcag gaatccacag cctttcattt aatttaaaag tgtgcctccc a    51

<210> SEQ ID NO 370
<211> LENGTH: 37
<212> TYPE: DNA
<213> ORGANISM: Mus musculus

```
<400> SEQUENCE: 370
aatcttctgt taccttctca ttctgtgtct cattctg                                37

<210> SEQ ID NO 371
<211> LENGTH: 35
<212> TYPE: DNA
<213> ORGANISM: Mus musculus

<400> SEQUENCE: 371
taacctccct gatttctctg tggtgtctgt agctc                                  35

<210> SEQ ID NO 372
<211> LENGTH: 42
<212> TYPE: DNA
<213> ORGANISM: Mus musculus

<400> SEQUENCE: 372
acacccagac ccagcgtccc tccgttgact cgctcttgtc tc                          42

<210> SEQ ID NO 373
<211> LENGTH: 67
<212> TYPE: DNA
<213> ORGANISM: Mus musculus

<400> SEQUENCE: 373
ggagccgagc ccaagctttg ccggcacttt ccgcagcccc atctgcgagt gttttcgttt       60
tgttta                                                                  67

<210> SEQ ID NO 374
<211> LENGTH: 41
<212> TYPE: DNA
<213> ORGANISM: Mus musculus

<400> SEQUENCE: 374
gagcacccct gggagtggat cctctgcacc cagtttcacc a                           41

<210> SEQ ID NO 375
<211> LENGTH: 61
<212> TYPE: DNA
<213> ORGANISM: Mus musculus

<400> SEQUENCE: 375
tctacctctt ttatccccac tttcttttga gacaggattg ttcactgaac ctagggtttg       60
g                                                                       61

<210> SEQ ID NO 376
<211> LENGTH: 54
<212> TYPE: DNA
<213> ORGANISM: Mus musculus

<400> SEQUENCE: 376
actgtcatta cctctttgtt catctcacca atccatggac ttgttcagtg cttg             54

<210> SEQ ID NO 377
<211> LENGTH: 95
<212> TYPE: DNA
<213> ORGANISM: Mus musculus

<400> SEQUENCE: 377
cctgacccct catggccctg tagcctcggt acttggatga gaatgtacac ggggagccct       60
ggacccatcc tgacctctga gtcgagtcca ttcag                                  95
```

<210> SEQ ID NO 378
<211> LENGTH: 50
<212> TYPE: DNA
<213> ORGANISM: Mus musculus

<400> SEQUENCE: 378
acccgacgca gaatggagac atccatgggg gctctcggtg gagtgtgagg        50

<210> SEQ ID NO 379
<211> LENGTH: 70
<212> TYPE: DNA
<213> ORGANISM: Mus musculus

<400> SEQUENCE: 379
gaggaatgca tgacaaacgt gctgtcaggc tctctcttac tgcgttttac ttacttttct        60
gcctgctctg        70

<210> SEQ ID NO 380
<211> LENGTH: 30
<212> TYPE: DNA
<213> ORGANISM: Mus musculus

<400> SEQUENCE: 380
aaatctaatc aagtcccgtt tgtgtgtgtg        30

<210> SEQ ID NO 381
<211> LENGTH: 42
<212> TYPE: DNA
<213> ORGANISM: Mus musculus

<400> SEQUENCE: 381
atggcgtgca ttgaggaggg cagccctagg ccacgcagga gg        42

<210> SEQ ID NO 382
<211> LENGTH: 39
<212> TYPE: DNA
<213> ORGANISM: Mus musculus

<400> SEQUENCE: 382
tccctctggt gacccagctg ttgcttacgt taccgacat        39

<210> SEQ ID NO 383
<211> LENGTH: 66
<212> TYPE: DNA
<213> ORGANISM: Mus musculus

<400> SEQUENCE: 383
actagccgct acttgccttt ttcttttttt ctcaattact tatgcttgga ttccagctgt        60
gctctg        66

<210> SEQ ID NO 384
<211> LENGTH: 84
<212> TYPE: DNA
<213> ORGANISM: Mus musculus

<400> SEQUENCE: 384
gcagggtccc acatgtctaa acgcagtagt taggaacaaa actaaatcaa tgtccttttt        60
gctccatcta tccctcagct tctc        84

<210> SEQ ID NO 385

```
<211> LENGTH: 54
<212> TYPE: DNA
<213> ORGANISM: Mus musculus

<400> SEQUENCE: 385
agtgttgcca taactggtct ttcatactgt cttctgtacc acagatctca ccag          54

<210> SEQ ID NO 386
<211> LENGTH: 69
<212> TYPE: DNA
<213> ORGANISM: Mus musculus

<400> SEQUENCE: 386
attctacaca ctctcttgtg ttgtaactttt tgtcagtgca actagagacc tgttctacac   60
agtcaggga                                                            69

<210> SEQ ID NO 387
<211> LENGTH: 48
<212> TYPE: DNA
<213> ORGANISM: Mus musculus

<400> SEQUENCE: 387
tgggctagat agatggcttt tcttgaagac ccaagtttga ttcccacc                 48

<210> SEQ ID NO 388
<211> LENGTH: 74
<212> TYPE: DNA
<213> ORGANISM: Mus musculus

<400> SEQUENCE: 388
aagatgctct gtagtgaaca cagatttctg tttcctcgct cttccacgtt gtcttagtta   60
gggttttact gatg                                                      74

<210> SEQ ID NO 389
<211> LENGTH: 47
<212> TYPE: DNA
<213> ORGANISM: Mus musculus

<400> SEQUENCE: 389
atgggtacca gttctgattc ccttcagtaa attctgatct acggcct                 47

<210> SEQ ID NO 390
<211> LENGTH: 82
<212> TYPE: DNA
<213> ORGANISM: Mus musculus

<400> SEQUENCE: 390
ataacctagt ccttatggta cccaagtata tccagctcaa cctatctcat gacgggacag   60
ccttgatgct aaagagttca ag                                             82

<210> SEQ ID NO 391
<211> LENGTH: 88
<212> TYPE: DNA
<213> ORGANISM: Mus musculus

<400> SEQUENCE: 391
cacaacagtt actgaactcc tgcctccagc tcttaagtac tgagattata gataggtacc   60
catcaccttc ctgggctctt gctttatg                                       88

<210> SEQ ID NO 392
<211> LENGTH: 84
```

-continued

```
<212> TYPE: DNA
<213> ORGANISM: Mus musculus

<400> SEQUENCE: 392
catgggcagt ctcttgttta aactgctgtc ctttgtcatc ctacatttta atttacttat     60
tccactgtta ttttagatca ctag                                           84

<210> SEQ ID NO 393
<211> LENGTH: 76
<212> TYPE: DNA
<213> ORGANISM: Mus musculus

<400> SEQUENCE: 393
tacttgctcc tacttcctcc atgggcttct ccttttatag tcatctttgt ggtcctccat     60
ctcttctgtt cttaag                                                    76

<210> SEQ ID NO 394
<211> LENGTH: 86
<212> TYPE: DNA
<213> ORGANISM: Mus musculus

<400> SEQUENCE: 394
aaggcactgc gcagggcgtg atgctgtttc cagatccact tctgtttatc tccattttg      60 tttgtatccc ccccttgta atgttt                                          86

<210> SEQ ID NO 395
<211> LENGTH: 37
<212> TYPE: DNA
<213> ORGANISM: Mus musculus

<400> SEQUENCE: 395
atcaggctgg cctggccttg tcagctcctg tcttcca                             37

<210> SEQ ID NO 396
<211> LENGTH: 58
<212> TYPE: DNA
<213> ORGANISM: Mus musculus

<400> SEQUENCE: 396
tctaggtgga tcaacaatat gaactagcca gtgcccccag aactcacgtc tctagctg      58

<210> SEQ ID NO 397
<211> LENGTH: 54
<212> TYPE: DNA
<213> ORGANISM: Mus musculus

<400> SEQUENCE: 397
catcttaacc aactctcagc atttttattt tctattttta gccatttatt acac          54

<210> SEQ ID NO 398
<211> LENGTH: 59
<212> TYPE: DNA
<213> ORGANISM: Mus musculus
<220> FEATURE:
<221> NAME/KEY: misc_feature
<222> LOCATION: (6)..(6)
<223> OTHER INFORMATION: n is a, c, g, t or u

<400> SEQUENCE: 398
cctcancaat gctggtactc ctgacttgcc tcctactctg ttaagacaac cgcaaccac      59

<210> SEQ ID NO 399
```

```
<211> LENGTH: 73
<212> TYPE: DNA
<213> ORGANISM: Mus musculus

<400> SEQUENCE: 399
atccaccagt ttttattaaa ttaacatttt tgctgtagtc ttgcttgccc aggtgtacct      60
acataacata aat                                                        73

<210> SEQ ID NO 400
<211> LENGTH: 55
<212> TYPE: DNA
<213> ORGANISM: Mus musculus

<400> SEQUENCE: 400
cacagtgctg acttaatcca gcctggtgtt ctttctacac atgccacaca cagac           55

<210> SEQ ID NO 401
<211> LENGTH: 48
<212> TYPE: DNA
<213> ORGANISM: Mus musculus

<400> SEQUENCE: 401
acacagcagc cacagcagtc acgcagcata ctcgccgcag acatgtag                   48

<210> SEQ ID NO 402
<211> LENGTH: 47
<212> TYPE: DNA
<213> ORGANISM: Mus musculus

<400> SEQUENCE: 402
cacaccccat ctccctgcct ctggctctgg gggacctcat gcagatt                    47

<210> SEQ ID NO 403
<211> LENGTH: 32
<212> TYPE: DNA
<213> ORGANISM: Mus musculus

<400> SEQUENCE: 403
aaaatgcctc tcccactcct tgcttttcca tt                                    32

<210> SEQ ID NO 404
<211> LENGTH: 60
<212> TYPE: DNA
<213> ORGANISM: Mus musculus

<400> SEQUENCE: 404
caggatctca ctaagtagct ctggccagct tagaacttgc tatgtagacc atgccagctt      60

<210> SEQ ID NO 405
<211> LENGTH: 61
<212> TYPE: DNA
<213> ORGANISM: Mus musculus

<400> SEQUENCE: 405
ccaccacgcc cggctctctc cttttttttaa agacaggttc ttgctatgta gctctgtcgt     60
g                                                                     61

<210> SEQ ID NO 406
<211> LENGTH: 43
<212> TYPE: DNA
<213> ORGANISM: Mus musculus

<400> SEQUENCE: 406
```
tattctaaga aaagtagatt ttataggctt tgtcgtgaca ctc            43

<210> SEQ ID NO 407
<211> LENGTH: 35
<212> TYPE: DNA
<213> ORGANISM: Mus musculus

<400> SEQUENCE: 407
tatccacacc aagcctaccc taaactaaac agcta                     35

<210> SEQ ID NO 408
<211> LENGTH: 26
<212> TYPE: DNA
<213> ORGANISM: Mus musculus

<400> SEQUENCE: 408
cttagtcctc tcgttgactc aggttc                               26

<210> SEQ ID NO 409
<211> LENGTH: 42
<212> TYPE: DNA
<213> ORGANISM: Mus musculus
<220> FEATURE:
<221> NAME/KEY: misc_feature
<222> LOCATION: (42)..(42)
<223> OTHER INFORMATION: n is a, c, g, t or u

<400> SEQUENCE: 409
agaccctgct tgcctgctcg ccctgctcac caccttttat an             42

<210> SEQ ID NO 410
<211> LENGTH: 76
<212> TYPE: DNA
<213> ORGANISM: Mus musculus

<400> SEQUENCE: 410
cccctcttgt gcccacttcc tcctcaaatt cccccctttt ccccagtcc tagttgtcta    60 tctttttttt tcttcc                                          76

<210> SEQ ID NO 411
<211> LENGTH: 36
<212> TYPE: DNA
<213> ORGANISM: Mus musculus

<400> SEQUENCE: 411
ttagcttacc ctttctcctc tcttcgtcaa gctact                    36

<210> SEQ ID NO 412
<211> LENGTH: 87
<212> TYPE: DNA
<213> ORGANISM: Mus musculus

<400> SEQUENCE: 412
cctggcctgg cctgaaattt gctgtgtaga ccaggttggc cttgaactca aagagatcta    60
cctgtttctg cctcgtgacg atgcggg                              87

<210> SEQ ID NO 413
<211> LENGTH: 72
<212> TYPE: DNA
<213> ORGANISM: Mus musculus

<400> SEQUENCE: 413

```
caatctgtta gcaattctgt aggttccta agctagccag gagtgagtcg tgtgcaatcg    60
gtatttattg cc                                                      72
```

```
<210> SEQ ID NO 414
<211> LENGTH: 52
<212> TYPE: DNA
<213> ORGANISM: Mus musculus

<400> SEQUENCE: 414
ggtgcgaacg aaccggaggg gggagagaga aatcaaacag ctaagcgtgg ag          52
```

```
<210> SEQ ID NO 415
<211> LENGTH: 75
<212> TYPE: DNA
<213> ORGANISM: Mus musculus

<400> SEQUENCE: 415
aacaagcaat ggacctcaaa tatacaagca tatatgttag tgagtatgtg ccccacactt  60
tcgagtcaca ctctg                                                   75
```

```
<210> SEQ ID NO 416
<211> LENGTH: 45
<212> TYPE: DNA
<213> ORGANISM: Mus musculus

<400> SEQUENCE: 416
tagtgcttgg cccacgctca gtattattct ctctttccag gaagc                  45
```

```
<210> SEQ ID NO 417
<211> LENGTH: 58
<212> TYPE: DNA
<213> ORGANISM: Mus musculus

<400> SEQUENCE: 417
tgtcaggatc ccagtgaccc ccaagactct gcctttggca cctgcctagc cgcttctg    58
```

```
<210> SEQ ID NO 418
<211> LENGTH: 80
<212> TYPE: DNA
<213> ORGANISM: Mus musculus

<400> SEQUENCE: 418
atatgaatga cctcccggga ccaccatcca aacctcaggt cactgatgtt tctaagaaca  60
gtgtcacctt atcctggcag                                              80
```

```
<210> SEQ ID NO 419
<211> LENGTH: 70
<212> TYPE: DNA
<213> ORGANISM: Mus musculus

<400> SEQUENCE: 419
atgagctcac agtgccccga taccgcacag agaagccctc caagtcatcc ccgccacccc  60 ctcccccgccg                                                        70
```

```
<210> SEQ ID NO 420
<211> LENGTH: 85
<212> TYPE: DNA
<213> ORGANISM: Mus musculus

<400> SEQUENCE: 420
atgcaagctg cctacatcca aacacagttt gaaagcaaaa accgctcacc caacaaagaa  60
```

-continued atttactgtc acatgacttg tgcca					85

<210> SEQ ID NO 421
<211> LENGTH: 76
<212> TYPE: DNA
<213> ORGANISM: Mus musculus

<400> SEQUENCE: 421
caaatcaaga cagcacgtac caccatggcg ggcctgacca tggaggaact aatccaactg		60 gtagccgcac gactgg					76

<210> SEQ ID NO 422
<211> LENGTH: 35
<212> TYPE: DNA
<213> ORGANISM: Mus musculus

<400> SEQUENCE: 422
tgagagctac cccattgagc tccgttgtcc gggca					35

<210> SEQ ID NO 423
<211> LENGTH: 55
<212> TYPE: DNA
<213> ORGANISM: Mus musculus

<400> SEQUENCE: 423
acagctaccc accatccacc ccacagcccc ctggtgagac agctctccac ctcat		55

<210> SEQ ID NO 424
<211> LENGTH: 50
<212> TYPE: DNA
<213> ORGANISM: Mus musculus

<400> SEQUENCE: 424
cctgtctgca ggaagggtcc ccctgtgggg cggagtcctc atcaccatcg		50

<210> SEQ ID NO 425
<211> LENGTH: 36
<212> TYPE: DNA
<213> ORGANISM: Mus musculus

<400> SEQUENCE: 425
acagatttct tgttccttc tccgctccca ctgctt		36

<210> SEQ ID NO 426
<211> LENGTH: 41
<212> TYPE: DNA
<213> ORGANISM: Mus musculus

<400> SEQUENCE: 426
aaacctttac ccaatgtatt ttgaagctct agtttaataa g		41

<210> SEQ ID NO 427
<211> LENGTH: 52
<212> TYPE: DNA
<213> ORGANISM: Mus musculus

<400> SEQUENCE: 427
tgccccttct ctctcctgaa tcattgttct ctgggaaatt ctttgctctg cc		52

<210> SEQ ID NO 428
<211> LENGTH: 55
<212> TYPE: DNA

<213> ORGANISM: Mus musculus

<400> SEQUENCE: 428
atgtatctgt cattcccagc aggaggtaga tggatccaca gacttccatt atgat    55

<210> SEQ ID NO 429
<211> LENGTH: 40
<212> TYPE: DNA
<213> ORGANISM: Mus musculus

<400> SEQUENCE: 429
agccagttgt ccagaatttt tatttctttt tgcttgtttg    40

<210> SEQ ID NO 430
<211> LENGTH: 33
<212> TYPE: DNA
<213> ORGANISM: Mus musculus

<400> SEQUENCE: 430
cctgtttcct tttgtatttt tccttctatt ttc    33

<210> SEQ ID NO 431
<211> LENGTH: 38
<212> TYPE: DNA
<213> ORGANISM: Mus musculus

<400> SEQUENCE: 431
catctgatgt atgattttca cacattttct ctgctctg    38

<210> SEQ ID NO 432
<211> LENGTH: 104
<212> TYPE: DNA
<213> ORGANISM: Mus musculus

<400> SEQUENCE: 432
gaagaaatta aagactttt agattttagt gaaaatgaag acacatcatt ccaaaattta    60
tttacttaca caatgaaagt agtaggagga ggaaactcat agct    104

<210> SEQ ID NO 433
<211> LENGTH: 91
<212> TYPE: DNA
<213> ORGANISM: Mus musculus

<400> SEQUENCE: 433
agaagcccac ataggaaggt ccacttgtca aggaaccttg tcaggaatag cagaaagtct    60
ggccattcat ttactcattt actaaccacc t    91

<210> SEQ ID NO 434
<211> LENGTH: 62
<212> TYPE: DNA
<213> ORGANISM: Mus musculus

<400> SEQUENCE: 434
aagtcagtgg tgtaggcctg gcttttgctg tttccggaag tgttcttttg tattttacgc    60
tg    62

<210> SEQ ID NO 435
<211> LENGTH: 69
<212> TYPE: DNA
<213> ORGANISM: Mus musculus

<400> SEQUENCE: 435

```
accctgttcc tctcagcact gctgtgctac ctggtatcca agtcctttcc actttgtaac    60
tgtctcttg                                                            69

<210> SEQ ID NO 436
<211> LENGTH: 104
<212> TYPE: DNA
<213> ORGANISM: Mus musculus

<400> SEQUENCE: 436
gaagaaatta aagactttt agatttagt gaaaatgaag acacatcatt ccaaaattta    60
tttacttaca caatgaaagt agtaggagga ggaaactcat agct                    104

<210> SEQ ID NO 437
<211> LENGTH: 91
<212> TYPE: DNA
<213> ORGANISM: Mus musculus

<400> SEQUENCE: 437
agaagcccac ataggaaggt ccacttgtca aggaaccttg tcaggaatag cagaaagtct    60
ggccattcat ttactcattt actaaccacc t                                   91

<210> SEQ ID NO 438
<211> LENGTH: 82
<212> TYPE: DNA
<213> ORGANISM: Mus musculus

<400> SEQUENCE: 438
accagaagag ggcatcagat cccattactg atgtttgtga gccaccatgt ggttcatcgt    60
tctagaaggt ttttttttt tg                                              82

<210> SEQ ID NO 439
<211> LENGTH: 66
<212> TYPE: DNA
<213> ORGANISM: Mus musculus

<400> SEQUENCE: 439
gttacaaagt cagacagcgg accttgacac taatggcact tcacatttcc cacagaattg    60
gctcag                                                               66

<210> SEQ ID NO 440
<211> LENGTH: 67
<212> TYPE: DNA
<213> ORGANISM: Mus musculus

<400> SEQUENCE: 440
aaaggcctct agtagctgtc aatgcaggtg ccctttatg ttgtacaggt acaaatttgc     60
agaatag                                                              67

<210> SEQ ID NO 441
<211> LENGTH: 73
<212> TYPE: DNA
<213> ORGANISM: Mus musculus

<400> SEQUENCE: 441
gtctctgcac ctgaatctgt tcttatgaa ttttcttggg cttttttcct tctgtttgtt     60
tcttttgctc aat                                                       73

<210> SEQ ID NO 442
```

```
<211> LENGTH: 57
<212> TYPE: DNA
<213> ORGANISM: Mus musculus

<400> SEQUENCE: 442
ctaattgatc acaaccagtt acagatttct tgttccttc tctgctccca ctgcttc        57

<210> SEQ ID NO 443
<211> LENGTH: 35
<212> TYPE: DNA
<213> ORGANISM: Mus musculus

<400> SEQUENCE: 443
caccgcccgg cttgtttgtt tgtttttaa cctac                                35

<210> SEQ ID NO 444
<211> LENGTH: 48
<212> TYPE: DNA
<213> ORGANISM: Mus musculus

<400> SEQUENCE: 444
caactgggcg ctgtgacttt gcgtgtcaga cgtttcccga tttccccg                 48

<210> SEQ ID NO 445
<211> LENGTH: 60
<212> TYPE: DNA
<213> ORGANISM: Mus musculus

<400> SEQUENCE: 445
acaaccagtt acagatttct tgttccttc tccgctccca ctgcttcact tgaccagcct     60

<210> SEQ ID NO 446
<211> LENGTH: 47
<212> TYPE: DNA
<213> ORGANISM: Mus musculus

<400> SEQUENCE: 446
aggcagaggc aggaggatca cgagttcgag gccagcctgg gctacac                  47

<210> SEQ ID NO 447
<211> LENGTH: 55
<212> TYPE: DNA
<213> ORGANISM: Mus musculus

<400> SEQUENCE: 447
ccgcccccac attcgccgtc acaagatggc gctgacatcc tgtgttctaa gttgg         55

<210> SEQ ID NO 448
<211> LENGTH: 87
<212> TYPE: DNA
<213> ORGANISM: Mus musculus

<400> SEQUENCE: 448
atccatcaag gccacaattc ctaatagtgt catttcctgt tccaagcata tacaaaccat    60
cacaatgagt ctgttggttt atttctg                                        87

<210> SEQ ID NO 449
<211> LENGTH: 78
<212> TYPE: DNA
<213> ORGANISM: Mus musculus

<400> SEQUENCE: 449
tccactggat ggttttagct cccttgtcaa agatcaagtg accataggtg tgtgggttca    60
```
tctctgggtc ttcaattc                                                        78

<210> SEQ ID NO 450
<211> LENGTH: 4
<212> TYPE: DNA
<213> ORGANISM: Mus musculus

<400> SEQUENCE: 450 ccau                                                                        4

<210> SEQ ID NO 451
<211> LENGTH: 4
<212> TYPE: DNA
<213> ORGANISM: Mus musculus

<400> SEQUENCE: 451 ucau                                                                        4

<210> SEQ ID NO 452
<211> LENGTH: 4
<212> TYPE: DNA
<213> ORGANISM: Mus musculus

<400> SEQUENCE: 452 ucac                                                                        4

<210> SEQ ID NO 453
<211> LENGTH: 4
<212> TYPE: DNA
<213> ORGANISM: Mus musculus

<400> SEQUENCE: 453 ccac                                                                        4

<210> SEQ ID NO 454
<211> LENGTH: 6
<212> TYPE: DNA
<213> ORGANISM: Mus musculus

<400> SEQUENCE: 454 uccauc                                                                      6

<210> SEQ ID NO 455
<211> LENGTH: 6
<212> TYPE: DNA
<213> ORGANISM: Mus musculus

<400> SEQUENCE: 455 ccaucc                                                                      6

<210> SEQ ID NO 456
<211> LENGTH: 6
<212> TYPE: DNA
<213> ORGANISM: Mus musculus

<400> SEQUENCE: 456 auccau                                                                      6

<210> SEQ ID NO 457
<211> LENGTH: 6
<212> TYPE: DNA
<213> ORGANISM: Mus musculus

```
<400> SEQUENCE: 457 caucca                                                              6

<210> SEQ ID NO 458
<211> LENGTH: 6
<212> TYPE: DNA
<213> ORGANISM: Mus musculus

<400> SEQUENCE: 458 ucaucc                                                              6

<210> SEQ ID NO 459
<211> LENGTH: 6
<212> TYPE: DNA
<213> ORGANISM: Mus musculus

<400> SEQUENCE: 459 caucau                                                              6

<210> SEQ ID NO 460
<211> LENGTH: 6
<212> TYPE: DNA
<213> ORGANISM: Mus musculus

<400> SEQUENCE: 460 ccaucu                                                              6

<210> SEQ ID NO 461
<211> LENGTH: 6
<212> TYPE: DNA
<213> ORGANISM: Mus musculus

<400> SEQUENCE: 461 ccuccc                                                              6

<210> SEQ ID NO 462
<211> LENGTH: 6
<212> TYPE: DNA
<213> ORGANISM: Mus musculus

<400> SEQUENCE: 462 cucauc                                                              6

<210> SEQ ID NO 463
<211> LENGTH: 6
<212> TYPE: DNA
<213> ORGANISM: Mus musculus

<400> SEQUENCE: 463 cauccu                                                              6

<210> SEQ ID NO 464
<211> LENGTH: 6
<212> TYPE: DNA
<213> ORGANISM: Mus musculus

<400> SEQUENCE: 464 cucacc                                                              6

<210> SEQ ID NO 465
<211> LENGTH: 6
<212> TYPE: DNA
<213> ORGANISM: Mus musculus
```

```
<400> SEQUENCE: 465 aucauc                                                              6

<210> SEQ ID NO 466
<211> LENGTH: 6
<212> TYPE: DNA
<213> ORGANISM: Mus musculus

<400> SEQUENCE: 466 ccauca                                                              6

<210> SEQ ID NO 467
<211> LENGTH: 6
<212> TYPE: DNA
<213> ORGANISM: Mus musculus

<400> SEQUENCE: 467 cccauc                                                              6

<210> SEQ ID NO 468
<211> LENGTH: 4
<212> TYPE: DNA
<213> ORGANISM: Mus musculus

<400> SEQUENCE: 468 ycay                                                                4

<210> SEQ ID NO 469
<211> LENGTH: 5
<212> TYPE: DNA
<213> ORGANISM: Mus musculus

<400> SEQUENCE: 469 ycayy                                                               5

<210> SEQ ID NO 470
<211> LENGTH: 8
<212> TYPE: PRT
<213> ORGANISM: unknown
<220> FEATURE:
<223> OTHER INFORMATION: don't know source

<400> SEQUENCE: 470

Asp Tyr Lys Asp Asp Asp Asp Lys
1               5

<210> SEQ ID NO 471
<211> LENGTH: 8
<212> TYPE: PRT
<213> ORGANISM: Unknown
<220> FEATURE:
<223> OTHER INFORMATION: don't know source

<400> SEQUENCE: 471

Asp Tyr Leu Asp Glu Asp Asp Lys
1               5

<210> SEQ ID NO 472
<211> LENGTH: 9
<212> TYPE: PRT
<213> ORGANISM: Unknown
<220> FEATURE:
<223> OTHER INFORMATION: don't know source
```

```
<400> SEQUENCE: 472

Ala Trp Arg His Pro Gln Phe Gly Gly
1               5

<210> SEQ ID NO 473
<211> LENGTH: 13
<212> TYPE: PRT
<213> ORGANISM: Influenza A virus

<400> SEQUENCE: 473

Tyr Pro Tyr Asp Val Pro Asp Tyr Ala Ile Glu Gly Arg
1               5                   10

<210> SEQ ID NO 474
<211> LENGTH: 6
<212> TYPE: PRT
<213> ORGANISM: artificial
<220> FEATURE:
<223> OTHER INFORMATION: artificial sequence

<400> SEQUENCE: 474

His His His His His His
1               5

<210> SEQ ID NO 475
<211> LENGTH: 11
<212> TYPE: PRT
<213> ORGANISM: homo sapiens

<400> SEQUENCE: 475

Glu Gln Lys Leu Leu Ser Glu Glu Asp Leu Asn
1               5                   10

<210> SEQ ID NO 476
<211> LENGTH: 3
<212> TYPE: PRT
<213> ORGANISM: unknown
<220> FEATURE:
<223> OTHER INFORMATION: source unknown

<400> SEQUENCE: 476

Glu Glu Phe
1

<210> SEQ ID NO 477
<211> LENGTH: 16
<212> TYPE: RNA
<213> ORGANISM: Artificial
<220> FEATURE:
<223> OTHER INFORMATION: synthetic oligo

<400> SEQUENCE: 477
agggaggacg augcgg                                                   16

<210> SEQ ID NO 478
<211> LENGTH: 16
<212> TYPE: RNA
<213> ORGANISM: Artificial
<220> FEATURE:
<223> OTHER INFORMATION: synthetic oligo

<400> SEQUENCE: 478
cagacgacga gcggga                                                   16

<210> SEQ ID NO 479
```

```
<211> LENGTH: 16
<212> TYPE: DNA
<213> ORGANISM: Artificial
<220> FEATURE:
<223> OTHER INFORMATION: synthetic linker

<400> SEQUENCE: 479
agggaggacg atgcgg                                                          16

<210> SEQ ID NO 480
<211> LENGTH: 16
<212> TYPE: DNA
<213> ORGANISM: Artificial
<220> FEATURE:
<223> OTHER INFORMATION: synthetic oligo

<400> SEQUENCE: 480
tcccgctcgt cgtctg                                                          16

<210> SEQ ID NO 481
<211> LENGTH: 33
<212> TYPE: DNA
<213> ORGANISM: Artificial
<220> FEATURE:
<223> OTHER INFORMATION: synthetic oligo

<400> SEQUENCE: 481
cagtgctgcg cggccgcagg gaggacgatg cgg                                       33

<210> SEQ ID NO 482
<211> LENGTH: 33
<212> TYPE: DNA
<213> ORGANISM: Artificial
<220> FEATURE:
<223> OTHER INFORMATION: synthetic oligo

<400> SEQUENCE: 482
tcaagtcagg gcgcgcctcc cgctcgtcgt ctg                                       33

<210> SEQ ID NO 483
<211> LENGTH: 16
<212> TYPE: DNA
<213> ORGANISM: artificial
<220> FEATURE:
<223> OTHER INFORMATION: synthetic primer

<400> SEQUENCE: 483
tcgggcgagt cgtctg                                                          16

<210> SEQ ID NO 484
<211> LENGTH: 15
<212> TYPE: DNA
<213> ORGANISM: Artificial
<220> FEATURE:
<223> OTHER INFORMATION: synthetic oligo

<400> SEQUENCE: 484
ccgcatcgtc ctccc                                                           15

<210> SEQ ID NO 485
<211> LENGTH: 16
<212> TYPE: DNA
<213> ORGANISM: Artificial
<220> FEATURE:
<223> OTHER INFORMATION: synthetic oligo

<400> SEQUENCE: 485
```

```
tcgggcgagt cgtctg                                                16

<210> SEQ ID NO 486
<211> LENGTH: 15
<212> TYPE: DNA
<213> ORGANISM: Artificial
<220> FEATURE:
<223> OTHER INFORMATION: synthetic oligo

<400> SEQUENCE: 486
gggaggacga tgcgg                                                 15

<210> SEQ ID NO 487
<211> LENGTH: 19
<212> TYPE: DNA
<213> ORGANISM: Artificial
<220> FEATURE:
<223> OTHER INFORMATION: primer

<400> SEQUENCE: 487
cgaccugcag gcuuccugc                                             19

<210> SEQ ID NO 488
<211> LENGTH: 20
<212> TYPE: DNA
<213> ORGANISM: Artificial
<220> FEATURE:
<223> OTHER INFORMATION: primer

<400> SEQUENCE: 488
cuuaggugga agggcaagcg                                            20

<210> SEQ ID NO 489
<211> LENGTH: 20
<212> TYPE: DNA
<213> ORGANISM: Artificial
<220> FEATURE:
<223> OTHER INFORMATION: linker

<400> SEQUENCE: 489
gggcaacagg uaccaaacuc                                            20

<210> SEQ ID NO 490
<211> LENGTH: 20
<212> TYPE: DNA
<213> ORGANISM: Artificial
<220> FEATURE:
<223> OTHER INFORMATION: linker

<400> SEQUENCE: 490
cuuagguggu accgcaagcg                                            20

<210> SEQ ID NO 491
<211> LENGTH: 20
<212> TYPE: DNA
<213> ORGANISM: Artificial
<220> FEATURE:
<223> OTHER INFORMATION: linker

<400> SEQUENCE: 491
gggcaacagu agauaaacuc                                            20

<210> SEQ ID NO 492
<211> LENGTH: 19
<212> TYPE: DNA
```

```
<213> ORGANISM: Artificial
<220> FEATURE:
<223> OTHER INFORMATION: linker

<400> SEQUENCE: 492
cgagauggcg gcuuccugc                                                  19

<210> SEQ ID NO 493
<211> LENGTH: 16
<212> TYPE: DNA
<213> ORGANISM: Artificial
<220> FEATURE:
<223> OTHER INFORMATION: primer

<400> SEQUENCE: 493
agggaggacg atgcgg                                                     16

<210> SEQ ID NO 494
<211> LENGTH: 19
<212> TYPE: DNA
<213> ORGANISM: Artificial
<220> FEATURE:
<223> OTHER INFORMATION: primer

<400> SEQUENCE: 494
gcaggaagcc gccatctcg                                                  19

<210> SEQ ID NO 495
<211> LENGTH: 22
<212> TYPE: DNA
<213> ORGANISM: Artificial
<220> FEATURE:
<223> OTHER INFORMATION: primer

<400> SEQUENCE: 495
gaattcaggg aggacgatgc gg                                              22

<210> SEQ ID NO 496
<211> LENGTH: 23
<212> TYPE: DNA
<213> ORGANISM: Artificial
<220> FEATURE:
<223> OTHER INFORMATION: primer

<400> SEQUENCE: 496
gctagcagga agccgccatc tcg                                             23

<210> SEQ ID NO 497
<211> LENGTH: 25
<212> TYPE: DNA
<213> ORGANISM: Artificial
<220> FEATURE:
<223> OTHER INFORMATION: primer

<400> SEQUENCE: 497
tgatgactcc ctatgtggta actcg                                           25

<210> SEQ ID NO 498
<211> LENGTH: 27
<212> TYPE: DNA
<213> ORGANISM: Artificial
<220> FEATURE:
<223> OTHER INFORMATION: primer

<400> SEQUENCE: 498
tctctggctt gacttgtttt tattttg                                         27
```

<210> SEQ ID NO 499
<211> LENGTH: 20
<212> TYPE: DNA
<213> ORGANISM: Artificial
<220> FEATURE:
<223> OTHER INFORMATION: primer

<400> SEQUENCE: 499
acactggctg gaaggagggg                                               20

<210> SEQ ID NO 500
<211> LENGTH: 21
<212> TYPE: DNA
<213> ORGANISM: Artificial
<220> FEATURE:
<223> OTHER INFORMATION: primer

<400> SEQUENCE: 500
tgggctgtgg gaagactctg g                                             21

<210> SEQ ID NO 501
<211> LENGTH: 24
<212> TYPE: DNA
<213> ORGANISM: Artificial
<220> FEATURE:
<223> OTHER INFORMATION: primer

<400> SEQUENCE: 501
tgtggaataa gggggaaaac tctg                                          24

<210> SEQ ID NO 502
<211> LENGTH: 20
<212> TYPE: DNA
<213> ORGANISM: Artificial
<220> FEATURE:
<223> OTHER INFORMATION: primer

<400> SEQUENCE: 502
tcgtgggagc acctgaacac                                               20

<210> SEQ ID NO 503
<211> LENGTH: 5
<212> TYPE: DNA
<213> ORGANISM: Mus musculus

<400> SEQUENCE: 503 gtttt                                                                5

<210> SEQ ID NO 504
<211> LENGTH: 4
<212> TYPE: DNA
<213> ORGANISM: Mus musculus

<400> SEQUENCE: 504 gttt                                                                 4

<210> SEQ ID NO 505
<211> LENGTH: 5
<212> TYPE: DNA
<213> ORGANISM: Mus musculus

<400> SEQUENCE: 505 ctttt                                                                5

```
<210> SEQ ID NO 506
<211> LENGTH: 4
<212> TYPE: DNA
<213> ORGANISM: Mus musculus

<400> SEQUENCE: 506 cttt                                                                    4

<210> SEQ ID NO 507
<211> LENGTH: 5
<212> TYPE: DNA
<213> ORGANISM: Mus musculus

<400> SEQUENCE: 507 gtttc                                                                   5

<210> SEQ ID NO 508
<211> LENGTH: 5
<212> TYPE: DNA
<213> ORGANISM: Mus musculus

<400> SEQUENCE: 508 ctttc                                                                   5

<210> SEQ ID NO 509
<211> LENGTH: 16
<212> TYPE: DNA
<213> ORGANISM: Artificial
<220> FEATURE:
<223> OTHER INFORMATION: primer

<400> SEQUENCE: 509
gtaaaacgac ggccag                                                      16

<210> SEQ ID NO 510
<211> LENGTH: 16
<212> TYPE: PRT
<213> ORGANISM: Artificial
<220> FEATURE:
<223> OTHER INFORMATION: synthetic construct

<400> SEQUENCE: 510

Ala Gly Thr Ala Ala Thr Ala Cys Gly Ala Cys Thr Cys Ala Cys Thr
1               5                   10                  15

<210> SEQ ID NO 511
<211> LENGTH: 75
<212> TYPE: RNA
<213> ORGANISM: Mus musculus

<400> SEQUENCE: 511
gggccaguuc aaccacaggu ccccagcuuc cauccauugg uugggugcua guaucugcau       60
cugacucuuu cagcu                                                       75

<210> SEQ ID NO 512
<211> LENGTH: 75
<212> TYPE: RNA
<213> ORGANISM: Artificial
<220> FEATURE:
<223> OTHER INFORMATION: synthetic construct

<400> SEQUENCE: 512
gggagcugau guaugcugcc ugguuggugg cucaguaucc uagagaucuc gggauccagg       60
```

```
ucaguugaga cugcc                                              75

<210> SEQ ID NO 513
<211> LENGTH: 77
<212> TYPE: RNA
<213> ORGANISM: Mus musculus

<400> SEQUENCE: 513
gggccaacca caaaugccag caccucuuaa uaacaaucag caugaccucu gccuaagucu   60
uggcuucuuc cucagaa                                            77

<210> SEQ ID NO 514
<211> LENGTH: 76
<212> TYPE: RNA
<213> ORGANISM: Artificial
<220> FEATURE:
<223> OTHER INFORMATION: synthetic construct

<400> SEQUENCE: 514
ggggaggaug cccugcacca guacaguaaa ugagugcuug gaggagauca guguggcacu   60
guaaagccua gugugc                                             76

<210> SEQ ID NO 515
<211> LENGTH: 52
<212> TYPE: RNA
<213> ORGANISM: Mus musculus

<400> SEQUENCE: 515
gggguguucu uccauuuucc acauucuuca cacuaacaug cgucuucaug cu         52

<210> SEQ ID NO 516
<211> LENGTH: 52
<212> TYPE: RNA
<213> ORGANISM: Artificial
<220> FEATURE:
<223> OTHER INFORMATION: synthetic construct

<400> SEQUENCE: 516
gggguuuugu aagggagcc gacggcauag ggcacuagcu cugcccuc gu            52

<210> SEQ ID NO 517
<211> LENGTH: 64
<212> TYPE: RNA
<213> ORGANISM: Mus musculus

<400> SEQUENCE: 517
gggcugugau uagugcccau cccauccauu cccucgauaa cccucaccau cauuccacu   60 ccag                                                          64

<210> SEQ ID NO 518
<211> LENGTH: 64
<212> TYPE: RNA
<213> ORGANISM: Artificial
<220> FEATURE:
<223> OTHER INFORMATION: synthetic construct

<400> SEQUENCE: 518
ggggucuaca cuggcuggaa ggaggggaau gagaccaaaa augaugaugc ccuuugacuc   60
ucag                                                          64

<210> SEQ ID NO 519
<211> LENGTH: 62
```

```
<212> TYPE: RNA
<213> ORGANISM: Mus musculus

<400> SEQUENCE: 519
ccugacggau ccugugacgc ccacaguauc ccuguagcag acuggcaugg ccuugccugu        60
ga                                                                       62

<210> SEQ ID NO 520
<211> LENGTH: 49
<212> TYPE: RNA
<213> ORGANISM: Mus musculus

<400> SEQUENCE: 520
guguucuucc auuuccaca uucuucacgc uaacaugcgu cuucaugcu                     49

<210> SEQ ID NO 521
<211> LENGTH: 24
<212> TYPE: RNA
<213> ORGANISM: Mus musculus

<400> SEQUENCE: 521
cucauuuuca gauucaucau cuca                                               24

<210> SEQ ID NO 522
<211> LENGTH: 20
<212> TYPE: RNA
<213> ORGANISM: Mus musculus

<400> SEQUENCE: 522
ucucaucauc auuuucauuu                                                    20
```

METHOD OF PURIFYING RNA BINDING PROTEIN-RNA COMPLEXES

CROSS REFERENCE TO RELATED APPLICATIONS

This application is a continuation of, and claims priority to U.S. application Ser. No. 12/509,856 filed Jul. 27, 2009, which is now abandoned, which is a continuation of and claims priority to U.S. application Ser. No. 10/971,736 filed on Oct. 25, 2004 which is now abandoned, which claims priority to U.S. Provisional Application No. 60/513,183, filed on Oct. 23, 2003.

FIELD OF THE INVENTION

The present invention provides methods for purifying RNA molecules interacting with an RNA binding protein (RBP), and the use of such methods to analyze a gene expression profile of a cell. The invention also provides sequences of RNA molecules that methate binding to an RBP, proteins encoded by the sequences, a method of identifying the sequences, and the use of the sequences in a screen to identify bioactive molecules. The invention also provides RNA motifs found among the sequences and compounds that bind the RNA motifs. In addition, the invention provides methods of treating diseases associated with a function of an RNA binding protein.

BACKGROUND OF THE INVENTION

RNA binding proteins (RBPs) are frequently targets of human autoimmune or genetic neurologic diseases. Notable examples among autoimmune disease include systemic lupus erythematosis, primary biliary cirrhosis (PBC) and Sjogren's syndrome, and among neurologic disease include the paraneoplastic neurologic antigens Nova and Hu, and the Fragile X mental retardation FMR1 protein, the spinal muscular atrophy SMN protein, the myotonic dystrophy CELF proteins, and the spinocerebellar ataxia SCA1 protein. Understanding the role these proteins play in disease, normal biology, and in the brain requires methods to identify the set of RNAs they bind to in vivo, and the use of mouse models of these disorders for RNA target validation. The targets of RBPs involved in a number of autoimmune and genetic diseases have been difficult to identify, however. Accordingly, the present invention provides methods for purifying RNA molecules interacting with an RNA

SUMMARY OF THE INVENTION

In one embodiment, the present invention provides a method for purifying an RNA molecule interacting with an RBP of interest in a biological sample, comprising the steps of: (a) contacting the biological sample with an agent that creates a covalent bond between the RNA molecule and the RBP of interest, thereby generating a covalently bound RBP-RNA complex containing the RNA molecule; (b) cleaving the RNA molecule by contacting the RBP-RNA complex with an agent capable of cleaving a bond thereof, thereby generating a fragment of the RNA molecule, wherein the fragment is at least 22 nucleotide bases in length; (c) selecting the RBP-RNA complex with a molecule that specifically interacts with a component of the RBP-RNA complex; and (d) purifying the RBP-RNA complex under stringent conditions, thereby purifying an RNA molecule interacting with an RBP of interest.

In another embodiment, the present invention provides a method for purifying an RNA molecule interacting with an RBP of interest in a biological sample, comprising the steps of (a) contacting the biological sample with an agent that creates a covalent bond between the RNA molecule and the RBP of interest, thereby generating a covalently bound RBP-RNA complex containing the RNA molecule; (b) cleaving the RNA molecule with an agent capable of cleaving a bond thereof, thereby generating a fragment of the RNA molecule, wherein the fragment is at least 22 nucleotide bases in length; (c) selecting the RBP-RNA complex with a molecule that specifically interacts with a component of the RBP-RNA complex; and (d) purifying the RBP-RNA complex, wherein the purifying step comprises an agent that disrupts an intermolecular interaction, thereby purifying an RNA molecule interacting with an RBP of interest.

In another embodiment, the present invention provides a method for purifying an RNA molecule interacting with an RBP of interest in a biological sample, comprising the steps of (a) contacting the biological sample with an agent that creates a covalent bond between the RNA molecule and the RBP of interest, thereby generating a covalently bound RBP-RNA complex containing the RNA molecule; (b) cleaving the RNA molecule with an agent capable of cleaving a bond thereof, thereby generating a fragment of the RNA molecule, wherein the fragment is at least 22 nucleotide bases in length; (c) selecting the RBP-RNA complex with a molecule that specifically interacts with a component of the RBP-RNA complex; and (d) purifying the RBP-RNA complex, wherein the purifying comprises a chromatographic method, thereby purifying an RNA molecule interacting with an RBP of interest.

In another embodiment, the present invention provides a method for identifying a plurality of RNA molecules interacting with a known RBP in a biological sample, comprising the following steps: (a) contacting the biological sample with an agent that results in a plurality of covalently bound RBP-RNA complexes in the biological sample; (b) obtaining RNA fragments of at least 22 bases in length from the biological sample; selecting a plurality of RBP-RNA complexes of interest with a molecule that specifically interacts with the known RBP; purifying the plurality of RBP-RNA complexes of interest under stringent conditions; and identifying a plurality of RNA molecules in the RBP-RNA complexes of interest; thereby identifying a plurality of RNA molecules interacting with a known RBP in a biological sample.

In another embodiment, the present invention provides a method of screening a test compound for its ability to modulate expression of a gene in a cell, comprising the steps of: (a) purifying a first plurality of RNA binding protein-RNA complexes from the cell by the CLIP method, wherein the cell has been contacted with the test compound; (b) identifying a first plurality of RNA molecules in the first plurality of RBP-RNA complexes; (c) assessing an amount of the gene among the first plurality of RNA molecules; (d) purifying a second plurality of RNA binding protein-RNA complexes from the cell by the CLIP method, wherein the cell has not been contacted with the test compound; (e) identifying a second plurality of RNA molecules in the second plurality of RBP-RNA complexes; and (f) assessing an amount of the gene among the second plurality of RNA molecules; wherein a difference between the amount of the gene in the first plurality of RNA molecules and the amount of the gene in the second plurality of RNA molecules indicates an ability of the test compound to modulate expression of a gene in a cell.

In another embodiment, there are provided nucleotide linkers comprising a sequence as set forth in SEQ ID No 477-502.

In another embodiment, there is provided a compound which interacts with a motif of an isolated nucleic acid sequence as set forth in SEQ ID No 1-335.

In another embodiment, there is provided a compound which interacts with a motif of an isolated nucleic acid sequence as set forth in SEQ ID No 336-449.

In another embodiment, there is provided a compound which interacts with a motif of an isolated nucleic acid sequence as set forth in SEQ ID No 1-78.

In another embodiment, there is provided a method of generating a gene expression profile of a cell, tissue, or biological sample in vivo, comprising: purifying an RBP-RNA complex from the cell according the method for purifying RNA interacting with RBPs of interest, wherein RNA bound to the RBP-RNA complex comprises a subset of the mRNA of the cell; and then identifying the mRNAs of the subset, thereby generating the gene expression profile of the cell, tissue, or biological sample.

In another embodiment, the present invention provides a method of treating a disease or disorder in a subject, wherein the disease or disorder is associated with a function of an RNA binding protein, comprising contacting a cell in the subject with an agent that modulates an expression or activity of a gene, or a protein encoded by the gene, function of an RNA binding protein, comprising contacting a cell in the subject with an agent that modulates an expression or activity of a gene, or a protein encoded by the gene, wherein a transcript of the gene comprises a nucleic acid sequence set forth in SEQ ID No 1-335, thereby treating a disease or disorder in a subject.

In another embodiment, the present invention provides a method of treating a disease or disorder in a subject, wherein the disease or disorder is associated with a function of an RNA binding protein, comprising contacting a cell in the subject with an agent that modulates an expression or activity of a gene, or a protein encoded by the gene, wherein a transcript of the gene comprises a nucleic acid sequence set forth in SEQ ID No 336-449, thereby treating a disease or disorder in a subject.

In another embodiment, the present invention provides method of diagnosing a disease or disorder associated with an alternate splicing pattern of a gene in a subject, wherein a transcript of the gene comprises a nucleic acid sequence set forth in SEQ ID No 1-335, comprising assessing a splicing pattern of the transcript in a biological sample from the subject; assessing a splicing pattern of a reference standard; and comparing the splicing pattern of the transcript to the splicing pattern of a reference standard, thereby diagnosing a disease or disorder associated with an alternate splicing pattern of a gene in a subject.

In another embodiment, the present invention provides method of diagnosing a disease or disorder associated with an alternate splicing pattern of a gene in a subject, wherein a transcript of the gene comprises a nucleic acid sequence set forth in SEQ ID No 336-449, comprising assessing a splicing pattern of the transcript in a biological sample from the subject; assessing a splicing pattern of a reference standard; and comparing the splicing pattern of the transcript to the splicing pattern of a reference standard, thereby diagnosing a disease or disorder associated with an alternate splicing pattern of a gene in a subject.

In another embodiment, the present invention provides a method of assessing a level of association of an RNA transcript of interest with an RBP of interest, comprising the steps of: (a) contacting an RBP-RNA complex containing said RBP of interest with an agent that creates a covalent bond between two components of said RBP-RNA complex; (b) cleaving an RNA molecule of said RBP-RNA complex with an agent capable of cleaving a bond of said RNA molecule, thereby generating a fragment of said RNA molecule, wherein said fragment is at least 22 nucleotide bases in length; (c) selecting said RBP-RNA complex with a molecule that specifically interacts with a component thereof; (d) purifying said RBP-RNA complex, wherein said purifying comprises a chromatographic method; and (e) assessing a presence or amount of said RNA transcript of interest or a fragment thereof in said plurality of RNA molecules, thereby assessing a level of association of an RNA transcript of interest with an RBP of interest.

In another embodiment, the present invention provides a method of screening a test compound for its ability to modulate a level of association between an RBP and an RNA transcript, comprising the steps of: (a) assessing a first level of association between said RBP and said RNA transcript in a first cell by the method of claim 112, wherein said first cell has been contacted with said test compound; (b) assessing a second level of association between said RBP and said RNA transcript in a second cell by the method of claim 112, wherein said second cell has not been contacted with said test compound; and (c) comparing said first level of association with said second level of association, wherein a difference between said first level of association and said second level of association indicates an ability of said test compound to modulate a level of association between said RBP and said RNA transcript.

In another embodiment, there is provided an RBP binding site comprised of a nucleic acid comprising a sequence as set forth in SEQ ID No 1-335 and 450-469.

In another embodiment, there is provided an RBP binding site comprised of a nucleic acid comprising a sequence as set forth in SEQ ID No 336-449 and 503-508.

In another embodiment, there is provided a method of modifying an expression profile of a gene of interest comprising engineering the gene of interest to comprise an RBP binding site comprising a nucleic acid sequence as set forth in SEQ ID No 1-449, 450-469, and 503-508, thereby modifying the expression profile of the gene of interest.

In another embodiment, there is provided the use of a gene that has been engineered to comprise an RBP binding site comprising a nucleic acid sequence as set forth in SEQ ID NO 1-449, 450-469, and 503-508, in order to compete for biological factors that bind the sites of a gene of interest, thus modifying the splicing pattern of the gene of interest.

In another embodiment, there is provided an isolated nucleic acid that comprises a sequence set forth in SEQ ID NO 63, 64, 76, 77, 78, 84, or 292-335.

In another embodiment, there is provided an isolated nucleic acid that comprises a sequence set forth in SEQ ID No 374, 377, 378, 380, 382, 384, 387, 394-396, 415, or 416, 421.

In another embodiment, there is provided an oligonucleotide of at least 15 bases, with a nucleic acid sequence corresponding to SEQ ID NO 1-335, or 336-449, or a complementary sequence thereof.

In another embodiment, there is provided an isolated peptide encoded by a nucleic acid sequence as set forth in SEQ ID No 63, 64, 76, 77, 78, 84, or 292-335.

In another embodiment, there is provided an isolated peptide encoded by a nucleic acid sequence as set forth in SEQ ID No 374, 377, 378, 380, 382, 384, 387, 394-396, 415, or 416, 421.

In another embodiment, there is provided a transgenic mouse comprising a mutation in a Nova-2 gene.

In another embodiment, the present invention provides a method for purifying an RBP present in an RBP-RNA complex containing a known component, comprising the steps of (a) contacting said RBP-RNA complex with an agent that creates a covalent bond between two components of said RBP-RNA complex; (b) cleaving an RNA molecule of said RBP-RNA complex with an agent capable of cleaving a bond of said RNA molecule, thereby generating a fragment of said RNA molecule, wherein said fragment is at least 22 nucleotide bases in length; (c) selecting said RBP-RNA complex with a molecule that specifically interacts with said known component; (d) purifying said RBP-RNA complex under stringent conditions; and (e) removing said RBP from said RBP-RNA complex, thereby purifying an RBP present in an RBP-RNA complex containing a known component.

A method for identifying an unknown RBP present in an RBP-RNA complex containing a known component, comprising the steps of:
 contacting a biological sample with an agent that results in a covalently bound RBP-RNA complex in the biological sample;
 obtaining RNA fragments from the biological sample;
 selecting the RBP-RNA complex containing the known component with a molecule that specifically interacts with the known component;
 purifying the RBP-RNA complex containing the known component under stringent conditions; and
 identifying the unknown RBP from the RBP-RNA complex containing the known component.

BRIEF DESCRIPTION OF THE DRAWINGS

FIG. 1A is a Schematic of CLIP method. FIG. 1B is the Purification of Nova-1-RNA covalent complexes by SDS-PAGE. Adult mouse hindbrain tissue was UV irradiated (+XL), protein-RNA complexes immunoprecipitated with Nova antiserum, RNA labeled with $^{32}$P, and complexes visualized by autoradiography. Without UV irradiation (—XL), no protein-RNA complexes were detected. FIG. 1C shows CLIP performed using mouse forebrain (postnatal day 6; $N^{+/+}$) revealed ~70 kilodalton (kDa) and ~55 kD RNA-protein complexes cross-linked to Nova-2 (N2) (~70 kDa upper band) and smaller isoforms of Nova-1 and Nova-2 (~55 kDa lower band). When Nova-$2^{-/-}$ forebrain was used for CLIP, the 70 kDa Nova-2 band was absent. When the UV cross-linked sample was immunoprecipitated with normal rabbit serum (Control IP), no cross-linked protein-RNA complex was apparent.

FIGS. 2A-2D are Directional cloning of purified cross-linked RNA using RNA primers and T4 RNA ligase. FIG. 2A shows $^{32}$P-labeled RNA was purified from N2A cells following UV cross-linking and IP with anti-Nova antiserum. The size of the RNA fragments ranged from 24-150 bases; the modal size of the RNA was approximately 60 bases. FIG. 2B shows the purified RNA fragments were ligated to 5' and 3' linker oligonucleotides, which added 16 bases to each end of the molecule. The majority of the labeled RNA fragments shifted in size by 32 bases, indicating successful ligation. FIG. 2C is RNA isolated from regions 1 and 2 in B were amplified by RT-PCR with specific primers. The prominent band at 32 bases was product from the ligation of the two RNA oligonucleotides without insert. FIG. 2D shows the products in C were further divided and further amplified by PCR. These products are then used for cloning and sequencing of the RNA insert tags.

FIGS. 3A-3H are the analysis of 340 Nova CLIP fragments. FIG. 3A shows Genomic location of the tags. Tags belonging to genomic regions with no annotated transcripts were labeled as 'unclassified'. 189 fragments aligned to introns within pre-mRNA, 107 to mature mRNA, and 55 to genomic regions to which no transcript has been assigned as yet. FIG. 3B is YCAY tetramer abundance in Nova and Hu CLIP fragments in comparison to control tags. The average number of YCAY tetramers per Nova CLP fragment was 4.18 (99% confidence interval±0.39, average tag length 71±18 nucleotides; n=340) compared with 1.7 per CLIP fragment of an unrelated RBP, Hu (99% confidence interval±0.21, average tag length 62±16 nucleotides; n=94) and 1.1 per random fragment of transcribed genomic sequence (Control; 99% confidence interval±0.03, average tag length 71±18 nucleotides; n=3400). FIG. 3C shows the frequency of nucleotides flanking all CA dimers in Nova CLIP and genomic tags. Certain nucleotides (A in position 1, U in position 3, C in position 4, A in position 5, U in position 6, and C in position 7; in the control sequence, C in position 4 and A in position 5) had a frequency 25% higher than expected on the basis of total nucleotide composition of 29% U, 35% C, 20% A and 17% G in Nova CLIP fragments. FIG. 3D is the 5 most frequent hexamers in Nova CLIP fragments, and the ratio of the average observed/expected abundance compared to control tags; even the least abundant of these, UCAUCC, was in 10 fold excess relative to the average control tag (p=0.013, z-test). FIG. 3E shows filter binding assay results, using Nova-2 fusion protein at the indicated concentrations, and synthetic RNAs shown in (F). FIG. 3F is the sequences of transcribed CLIP fragment RNAs, and control RNAs corresponding to genomic sequence immediately 5' to the CLIP fragments, used in filter binding assay (SEQ ID NOS: 511-518). FIG. 3G is the Distribution of tags relative to number of YCAY tetramers they contain. FIG. 3H is the Annotated list of Nova CLIP fragments.

FIGS. 4A-4D is Nova-dependent regulation of JNK2. FIG. 4A shows neogenin. FIG. 4B shows gephyrin. FIG. 4C shows alternative splicing. Schematic of pre-mRNA alternative splicing in the vicinity of the Nova CLIP fragments are shown on left. Autoradiograms (center) of RT-PCR products for each transcript, which were generated using RNA isolated from Nova $2^{+/+}$ (WT) and Nova $2^{-/-}$ (KO) P6-7 brain cortex, show the migration of bands corresponding to specific spliced isoforms. Each autoradiogram was quantitated and plotted with the standard error from 3 litters. FIG. 4A are asterisk marks a minor splice variant (isoform IV), and JNK2 PCR products present after digestion with AluI are illustrated. FIG. 4C depicts Western blot analysis of gephyrin protein in Nova 2 P1 WT and KO cortex. FIG. 4D shows RT-PCR analysis of gephyrin exon 9 splicing in indicated mouse tissues.

FIGS. 5A and 5B is the list of 21 multiple-hit Nova CLIP fragments organized by primary encoded function and list of Nova CLIP fragments belonging to transcripts coding for proteins with a role in inhibitory control (SEQ ID NOS: 11, 12, 68, 69, 60-62, 519, 95, 7, 8, 87, 207 and 520-522, respectively.

FIG. 6A shows Immunoblot analysis of Nova distribution in cytoplasmic and nuclear fractions from P7 mouse brain (equal volumes of each fraction were loaded in lanes 1 and 2; 50 micrograms (µg) of protein was loaded in lanes 3 and 4). Hsp90 was used as a cytoplasmic marker, and brPTB as nuclear marker. FIG. 6B is Nova immunoreactivity within the post-synaptic dendrite; gold particles associated with small cisternae. FIG. 6C-1 is Nova immunoreactivity in motor neurons was within the nucleus and somatodendritic compartments; in dendrites Nova accumulated at the dendritic periphery (arrowheads) and branch points (arrow). FIG. 6C2-4 are Colocalization of Nova (in red-2 and 3; red areas in original color photo are indicated by arrowheads) (in green-4; green areas in original color photo are indicated by arrowheads) and synapsin (in green-2 and 3; green areas in original color photo are lighter areas not indicated by arrowheads) and gephyrin (in red-4; red areas in original color photo are lighter areas not indicated by arrowheads). Anti-Nova antibodies: affinity purified rabbit anti-Nova (CI and C3) human POMA serum (C2 and C4). Scale bar: 15 um (C1); 9 µm (C2, C3); 6 µm (C4).

FIGS. 7A-7F are Colocalization of Nova protein and GlyRα2 mRNA in motor neurons. FIGS. 7A and 7B depict Fluorescence microscopy and FISH demonstrated GlyRαt mRNA and Nova immunoreactivity at the dendritic periphery, which demonstrated accumulation of GlyRa mRNA and Nova protein at the site (arrows). Fluorescence microscopy and FISH demonstrated GlyRαt mRNA and Nova immunoreactivity at the dendritic periphery, which demonstrated accumulation of GlyRa mRNA and Nova protein at the site (arrows). [(C-F)] FIGS. 7C-7F depict Nova protein (HRP immuno-labeling) and GlyRαt2 mRNA ISH signal (gold particles) formed aggregates within the dendritic cytoplasm (arrows) and in front of synaptic boutons (arrowheads, b). Note in FIGS. 7D and 7F the association of the Nova protein and mRNA signals with small cisternae. Anti-Nova antibodies: human POMA serum. Scale bar: 0.2 µm (B-E); 0.35 µm (D).

FIGS. 8A and 8B are an annotated list of 114 neuronal Hu protein CLIP fragment sequences and a Sequence alignment of Hu CLIP fragment sequences.

FIG. 9A-9E shows Generation and characterization of Nova-2 knockout mice. FIG. 9A depicts a Cloning scheme. FIG. 9B depicts Southern blot showing deletion of Nova-2 from genomic DNA. FIG. 9C depicts Western blot showing elimination of 55 KDa and 70 KDa isoforms of Nova-2 from knockout animals. FIG. 9D depicts Size reduction of Nova-2 knockout mice. FIG. 9E depicts Survival curve of Nova-2 mice.

FIGS. 10A-10B are Alternative splicing defects in Nova-2 knockout Mice. FIG. 10A shows Nova-2 mice are deficient in inclusion of γ2L exon of GABAγ2 RNA. FIG. 10B shows Splicing pattern of alternately spliced exons in GABAγ2, GlyR α2, Nova, src, and ICH-1 in Nova-2 knockout mice.

DETAILED DESCRIPTION OF THE PRESENT INVENTION

The present invention provides, in one embodiment, methods of purifying an RNA molecule interacting with an RBP of interest, comprising covalent cross-linking and immunoprecipitation, and the use of such methods to analyze association of an RNA transcript with an RBP. The invention also provides sequences of RNA molecules that mediate binding to an RBP, proteins encoded by the sequences, methods of identifying the sequences, and the use of the sequences in a screening assay to identify bioactive molecules. The invention also provides RNA motifs found among the sequences and compounds that bind to the RNA motifs. In addition, the invention provides methods of treating diseases associated with a function of an RNA binding protein In another embodiment, the present invention provides a method for purifying an RNA molecule interacting with an RBP of interest in a biological sample, comprising the steps of: (a) contacting the biological sample with an agent that creates a covalent bond between the RNA molecule and the RBP of interest, thereby generating a covalently bound RBP-RNA complex containing the RNA molecule; (b) cleaving the RNA molecule by contacting the RBP-RNA complex with an agent capable of cleaving a bond thereof, thereby generating a fragment of the RNA molecule, wherein the fragment is at least 22 nucleotide bases in length; (c) selecting the RBP-RNA complex with a molecule that specifically interacts with a component of the RBP-RNA complex; and (d) purifying the RBP-RNA complex under stringent conditions, thereby purifying an RNA molecule interacting with an RBP of interest The general term for methods of the present invention for purifying an RNA molecule interacting with an RBP of interest comprising covalent cross-linking and immunoprecipitation, is "the CLIP method" (cross-linking and immunoprecipitation method).

In another embodiment, the present invention provides a method of identifying an RNA molecule interacting with an RBP of interest, comprising purifying an RNA molecule interacting with the RBP of interest by the CLIP method, and identifying the RNA molecule, thereby identifying an RNA molecule interacting with an RBP of interest.

In one embodiment, the plurality of RNA molecules interacting with the known RBP are analyzed to generate a profile of RNA molecules interacting with the known RBP in the biological sample.

In one embodiment, the RNA fragments that are generated, or the RNA in the RBP-RNA complex, is any type of RNA known in the art, such as, for example, tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes.

Figure 1A:
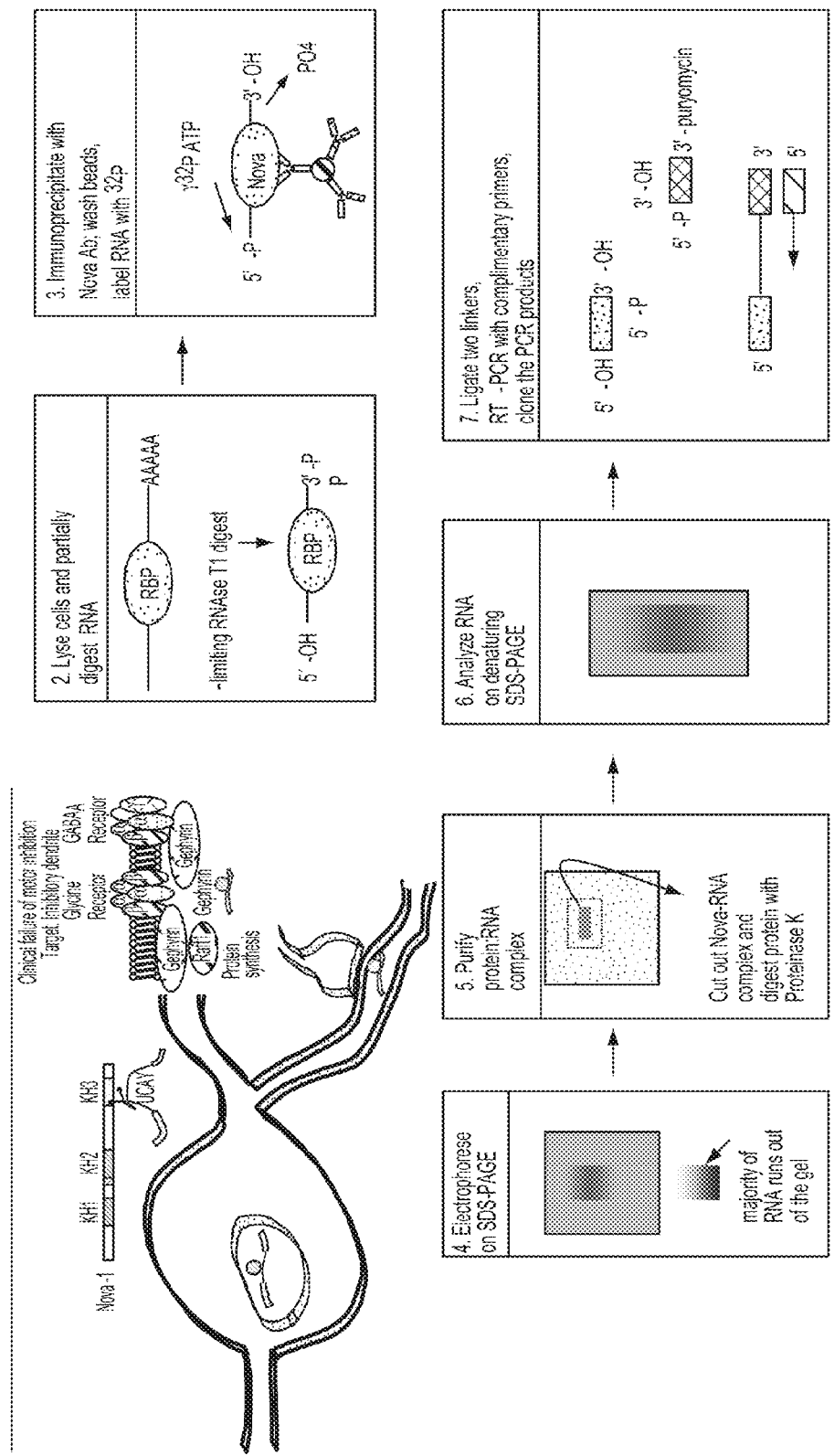
FIGS. 1A-1C depict the CLIP method.

In one embodiment, as shown in FIG. 1A, a biological sample is contacted with an agent that results in a covalently bound RBP-RNA complex (step 1 of FIG. 1A). In this embodiment, the biological sample is mouse brain tissue that has been disassociated into a cell suspension, and the agent is UV irradiation of 254 nm wavelength. As a result of contact with the agent, a covalent bond is formed between an RNA molecule and a protein molecule in close contact with the RNA molecule. This RNA molecule covalently bound to a protein molecule is referred to herein as a covalently bound RBP-RNA complex. In this embodiment, cells are collected and lysed with detergent and high salt, which disassociates RNA from protein in some RBP-RNA complexes that are not covalently bound.

Covalent cross-linking has the advantage of forming bonds between RBP-RNA complexes that are in direct contact. Covalent binding enables the use, in some embodiments of the present invention, of rigorous purification schemes for obtaining highly purified RBP-RNA complexes. In one embodiment, the purification scheme may comprise immunoprecipitation. In another embodiment, the purification scheme may comprise rigorous washing of immunoprecipitates. In another embodiment, the purification scheme may comprise boiling complexes in SDS. In another embodiment, the purification scheme may comprise separating complexes on SDS-PAGE. In another embodiment, the purification scheme may comprise transferring samples to NC, which retains RNA-protein complexes, but not free RNA.

In another embodiment, the covalent bond enables partial cleavage of RNA molecules without affecting their protein binding, such that only short RNA fragments can be purified. In another embodiment, this partial cleavage enables identification of the region of the RNA responsible for binding to the RBP or another. In another embodiment, this partial cleavage facilitates purification of the RBP-RNA complex. Following purification of RNA-protein complexes that have been covalently cross-linked, protein can be digested with nucleases, and RNA can be cloned using linker ligation and RT-PCR. Each of these methods represents a separate embodiment of the present invention, and is described in more detail herein.

In another embodiment, the present invention provides a method for purifying an RNA molecule interacting with an RBP of interest in a biological sample, comprising the steps of (a) contacting the biological sample with an agent that creates a covalent bond between the RNA molecule and the RBP of interest, thereby generating a covalently bound RBP-RNA complex containing the RNA molecule; (b) cleaving the RNA molecule with an agent capable of cleaving a bond thereof, thereby generating a fragment of the RNA molecule, wherein the fragment is at least 22 nucleotide bases in length; (c) selecting the RBP-RNA complex with a molecule that specifically interacts with a component of the RBP-RNA complex; and (d) purifying the RBP-RNA complex, wherein the purifying step comprises an agent that disrupts an intermolecular interaction, thereby purifying an RNA molecule interacting with an RBP of interest.

In another embodiment, the present invention provides a method for purifying an RNA molecule interacting with an RBP of interest in a biological sample, comprising the steps of (a) contacting the biological sample with an agent that creates a covalent bond between the RNA molecule and the RBP of interest, thereby generating a covalently bound RBP-RNA complex containing the RNA molecule; (b) cleaving the RNA molecule with an agent capable of cleaving a bond thereof, thereby generating a fragment of the RNA molecule, wherein the fragment is at least 22 nucleotide bases in length; (c) selecting the RBP-RNA complex with a molecule that specifically interacts with a component of the RBP-RNA complex; and (d) purifying the RBP-RNA complex, wherein the purifying comprises a chromatographic method, thereby purifying an RNA molecule interacting with an RBP of interest.

In another embodiment, the present invention provides a method for purifying an RBP present in an RBP-RNA complex containing a known component, comprising the steps of (a) contacting said RBP-RNA complex with an agent that creates a covalent bond between two components of said RBP-RNA complex; (b) cleaving an RNA molecule of said RBP-RNA complex with an agent capable of cleaving a bond of said RNA molecule, thereby generating a fragment of said RNA molecule, wherein said fragment is at least 22 nucleotide bases in length; (c) selecting said RBP-RNA complex with a molecule that specifically interacts with said known component; (d) purifying said RBP-RNA complex under stringent conditions; and (e) removing said RBP from said RBP-RNA complex, thereby purifying an RBP present in an RBP-RNA complex containing a known component.

In one embodiment, the term "contacting", "contact" or "contacted" when in reference to a cell refers to direct exposure of the cell to an agent, compound or composition of the invention. In another embodiment, the term "contacting", "contact" or "contacted" when in reference to a cell refers to indirect exposure of the cell to an agent, compound or composition of the invention. In one embodiment, contacting a cell may comprise subjecting the cell to electromagnetic radiation. In another embodiment, a cell is exposed directly to a chemical that forms the covalent bond. In another embodiment, supply to the cell is indirect, such as via provision in a culture medium that surrounds the cell. In another embodiment, contacting a cell may comprise direct injection of the cell through any means well known in the art, such as microinjection.

In one embodiment, a "target cell" can be, for example, a type of cell or tissue in an organism, or a single cell type, e.g., grown in tissue culture. In another embodiment, an expression vector-ligand complex can be formed in which the ligand comprises a fusogenic viral peptide to disrupt endosomes, allowing the expression vector to avoid lysosomal degradation. In yet another embodiment, the expression vector can be targeted in vivo for cell specific uptake and expression, by targeting a specific receptor (see, e.g., PCT Publications WO 92/06180 dated Apr. 16, 1992; WO 92/22635 dated Dec. 23, 1992; WO92/20316 dated Nov. 26, 1992; WO93/14188 dated Jul. 22, 1993; WO 93/20221 dated Oct. 14, 1993). Alternatively, the expression vector can be introduced intracellular and incorporated within host cell DNA for expression, by homologous recombination (Koller and Smithies, 1989, Proc. Natl. Acad. Sci. USA 86:8932-8935; Zijistra et al., 1989, Nature 342:435-438). Each of these methods represents a separate embodiment of the present invention.

In one embodiment, the biological sample of step (a) is from a healthy source. In another embodiment, the biological sample of step (a) is from a diseased source. In another embodiment, the biological sample of step (a) may comprise a cell culture. In another embodiment, the biological sample of step (a) may comprise a cell line. In another embodiment, the biological sample may comprise a cell extract. In another embodiment, the biological sample may comprise a cell lysate. In another embodiment, the biological sample may comprise whole tissue. In another embodiment, the biological sample may comprise a tissue extract. In another embodiment, the biological sample is a tissue sample, such as, for example, a biopsy. In another embodiment, the biological sample may comprise a whole organ. In another embodiment, the biological sample may comprise a tumor. In another embodiment, the biological sample may comprise a tumor cell. In another embodiment, the biological sample may comprise a cell mass. In another embodiment, the tissue sample may comprise diseased tissue. In another embodiment, the biological sample may comprise a tumor cell or tumor cell extract. In another embodiment, the biological sample may comprise a pre-cancerous lesion, polyp, or cyst. In another embodiment, the biological sample may comprise a combination thereof. Each possibility represents a separate embodiment of the present invention.

In another embodiment, the biological sample may comprise a cellular component or compartment. In one embodiment, the cellular component or compartment is neuronal dendrites. In one embodiment, laser capture micro-dissection is used in conjunction with the CLIP method to purify RBP-RNA complexes, from, for example, molecular layers of brain, tumor sections, or tumor cells. Laser capture micro-dissection is, in one embodiment, performed by any technique known to those skilled in the art, such as, for example, the techniques described in Biotechniques. 34:42-46. Each such technique represents a separate embodiment of the present invention.

In one embodiment, cells comprising the biological sample are suspension cells. In another embodiment, the cells are adherent cells. In another embodiment, the cells are transformed cells. In another embodiment, the cells are tissue culture cells. In another embodiment, the cells are primary cell lines. Cells comprising the biological sample are, in one embodiment, grown in any method known to one skilled in the art. Each such method represents a separate embodiment of the invention.

In one embodiment, the biological sample is disrupted, disaggregated, homogenized, or lysed by any technique known in the art. For example, the biological sample may be made into a single-cell suspension using a nylon filter or mesh. Cells or tissue comprising the biological sample may, in one embodiment, be adhered to a substrate such as a chip, a slide, a dish, etc. The cells are, in one embodiment, washed according to techniques known to one skilled in the art. Each such technique represents a separate embodiment of the present invention.

In one embodiment, the covalent bond of step (a) is formed with irradiation. The source of irradiation may emit, in one embodiment, radiation of a discrete wavelength. In another embodiment, the source may emit radiation dispersed throughout a region of the electromagnetic radiation spectrum. In another embodiment, the source may emit a mixture of radiation, some of which is of a discrete wavelength, and some of which is dispersed throughout a region of the electromagnetic radiation spectrum.

In one embodiment, the irradiation may result from a polychromatic irradiation source. Polychromatic refers, in one embodiment, to a source that emits radiation of various wavelengths. Such wavelengths may be anywhere in the electromagnetic radiation spectrum. The radiation emission spectra of various types of irradiation sources are known in the art.

In another embodiment, the irradiation may result from a monochromatic irritation source. Monochromatic refers, in one embodiment, to a source that emits radiation of a single wavelength. In another embodiment, monochromatic refers to a source that emits radiation primarily of a single wavelength.

In another embodiment, the irradiation may result from a mercury light. Mercury lamps emit radiation of 254 nm, and may also have polychromatic background emissions at other discrete wavelengths, e.g., 313 nm, 365 nm, 405 nm, 436 nm, 546 nm, 579 nm, 1015 nm and 1140 nm. This is a fairly unique characteristic of these types of lamps (see U.S. Pat. No. 6,611,375).

In another embodiment, the irradiation may result from a two-photon excitation apparatus (So P T et al, Cell Mol Bio (Noisy le grand) 44:771). In this technique, small structures are formed by multiple photon-induced polymerization or cross-linking of a precursor composition. "Multiple photon" as used herein means, in one embodiment, the simultaneous absorption of multiple photons by a reactive molecule. This method is described in detail in U.S. Pat. No. 6,316,153 and references therein.

In one embodiment, the irradiation used to form the covalent bond of step (a) is ultraviolet irradiation. Ultraviolet radiation, in one embodiment, is a form of energy that occupies a portion of the electromagnetic radiation spectrum (the electromagnetic radiation spectrum ranges from cosmic rays to radio waves). Ultraviolet radiation can come from many natural and artificial sources. Depending on the source of ultraviolet radiation, it may be accompanied by other (non-ultraviolet) types of electromagnetic radiation (e.g. visible light).

Particular types of ultraviolet radiation are herein described in terms of wavelength. Wavelength is herein described in terms of nanometers ("nm"). In one embodiment, ultraviolet radiation extends from approximately 180 nm to 400 nm. In another embodiment, the ultraviolet radiation has a wavelength of about 254 nm. In another embodiment, the ultraviolet radiation has a different wavelength. When a radiation source, by virtue of filters or other means, does not allow radiation below a particular wavelength (e.g. 320 nm), it is said to have a low end "cutoff" at that wavelength (e.g. "a wavelength cutoff at 300 nanometers"). Similarly, when a radiation source allows only radiation below a particular wavelength (e.g. 360 nm), it is the to have a high end "cutoff" at that wavelength (e.g. "a wavelength cutoff at 360 nanometers"). In another embodiment, the source of ultraviolet radiation is a fluorescent source. All of these sources represent separate embodiments of the present invention. In one embodiment, the device of the present invention comprises an additional filtering means. In one embodiment, the filtering means comprises a liquid filter solution that transmits only a specific region of the electromagnetic spectrum. The use of sources of irradiation is well known to those skilled in the art (see, for example Diffey, B L, Methods 28:4-13; and Chen J et al, Cancer J. 8:154-63). Each type of radiation represents a separate embodiment of the present invention.

In one embodiment, a chemical group such as, for example, puromycin is added to RNA to facilitate formation of the covalent bond of step (a). This method is described in Rodriguez-Fonseca C et al (RNA 6:744-54).

In one embodiment, the covalent bond of step (a) is formed with a chemical. In one embodiment, the chemical is formaldehyde. In another embodiment, the chemical is a derivative of formaldehyde. In another embodiment, the chemical is paraformaldehyde. In another embodiment, the chemical is glutaraldehyde. In another embodiment, the chemical is osmium tetroxide. In another embodiment, the chemical is acetone. In another embodiment, the chemical is an alcohol. In another embodiment, the chemical is an NHS ester. In another embodiment, the chemical is a Maleimides. In another embodiment, the chemical is a haloacetyl. In another embodiment, the chemical is a pyridyl disulfide. In another embodiment, the chemical is a sulfhydryl modifier such as SATA, SPDP or Traut's Reagent. In another embodiment, the chemical is hydrazide. In another embodiment, the chemical is 1-Ethyl-3-(3-Dimethylaminopropyl)-Carbodiimide Hydrochloride. In another embodiment, the chemical is an aryl azide or a derivative thereof. In another embodiment, the chemical is any other cross-linking compound known in the art. The cross-linking compound may, in one embodiment, be applied over a broad range of concentrations. Each type of chemical represents a separate embodiment of the present invention.

In one embodiment, the cross-linking compound is photoactivated. Chemical cross-linking methods are known to those skilled in the art (see, for example, Hecht A et al, Methods Mol Biol. (1999) 119:469-79; and Strutt H et al, Methods Mol Biol. (1999) 119:455-67.

In one embodiment, the covalent bond is a reversible bond. In another embodiment, the covalent bond may be an irreversible bond. In another embodiment, a reversible bond is a bond capable of being broken or disrupted by exposure to heat, acid, base, or another means without destroying the remainder of the molecule.

In step (b) of the present invention, RNA molecules in the biological sample are cleaved (digested, broken, or fragmented) to obtain fragments of at least 22 bases in length (FIG. 1A, step 2). Step (b) may, in some embodiments, facilitate the selection of RBP-RNA complexes. In another embodiment, step (b) may facilitate identification of binding sites on RNA molecules that are isolated by this method.

In one embodiment, the digestion of step (b) generates a modified RBP-RNA complex of interest containing a fragment of the RNA molecule present in the original RBP-RNA complex. In one embodiment, step (c) and subsequent steps are performed on the modified RBP-RNA complex. In another embodiment, step (c) is performed prior to the modification performed in step (b). Each possibility represents a separate embodiment of the present invention.

In one embodiment, cleavage of the RNA molecules is performed by contact with an agent capable of breaking a bond of an RNA molecule. In one embodiment, the agent is capable of breaking a bond of any RNA molecule in a sequence-specific manner. In another embodiment, the agent preferentially breaks bonds of RNA molecules having a particular sequence. In one embodiment, the bond is a phosphodiester bond.

In one embodiment, as depicted in FIG. 1A, the biological sample is a lysate at this point in the method. In the embodiment depicted, the fragments are obtained by digestion with limiting amounts of RNAse T1, which cleaves RNA molecules in a largely random fashion, leaving RNA fragments of approximately 100 bases. In the embodiment depicted, the lysate is then subjected to a high-speed centrifugation, which removes high molecular weight material from the cell. In one embodiment, the fragments average about 70-100 nucleotides in length.

Some of the RNA fragments obtained by step (b) of the present invention may contain the RBP binding site. In one embodiment, an RBP is bound to the binding site. It will be understood to one skilled in the art that, in one embodiment, the size of the RNA fragments may reflect the fact that an RBP is bound.

In one embodiment, the biological sample is treated with a DNAse prior to step (b). In another embodiment, the DNAse treatment may follow step (b). In another embodiment, the DNAse treatment is simultaneous with step (b). In another embodiment, any DNAse known in the art may be used. The use of such enzymes is well known to those skilled in the art, and is described, for example, in Molecular Cloning, (2001), Sambrook and Russell, eds. The use of each DNAse represents an additional embodiment of this invention.

In another embodiment, step (b) is carried out with a nuclease. In one embodiment, the nuclease is RNAse T1. T1 digestion yields —OH groups on the 5' ends and 2', 3' cyclic phosphate groups on the 3' ends of RNA fragments (FIG. 1A). In one embodiment, fragments generated by RNAse T1 digestion are suitable for labeling with T4 PNK and $^{32}$P phosphate, as disclosed herein. In another embodiment, fragments generated by RNAse T1 digestion are suitable for directional ligation of nucleotide linkers onto the fragments. In another embodiment, fragments generated by RNAse T1 digestion are suitable for directional subcloning of the fragments into a vector.

In one embodiment, titrations of RNAse T1 are performed to ascertain dilutions which yield RNA CLIP fragments of the desired length. Techniques for titrating enzymes are known to those skilled in the art.

The covalent bond formed in step (a) enables, in one embodiment, the use of nucleases such as RNAse T1 in the CLIP method. In another embodiment, the covalent bond formed in step (a) enables fragmentation of the RNA (by a variety of means) without separating the RNA from its RBP-RNA complex. Fragmentation facilitates, in one embodiment, extrication and subsequent purification of RBP-RNA complexes that bound to ribosome and other cellular structures. Nucleases such as RNAse T1 in the CLIP method RNAse T1 cleaves RNA molecules in a relatively sequence non-specific fashion. Each of these properties of CLIP contribute to its ability to purify a representative sample of RNA molecules interacting with a given RBP.

In one embodiment, the nuclease is an endonuclease. In another embodiment, the nuclease is an exonuclease. In another embodiment, the nuclease is S1 Nuclease. In another embodiment, the nuclease is Mung Bean Nuclease. In another embodiment, the nuclease is Bal3I nuclease. In another embodiment, the nuclease is S1 nuclease. In another embodiment, the nuclease is T7 gene 6 exonuclease. In another embodiment, the nuclease is Exonuclease III. In another embodiment, the nuclease is the 3'-5' exonuclease activity of a polymerase, such as T4 DNA polymerase, a Klenow fragment, and f1 gene product II or homologous enzymes from other filamentous bacteriophage (Meyer and Geider, J. Biol. Chem. 254:12636). In another embodiment, the nuclease is any nuclease known in the art.

A nuclease, according to one embodiment of the invention, also includes *Saccharomyces cerevisiae* RAD27, and *Schizosaccharomyces pombe* RAD2, Pol I DNA polymerase associated 5' to 3' exonuclease domain, (e.g. *E. coli, Thermus aquaticus* (Taq), *Thermus flavus* (Tfl), *Bacillus caldotenax* (Bca), *Streptococcus pneumoniae*) and phage functional homologues of FEN including but not limited to T5 5' to 3' exonuclease, T7 gene 6 exonuclease and T3 gene 6 exonuclease. The use of these nucleases is familiar to those skilled in the art (see, for example, Molecular Cloning, (2001), Sambrook and Russell, eds.). Each of these nucleases represents a separate embodiment of this invention.

In other embodiments, obtaining RNA fragments in step (b) is performed using a cleaving agent. In another embodiment, the cleaving agent is a single-stranded-specific endonucleases. In another embodiment, the cleaving agent is a double-stranded-specific endonuclease. In another embodiment, the cleaving agent is a chemical cleaving agent which preferentially cleaves single-stranded molecules. In another embodiment, the cleaving agent is a chemical cleaving agents which preferentially cleaves double-stranded molecules. In another embodiment, the cleaving agent is S1 Nuclease. In another embodiment, the cleaving agent is Mung Bean Nuclease. In another embodiment, the cleaving agent is potassium permanganate. In another embodiment, the cleaving agent is a cleaving agents, which cleaves double-stranded oligonucleotides in a random or pseudorandom way. In another embodiment, the cleaving agent is DNase I. The concentration and cutting time of the cleaving agent must, in one embodiment, be determined experimentally for each hybridization procedure. Each type of cleaving agent represents a separate embodiment of the present invention.

In one embodiment, step (b) is performed by fragmentation. The sequences can be, for example, either randomly fragmented or fragmented at specific sites in the nucleic acid sequence. Any known method of fragmentation may be employed in step (b), according to this embodiment. Various methods of fragmenting nucleic acids will be known to those of skill in the art. These methods may be, for example, either chemical or physical in nature.

In alternate embodiments, fragmentation may include partial degradation with a DNAse, RNAse, partial depurination with acid followed by heating, and restriction enzymes or other enzymes, which cleave nucleic acid at known or unknown locations. Physical fragmentation methods may involve subjecting the nucleic acid to a high shear rate. High shear rates are produced, in one embodiment, by moving nucleic acid through a chamber or channel with pits or spikes, or forcing the nucleic sample through a restricted size flow passage, e.g. an aperture having a cross sectional dimension in the micron or submicron scale. Each of these methods represents a separate embodiment of this invention.

In other embodiments of this invention, step (b) is performed by using radical-generating coordination complexes or with a syringe-operated silica micro-column. Those of skill in the art will be familiar with methods of fragmenting RNA (see, for example, Current Protocols in Molecular Biology, (1998) Ausubel, et al, eds.), each of which represents another embodiment of this invention. In another embodiment, RNA is fragmented by heat and ion-mediated hydrolysis.

In another embodiment, step (b) is performed by physical or chemical means. The sequences can be randomly fragmented or fragmented at specific sites in the nucleic acid sequence. In another embodiment, step (b) is performed by breaking the nucleic acid in the biological sample. In another embodiment, step (b) is performed exposing it to harsh physical treatment (e.g., shearing or irradiation). In another embodiment, step (b) is performed or harsh chemical agents (e.g., by free radicals, including, but not limited to hydroxyl radicals; metal ions; acid treatment). The reaction conditions suitable for fragmenting nucleic acid molecules by physical or chemical methods are well known in the art. Furthermore, partial PCR extension, PCR stuttering, and other related methods for producing partial length copies of a parental sequence can be used to effect "fragmentation", e.g., to obtain a hybrid product which contains segments derived from different parental sequences. Any method of fragmenting nucleic acid known in the art represents an additional embodiment of this invention.

As mentioned, in one embodiment fragmentation of the RNA molecules present in the RBP-RNA complexes render it suitable for subsequent subcloning. "Subcloning," refers, in one embodiment, to inserting an oligonucleotide into a nucleotide molecule. In one embodiment, isolated DNA encoding an RNA transcript can be inserted into an appropriate expression vector that is suitable for the host cell to be employed such that the DNA is transcribed to produce the RNA. A large number of vector-host systems known in the art may be used in this embodiment. A vector may include, in some embodiments, an appropriate selectable marker. The vector may further include an origin of replication, and may be a shuttle vector, which can propagate both in bacteria, such as, for example, *E. coli* (wherein the vector comprises an appropriate selectable marker and origin of replication) and be compatible for propagation in vertebrate cells, or integration in the genome of an organism of choice. The vector according to this aspect of the present invention can be, for example, a plasmid, a bacmid, a phagemid, a cosmid, a phage, a modified or unmodified virus or an artificial chromosome. Many such vectors are commercially available, and their use is well known to those skilled in the art (see, for example, Molecular Cloning, (2001), Sambrook and Russell, eds.).

The insertion into a vector can, for example, be accomplished by ligating the DNA fragment into a vector which has complementary cohesive termini. However, if the complementary restriction sites used to fragment the DNA are not present in the cloning vector, the ends of the DNA molecules may be enzymatically modified. In another embodiment, any site desired may be produced by ligating nucleotide sequences (linkers) onto the DNA termini; these ligated linkers may comprise specific chemically synthesized oligonucleotides encoding restriction endonuclease recognition sequences.

In another embodiment, the nucleotide molecule into which the oligonucleotide is inserted may be a plasmid, cosmid, or the like, or a vector or strand of nucleic acid. In another embodiment, the nucleotide molecule is genetic material of a living organism, virus, phage, or material derived from a living organism, virus, or phage. In one embodiment, the nucleotide molecule is linear. In another embodiment, the nucleotide molecule is circular. In another embodiment, the nucleotide molecule is concatemerized. In another embodiment, the nucleotide molecule may be of any length. Each of these types of nucleotide molecules represents a separate embodiment of the invention. Methods for subcloning are known to those skilled in the art, and are described, for example in Molecular Cloning, (2001), Sambrook and Russell, eds.

In one embodiment, the biological sample is subjected to a centrifugal force at some point after step (a). In one embodiment, the centrifugation or settling step removes high-molecular weight (MW) material from the biological sample. In another embodiment, the centrifugation or settling step removes ribosomes from the biological sample. In another embodiment, the biological sample is allowed to settle. Each method represents a separate embodiment of the present invention.

In one embodiment, step (b) is performed before step (c). In another embodiment, step (b) is performed after part or all of step (c). In another embodiment, step (b) is performed concurrently with all or part of step (c).

In step (c) of the present invention, an RBP-RNA complex of interest is selected with a molecule that specifically interacts with a component of the RBP-RNA complex of interest (FIG. 1A, step 3). In one embodiment, as depicted in FIG. 1A, the method of selection is immunoprecipitation and the molecule that specifically interacts with a component of the RBP-RNA complex of interest is antisera directed against the protein of interest, in this case Nova-1 or Nova-2 protein. The immunoprecipitation method depicted in FIG. 1A comprises thorough washing of RBP-RNA complexes of interest, resulting in the selective removal of unwanted molecules. In the embodiment depicted in FIG. 1A, RNA molecules remaining after the washing are phosphorylated and labeled with $\gamma$-$^{32}$P ATP, allowing detection at a later step.

In one embodiment, the biological sample is pre-cleared prior to step (c). "Pre-clearing" comprises, in one embodiment, immunoprecipitating the sample using pre-immune serum or an irrelevant antibody, and is typically used to remove proteins and other substances that tend to stick non-specifically to other molecules ("sticky molecules"). In another embodiment, a similar method of removing sticky molecules is employed. In another embodiment, sticky molecules are "blocked", or rendered less sticky, by the addition of a blocking agent such as milk powder to the solution used in step (c). Each such method represents a separate embodiment of the present invention.

In one embodiment, the component of the RBP-RNA complex of interest selected in step (c) is an RBP. In another embodiment, the component is an RNA-associated protein. In another embodiment, the component is a nucleic acid associated with the RBP-RNA complex. In another embodiment, the component of the RBP-RNA complex of interest selected in step (c) is an mRNA molecule associated with the RBP-RNA complex. In another embodiment, the component is another molecule or compound (e.g., carbohydrate, lipid, vitamin, etc.) that associates with the RBP-RNA complex.

In one embodiment, the component of the RBP-RNA complex of interest selected in step (c) is Nova-1 protein, Nova-2 protein, or a combination thereof. According to this aspect of the invention, the Nova-1 and Nova-2 may include wild-type protein sequences, as well as other variants (including alleles) of the native protein sequence. In another embodiment, the component selected is a 55 KDa isoform of Nova-2. In another embodiment, the component selected is a 70 KDa isoform of Nova-2. Nova-1 and Nova-2 proteins are homologous to one another, and have similar or identical function (FIGS. 9-10).

In one embodiment, "variants" refers to proteins or genes that result from natural polymorphisms. In another embodiment, "variants" refers to proteins or genes that are synthesized by recombinant methodology. In another embodiment, "variants" refers to proteins or genes that differ from wild-type protein by one or more amino acid substitutions, insertions, deletions, or the like. As will be appreciated by those skilled in the art, a nucleotide sequence encoding a protein mentioned herein or a variant may differ from the known native sequences, due to codon degeneracies, nucleotide polymorphisms, or amino acid differences. Each of these represents an additional embodiment of the invention.

In another embodiment, the component of the RBP-RNA complex of interest selected in step (c) is an ELAV/Hu protein such as HuA, HuB, HuC, HuD or mHuR, or a combination thereof. Hu family proteins are RNA-binding proteins, antibodies against which are found in patients with small-cell lung carcinoma, are associated with sensory neuronopathy (PEM/SN), paraneoplastic cerebellar degeneration and MS. HuD, a neuronal Hu protein, is an RBP that is believed to shuttle between the nucleus and cytoplasm. In another embodiment, the component of the RBP-RNA complex of interest bound to in step (c) is a FXRP family protein such as FMRP, FXRP1, or FXRP2, or a combination thereof. FMRP is a family of RBPs that are implicated in Fragile X Syndrome. In another embodiment, the component of the RBP-RNA complex of interest bound to in step (c) is Sjogren's Syndrome related antigen Ro (SS-A), Sjogren's Syndrome related antigen La (SS-B), or a protein belonging of the ribonuclear proteins (RNP) family, or a combination thereof. SS-A, SS-B, and RNP proteins are antigens that have been implicated in autoimmune disorders such as SLE, Sjogren's Syndrome, JRA, and HAM/TSP. In another embodiment, the component of the RBP-RNA complex of interest bound to in step (c) is calreticulin. Calredculin is an RBP that has been implicated in Sjogren's syndrome, PBC, autoimmune hepatitis type 1, MS, coeliac disease, and yersinosis. In another embodiment, the component of the RBP-RNA complex of interest bound to in step (c) is SMN protein, a protein belonging to the CELF proteins family, or SCAT protein, or a combination thereof. In another embodiment, the component of the RBP-RNA complex of interest bound to in step (c) is SF2/ASF. SF2/ASF is a protein that has been implicated in spinal muscular atrophy. In another embodiment, the component of the RBP-RNA complex of interest bound to in step (c) is a small nucleolar ribonucleoprotein complex (snoRNP). SnoRNP have been implicated in SLE and SSc. In another embodiment, the component of the RBP-RNA complex of interest bound to in step (c) is heterogeneous nuclear ribonuclear protein-A1 (hnRNP-A1). hnRNA-A1 has been implicated in HAM/TSP.

The term "homology", as used herein, when in reference to any protein or peptide, may indicate, in one embodiment, a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. In another embodiment, conservative substitutions are considered as part of sequence identity when determining homology. Neither N- or C-terminal extensions nor insertions shall be construed as reducing identity or homology. Methods and computer programs for the alignment are well known in the art.

In one embodiment, "corresponding" refers to identity of greater than 70%. In another embodiment, "corresponding" refers to identity of greater than 75%. In another embodiment, "corresponding" refers to identity of greater than 80%. In another embodiment, "corresponding" refers to identity of greater than 85%. In another embodiment, "corresponding" refers to identity of greater than 90%. In another embodiment, "corresponding" refers to identity of greater than 95%. In another embodiment, "corresponding" refers to identity of greater than 97%. In another embodiment, "corresponding" refers to identity of greater than 98%. In another embodiment, "corresponding" refers to identity of greater than 99%. In another embodiment, "corresponding" refers to identity of 100%.

The term "homology", as used herein, when in reference to any nucleic acid sequence similarly may indicate, in one embodiment, a percentage of nucleotides in a candidate sequence that are identical with the nucleotides of a corresponding native nucleic acid sequence.

Homology may be determined in the latter case by computer algorithm for sequence alignment, by methods well described in the art. For example, computer algorithm analysis of nucleic acid sequence homology may include the utilization of any Number of software packages available, such as, for example, the BLAST, DOMAIN, BEAUTY (BLAST Enhanced Alignment Utility), GENPEPT and TREMBL packages.

An additional means of determining homology is via determination of candidate sequence hybridization, methods of which are well described in the art (See, for example, "Nucleic Acid Hybridization" Hames, B. D., and Higgins S. J., Eds. (1985); Molecular Cloning, (2001), Sambrook and Russell, eds.; and Current Protocols in Molecular Biology, (1998) Ausubel, et al, eds.). In one embodiment, methods of hybridization are carried out under moderate to stringent conditions, to the complement of a DNA encoding a native peptide derived from Nova-1, Nova-2, an ELAV/Hu protein, FXRP, SS-A, SS-B, an RNP protein, calreticulin, SMN protein, a protein belonging to the CELF proteins family, or SCAT protein. Hybridization conditions being, for example, overnight incubation at 42° C. in a solution comprising: 10-20% formamide, 5×SSC (150 millimolar (mM) NaCl, 15 mM trisodium citrate), 50 mM sodium phosphate (pH 7.6), 5×Denhardt's solution, 10% dextran sulfate, and 20 μg/ml denatured, sheared salmon sperm DNA.

Protein and/or peptide homology for any amino acid sequence listed herein are, in one embodiment, determined by methods well described in the art, including immunoblot analysis, or via computer algorithm analysis of amino acid sequences, utilizing any of a Number of software packages available, via established methods. Some of these packages may include the FASTA, BLAST, MPsrch or Scanps packages, and may employ the use of the Smith and Waterman algorithms, and/or global/local or BLOCKS alignments for analysis, for example. In another embodiment, the web site clustalw is used for analysis (FIG. 8B). The use of each of these methods is known to those skilled in the art. Each method for determining homology represents an additional embodiment of the present invention.

In one embodiment, step (c) comprises selecting the RBP-RNA complex by immunoprecipitation (IP). In another embodiment, the RBP-RNA complex is selected by magnetic separation. In one embodiment, the IP is performed in a similar manner to one of the embodiments described in Example 1.

The term "IP" herein, refers, in one embodiment, to a technique for selecting a molecule of interest from a biological sample. Briefly, the biological sample is contacted with a molecule that interacts with the molecule of interest and attaching or adhering the molecule that interacts with the molecule of interest to a substrate. IP may include a step of washing the substrate to remove impurities. IP may, in one embodiment, comprise protein A/sepharose beads. In another embodiment, IP may comprise protein G/sepharose beads. In one embodiment, IP comprises magnetic beads such as Dynabeads. In another embodiment, IP may comprise any type of solid support, such as any type of bead, plate, column, a fiber, or an array. The molecule that specifically interacts with a component of the RBP-RNA complex of interest may be attached, in one embodiment, to the substrate using any known method, including chemical or physical attachment in some embodiments, as known in the art. Techniques for performing IP are known to those skilled in the art (see, for example, Current Protocols in Molecular Biology, (1998) Ausubel, et al, eds.) Each such method represents a separate embodiment of the present invention.

In one embodiment, step (c) comprises solid phase absorption using calcium phosphate gel or hydroxyapatite, or solid phase binding. Solid phase binding is performed, in one embodiment, through ionic bonding, with either an anion exchanger, such as diethylaminoethyl (DEAE), or diethyl aminoethyl (QAE) SEPHADEX or cellulose; or with a cation exchanger such as carboxymethyl (CM) or sulfopropyl (SP) SEPHADEX or cellulose. Alternative means of solid phase binding include the exploitation of hydrophobic interactions e.g., the using of a solid support such as phenyl-SEPHAROSE and a high salt buffer; affinity-binding, using, e.g., placing a specific DNA binding site of a Stat protein to an activated support; immuno-binding, using e.g., an antibody to the Stat protein bound to an activated support; as well as other solid phase supports including those that contain specific dyes or lectins etc. A further solid phase support technique that is often used at the end of the purification procedure relies on size exclusion, such as SEPHADEX and SEPHAROSE gels, or pressurized or centrifugal membrane techniques, using size exclusion membrane filters. Each of these methods represents a separate embodiment of the invention.

In another embodiment, a silaceous or silane-containing substrate such as, for example, glass, porous silica, or oxidized silicon materials is used as a solid support. This technique may be effected by any method well known to one skilled in the art, such as, for example, the method cited in U.S. Pat. No. 6,426,183.

In one embodiment, selecting the RBP-RNA complex of interest in step (c) comprises a separation step. In one embodiment, solid phase support separations are generally performed batch-wise with low-speed centrifugations or by column chromatography. In another embodiment, magnetic separation methods such as Dynabeads are used. In another embodiment, liquid chromatography separation is performed, using, for example, high performance liquid chromatography (HPLC), including such related techniques as FPLC. In another embodiment, size exclusion techniques may also be accomplished with the aid of low speed centrifugation. In addition, size permeation techniques such as gel electrophoretic techniques may be employed for separation. These techniques are generally performed in tubes, slabs or by capillary electrophoresis. Each of these methods represents a separate embodiment of the invention.

In one embodiment, the molecule that specifically interacts with a component of the RBP-RNA complex of interest of step (c) is an antibody that specifically binds the component. In another embodiment, the molecule is a nucleic acid that binds the component (e.g., an antisense molecule, an RNA molecule that binds the component). In another embodiment, the molecule is any other compound or molecule that binds a component of the complex. Each type of molecule represents a separate embodiment of the present invention.

The term "antibody" refers, in one embodiment, to an antiserum. In another embodiment, "antibody" refers to a purified antibody. In another embodiment, "antibody" refers to a modification of a purified antibody. In another embodiment, the antibody is polyclonal. In another embodiment, the antibody is monoclonal. Each type of antibody represents a separate embodiment of the present invention.

In one embodiment, the molecule that specifically interacts with a component of the RBP-RNA complex of interest binds the component directly (e.g., may be, in one embodiment, an antibody specific for the component), or binds the component indirectly (e.g., may be, in one embodiment, an antibody or binding partner for a tag on the component). The molecule that specifically interacts with a component of the RBP-RNA complex of interest of step (c) is attached, in one embodiment, to a solid support, such as a bead, plate, a column, a fiber, or an array. The molecule that specifically interacts with a component of the RBP-RNA complex of interest may be attached to the solid support using any known method, including chemical or physical attachment in some embodiments, as known in the art. Each molecule represents a separate embodiment of the present invention.

In another embodiment, the component is modified with a selectable element, the properties of which may then be exploited in order to remove the RBP-RNA complex from the mixed population. Non-limiting examples of selectable elements include: nucleic acid sequences, ligands, receptors, antibodies, hapten groups, antigens, biotin, streptavidin, enzymes and enzyme inhibitors. Once a component containing a selectable element is complexed to the target sequence, the RBP-RNA complex is exposed to a reagent capable of binding the selectable element and the RBP-RNA complex is removed from the mixed population. In another embodiment, glutathione-S-transferase/protease fusion proteins can be adsorbed onto glutathione sepharose beads. Each of these methods represents a separate embodiment of the present invention.

The term "biotin" herein includes, in one embodiment, any of the biotin derivatives that are described in the art. See, for example, U.S. Pat. No. 6,613,516 and references cited therein.

In another embodiment, the molecule that specifically interacts with a component of the RBP-RNA complex of interest is bound by a secondary binding molecule. The secondary binding molecule may bind the molecule that specifically interacts with a component of the RBP-RNA complex of interest directly or indirectly. Examples of direct-binding secondary molecules comprise antibodies. For example, an RBP-RNA complex of interest is bound by a primary antibody, and an antibody recognizing the immunoglobulin chain of the primary antibody is then used to select the bound complex. Examples of indirect-binding secondary molecules comprise antibodies or binding partners for a tag on the molecule that specifically interacts with a component of the RBP-RNA complex of interest. For example, an RBP-RNA complex of interest is bound by a primary antibody that contains an epitope tag, and an antibody recognizing the epitope tag of the primary antibody is then used to select the bound complex. Accordingly, in the aforementioned embodiments, the RBP-RNA complex is attached to the solid support via the ligand and binding molecule.

Alternatively, the molecule that specifically interacts with a component of the RBP-RNA complex of interest can be modified with a selectable element, the properties of which may then be exploited in order to remove the RBP-RNA complex from the mixed population. Non-limiting examples of selectable elements include: nucleic acid sequences, ligands, receptors, antibodies, hapten groups, antigens, biotin, streptavidin, enzymes and enzyme inhibitors. Once a molecule that specifically interacts with a component of the RBP-RNA complex of interest containing a selectable element is complexed to the RBP-RNA complex, the biological sample is exposed to a reagent capable of binding the selectable element and the RBP-RNA complex is removed from the mixed population.

The RBP-RNA complex of interest is selected in step (c), in one embodiment, by removing it from the solid support (i.e., the complex is washed off the solid support using suitable conditions and solvents). In another embodiment, the RBP-RNA complex of interest may remain on the solid support.

A variety of epitopes may be used to tag a protein, while retaining at least part of the biological activity of the unmodified protein. Such epitopes may be naturally-occurring amino acid sequences found in nature, artificially constructed sequences, or modified natural sequences. Recently, a variety of artificial epitope sequences have been described that have been shown to be useful for tagging and detecting recombinant proteins. In one embodiment, an artificial epitope sequence with the eight amino acid FLAG marker peptide (Asp-Tyr-Lys-Asp-Asp-Asp-Asp-Lys) (SEQ ID No 470), has been useful for detection as well as affinity purification of recombinant proteins, with antibodies recognizing the epitope readily available (Brewer et al Bioprocess Technol. 2:239-266; Kunz et al J. Biol. Chem. 267:9101-9106).

Additional artificial epitope tags include an improved FLAG tag having the sequence Asp-Tyr-Lys-Asp-Glu-Asp-Asp-Lys (SEQ ID No 471), a nine amino acid peptide sequence Ala-Trp-Arg-His-Pro-Gln-Phe-Gly-Gly (SEQ ID No 472) referred to as the "Strep tag" (Schmidt et al, J. Chromatography 676:337-345), poly-histidine sequences, e.g., a poly-His of six residues which is sufficient for binding to IMAC beads, an eleven amino acid sequence from human c-myc recognized by monoclonal antibody 9E10, or an epitope represented by the sequence Tyr-Pro-Tyr-Asp-Val-Pro-Asp-Tyr-Ala-Ile-Glu-Gly-Arg (SEQ ID No 473) derived from an influenza virus hemagglutinin (HA) subtype, recognized by the monoclonal antibody 12CA5. Also, the Glu-Glu-Phe sequence recognized by the anti-alpha-tubulin monoclonal antibody YL1/2 has been used as an affinity tag for purification of recombinant proteins (Stammers et al., FEBS Lett. 283:298302).

Another commonly used artificial epitope is a poly-His sequence having six histidine residues (His-His-His-His-His-His) (SEQ ID No 474). Naturally occurring epitopes include the eleven amino acid sequence from human c-myc recognized by the monoclonal antibody 9E10 (Glu-Gln-Lys-Leu-Leu-Ser-Glu-Glu-Asp-Leu-Asn) (SEQ ID No 475) (Manstein et al. (1995) Gene 162:129-134). Another useful epitope is the tripeptide Glu-Glu-Phe (SEQ ID No 476) which is recognized by the monoclonal antibody YL 1/2 against alpha-tubulin. This tripeptide has been used as an affinity tag for the purification of recombinant proteins.

In one embodiment, selecting the RBP-RNA complex in step (c) is performed in the presence of an agent capable of disrupting non-covalent interactions. In one embodiment, the agent is a detergent. In one embodiment, the detergent is ionic. In another embodiment, the detergent is non-ionic. In certain embodiments, the detergent is selected from sodium dodecyl sulfate (SDS) and sodium deoxycholate. In certain other embodiments, the detergent is NP-40, tergitol, Tween 20, Saponin, or triton X-100. Disruption of non-covalent interactions may also be achieved using aprotic solvents such as dimethyl sulfoxide and hexamethylphosphoramide. The use of detergents and other agents to disrupt non-covalent interactions is well known in the art (see, for example Molecular Cloning, (2001), Sambrook and Russell, eds.; Methods in Enzymology: Guide to Molecular Cloning Techniques (1987) Berger and Kimmel, eds.; and Current Protocols in Molecular Biology, (1998) Ausubel, et al, eds.). Each of the various agents that disrupts non-covalent interactions that are described in the art represents a separate embodiment of this invention.

"Intermolecular" and "non-covalent" are, in one embodiment, interchangeable terms that refer to bonds between biological macromolecules. In one embodiment, "intermolecular" refers to bonds between components of a complex such as an RBP-RNA complex. In one embodiment, the agent utilized in step (d) only disrupt certain types of intermolecular bonds. Each possibility represents a separate embodiment of the present invention.

In one embodiment, step (c) is performed with a buffer. The use of buffers is well known to those skilled in the art. Typical buffers can be purchased from most biochemical catalogues and include the classical buffers such as Tris, pyrophosphate, monophosphate and diphosphate. A number of references (Current Protocols in Molecular Biology, (1998) Ausubel, et al, eds.; Good, N. E., et al., Biochemistry, 5, 467; Good, N. E. and Izawa, S., Meth. Enzymol., 24:3; and Fergunson, W. J. and Good, N. E., Anal. Biochem. 104:300) describe the use of pH buffers such as Mes, Hepes, Mops, tricine and Ches. Buffers described in the literature that may be useful may be referred to as SDS buffer, lysis buffer, PJPA buffer, RIP buffer, IP buffer, washing buffer, binding buffer, storage buffer, and blocking buffer. Buffer may contain, for example, detergents, pH buffering agents, salts, blocking agents, ion chelators, preservatives, such as, for example, sodium azide, dyes, glycerol, protease inhibitor, phosphatase inhibitors, among other substances. In one embodiment, step (c) comprises the use of a high-salt buffer. In one embodiment, a high-salt buffer has an osmolarity greater than physiologic osmolarity. In another embodiment, a high salt buffer has a salt content greater than physiological salt content Methods for calculating the osmolarity and salt content of a buffer are well known to those skilled in the art. Each buffer disclosed in the art represents a separate embodiment of this invention.

In one embodiment, the RBP-RNA complex of interest is first washed with a buffer containing an agent that disrupts non-covalent interactions, and is subsequently washed with a high-salt buffer. In another embodiment, the RBP-RNA complex of interest is first washed with a high-salt buffer, and is subsequently washed with a buffer containing an agent that disrupts non-covalent interactions. In one embodiment, the high salt buffer also contains an agent that disrupts non-covalent interactions. In another embodiment, the high salt buffer does not contain an agent that disrupts non-covalent interactions. The high salt buffer may also contain any of the other buffer components listed hereinabove. Each of these techniques represents a separate embodiment of the present invention.

In another embodiment, RNA in the RBP-RNA complexes selected in step (c) is labeled. In one embodiment, the labeling comprises the use of gamma-$^{32}$P ATP and T4 polynucleotide kinase (PNK). T4 PNK leaves a 5' phosphate on RNA molecules. Also, T4 PNK has a "resolving" activity that opens up a 2', 3' cyclic phosphate at the 3' end of the RNA fragments (for example, as remains after T1 RNAse digestion) to yield a fraction of molecules with free 3'-OH (FIG. 1A, step 3) (Walker et al, PNAS 72:122-6). In one embodiment, fragments treated with T4 PNK are suitable for directional ligation of nucleotide linkers onto the fragments. For example, a linker containing a 5'-OH and a 3'-OH group may only be able to be coupled to the 5' phosphorylated end of the RNA fragment. By contrast, a nucleotide linker containing a 5' phosphate and a 3' end blocked with puromycin, may only be able to be linked to 3' end of the RNA fragment (FIG. 1A, step 7). In another embodiment, fragments treated with T4 PNK are suitable for directional subcloning of the fragments into a vector.

In one embodiment, the sample is labeled with gamma-$^{32}$P ATP. Other detectable signal moieties suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, Texas red, rhodamine, green fluorescent protein, and the like), radiolabels (e.g., 3H, 125I, 35S, 14C, or 32P), enzymes (e.g., horseradish peroxidase, alkaline phosphatase and others commonly used in an ELISA), colorimetric labels such as colloidal gold or colored glass or plastic (e.g., polystyrene, polypropylene, latex, etc.) beads, and electron-dense labels such as gold, silver, lead and other metals. Methods employing the use of such labels are described in, for example, U.S. Pat. Nos. 3,817,837; 3,850,752; 3,939,350; 3,996,345; 4,277,437; 4,275,149; and 4,366,241 and references cited therein, or others well known to one skilled in the art. The use of each of these methods represents a separate embodiment of the present invention.

In one embodiment of the present invention, a detectable signal moiety is then reacted with the modified or unmodified 5' end of the fragments to produce labeled fragments. For example, a biotin group such as PEO-Iodoacetyl Biotin may be conjugated to 5'-ends of the fragments which have been modified by T4 polynucleotide kinase and gamma-S-ATP. In one such embodiment, the label is supplied to the nucleic acid by the addition of oxide biotinyl-iodacetamidyl-3,6-dioxaoctanediamine (Iodoacetyl Biotin), for example, by the addition of polyethylene oxide biotinyl-iodacetamidyl-3,6-dioxaoctanediamine (PEO-Iodoacetyl Biotin). PEO-Iodoacetyl Biotin (Pierce Chemical Co. Product #21334ZZ) is a long-chain, water-soluble, sulfhydryl (—SH)-reactive biotinylation reagent. The PEO spacer arm imparts high water solubility. Iodoacetyl Biotin (Pierce Chemical Co. Product #21333ZZ) is generally dissolved in DMSO or DMF before use. The iodoacetyl functional group reacts predominantly with free —SH groups. The reaction occurs by nucleophilic substitution of iodine with a thiol group, resulting in a stable thio-ether bond. The use of PEO-Iodoacetyl Biotin as a biotinylation reagent for proteins and antibodies has been described previously. See, for example, Instructions for EZ-Link™ PEO-Iodoacetyl Biotin, Pierce Chemical Co. PEO-Iodoacetyl Biotin is also a suitable label for nucleic acids. The use of Iodoacetyl Biotin as a biotinylation reagent for antibodies is described in, for example, U.S. Pat. No. 5,137,804. The use of Iodoacetyl Biotin as a label for the enzyme kinase is described in, for example, (Jeong et al. Kinase "Assay Based on Thiophosphorylation and Biotinylation," Biotechniques 27:1232-1238 (December 1999)). We have also found that PEO-Iodoacetyl Biotin can be conjugated to a nucleic acid fragment without 5' modification. The use of each of these methods represents a separate embodiment of the present invention.

Means of detecting such labels are well known to those of skill in the art. In one embodiment, radiolabels are detected using photographic film or scintillation counters, fluorescent markers may be detected using a photodetector to detect emitted light. Enzymatic labels are, in one embodiment, detected by providing the enzyme with a substrate and detecting the reaction product produced by the action of the enzyme on the substrate, and colorimetric labels are detected by simply visualizing the colored label. Colloidal gold and other electron-dense labels can be detected by measuring scattered light. Each of these techniques represents a separate embodiment of the present invention.

Methods for labeling the 5' end of an oligonucleotide, which may be used in other embodiments, include, but are not limited to, the following: (i) periodate oxidation of a 5'-to-5'-coupled ribonucleotide, followed by reaction with an amine-reactive label (Heller & Morisson (1985) in Rapid Detection and Identification of Infectious Agents, D. T. Kingsbury and S. Falkow, eds., pp 245-256, Academic Press); (ii) condensation of ethylenediamine with 5'-phosphorylated polynucleotide, followed by reaction with an amine reactive label (Morrison, European Patent Application 232 967 and references cited therein); and (iii) introduction of an aliphatic amine substituent using an aminohexyl phosphite reagent in solid-phase DNA synthesis, followed by reaction with an amine reactive label (Cardullo et al. (1988) Proc. Natl. Acad. Sci. USA, 85:8790-8794).

Figure 1B:
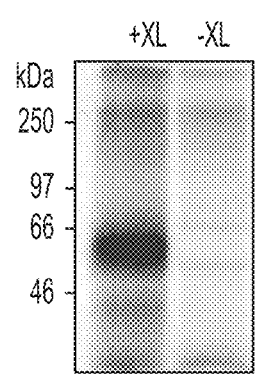
Figure 1C:
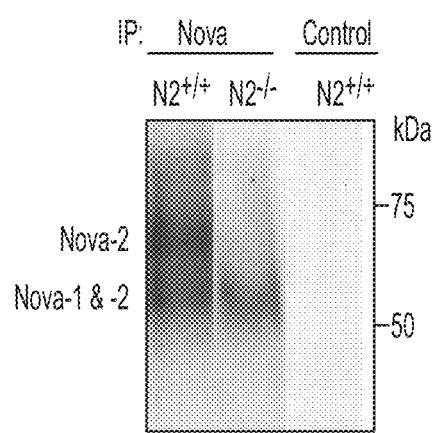

In step (d) of the present invention, the RBP-RNA complex of interest is purified under stringent conditions (FIG. 1A, steps 4-5). In one embodiment, as depicted in FIG. 1A, the stringent conditions consist of SDS-PAGE, transfer to a nitrocellulose (NC) filter, and digestions with Proteinase K. SDS-PAGE separates covalently linked RBP-RNA complexes from free RNA and RBP-RNA complexes that are not covalently linked. The radioactive label of this embodiment allows visualization of these different populations of RNA, and of a band containing the RBP-RNA complexes of interest (FIG. 1B-C). Transfer of the material in the gel to the NC filter constitutes a further purification step, as NC binds protein-bound but not free RNA. Digestion of the protein with Proteinase K results in extraction from the NC filter of RNA molecules of the RBP-RNA complexes.

In one embodiment, "purification" refers to removal of the RNA molecule of interest from the RBP-RNA complex. In one embodiment, this removal comprises digestion of one or more other components of the RBP-RNA complex. In another embodiment, "purification" refers to purification of the RNA molecule of interest together with one or more components of the RBP-RNA complex.

In one embodiment, the purification of step (d) is performed in the presence of an agent capable of disrupting non-covalent interactions as disclosed herein. In another embodiment, the RBP-RNA complex of interest is heated in the presence of a buffer as part of step (d). In one embodiment, the biological sample is heated to a temperature of about 100° Celsius (C). In one embodiment, the biological sample is heated to a temperature greater than about 25° C. In one embodiment, the biological sample is heated to a temperature greater than about 4° C. Each of these techniques represents a separate embodiment of the present invention.

In one embodiment, the RBP-RNA complex is purified by a chromatographic method. In another embodiment, the purification may utilize other methods known in the art.

Other embodiments of techniques which can be applied or combined to purify the RBP-RNA complex of interest comprise chemical extraction, such as phenol or chloroform extract, dialysis, precipitation such as ammonium sulfate cuts, electrophoresis, and chromatographic techniques. In another embodiment, chemical isolation techniques are used for removal of bulk quantities of non-proteinaceous material, and may therefore be used for purifying an RBP-RNA complex of interest. Electrophoretic separation involves placing the biological sample into wells of a gel. In one embodiment, the gel is a denaturing gel. In another embodiment, the gel is a non-denaturing gel. In another embodiment, the gel is a polyacrylamide gel. In another embodiment, the gel is an agarose gel. Direct or pulsed current is applied to the gel and the various components of the system separate according to molecular size, configuration, charge or a combination of their physical properties. Methods for the purification of protein from acrylamide and agarose gels are known and commercially available. Each of these techniques represents a separate embodiment of the current invention.

In one embodiment, the chromatographic method is performed in the presence of an agent capable of disrupting non-covalent interactions. In one embodiment, the agent is a detergent. In one embodiment, the detergent is ionic. In yet another embodiment, the detergent is non-ionic. In certain embodiments, the detergent is selected from sodium dodecyl sulfate (SDS) and sodium deoxycholate. In certain other embodiments, the non-ionic detergent is NP-40, tergitol, Tween 20, or triton X-100. Disruption of non-covalent interactions may also be achieved using aprotic solvents such as dimethyl sulfoxide and hexamethylphosphoramide. The use of detergents and other agents to disrupt non-covalent interactions is well known in the art (see, for example Molecular Cloning, (2001), Sambrook and Russell, eds.; and Current Protocols in Molecular Biology, (1998) Ausubel, et al, eds.). Each of the agents that disrupts non-covalent interactions represents a separate embodiment of this invention.

In one embodiment, the chromatographic method is gel filtration. In another embodiment, the chromatographic method is fast-pressure liquid chromatography. In another embodiment, the chromatographic method is high-pressure liquid chromatography. In another embodiment, the chromatographic method is reverse-phase chromatography. In another embodiment, the chromatographic method is affinity chromatography. In another embodiment, the chromatographic method is ion exchange chromatography.

The chromatographic method utilizes, in one embodiment, a gel. In another embodiment, the chromatographic method utilizes a column. In another embodiment, the chromatographic method utilizes a liquid phase apparatus. In another embodiment, the chromatographic methods utilizes a thin-layer apparatus. In another embodiment, the chromatographic methods utilizes any other chromatographic method known in the art. Each type of chromatographic method represents a separate embodiment of the current invention.

In one embodiment, the gel utilized in the chromatographic method may comprise acrylamide. In another embodiment, the gel utilized may comprise agarose. In another embodiment, the gel utilized may comprise any other matrix constituent known in the art. The use of such constituents is well known to those skilled in the art. Each of these techniques represents a separate embodiment of the current invention.

In another embodiment, the chromatographic method is performed in the presence of a pH buffering agent. In another embodiment, the pH buffering agent prevents or reduces alkalinization. In one embodiment, purifying the RBP-RNA complex of interest in step (d) is performed in the presence of a reducing agent. In another embodiment, step (d) is performed in the absence of reducing agent. Each of these techniques represents a separate embodiment of the current invention.

In one embodiment of the current invention, purifying the RBP-RNA complex of interest in step (d) comprises transferring the RBP-RNA complex of interest to a substrate. In one embodiment, the substrate is a membrane. In one embodiment, the substrate is composed of, for example, NC (Example 1), nylon (Stahl et al., Appl. Environ. Microbiol., 54:1079-1084), a silaceous or silane-containing substrate such as for example, glass, porous silica, or oxidized silicon materials, (U.S. Pat. No. 6,426,183 and references cited therein) silica gel, glass fibers, quartz fibers, and zeolites (U.S. Pat. No. 6,383,393 and references cited therein), or any other substrate known in the art, as described, for example in Molecular Cloning, (2001), Sambrook and Russell, eds.; Methods in Enzymology: Guide to Molecular Cloning Techniques (1987) Berger and Kimmel, eds.; or in Current Protocols in Molecular Biology (1998) Ausubel, et al, eds.). Each of these techniques represents a separate embodiment of the current invention.

In one embodiment, the substrate may preferentially bind RNA covalently bound to protein over RNA not covalently bound to protein. In another embodiment, the substrate may exclusively bind RNA covalently bound to protein over RNA not covalently bound to protein.

In one embodiment, the RBP-RNA complex of interest is transferred to the substrate by electrophoresis. The use of electrophoresis is well known to those skilled in the art. In some embodiments, the RBP-RNA complex of interest is transferred to the substrate using, for example, electroblotting, capillary electrophoresis, positive pressure blotting, vacuum blotting, direct blotting, mechanical blotting, or, for example, any of the methods described in U.S. Pat. No. 6,602,391 and references cited therein. Each of these techniques represents a separate embodiment of the current invention. In another embodiment, the RBP-RNA complex of interest is transferred to the substrate using the methods described in U.S. Pat. No. 6,383,393 and references cited therein. Each of these methods represents a separate embodiment of the present invention.

In one embodiment, the transfer of the RBP-RNA complex of interest to a substrate may involve a semipermeable membrane. In another embodiment, the transfer may involve a micro-porous composites or a micro-porous membrane. In one embodiment, the transfer apparatus may be vertical. In another embodiment, the transfer apparatus may be horizontal. Each of these methods represents a separate embodiment of the present invention.

Figure 2:
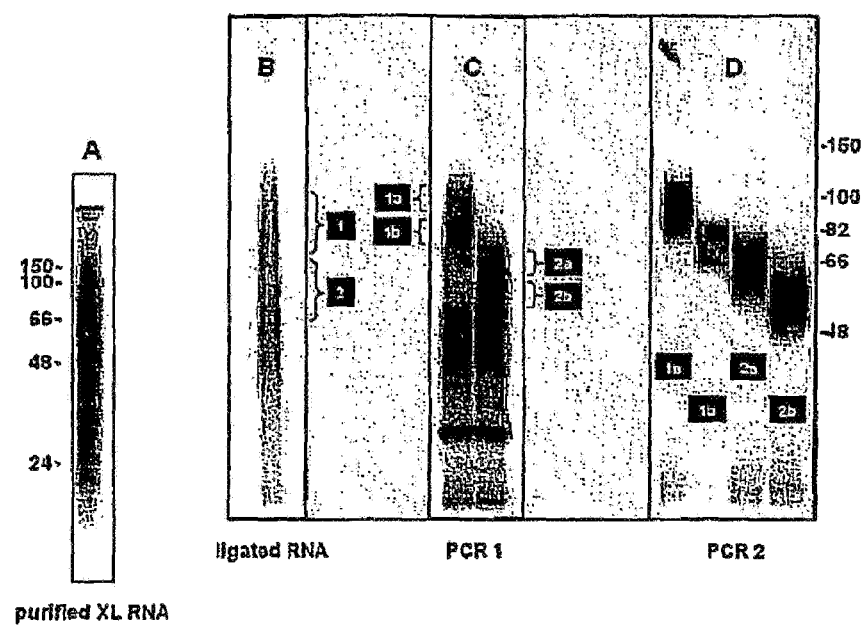

In one embodiment, purifying the RBP-RNA complex of interest in step (d) comprises eluting the RBP-RNA complex from the substrate. In one embodiment, the elution comprises physically removing the section of the substrate containing the RBP-RNA complex of interest. In one embodiment, the elution comprises, for example, digestion with Proteinase K or a homologous enzyme. Proteinase K is capable of efficiently digesting protein in an RBP-RNA complex, liberating RNA in the complex from a substrate and yielding products that can be used for ligation and amplification (FIG. 2).

In another embodiment, the RBP-RNA complex of interest is eluted from the substrate by digestion with a member of one of the following classes of proteases or their homologues: Aspartyl proteases, caspases, thiol proteases, Insulinase family proteases, zinc binding proteases, Cytosol Aminopeptidase family proteases, Zinc carboxypeptidases Neutral Zinc Metallopeptidases, extracellular matrix metalloproteinases, matrixins, Prolyl oligopeptidases, Aminopeptidases, Proline Dipeptidases, Methionine aminopeptidases, Serine Carboxypeptidases, Cathepsins, Subtilases, Proteasome A-type Proteases, Proteosome B-type Proteases, Trypsin Family Serine Proteases, Subtilase Family Serine Proteases, Peptidases, Ubiquitin carboxyl-terminal hydrolases, or other proteases described in U.S. Pat. No. 6,395,889 and references cited therein. In another embodiment, the elution comprises the methods described in U.S. Pat. No. 6,383,393 and references cited therein. A number of these proteases are commercially available. The use of these proteases is known to those skilled in the art, and is described in, for example, Lundell et al (Anal Biochem 266: 31-47) and product literature from Roche and Sigma-Aldrich. Each of these techniques represents a separate embodiment of the current invention.

In one embodiment, RNA molecules from RNA-protein complexes of interest are analyzed. In one embodiment, the analysis may comprise electrophoresis. In one embodiment, the electrophoresis may be carried out with SDS-PAGE (FIG. 1A, step 6 and FIG. 2). SDS-PAGE electrophoresis reveals the approximate size of nucleic acid molecules. This technique is well known to those skilled in the art, and is described in, for example, Molecular Cloning, (2001), Sambrook and Russell, eds. In another embodiment, RNA from the RBP-RNA complex of interest is size purified. The analysis or size purification may utilize any chromatography method described herein, or any other method described in the art. Each such method represents a separate embodiment of the current invention.

Size purification is, in one embodiment, an effective method of following the various steps involved in amplifying and identifying RNA molecules of interest. In another embodiment, size purification may increase the purity of products obtained (FIG. 1A, step 6 and FIG. 2).

In one embodiment (depicted in FIG. 1A), RNA molecules from the RBP-RNA complexes of interest are then identified. Identification is accomplished, according to this aspect, by linker ligation, reverse transcriptase-polymerase chain reaction (RT-PCR), which amplifies the RNA molecules, ligation into a vector, and sequencing (step 7). In another embodiment, the RBP-RNA complex of interest is not identified. Analysis of RNA molecules (step 6) may also be useful at one or more stages in the steps comprising the identification process, as described herein. In one embodiment, this method is used to identify RNA molecules that affect gene silencing or post-transcriptional regulation of gene expression.

In one embodiment of the current invention, nucleotide linkers are ligated to an RNA molecule in the RBP-RNA complex of interest. "Ligation", in all the applications described herein, refers, in one embodiment, to attaching an end of a nucleotide molecule to another end of a nucleotide molecule. The two ends that are joined may be from separate molecules or the same molecule. Ligation of nucleotide linkers facilitates subsequent amplification (FIG. 1A, step 7). In one embodiment, the ligation is performed with T4 RNA ligase or a homologous enzyme. Alternately, the ligation can be performed by any RNA ligase known in the art. Methods of ligation and the use of various ligases and methods for using them are described in, for example, Molecular Cloning, (2001), Sambrook and Russell, ed. or Methods in Enzymology: Guide to Molecular Cloning Techniques (1987) Berger and Kimmel, eds. Each such ligase represents an additional embodiment of the current invention.

In another embodiment, there are provided nucleotide linkers comprising a nucleic acid having a sequence selected from the group consisting of: 5' P-CGACCUGCAGGC-UUCCUGC-puromycin (SEQ ID No 487); 5' OH-CUUAG-GUGGAAGGGCAAGCG-OH 3' (SEQ ID No 488); 5' P-GGG CAACAGGUACCAAACUC-puromycin (SEQ ID No 489); 5' OH-CUUAGGUGGUACCGCAAGCG-OH 3' (SEQ ID No 490); 5' P-GGGCAACAGUAGAUAAA-CUC-puromycin (SEQ ID No 491); 5'-OH TCGGGC-GAGTCGTCTG-OH 3' (SEQ ID No 483); 5'-P CCG-CATCGTCCTCCC puromycin) (SEQ ID No 484); 5'-TCGGGCGAGTCGTCTG (SEQ ID No 485); and GGGAGGACGATGCGG (SEQ ID No 486); 3' link RNA (5'-P CAG ACG ACG AGC GGG A 3'-puromycin) (SEQ ID No 478); GL5 DNA (AGG GAG GAC GAT GCG G) (SEQ ID No 479); GL3 DNA (TCC CGC TCG TCG TCT G) (SEQ ID No 480); 5CLIPcloneNofl (CAGTGCTGCGCGGC-CGCAGGGAGGACGATGCGG) (SEQ ID No 481); 3CLEPcloneAscI (TCAAGTCAGGGCGCGCCTC-CCGCTCGTCGTCTG) (SEQ ID No 482); and a sequence as set forth in (SEQ ID No 477-486 and 497-502). In one embodiment, the linkers may be useful in methods comprising ligation to a nucleotide molecule. In one embodiment (depicted in FIGS. 1 and 2), the linkers may be directionally ligated to the ends of RNA fragments to facilitate cDNA synthesis and RT-PCR. In another embodiment, the linkers may be used in a non-directional manner. In another embodiment, the linkers may be used to facilitate a different later step other than cDNA synthesis or RT-PCR.

In one embodiment of the current invention, the nucleotide linkers are directionally oriented. In another embodiment of the current invention, the nucleotide linkers are not directionally oriented.

The term "nucleotide linker", in one embodiment, refers to an oligonucleotide ligated onto the end of an RNA fragment. In another embodiment, "nucleotide linker" refers to an oligonucleotides used as primers in a polymerase chain reaction (PCR) reaction. In one embodiment, the nucleotide linkers are suitable for directional ligation. In one embodiment, the nucleotide linkers are suitable for PCR amplification. In another embodiment, the nucleotide linkers are suitable for subcloning.

In one embodiment, the nucleotide linkers comprise RNA or a derivative thereof. In one embodiment, the nucleotide linkers comprise DNA or a derivative thereof. In one embodiment, the nucleotide linkers comprise any other nucleic acid or nucleic acid derivative disclosed herein.

In another embodiment of the current invention, there is provided a method of using linkers comprising a sequence as set forth in SEQ ID No 477-502 to amplify a nucleic acid molecule. The method may comprise, in one embodiment, the following steps: (a) ligating the nucleic acid molecule to one or more of the linkers; (b) synthesizing a nucleic acid strand complementary to a product of step (a) using one or more of the linkers as a primer; (c) amplifying a product of step (b) by PCR, using one or more of the linkers as a primer. In another embodiment, an amplification step other than PCR may be used. In another embodiment, the method may further comprise size separation, phenol/chloroform purification, or ethanol precipitation. Methods for these techniques are known in the art and are described, for example, in Example 1 and in Molecular Cloning, (2001), Sambrook and Russell, eds. Each such method represents a separate embodiment of the present invention.

In one embodiment of the current invention, an RNA molecule in the RBP-RNA complex of interest is amplified. In one embodiment, the amplification utilizes PCR. "PCR", in one embodiment, is a process in which nucleic acid is amplified (i.e., the copy number is increased). Briefly, a nucleic acid molecule desired to be amplified is incubated with oligonucleotides known as "primers", mononucleotides, and a polymerase, and is put though a cycle of temperature changes that facilitate denaturation, annealing of the primers to the molecule desired to be amplified, and extension of the primers to create additional copies of the molecule. Generally, PCR primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. In some embodiments, the XL-PCR kit (PE Biosystems), nested primers, and commercially available cDNA or genomic DNA libraries may be used to extend the nucleic acid sequence. In some embodiments, primers may be designed using commercially available software, such as OLIGONUCLEOTIDE 4.06 primer analysis As used herein, PCR is considered to be one, but not the only, example of a nucleic acid polymerase reaction method for amplifying a nucleic acid test sample. Methods for amplification of nucleic acid are known to those skilled in the art (see, for example, Mullis et al., Cold Spring Harbor Symp. Quant. Biol., 51:263; Erlich et al, PCR Technology (Stockton Press, N.Y., 1989); and U.S. Pat. No. 4,683,195 and references cited therein). Each such method represents a separate embodiment of the current invention.

In one embodiment, "cDNA" refers to a DNA molecule that is complementary to an RNA molecule. In one embodiment, the RNA molecule serves as a substrate for the synthesis of the DNA molecule.

In one embodiment, the present invention provides a method of detecting an RNA motif which represents a binding site on the RNA molecule for the RBP. In one embodiment, the motif may be detected. In one embodiment, the detection comprises partial fragmentation, digestion, hydrolysis, or physical or chemical treatment, as described for step (b) hereinabove. Each of these methods represents a separate embodiment of the invention.

A method for identifying a candidate RNA motif that may mediate binding to an RNA binding protein of interest, comprising the steps of (a) purifying a plurality of RNA molecules interacting with said RNA binding protein of interest by the CLIP method; (b) obtaining sequences from a subset of said plurality of RNA molecules; and (c) detecting a presence of said candidate RNA motif in two of said sequences, thereby identifying a candidate RNA motif that may mediate binding to an RNA binding protein of interest.

In one embodiment, said motif interacts with a Nova-1 protein. In another embodiment, said motif interacts with a Nova-2 protein. In another embodiment, said motif interacts with a HuA. In another embodiment, said motif interacts with a HuB. In another embodiment, said motif interacts with a HuC. In another embodiment, said motif interacts with a HuD. In another embodiment, said motif interacts with a FMRP. In another embodiment, said motif interacts with a FXRP1. In another embodiment, said motif interacts with a FXRP2. In another embodiment, said motif interacts with a combination of any of the above. In another embodiment, said motif interacts with any other RBP known in the art. Each possibility represents a separate embodiment of the present invention.

In one embodiment, the detection comprises determining the sequence of an RNA molecule from the RBP-RNA complex of interest. In one embodiment, the detection comprises analysis or comparison of multiple sequences identified by the present invention (Example 3). Analysis or comparison of multiple sequences may be performed manually, or using one of various methods for determining homology described hereinabove. Each of these methods represents a separate embodiment of the invention.

In one embodiment, the detection comprises amplification, as described herein. In one embodiment, the detection comprises inserting a nucleic acid molecule from the RBP-RNA complex of interest into a vector. In one embodiment, the detection comprises inserting an amplified product of a nucleic acid molecule from the RBP-RNA complex of interest into a vector. The insertion may be performed by any technique known in the art. Such techniques are described, for example, in Molecular Cloning, (2001), Sambrook and Russell, ed. or Methods in Enzymology: Guide to Molecular Cloning Techniques (1987) Berger and Kimmel, eds. Each such technique represents a separate embodiment of the present invention.

In one embodiment, the detection involves RNA footprinting. Methods for RNA footprinting are known to those skilled in the art, and comprise the use of chemical or enzymatic means of nicking RNA. Such methods are described in Curr Opin Struct Biol 12:648-53 and references cited therein, and in Molecular Cloning, (2001), Sambrook and Russell, ed. or Methods in Enzymology: Guide to Molecular Cloning Techniques (1987) Berger and Kimmel, eds. Each of these methods represents a separate embodiment of the invention In one embodiment, the component that interacts with the RNA motif may be a protein. In another embodiment, the component that interacts with the RNA motif may be a nucleic acid. In another embodiment, the component that interacts with the RNA motif may be another molecule or compound (e.g., carbohydrate, lipid, vitamin, etc.) that associates with the RBP-RNA complex.

In one embodiment, the word "motif" refers to a portion of an RNA molecule. In another embodiment, the word "motif" refers to an entire RNA molecule. In another embodiment, the word "motif" refers to a portion of an RNA molecule that exhibits a particular structure. In another embodiment, the word "motif" refers to a particular structure. In another embodiment, the word "motif" refers to an element of structure that recurs in more than one context. In another embodiment, the word "motif" refers to a sequence that recurs in more than one context. Each of these represents a separate embodiment of the present invention.

In one embodiment of the present invention, the step of identifying an RNA molecule or motif in the RBP-RNA complex of interest comprises the use of hybridization to nucleic acid arrays. Those of skill in the art will appreciate that an enormous Number of array designs are suitable for the practice of this invention. High-density arrays may be used for a variety of applications, including, for example, gene expression analysis, genotyping, variant detection, and analysis of alternate splicing patterns.

Any of various techniques for large-scale polymer synthesis and probe array manufacturing known to one skilled in the art may be utilized, such as, for example, U.S. Pat. Nos. 5,143,854, 5,242,979, 5,252,743, 5,324,663, 5,384,261, 5,405,783, 5,412,087, 5,424,186, 5,445,934, 5,451,683, 5,482,867, 5,489,678, 5,491,074, 5,510,270, 5,527,681, 5,550,215, 5,571,639, 5,593,839, 5,599,695, 5,624,711, 5,631,734, 5,677,195, 5,744,101, 5,744,305, 5,753,788, 5,770,456, 5,831,070, 6,040,193 and 5,856,011. Each of these techniques represents a separate embodiment of the present invention.

In another embodiment, the present invention provides a method of assessing a level of association of an RNA transcript of interest with an RBP of interest, comprising the steps of: (a) contacting an RBP-RNA complex containing said RBP of interest with an agent that creates a covalent bond between two components of said RBP-RNA complex; (b) cleaving an RNA molecule of said RBP-RNA complex with an agent capable of cleaving a bond of said RNA molecule, thereby generating a fragment of said RNA molecule, wherein said fragment is at least 22 nucleotide bases in length; (c) selecting said RBP-RNA complex with a molecule that specifically interacts with a component thereof; (d) purifying said RBP-RNA complex, wherein said purifying comprises a chromatographic method; and (e) assessing a presence or amount of said RNA transcript of interest or a fragment thereof in said plurality of RNA molecules, thereby assessing a level of association of an RNA transcript of interest with an RBP of interest.

In another embodiment, the present invention provides a method of screening a test compound for its ability to modulate a level of association between an RBP and an RNA transcript, comprising the steps of: (a) assessing a first level of association between said RBP and said RNA transcript in a first cell by the method described in the previous paragraph, wherein said first cell has been contacted with said test compound; (b) assessing a second level of association between said RBP and said RNA transcript in a second cell by the method described in the previous paragraph, wherein said second cell has not been contacted with said test compound; and (c) comparing said first level of association with said second level of association, wherein a difference between said first level of association and said second level of association indicates an ability of said test compound to modulate a level of association between said RBP and said RNA transcript.

In another embodiment, the present invention provides a method of treating a disease or disorder in a subject, wherein the disease or disorder is associated with a function of an RNA binding protein, comprising contacting a cell in the subject with an agent that modulates an expression or activity of a gene, or a protein encoded by the gene, wherein a transcript of the gene comprises a nucleic acid sequence set forth in SEQ ID No 1-335, thereby treating a disease or disorder in a subject.

In another embodiment, the present invention provides a method of treating a disease or disorder in a subject, wherein the disease or disorder is associated with a function of an RNA binding protein, comprising contacting a cell in the subject with an agent that modulates an expression or activity of a gene, or a protein encoded by the gene, wherein a transcript of the gene comprises a nucleic acid sequence set forth in SEQ ID No 336-449, thereby treating a disease or disorder in a subject.

In another embodiment, the present invention provides method of diagnosing a disease or disorder associated with an alternate splicing pattern of a gene in a subject, wherein a transcript of the gene comprises a nucleic acid sequence set forth in SEQ ID No 1-335, comprising assessing a splicing pattern of the transcript in a biological sample from the subject; assessing a splicing pattern of a reference standard; and comparing the splicing pattern of the transcript to the splicing pattern of a reference standard, thereby diagnosing a disease or disorder associated with an alternate splicing pattern of a gene in a subject.

In another embodiment, the present invention provides method of diagnosing a disease or disorder associated with an alternate splicing pattern of a gene in a subject, wherein a transcript of the gene comprises a nucleic acid sequence set forth in SEQ ID No 336-449, comprising assessing a splicing pattern of the transcript in a biological sample from the subject; assessing a splicing pattern of a reference standard; and comparing the splicing pattern of the transcript to the splicing pattern of a reference standard, thereby diagnosing a disease or disorder associated with an alternate splicing pattern of a gene in a subject.

"Associated with," in one embodiment, refers to a correlation of a parameter associated with the RNA binding protein with the presence of the disease or disorder. In another embodiment, "associated with" refers to a correlation of a parameter associated with the RNA binding protein with the progress of the disease or disorder. In another embodiment, "associated with" refers to a correlation of a parameter associated with the RNA binding protein with a predisposition to the disease or disorder.

In another embodiment, the present invention provides a method of analyzing one or more RNA sequences identified by a method of the invention. Such analysis may, in one embodiment, be used to reveal motifs or patterns among the RNA sequences (Example 3). In another analysis, such analysis may be used to reveal RNA molecules that were not previously known to interact with the component of the RBP-RNA complex that was selected (Examples 3-5). In another analysis, such analysis may be used to reveal information about the expression pattern or splicing pattern of a gene encoded by the parent RNA molecules of the RNA fragments analyzed (Example 3).

In another embodiment, the present invention provides a method of identifying a motif on an RNA of the RBP-RNA complex of interest that interacts with a component of the RBP-RNA complex of interest. In one embodiment, the motif may be a protein-binding site (Example 3). In another embodiment, the analysis may reveal a previously unknown binding motif. In another embodiment, the analysis may improve existing knowledge about a binding motif, such as information about the role of surrounding sequence (Example 3). In another embodiment, information from the location of binding sites may, in conjunction with information about the splicing or expression pattern of the parent RNA molecules of the fragments, reveal information about the role of the selected component of the RBP-RNA complex in regulating the expression or splicing pattern of RNA molecules.

In one embodiment, identification or analysis of RNA fragments purified by the present invention may comprise the use of nucleic acid arrays. In one embodiment, the nucleic acid array may be a high-density array. A high-density array will typically include a number of probes that specifically hybridize to the nucleic acid(s) whose expression is to be detected. Array based methods for monitoring gene expression such as those described in U.S. Pat. Nos. 5,800,992, 5,871,928, 5,925,525, 6,040,138 and PCT Application WO92/10588 (published on Jun. 25, 1992), may be utilized, in another embodiment of this invention. In some embodiments, these methods of monitoring gene expression involve (1) providing a pool of target nucleic acids identified by the present invention (2) hybridizing the nucleic acid sample to a high density array of probes and (3) detecting the hybridized nucleic acids and calculating a relative or absolute Number of each transcript detected. Each of these techniques represents a separate embodiment of the present invention.

For genotyping and variant detection, the high-density array may, in some embodiments, include a number of probes which are designed to assay a particular position which is believed or known to be associated with sequence variation. Array based methods for variant detection used according to this aspect of the invention may be as described, for example, in U.S. Pat. Nos. 5,837,832, 5,856,104, 5,856,092, 5,858,659, 6,027,880 and 5,925,525. In some embodiments, these methods of variant detection involve (1) providing a pool of target nucleic acids comprising DNA from the region(s) to be interrogated (2) hybridizing the nucleic acid sample to a high density array of probes and (3) detecting the hybridized nucleic acids and determining the presence or absence of a sequence variant. Each of these techniques represents a separate embodiment of the present invention.

In another embodiment, the design and use of nucleic acid arrays is carried out as described, for example, in Bunney et al (Am J Psychiatry 160: 657-66) or Ahmed (J Environ Sci Health Part C Environ Carcinog Ectoxicol Rev. 20: 77-116). Each of these techniques represents a separate embodiment of the present invention.

In another embodiment, an embodiment of the CLIP method may be combined with laser capture micro-dissection (LCM). LCM under direct microscopic visualization permits rapid one-step procurement of selected cell populations from a section of complex, heterogeneous tissue. The method entails placing a thin thermoplastic film (such as, for example, ethylene vinyl acetate polymer) over a tissue section, visualizing the tissue microscopically, and selectively adhering the cells of interest to the film with a fixed-position, short-duration, focused pulse from an infrared laser. Strong focal adhesion allows selective procurement of the targeted cells. The film with the procured tissue is then removed from the section and placed directly into DNA, RNA, or enzyme buffer for processing. The technique is known to those skilled in the art (see, for example, Emmert-Buck M R et al, Science 274: 998-1001). The cellular material detaches from the film and is ready for standard processing.

The use of LCM in combination with an embodiment of the CLP method would facilitate, in one embodiment, the purification of RNA interacting with an RBP of interest from a specific region of tissue visualized in a microscope. In one embodiment, the specific region may be, for example, neuronal dendritic layers.

In another embodiment, LCM, or a similar technology, may be combined with Deep UV microscopy technology to facilitate the formation of covalently bound protein-RNA complexes from a specific region visualized in a microscope. In one embodiment, laser wavelength in the range of 245-260 nm may be used in Deep UV microscopy, a range of wavelengths that may be used to catalyze the formation of covalent bonds. The use of Deep UV microscopy is known to those skilled in the art (see, for example, U.S. Pat. No. 5,482,817).

In another embodiment, there is provided a method for isolating an unknown RBP present in an RBP-RNA complex containing a known component. This method is similar, in one embodiment, to the CLIP method described above, but the target to be identified is an RBP that may be different from the known component used to select the RBP-RNA complex. In one embodiment, the unknown RBP may be bound to an RNA or other nucleic acid molecule at the same time that the known component is bound to the same molecule. In another embodiment, the unknown RBP may bind a different RNA that can exist in an RBP-RNA complex also containing the known component. This method comprises the steps of contacting a biological sample with an agent that results in a covalently bound RBP-RNA complex in the biological sample; obtaining RNA fragments from the biological sample; selecting the RBP-RNA complex containing the known component with a molecule that specifically interacts with the known component; purifying the RBP-RNA complex containing the known component under stringent conditions; and isolating the unknown RBP from the RBP-RNA complex containing the known component.

In another embodiment, there is provided a method for identifying an unknown RBP present in an RBP-RNA complex containing a known component, comprising the steps of contacting a biological sample with an agent that results in a covalently bound RBP-RNA complex in the biological sample; obtaining RNA fragments from the biological sample; selecting the RBP-RNA complex containing the known component with a molecule that specifically interacts with the known component; purifying the RBP-RNA complex containing the known component under stringent conditions; and identifying the unknown RBP from the RBP-RNA complex containing the known component.

It is to be understood that any embodiment listed herein for effecting the CLIP methods of this invention may be utilized for isolating and/or identifying an unknown RBP present in an RBP-RNA complex containing a known component, and represent additional embodiments of this invention. In one embodiment, the unknown RBP may be identified, by antibody detection, mass spectrometry, or any other method well known in the art. Mass spectrometry may be carried out by any method well known to those skilled in the art, such as those described in U.S. Pat. No. 6,586,727. Each method of mass spectrometry or protein identification represents a separate embodiment of the present invention.

In one embodiment of this method, "unknown RBP" refers to an RBP that has not been previously identified. In another embodiment, "unknown RBP" refers to a previously identified protein not known to be an RBP. In another embodiment, "unknown RBP" refers to a previously identified RBP not known to be present in an RBP-RNA complex with the known component of the RBP-RNA complex. In another embodiment, "unknown RBP" refers to the fact that information is lacking about conditions permitting association of the RBP with complexes containing the known component. In another embodiment, "unknown RBP" refers to the fact that information is lacking about the stoichiometry, affinity, binding site of the RBP, or any other aspect of complexes containing the RBP and the known component In one embodiment, a covalent bond is created between the known component and an RNA in the complex, and another covalent bond is created between the unknown RBP and an RNA in the complex. The presence of these covalent bonds allows the known component, the RNA, and the unknown RBP to remain associated throughout stringent purification steps. The use of these stringent steps increases the purity of the isolated product relative to schemes using less stringent purification steps.

In one embodiment, the unknown RBP is isolated from the RBP-RNA complex. In one embodiment, isolation may comprise selectively removing the unknown RBP from the RBP-RNA complex. In another embodiment, isolation may comprise removing the unknown RBP from the RBP-RNA complex by a technique that also removes one or more other proteins. In another embodiment the amount of the unknown RBP is assessed. In another embodiment, the presence of the unknown RBP under various conditions is assessed. In another embodiment, the binding site of the unknown RBP is characterized or identified.

In another embodiment, the unknown RBP can be analyzed, for example, by SDS-PAGE gel electrophoresis, Western blotting and detection with specific antibodies, phosphoamino acid analysis, protease digestion, protein sequencing, or isoelectric focusing. The use of these techniques is known to those skilled in the art, and is described in, for example, Methods in Enzymology: Guide to Molecular Cloning Techniques (1987) Berger and Kimmel, eds. Each technique represents a separate embodiment of the present invention.

In another embodiment, the invention provides a material that may be used in a screen to identify bioactive molecules. In one embodiment, the material may comprise a motif on an RNA of the RBP-RNA complex of interest. In another embodiment, the material may comprise a derivative of the motif. In another embodiment, the material may comprise a sequence homologous to the motif. In another embodiment, the material may comprise a molecule containing the motif. In another embodiment, the material may comprise a sequence fragment identified by the method of this invention. In another embodiment, the material may comprise a sequence identified by the method of this invention (SEQ ID No 1-449).

As used herein, the terms "homology", "homologue" or "homologous", in any instance, indicate that the sequence referred to, whether an amino acid sequence, or a nucleic acid sequence, exhibits, in one embodiment at least 70% correspondence with the indicated sequence. In another embodiment, the amino acid sequence or nucleic acid sequence exhibits at least 72% correspondence with the indicated sequence. In another embodiment, the amino acid sequence or nucleic acid sequence exhibits at least 75% correspondence with the indicated sequence. In another embodiment, the amino acid sequence or nucleic acid sequence exhibits at least 77% correspondence with the indicated sequence. In another embodiment, the amino acid sequence or nucleic acid sequence exhibits at least 80% correspondence with the indicated sequence. In another embodiment, the amino acid sequence or nucleic acid sequence exhibits at least 82% correspondence with the indicated sequence. In another embodiment, the amino acid sequence or nucleic acid sequence exhibits at least 85% correspondence with the indicated sequence. In another embodiment, the amino acid sequence or nucleic acid sequence exhibits at least 87% correspondence with the indicated sequence. In another embodiment, the amino acid sequence or nucleic acid sequence exhibits at least 90% correspondence with the indicated sequence. In another embodiment, the amino acid sequence or nucleic acid sequence exhibits at least 92% correspondence with the indicated sequence. In another embodiment, the amino acid sequence or nucleic acid sequence exhibits at least 95% or more correspondence with the indicated sequence. In another embodiment, the amino acid sequence or nucleic acid sequence exhibits 95%-100% correspondence to the indicated sequence. Similarly, as used herein, the reference to a correspondence to a particular sequence includes both direct correspondence, as well as homology to that sequence as herein defined.

In another embodiment, the invention provides compounds that interact with a motif of an isolated nucleic acid sequence. In one embodiment, the nucleic acid is RNA or a derivative thereof. In one embodiment, the sequences comprise SEQ ID No 1-335.

In another embodiment, the sequences comprise SEQ ID No 336-449.

In another embodiment, the sequences comprise 63, 64, 76, 77, 78, 84, and 292-335.

In another embodiment, the present invention provides the use of the RNA motifs, sequence fragments, or sequences in a screening assay to identify bioactive molecules that interact with the RNA motifs, sequence fragments, or sequences. A molecule found to interact with the an RNA motif, sequence fragment, or sequence is likely, in one embodiment, to modulate the activity of an RNA molecule containing the motif, sequence fragment, or sequence in vivo.

In one embodiment, the screening assay can be performed in a cell-based system. In one embodiment, the screening assay can be performed in a cell-free system. Cell-based assays can be native, i.e., cells that normally express the enzyme, as a biopsy or expanded in cell culture. In an alternate embodiment, the cell-based assay involves recombinant host cells expressing the enzyme protein. In one embodiment, the screening assay can be a high-throughput screen. Each such system represents a separate embodiment of the present invention.

To perform cell free drug screening assay, it is sometimes desirable, in one embodiment, to immobilize either the material or its target molecule to facilitate separation of complexes from un-complexed forms of one or both of the proteins, as well as to accommodate automation of the assay. Techniques for immobilizing nucleic acids on matrices can be used in the drug screening assay. Matrices are then combined with the cell lysates (e.g., 35 S-labeled) and the candidate compound, and the mixture incubated under conditions conducive to complex formation (e.g., at physiological conditions for salt and pH), Following incubation, the beads are washed to remove any unbound label, and the matrix immobilized and radiolabel determined directly, or in the supernatant after the complexes are dissociated. Alternatively, the complexes can be dissociated from the matrix and separated by SDS-PAGE, and the level of target molecule bound to the material found in the bead fraction can be quantitated from the gel using standard electrophoretic techniques. For example, either the material or its target molecule can be immobilized utilizing conjugation of biotin and streptavidin using techniques well known in the art. Alternatively, antibodies reactive with the material but which do not interfere with binding of the material to its target molecule can be derivatized to the wells of the plate, and the material trapped in the wells by antibody conjugation. Methods for detecting such complexes include immuno-detection of complexes using antibodies reactive with the target molecule, or which are reactive with the material and compete with the target molecule, as well as enzyme-linked assays, which rely on detecting an enzymatic activity associated with the target molecule. These methods represent additional embodiments of the present invention.

Candidate compounds include, for example, 1) peptides such as soluble peptides, including Ig-tailed fusion peptides and members of random peptide libraries (see, e.g., Lam et al, Nature 354:82-84; Houghten et al., Nature 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767-778); 3) antibodies (e.g., polyclonal, monoclonal, humanized, anti-idiotypic, chimeric, and single chain antibodies as well as Fab, F(ab') sub.2, Fab expression library fragments, and epitope-binding fragments of antibodies); and 4) small organic and inorganic molecules (e.g., molecules obtained from combinatorial and natural product libraries). The use of each such group of compounds, as well as any other used in the art, represents a separate embodiment of the current invention.

The motifs, sequence fragments, or sequences claimed for use in a screen to identify bioactive molecules may, in one embodiment, be used in competition binding assays in methods designed to discover compounds that interact with the motifs, sequence fragments, or sequences (e.g. binding partners and/or ligands). Thus, a compound is exposed to the material under conditions that allow the compound to bind or to otherwise interact with the motifs, sequence fragments, or sequences. A molecule that normally interacts with the materials is also added to the mixture. If the test compound interacts with the material, it decreases the amount of complex formed. This type of assay may be used in cases in which compounds are sought that interact with specific regions of the material. In another embodiment, the screening method involves contacting a biological sample with a compound capable of interacting with the RNA motifs, sequence fragments, or sequences such that the interaction can be detected. Such an assay can be provided in a single detection format or a multi-detection format such as an antibody chip array. These methods represent separate embodiments of the present invention.

In another embodiment, the motifs, sequence fragments, or sequences of the present invention can be used to screen a compound for its ability to stimulate or inhibit an interaction between RNA motifs, sequence fragments, or sequences of the present invention and a molecule that normally interacts with the motifs, sequence fragments, or sequences. In one embodiment, the molecule is a protein. In another embodiment, the molecule is an RBP. In another embodiment, the molecule interacts with an RBP. In another embodiment, the molecule may be a different molecule. Such an assay may include the steps of contacting a biological sample with a candidate molecule under conditions that allow the motifs, sequence fragments, or sequences to interact with the respective molecule, and to detect the formation of a complex between the motifs, sequence fragments, or sequences and the interacting molecule or to detect the biochemical consequence of the interaction with the motifs, sequence fragments, or sequences and the interacting molecule, such as, for example, splicing, export, or localization of a parent RNA or expression, activity, or concentration of a protein encoded by a parent RNA. Each such assay represents a separate embodiment of the current invention.

As used herein, the phrase "parent RNA" or "parent RNA molecule", in one embodiment, refers to a larger RNA molecule which comprises the material. In another embodiment, "parent RNA" or "parent RNA molecule" can be the material itself.

It will be appreciated by one skilled in the art that bioactive molecules identified by a screen of the present invention may be further assayed to gain information about their biological activities. For example, the bioactive molecules may be assayed for their effect on the RNA splicing, export, or localization or protein expression, activity, or concentration, of RNA or protein molecules in the cell. In one embodiment, the RNA or protein molecules used in the assay may comprise the motifs, sequence fragments, or sequences of the present invention. The effect of the bioactive molecules may be assessed for the RNA or protein in its natural state. In another embodiment, the effect of the bioactive molecules may be assessed for the RNA or protein in an altered form that causes a specific disease or pathology associated with the enzyme.

Bioactive molecules identified in these screens can be further screened to determine their effect of a parent RNA or protein as described herein. Further, these compounds can be tested in animal or invertebrate systems to determine activity/effectiveness. Compounds can be identified that activate (agonist) or inactivate (antagonist) a parent RNA or protein to a desired degree.

In one embodiment, bioactive molecules identified in these screens may modulate splicing of a parent RNA molecule of the material. In another embodiment, bioactive molecules identified in these screens may modulate export of a parent RNA molecule from the nucleus. In another embodiment, bioactive molecules identified in these screens may modulate localization of a parent RNA molecule to or near the inhibitory synapse. In another embodiment, bioactive molecules identified in these screens may modulate export of a parent RNA molecule from the cell. In another embodiment, bioactive molecules identified in these screens may modulate expression of a protein encoded by a parent RNA molecule. In another embodiment, bioactive molecules identified in these screens may modulate steady-state concentration of a protein encoded by a parent RNA molecule. In another embodiment, bioactive molecules identified in these screens may modulate activity of a protein encoded by a parent RNA molecule. Methods for assessment of RNA splicing, export, or localization or protein expression, activity, or concentration are known to those skilled in the art (FIG. 4; also see Suzuki et al, Am J Med Genet. 121B:7-13).

The invention further includes, in another embodiment, end point assays to further characterize bioactive molecules for their biological function. The assays may, in one embodiment, involve an assay of events in a signal transduction pathway. Thus, the phosphorylation of a substrate, activation of a protein, and a change in the expression of genes that are up- or down-regulated in response to the enzyme protein dependent signal cascade can be assayed. In one embodiment, any of the biological or biochemical functions mediated by a protein encoded by the motifs, sequence fragments, or sequences of the present invention can be used as an endpoint assay. Specifically, a biological function of a cell or tissues that expresses the motifs, sequence fragments, or sequences of the present invention can be assayed. Each such assay represents a separate embodiment of the current invention.

Bioactive molecules identified by a screen of the present invention can be used to treat a subject with a disorder or disease, as will be appreciated by one skilled in the art. For example, bioactive molecules may be identified that modulate splicing or expression of RNA molecules comprising a binding site. If an aberrant splicing or expression pattern of a gene is associated with a disease state or disorder, and that gene contains a binding site that interacts with the bioactive molecule identified, the bioactive molecule might constitute a therapy or treatment for the disease or disorder. In another embodiment, a bioactive molecule that modulates the export or localization of an RNA molecule, or the activity or concentration of a protein might similarly constitute a therapy or treatment for a disease associated with aberrant export or localization an RNA molecule, provided that the RNA molecule contains a binding site that interacts with the bioactive molecule identified. In another embodiment, a bioactive molecule that modulates the activity or concentration of a protein might similarly constitute a therapy or treatment for a disease associated with aberrant activity or concentration of a protein, provided that the RNA molecule encoding the protein contains a binding site that interacts with the bioactive molecule identified. The therapy would include the steps of administering the bioactive molecule in a pharmaceutical composition to a subject in need of such treatment. These therapeutic methods represent embodiments of the present invention for all applications of therapeutic methods mentioned herein.

As used herein, the term "disorder" may refer, in one embodiment to any type of disease, disorder, or symptom This invention further pertains to novel bioactive molecules identified by the above-described screening assay. Accordingly, it is within the scope of this invention to further use a bioactive molecules identified as described herein in an appropriate animal model. For example, an agent identified as described herein (e.g., an RNA modulating agent, protein modulating agent an antisense nucleic acid molecule, an antibody specific for the material, or a binding partner specific for the material) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assay for treatments as described herein. These agents, and their uses described herein, represent embodiments of the present invention.

In another embodiment, the invention provides a method of assessing an expression of a gene of a cell, tissue, or biological sample, comprising the following steps:
  a. purifying a plurality of RBP-RNA complexes from the cell, tissue, or biological sample by the CLIP method;
     identifying an RNA molecule in the plurality of RBP-RNA complexes; and
     assessing the presence or amount of the gene among the plurality of RBP-RNA complexes,
thereby assessing an expression of a gene of a cell, tissue, or biological sample.

In one embodiment, the preceding method of assessing an expression of a gene can be used to generate a gene expression profile of the cell, tissue, or biological sample. In one embodiment of this method, the expression of multiple genes of the cell, tissue, or biological sample is assessed. The expression data are then, in one embodiment, compiled to obtain a gene expression profile. Analysis or comparison of multiple sequences performed manually, in one embodiment. In another embodiment, the analysis is performed using one of various methods for determining homology described hereinabove.

In another embodiment, the present invention provides a method of screening a test compound for its ability to modulate expression of a gene in a cell, comprising the steps of: (a) purifying a first plurality of RNA binding protein-RNA complexes from the cell by the CLIP method, wherein the cell has been contacted with the test compound; (b) identifying a first plurality of RNA molecules in the first plurality of RBP-RNA complexes; (c) assessing an amount of the gene among the first plurality of RNA molecules; (d) purifying a second plurality of RNA binding protein-RNA complexes from the cell by the CLIP method, wherein the cell has not been contacted with the test compound; (e) identifying a second plurality of RNA molecules in the second plurality of RBP-RNA complexes; and (f) assessing an amount of the gene among the second plurality of RNA molecules; wherein a difference between the amount of the gene in the first plurality of RNA molecules and the amount of the gene in the second plurality of RNA molecules indicates an ability of the test compound to modulate expression of a gene in a cell.

In another embodiment, the invention provides a method of screening a test compound for its ability to modulate gene expression in a cell, tissue, or biological sample, comprising the steps of (a) generating a first gene expression profile of a cell, tissue, or biological sample according to the method of generating a gene expression profile described herein, wherein the cell, tissue, or biological sample has been contacted with a test compound; (b) generating a second gene expression profile of a cell, tissue, or biological sample according to the method of generating a gene expression profile described herein, wherein the cell, tissue, or biological sample has not been contacted with the test compound; and (c) identifying differences between the first and second gene expression profile, differences indicating that the test compound can modulate gene expression in the cell, tissue, or biological sample. The test compound need not be one identified by a screen of the current invention.

In another embodiment, there is provided a method of treating a disease or disorder in a subject, comprising contacting a cell in the subject with an agent that modulates the expression or activity of a gene, or a protein encoded by the gene, wherein the gene has a sequence comprising a nucleic acid sequence as set forth in SEQ ID No 1-335, thereby treating the disease or disorder.

In another embodiment, there is provided a method of treating a disease or disorder in a subject, comprising contacting a cell in the subject with an agent that modulates the expression or activity of a gene, or a protein encoded by the gene, wherein the gene has a sequence comprising a nucleic acid sequence as set forth in SEQ ID No 336-449, thereby treating the disease or disorder.

In another embodiment, the present invention provides a method of using the RNA binding motifs to diagnose or screen for disease or predisposition to a disease mediated by parent genes of RNA fragment sequences of the present invention. In one embodiment, the disease or ailment is Paraneoplastic Opsoclonus Myoclonus Ataxia (POMA). In another embodiment, the disease is another neurologic disorder. In another embodiment, the disease is a non-neurologic disorder. In another embodiment, the disease is an autoimmune disorder. Any of the methods for diagnosis described herein may be used. Each method represents a separate embodiment of the present invention.

Nova was the first mammalian tissue-specific splicing factor identified. Nova is a neuron-specific RBP targeted in patients with the autoimmune disorder paraneoplastic opsoclonus-myoclonus ataxia. Nova proteins were identified as the autoantigens in POMA using high titer antibodies to clone cDNAs encoding two highly homologous KH-type RBPs, Nova-1 and Nova-2. Antisera from 6/6 POMA patients were found to block the interaction of Nova protein with RNA. These antibodies have been hypothesized to gain access to neurons and play a role in provoking the neuronal degeneration in POMA by blocking critical RNA-protein interactions.

POMA, also known as opsoclonus-myoclonus-ataxia syndrome, is an autoimmune neurological disorder found in cancer patients, which is characterized by a failure of the inhibition of brainstem and spinal motor systems. The clinical syndrome of paraneoplastic opsoclonus is characterized by the acute onset of opsoclonus and truncal ataxia, often accompanied by encephalopathy, myoclonus and a cerebrospinal fluid pleocytosis, but with no accompanying loss of neurons from the cerebellum, brainstem, cerebral hemispheres, or spinal cord. Unlike most other paraneoplastic syndromes, the course is often remitting and relapsing.

As used herein, "neurologic disorder" refers, in one embodiment, to a disease or disorder selected from the group consisting of epilepsy, convulsions, and seizure disorders. In another embodiment, the neurological disease or disorder is associated with spasticity. In another embodiment, the neurological disease or disorder is a neurodegenerative disorder. In another embodiment, the neurological disease or disorder is selected from the group consisting of spasticity, skeletal muscle spasms, restless leg syndrome, anxiety, stress, multiple sclerosis (MS), Sjogren's Syndrome, stroke, head trauma, spinal cord injury, Parkinson's Disease, Huntington's Disease, Alzheimer's Disease, amyotrophic lateral sclerosis, myotonic dystrophy, spinocerebellar ataxia, Spinal Muscular Atrophy, paraneoplastic neurologic disorders, multiple system atrophy, amyotrophic lateral sclerosis, human T-lymphotropic virus type 1 (HTLV-1)-associated myelopathy/tropical spastic paraparesis (HAM/TSP), migraine, headaches, and bipolar disorder. In another embodiment, the treatment alleviates or prevents convulsions or spasticity. All of these represent separate embodiments of the present invention.

As used herein, "autoimmune disorder" refers, in one embodiment, to a disease or disorder selected from the group consisting of autoimmune endocarditis, SLE, rheumatoid arthritis (RA), systematic sclerosis (SSc), celiac disease, insulin dependent diabetes mellitus, and juvenile rheumatoid arthritis (JRA).

Another embodiment of the present invention provides a method of diagnosing a disease or disorder associated with an alternate splicing pattern of a gene in a subject, the gene having a sequence comprising a nucleic acid sequence set forth in SEQ ID No 1-335, comprising assessing a splicing pattern of a transcript of said gene, assessing a splicing pattern of a reference standard, and comparing said splicing pattern of a transcript of said gene to said splicing pattern of a reference standard, thereby diagnosing a disease or disorder associated with an alternate splicing pattern of a gene in a subject.

Another embodiment of the present invention provides a method of diagnosing a disease or disorder associated with an alternate splicing pattern of a gene in a subject, the gene having a sequence comprising a nucleic acid sequence set forth in SEQ ID No. 336-449, comprising assessing a splicing pattern of a transcript of said gene, assessing a splicing pattern of a reference standard, and comparing said splicing pattern of a transcript of said gene to said splicing pattern of a reference standard, thereby diagnosing a disease or disorder associated with an alternate splicing pattern of a gene in a subject.

If one embodiment, "associated with" refers to a correlation between the alternate splicing pattern and the disease or disorder. In another embodiment, "associated with" refers to a causation of the disease or disorder by the alternate splicing pattern. In another embodiment, "associated with" refers to a predisposition to the disease or disorder in subjects with the alternate splicing pattern. Each possibility represents a separate embodiment of the present invention.

In one embodiment, the splicing pattern is assessed by RT-PCR analysis as described herein. Alternately, the splicing pattern can be assessed by any method known to those skilled in the art, as described, for example, in Molecular Cloning, (2001), Sambrook and Russell, eds. or Methods in Enzymology: Guide to Molecular Cloning Techniques (1987) Berger and Kimmel, eds. Each such method represents a separate embodiment of the present invention.

In one embodiment, "reference standard" refers to a sample derived from one or more individuals that do not exhibit the disorder of interest. A significant departure in a pattern observed in a sample from a subject from a pattern observed in a reference standard may be indicative of a disorder, or predisposition for a disorder.

In one embodiment, the disorder is a neurological disorder. In another embodiment, the disorder is POMA. In another embodiment, the disorder is an autoimmune disorder.

In another embodiment, the disorder is a cancer or disorder involving neoplastic cells. "Neoplastic cells" refers, in one embodiment, to cells whose normal growth control mechanisms are disrupted (typically by accumulated genetic mutations), thereby providing potential for uncontrolled proliferation. Thus, "neoplastic cells" can include both dividing and non-dividing cells. For purposes of the invention, neoplastic cells include cells of tumors, neoplasms, carcinomas, sarcomas, leukemias, lymphomas, and the like. In another embodiment, "neoplastic cells" can include central nervous system tumors, especially brain tumors. These include glioblastomas, astrocytomas, oligodendrogliomas, meningiomas, neurofibromas, ependymomas, Schwannomas, neurofibrosarcomas, etc. In another embodiment, "neoplastic cells" can include either benign or malignant neoplastic cells.

Antibodies to Nova and Neuronal Hu proteins are elicited by tumors, linking expression or activity of each of these proteins to cancer. The present invention has disclosed that a set of RNA molecules with the sequences as set forth in SEQ ID No 1-335 interact with Nova in a transformed cell line (FIG. 3). Thus, the particular splicing pattern or the expression of these RNA molecules is also characteristic of neoplastic transformation. In another embodiment, the particular splicing or expression pattern of one or more of these sequences may be useful as a diagnostic marker for the presence of cancer or other such disorder involving neoplastic cells. In another embodiment, a particular splicing or expression pattern of one or more of these sequences may be useful as a diagnostic marker for a particular stage of cancer or associated disorders involving neoplastic cells.

In another embodiment, the disorder is arthritis. HuR, a homologue of Neuronal Hu proteins, regulates the stability and/or nuclear export of the RNA of early response genes (Gallouzi, I E et al, Science 294: 1895-1901), which are expressed in arthritic joints (Aicher W K et al, Arthritis Rheum 48:348-59), indicating that Neuronal Hu proteins and homologous proteins may play a role in the etiology of arthritis. Since RBPs regulate the splicing of multiple targets (Examples 3-8), the splicing pattern or the expression of other neuronal Hu protein targets may be characteristic of arthritis. Thus, a particular splicing or expression pattern or one or more of these sequences may be useful as a diagnostic marker of the presence of arthritis.

In another embodiment, the disorder is atherosclerosis. Early response gene-1 (erg-1), which is regulated by HuR, is upregulated in atherosclerotic lesions (Bea F et al, Atherosclerosis 167:187-194). These data indicate that Neuronal Hu proteins and homologous proteins may play a role in the etiology of atherosclerosis. Since RBPs regulate the splicing of multiple targets (Examples 3-8), the splicing pattern or the expression of other neuronal Hu protein targets may be characteristic of atherosclerosis. Thus, a particular splicing or expression pattern or one or more of these sequences may be useful as a diagnostic marker of the presence of atherosclerosis.

The term "arthritis", in one embodiment, refers to rheumatoid arthritis, ankylosing spondylitis, juvenile rheumatoid arthritis, psoriatic arthritis, or any other type of arthritis or arthritis-like disorder.

In another embodiment, the disease is a metabolic disease. In another embodiment, the disease is diabetes. Nova-2 knockout mice exhibit a diabetes-like phenotype (Example 9).

In one embodiment, splicing of the parent gene is assessed. In another embodiment, branch point recognition of the parent gene is assessed. In another embodiment, export from the nucleus of the parent gene is assessed. In another embodiment, the export from the cell of the parent gene is assessed. In another embodiment, localization of the parent gene or its RNA to or close to inhibitory synapses is assessed. In another embodiment, expression level of a protein encoded for by the gene is also assessed. In another embodiment, the steady-state concentration of a protein encoded for by the gene is also assessed. In another embodiment, activity of a protein encoded for by the gene is also assessed.

In another embodiment, a patient may have a variant sequence in the parent RNA or protein whose splicing, localization, export, activity, concentration, or expression is assessed. In another embodiment the patient may have a normal sequence in the parent RNA or protein. Thus, the material can be isolated from a biological sample and assayed for the presence of a genetic mutation that results in aberrant sequence. This includes amino acid substitution, deletion, insertion, rearrangement, (as the result of aberrant splicing events), and inappropriate post-translational modification. Analytic methods for determining the presence of mutations include altered restriction enzyme analysis, nucleotide sequencing, electrophoretic mobility, altered tryptic peptide digest, altered enzyme activity in cell-based or cell-free assay, alteration in substrate or antibody-binding pattern, altered isoelectric point, direct amino acid sequencing, and any other of the known assay techniques useful for detecting mutations in a polynucleotide or protein. Such an assay can be provided in a single detection format or a multi-detection format such as an antibody chip array. Each such method represents a separate embodiment of the present invention.

In vitro techniques for detection of the motifs, sequence fragments, or sequences of the present invention or the proteins they encode include enzyme linked immuno-absorbent assays (ELISAs), immunoprecipitations and immunofluorescence using a detection reagent, such as an antibody or protein binding agent. Alternatively, the material can be detected in vivo in a subject by introducing into the subject a labeled antibody against the material or another type of detection agent. For example, the antibody can be labeled with a radioactive marker whose presence and location in a subject can be detected by standard imaging techniques. In addition, methods that detect the allelic variant of a material expressed in a subject and methods which detect fragments of a material in a sample could also be used. Each such method represents a separate embodiment of the present invention.

The motifs, sequence fragments, or sequences of the present invention may be useful, in one embodiment, in pharmacogenomic analysis. Pharmacogenomics deal with clinically significant hereditary variations in the response to drugs due to altered drug disposition and abnormal action in affected persons. The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes affects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the enzyme protein in which one or more of the enzyme functions in one population is different from those in another population. The materials thus allow a target to ascertain a genetic predisposition that can affect treatment modality. Accordingly, substrate dosage would necessarily be modified to maximize the therapeutic effect within a given population containing a polymorphism. The use of materials of this invention pharmacogenomic analysis thus represents an additional embodiment of the present invention.

Another embodiment of the present invention provides a method of treating a symptom, disorder, or disease in a subject, comprising contacting a cell in the subject with an agent that modulates the expression or activity of a parent gene or a protein encoded by the parent gene of a gene motif, sequence fragment, or sequence, comprising a sequence as set forth in SEQ ID No 1-335, thereby treating the disorder. In another embodiment, the gene motif, sequence fragment, or sequence comprises a sequence as set forth in SEQ ID No 336-449. In one embodiment, the agent is a parent gene, gene motif, sequence fragment, or sequence of the present invention. In one embodiment, the cell that is contacted is a neuron. Any therapeutic method disclosed that may modulate one of the parent genes, gene motifs, sequence fragments, or sequences described here is considered a part of the present invention.

In one embodiment, the agent is a nucleic acid. Protocols for introducing a nucleic acid or vector of the invention into cells may comprise, for example: direct DNA uptake techniques, virus, plasmid, linear DNA or liposome mediated transduction, or transfection, direct injection, magnetoporation, receptor-mediated uptake and others. In another embodiment, recombinant molecules encoding the RNA molecules are introduced into host cells such that they become integrated into the host cell genome. In one embodiment, the recombinant molecule is flanked by sequences known to promote homologous recombination. In another embodiment, the integrated recombinant molecule is transcribed within the cell to produce a heterologous RNA molecule (see, for example, "Methods in Enzymology" Vol. 1-317, Academic Press, Current Protocols in Molecular Biology Ausubel et al, eds.; and in Molecular Cloning (2001), Sambrook and Russell, eds.; or other standard laboratory manuals). In another embodiment, a nucleic acid may be chemically modified to be a PNA or another nucleic acid, or conjugate to a Trojan peptide as described herein. It is to be understood that any direct means or indirect means of intracellular access of a nucleic acid or vector of the invention is contemplated herein, and represents an embodiment thereof, of any application of introducing a nucleic acid or vector of the invention into cells mentioned herein.

In one embodiment of the present invention, "nucleic acids" refers to a string of at least two base-sugar-phosphate combinations. The term includes, in one embodiment, deoxyribonucleic acid (DNA) and ribonucleic acid (RNA). "Nucleotides" refers, in one embodiment, to the monomeric units of nucleic acid polymers. RNA may be in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes. The use of siRNA and miRNA has been described (Caudy A A et al, Genes & Devel 16:2491-96 as references cited therein). DNA may be in form plasmid DNA, viral DNA, linear DNA, or chromosomal DNA or derivatives of these groups. In addition these forms of DNA and RNA may be single, double, triple, or quadruple stranded. The term also includes, in one embodiment, artificial nucleic acids that may contain other types of backbones but the same bases. Examples of artificial nucleic acids are PNAs (peptide nucleic acids), phosphorothioates, and other variants of the phosphate backbone of native nucleic acids. PNA contain peptide backbones and nucleotide bases, and are able to bind both DNA and RNA molecules. The use of phosphothioate nucleic acids and PNA are known to those skilled in the art, and are described in, for example, Neilsen P E, Curr Opin Struct Biol 9:353-57; and Raz N K et al Biochem Biophys Res Commun. 297:1075-84. The production and use of nucleic acids is known to those skilled in art and is described, for example, in Molecular Cloning. (2001), Sambrook and Russell, eds. and Methods in Enzymology: Guide to Molecular Cloning Techniques (1987) Berger and Kimmel, eds. Each nucleic acid derivative represents a separate embodiment of the present invention.

In another embodiment of the present invention, nucleic acids may be conjugated to "Trojan peptides" such as HTV TAT peptide (Tat), transporten, and Antennapedia peptide. These peptides facilitate entry of the nucleic acids into cells, and their use is described in the literature. (Derossi et al, Trends Cell Biol 8:84-87; Simmons C G et al, Bioorg Med Chem Lett 7:3001-6; Pooga H et al, Nat Biotechnol 16:857-61). This technology may be able to introduce nucleic acids to the splicing machinery of a cell (Sergueev et al, Pharm Res 19:744).

In another embodiment, nucleic acids may comprise at least one modified base moiety which is selected from the group including, but not limited to: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-memylaminomethyluracil, 5-memoxyaminomethyl-2-thiouracil, beta-D-mannosylqueosine, 5N-methoxycarboxymethyluracil, 5-methoxyuracil, 2-methylthio-N6-isopentenyladenine, uracil-5-oxyacetic acid, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, and 2,6-diaminopurine.

In one embodiment, the disorder is a neurological disorder as described herein. In another embodiment, the disorder is POMA, Multiple Sclerosis, Alzheimer's Disease, Huntington's Disease or Parkinson's Disease. In one embodiment, the disorder is an autoimmune disorder as described herein.

In another embodiment, the disorder may be a type of cancer or disorder involving neoplastic cells as described herein. Antibodies to Nova and Neuronal Hu proteins are elicited by tumors, linking expression or activity of each of these proteins to cancer. The present invention has shown that the RNA molecules as set forth in SEQ ID No 1-335 interact with Nova in a transformed cell line (FIG. 3), indicating that their splicing or expression pattern may play a role in the transformation or survival of transformed cells such as cancer cells. In addition, HuR, a homologue of Neuronal Hu proteins, is believed to regulate the stability and/or nuclear export of the RNA of early response genes, which have been implicated in angiogenesis (Tarnawski et al, J Mol Med 2003). In one embodiment, an antibody or other molecule that binds a protein encoded by a sequence as set forth in SEQ ID No 1-335 or 336-449 may be conjugated to a toxic compound or biological molecule for use in cancer chemotherapy.

In another embodiment, the disorder is arthritis. HuR, a homologue of Neuronal Hu proteins, regulates the stability and/or nuclear export of the RNA of early response genes, which are expressed in arthritic joints, indicating that Neuronal Hu proteins and homologous proteins may play a role in the etiology of arthritis through regulation of the splicing or expression of any of the genes containing the CLP fragments disclosed in this invention. Thus, modulating the splicing, expression, or activity of one or more of these sequences are therapeutic strategies for arthritis, and represent additional embodiments of this invention.

In another embodiment, the disorder is atherosclerosis. Erg-1, which is regulated by HuR, is upregulated in atherosclerotic lesions. These data indicate that Neuronal Hu proteins and homologous proteins may play a role in the etiology of atherosclerosis through regulation of the splicing or expression of any of the genes containing the CLP fragments disclosed in this invention. Thus, modulating the splicing, expression, or activity of one or more of these sequences are therapeutic strategies for atherosclerosis, and represent additional embodiments of this invention.

In another embodiment, the disease is a metabolic disease. In another embodiment, the disease is diabetes. Nova-2 knockout mice exhibit a diabetes-like phenotype (Example 9).

In one embodiment, the agent modulates the expression or activity of the gene via inhibition or abrogation of binding of a protein to an RNA transcript of the gene comprising a sequence as set forth in SEQ ID No 1-335. In another embodiment, the inhibition or abrogation of protein binding may occur via steric hindrance. In another embodiment, the inhibition or abrogation of protein binding may occur via competitive inhibition. In another embodiment, splicing of the gene is modulated. In another embodiment, export from the nucleus of the gene is modulated. In another embodiment, localization of the gene or its RNA transcript to or close to inhibitory synapses is modulated. In another embodiment, export of the gene from the cell is modulated. In another embodiment, expression level of a protein encoded for by the gene is modulated. In another embodiment, the steady-state concentration of a protein encoded for by the gene is modulated. In another embodiment, activity of a protein encoded for by the gene is modulated.

In one embodiment, "steric hindrance" describes an effect on relative occupancy of a binding site caused by the space-filling properties of those parts of a molecule attached at or near the binding site. For example, the agent described herein may, by binding to the nucleic acid sequence described herein, reduce the rate of occupancy by a natural ligand of a binding site on the nucleic acid molecule. In another embodiment, the agent may completely prevent binding of a natural ligand to the binding site.

In one embodiment, "competitive inhibition" refers to binding of the agent to the RNA transcript of the gene, at a site that overlaps with a site at which an RNA binding protein would otherwise bind, such that binding of the RBP is substantially reduced. In one embodiment, "competitive inhibition" refers to binding of the agent to the RNA transcript of the gene, at a site that is identical to a site at which an RNA binding protein would otherwise bind.

In another embodiment, an agent that modulates the expression or activity of the motifs, sequence fragments, or sequences of the present invention may be useful for treating a disorder characterized by, for example, an absence of, inappropriate, or unwanted expression of a parent gene of a motif, sequence fragment, or sequence. Accordingly, methods for treatment may involve, in one embodiment, contacting a cell of a patient with the motifs, sequence fragments, or sequences of the present invention, their agonists or their antagonists. Each such method represents a separate embodiment of the present invention.

In one embodiment, the motif, sequence fragment, or sequence, agonist, or antagonist may be targeted to a neuron. In another embodiment, the material, agonist, or antagonist may be targeted to neuronal tissue. In one embodiment, the material, agonist, or antagonist may be targeted to the nervous system or a part of the nervous system. Nova and many of the RBPs described herein are preferentially expressed in neuronal tissue such as neurons, and in the nervous system in general. In one embodiment, the material, agonist, or antagonist may be targeted to an inhibitory synapse. In another embodiment, the material, agonist, or antagonist may be targeted to a nucleus. In one embodiment, the material, agonist, or antagonist may be targeted to a cytoplasm. Nova was shown in this invention to be present in inhibitory synapses, nucleus, and cytoplasm of neurons (Examples 6 and 7). It is known to those skilled in the art that many proteins that mediate splicing are present in the cytoplasm.

The term "neuron" refers, in one embodiment, to any cell that functions in the central nervous system or the peripheral nervous system. In another embodiment, the term refers to any cell located in or near tissue of the central nervous system or the peripheral nervous system.

In another embodiment, the present invention provides a kit that comprises the method of assessing a splicing pattern of a gene comprising a nucleic acid sequence as set forth in SEQ ID No 1-335 or 336-449. Kits are packages that facilitate a diagnostic or other procedure by providing materials or reagents needed thereof in a convenient format. Many kits have been successfully commercialized.

Gephyrin is a protein that plays a key scaffolding role in the inhibitory synapse. Gephyrin is essential for the correct localization of $GABA_A$ $\gamma 2$ and $GlyR\alpha 2$ subunits to the synapse, the same subunits whose pre-mRNA splicing is regulated by Nova. Finally, gephyrin, like Nova, has been reported to be the target of a cancer-associated neurologic disorder, SMS, manifest by excess motor activity.

In one embodiment, modulating the expression or activity of a Nova protein may in turn affect the expression or activity of a gephyrin protein or gephyrin RNA. In one embodiment, the splicing, expression, export from the nucleus, localization, or export from the cell of gephyrin RNA may be affected. In another embodiment, the expression, concentration, or activity of gephyrin protein may be affected.

In another embodiment, the invention provides an RBP binding site comprised of nucleic acid having a sequence comprising n repeats of a sequence selected from the group consisting of CCAU, UCAU, UCAC, CCAC, UCCAUC, CCAUCC, AUCCAU, CAUCCA, UCAUCC, CAUCAU, CCAUCU, CCUCCC, CUCAUC, CAUCCU, CUCACC, AUCAUC, CCAUCA, CCCAUC (SEQ ID No 450-467, respectively), where an integer between 1 and 10, inclusive. Each of these sequences represents a separate embodiment of the present invention. These binding sites may be collectively referred to as a "YCAY motif" SEQ ID No 468, in which "Y" may refer to Cytosine, Uridine, Thymidine, or derivatives thereof. Another embodiment may be referred to as a "YCAYY motif" SEQ ID No 469.

It should be noted that the consensus Nova binding site is similar to the consensus sequence for branch site recognition in animal cells, linking the action of Nova to branch site recognition. Accordingly, this invention includes embodiments in which effects on splicing by Nova or other RBP are mediated by effects on branch point recognition.

In another embodiment, the invention provides an RBP binding site comprised of nucleic acid having a sequence comprising n repeats of a sequence selected from the group consisting of GTTTT, GTTT, CTTTT, CTTT, GTTTC, CTTTC (SEQ ID No 503-508, respectively), where n is an integer between 1 and 10, inclusive.

In one embodiment, n is between 1 and 9. In another embodiment, n is between 1 and 8. In another embodiment, n is between 1 and 7. In another embodiment, n is between 1 and 6. In another embodiment, n is between 1 and 5. In another embodiment, n is between 1 and 4. In another embodiment, n is between 1 and 3. In another embodiment, n is between 1 and 2. In another embodiment, n is between 1 and 5. In another embodiment, n is between 2 and 5. In another embodiment, n is between 3 and 5. In another embodiment, n is between 4 and 5. In another embodiment, n equals exactly 3.

It will be appreciated by one skilled in the art that nucleic acid substitutions, analogues, or derivatives of the binding sites that result in increased binding strength that can be detected by a method of the present invention are also included in the present invention. In another embodiment, sequences highly homologous to the claimed binding sites also form a part of the present invention.

In another embodiment, the invention provides an isolated nucleic acid comprising a sequence set forth in SEQ ID No 63, 64, 76, 77, 78, 84, or 292-335. In another embodiment, there is provided an isolated nucleic acid that comprises a sequence set forth in SEQ ID No 374, 377, 378, 380, 382, 384, 387, 394-396, 415, 416, or 421. In one embodiment, the nucleic acid is RNA or a derivative thereof. In another embodiment, the invention provides an oligonucleotide of at least 15 bases, with a nucleic acid sequence corresponding to SEQ ID NO 1-335, or a complementary sequence thereof. In another embodiment, the invention provides an oligonucleotide of at least 15 bases, with a nucleic acid sequence corresponding to SEQ ID NO 336-449, or a complementary sequence thereof. In one embodiment, the oligonucleotides may be either sense or antisense in orientation. Homologues of the isolated nucleic acid sequences and oligonucleotides are also included in the current invention.

In one embodiment, "oligonucleotides" are short-length, single- or double-stranded polydeoxynucleotides that are chemically synthesized by known methods (such as phosphotriester, phosphite, or phosphoramidite chemistry, using solid phase techniques such as described in EP 266,032 published 4 May 1988, or via deoxynucleoside H-phosphonate intermediates as described by Froehler et al, Nucl. Acids Res, 14: 5399-5407 [1986]). They may then, in one embodiment, be purified on polyacrylamide gels. Oligonucleotides may be composed of any of the embodiments of nucleic acids disclosed herein.

In another embodiment, the invention provides an isolated peptide having an amino acid sequence encoded by a nucleic acid sequence as set forth in SEQ ID No 63, 64, 76, 77, 78, 84, or 292-335. In another embodiment, the invention provides an isolated peptide encoded by a nucleic acid sequence as set forth in SEQ ID No 374, 377, 378, 380, 382, 384, 387, 394-396, 415, or 416, 421. Homologues of the isolated peptides are also included in the current invention.

The RNA sequences, oligonucleotides, and peptides may be used for a wide variety of purposes, including the diagnosis or treatment of a disease or disorder, screening methods to identify bioactive molecules, searches for homologous sequences, scientific experiments, or identification of useful consensus sequences that may not be exactly represented among the sequences. The RNA sequences, oligonucleotides, and peptides may be subcloned into a plasmid or vector, ligated into another molecule, amplified, or subjected to any other procedure for manipulated nucleic acids that is known in the art (see, for example, Molecular Cloning. (2001), Sambrook and Russell, eds.).

In another embodiment, the invention provides a method of modifying an expression profile of a gene of interest, comprising engineering the gene of interest to comprise an RNA motif comprising a sequence as set forth in SEQ ID No 1-335 and 450-469, thereby modifying the expression profile of the gene of interest. In one embodiment, the sequences are inserted alone. In another embodiment, the sequences are inserted together with surrounding sequence. Split up these; also comprising a motif identified by the method of . . . .

In one embodiment, the modification of the gene is tissue specific. In another embodiment, the modification is specific to neuronal tissue. In another embodiment, the tissue-specific modification is specific to for example, the nervous system. The nervous system may refer to, for example, the central nervous system, the peripheral nervous system, a portion of the nervous system, or any combination of these elements. In another embodiment, the modification is not tissue specific. Each of these represents a separate embodiment of the present invention.

A "tissue specific" modification refers, in one embodiment, to a modification that is only manifest in specific tissues. In another manifestation, "tissue specific" modification refers to a modification that is primarily manifest in specific tissues.

In one embodiment, the modification may affect the splicing of an RNA molecule. In one embodiment, the modification may affect the branch point recognition of an RNA molecule In another embodiment, the modification may affect the extent of export of an RNA molecule from the nucleus. In another embodiment, the modification may affect the localization of an RNA molecule to or near the inhibitory synapse. In another embodiment, the modification may affect the extent of export of an RNA molecule from the cell. In another embodiment, the modification may affect the expression of a protein encoded by an RNA molecule. In another embodiment, the modification may affect the steady-state concentration of a protein encoded by an RNA molecule. In another embodiment, the modification may affect the activity of a protein encoded by an RNA molecule. In one embodiment, a parent RNA molecule may be affected in one of the ways mentioned herein.

In one embodiment, the RBP binding site is introduced into an exon of a gene of interest. In another embodiment, the binding site is introduced into an intron of a gene of interest. In one embodiment, the binding site is introduced into a 5' untranslated region of a gene of interest. In one embodiment, the binding site is introduced into a 3' untranslated region of a gene of interest.

The binding sites can be inserted, in one embodiment, into a gene of interest by inserting the appropriate nucleotide sequences encoding the desired amino acid sequences to each other by methods commonly known in the art, such as, for example, ligation. The resulting nucleic acid can then be subcloned into an appropriate expression rector as described herein, or can be flanked by sequences that will promote intra-chromosomal insertion (e.g., by homologous recombination or random integration) and introduced into the desired host cell, where it may be expressed.

In one embodiment, the gene of interest is Nova-1, Nova-2, or a homologue thereof. In another embodiment, the gene is not a homologue of Nova-1 or Nova-2. In one embodiment, the gene is a reporter gene.

In another embodiment, the gene may be any nucleotide sequence, the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.). Each sequence represents a separate embodiment of the present invention.

A wide variety of genes can be modified by the binding sites of the present invention such as genes encoding vaccines, antigens, toxic gene products, potentially toxic gene products, and anti-proliferation or cytostatic gene products.

Reporter genes can also be modified including enzymes, (e.g. chloramphenicol acetyltransferase, beta-galactosidase, luciferase, beta-glucuronidase, Green Fluorescent Protein, HIS3), fluorescent proteins such as green fluorescent protein, or antigenic markers. Reporter genes, are one embodiment, are genes whose expression can be detected by detection methods known in the art.

In one embodiment, to comprise the nucleic acid sequence or RBP binding site inserted into the gene of interest may compete for a biological factor that binds a different molecule or binding site. When a molecule or binding site interacts with a biological factor that is present at limiting concentrations, it may, in one embodiment, reduce the number of copies of the biological factors that are available to interact with other molecules or binding sites, competing with the other molecules or binding sites for the biological factor. In another embodiment, competing for a biological factor may eliminate other copies of the biological factor that are available to interact with other molecules or binding sites. Thus, competition for a biological factor may reduce or eliminate the number of copies of the biological factor that interact with the other molecule or binding site.

There may be, in one embodiment, another binding site for the biological factor at a different portion of the gene of interest. In another embodiment, there may be another binding site for the biological factor on a different gene. In this case, competition for the biological factor by may reduce or eliminate the number of copies of the biological factor that interact with the alternate site of the gene of interest or other gene. In this way, the engineered binding site may thus indirectly affect the expression pattern of the gene of interest or other gene. In one embodiment, the splicing patter of the gene of interest or other gene may be affected. Competition for binding sites has been shown to affect the activity of the splicing factor Sub2P.

The present invention includes, in one embodiment, the use of the modified gene to diagnose, treat, ameliorate, or prevent a disease or ailment. In one embodiment, the disease or ailment is POMA. In another embodiment, the disease is another neurologic disorder as described herein. In another embodiment, the disease is a non-neurologic disorder. In another embodiment, the disease is an autoimmune disorder as described herein.

In one embodiment, the diagnosis, treatment, amelioration, or prevention of the disease may comprise administering the modified gene in a pharmaceutical composition to a subject in need of such treatment. In another embodiment, the diagnosis, treatment, amelioration, or prevention of the disease may comprise the use of a reporter gene modified as described herein. The use of the modified reporter gene may include, but is not limited to, diagnosis of defects in RNA splicing, export, localization or protein expression, concentration or activity of endogenous genes. Each of these methods represents a separate embodiment of the present invention.

In another embodiment of the invention, the aforementioned vector is introduced into an embryonic cell or other type of cell, for the construction of a transgenic animal to regulate the expression of a transgene in a tissue specific manner.

The modified genes can be introduced into animals by transgenic technology. Animals of any species, including, but not limited to, mice, rats, rabbits, guinea pigs, pigs, micro-pigs, goats, sheep, cattle, chickens, fish and non-human primates, e.g., baboons, monkeys and chimpanzees may be used to generate transgenic animals. The term "transgenic", in one embodiment, refers to animals expressing coding sequences from a different species (e.g., mice expressing human gene sequences), as well as animals that have been genetically engineered to no longer express, or express inactive versions of, endogenous gene sequences, (i.e., "knockout", or "null" animals). In transgenic animals that express coding sequences from a different species, as well as in the genetically engineered "knock out" transgenic animals, the altered coding sequences are present in a stably integrated form in their somatic cells, and may also be stably integrated into their germ cell lines so that the altered coding sequences are passed on to their progeny. The present invention encompasses transgenic animals whose progeny contain such stably integrated altered coding sequences as well as transgenic animals wherein the altered coding sequences are stably integrated only in their somatic cells, and therefore not passed on to their progeny. As used herein, "progeny" also refers to subsequent generations of single cells. Methods for the preparation and use of such animals are known in the art. A protocol for the production of a transgenic pig can be found in White and Yannoutsos, *Current Topics in Complement Research: 64th Forum in Immunology*, pp. 88-94; U.S. Pat. No. 5,523,226; U.S. Pat. No. 5,573,933; PCT Application WO93/25071; and PCT Application WO95/04744. A protocol for the production of a transgenic rat can be found in Bader and Ganten, Clinical and Experimental Pharmacology and Physiology, Supp. 3:S81-S87, 1996. Protocol for the production of a transgenic cow and a transgenic sheep can be found in Transgenic Animal Technology, A Handbook, (1994), Pinkert, C A ed., Academic Press, Inc.

Transgenic non-human animals may produced by introducing altered coding sequences into the germ line of the non-human animal. Embryonal target cells at various developmental stages may be used to introduce the altered coding sequences of the invention. Different methods may be used depending on the stage of development of the embryonal target cell(s). Such methods include, but are not limited to, microinjection of zygotes, viral integration, and transformation of embryonic stem cells as described below, and in U.S. Pat. No. 6,613,958 and references cited therein. Each such method represents a separate embodiment of the present invention.

Microinjection of zygotes is one method for incorporating altered coding sequences into animal genomes. A zygote, which is a fertilized ovum that has not undergone cell division, is the preferred target cell for microinjection of transgenic DNA sequences. The mouse male zygote nucleus reaches a size of approximately 20 micrometers in diameter, a feature which allows for the reproducible injection of 1-2 picoliters of a solution containing transgenic DNA sequences. The use of a zygote for introduction of altered coding sequences has the advantage that, in most cases, the injected transgenic DNA sequences will be incorporated into the host animal's genome before the first cell division (Brinster et al., Proc. Natl. Acad. Sci. USA 82:4438). As a consequence, all cells of the resultant transgenic animals (founder animals) stably carry an incorporated transgene at a particular genetic locus, referred to as a transgenic allele. The transgenic allele demonstrates Mendelian inheritance, i.e., half of the offspring resulting from the cross of a transgenic animal with a non-transgenic animal will inherit the transgenic allele, in accordance with Mendel's rules of random assortment.

Viral integration can also be used to introduce the altered coding sequences of the invention into an animal. This method is further described in Jaenich, Proc. Natl. Acad. Sci.

USA 73:1260). Introduction of altered coding sequences into germ line cells by this method is possible but probably occurs at a low frequency. However, once a transgene has been introduced into germ line cells by this method, offspring may be produced in which the transgenic allele is present in all of the animal's cells, i.e., in both somatic and germ line cells.

Embryonal stem (ES) cells can also serve as target cells for introduction of the transgenes of the invention into animals, as described in Evans et al., Nature 292:154. Once a transgene has been introduced into germ line cells by this method, offspring may be produced in which the transgenic allele is present in all of the animal's cells, i.e., in both somatic and genu line cells.

In another embodiment, the present invention provides a transgenic mouse comprising a mutation in a Nova-2 gene (FIGS. 4, 9, and 10). In one embodiment, the Nova-2 mutation may alter, diminish, or abrogate expression of Nova-2 RNA or Nova-2 protein. In another embodiment, the mutation may result in production of Nova-2 protein with an altered amino acid sequence. In another embodiment, the mutation may result in production of Nova-2 RNA with an altered nucleotide sequence. In another embodiment, the mutation is a null mutation. In another embodiment, the mutation is a temperature sensitive mutation. In another embodiment, the mutation, or expression of the transgenic Nova-2 protein, is manifest in a tissue-specific manner.

In one embodiment, the transgenic mouse may be generated by the technique of cre-lox recombination (FIG. 9A). In this system, the cre enzyme (also referred to as flp recombinase) is used to catalyze site-specific recombination of homologous sequences between a targeting vector and genomic DNA, such that either the genomic DNA is replaced by sequences from the targeting vector, or sequences from the targeting vector are inserted into genomic DNA sequences. Cre binds to sites known as loxP sites, catalyzing recombination between loxP sites on other molecules, or between multiple sites on the same molecule. "Recombination" refers, in one embodiment, to the breaking and rejoining of strands of DNA to produce a rearranged molecule. The use of cre-lox recombination is known to those skilled in the art (see, for example, Fuchs E C, et al, Proc Natl Acad Sci USA 98:3571-76).

In one embodiment of cre-lox recombination, the cre enzyme may be inserted into the genome of the transgenic mouse. In another embodiment, the cre enzyme may be under the control of an inducible promoter. In another embodiment, the sequence inserted into the mouse's genome may contain one or more selectable markers that confer antibiotic resistance, such as, for example, neomycin resistance. In another embodiment, the selectable markers may be removed subsequent to inserting the sequence into the genome. In another embodiment, cre-lox recombination may be performed on embryonic stem cells, which may, in one embodiment, be subsequently used to generate a transgenic mouse. In another embodiment, insertion of the foreign sequence into the mouse's DNA may be verified by Southern blot (FIG. 9B). Each of these methods represents another embodiment of the present invention.

Nova-2 knockout mice were shown to exhibit splicing defects in GABAγ2 RNA (FIG. 10), showing that Nova-1 and Nova-2 are capable of mediating similar functions. In addition, it was shown that the knockout mice had elevated circulating levels of IGF-1, and low levels of serum glucose. This shows that RBP in general, and Nova in particular, have implications in metabolic systems, and potentially those involving autoimmune diseases.

In another embodiment, cells may be isolated from the transgenic animals described herein. Transgenic animals, or cell isolated from them, may be used, in one embodiment, as disease models for POMA or other diseases, or for other purposes apparent to one skilled in the art. In one embodiment, the isolated cells, or their progeny, may be used for one of the purposed described herein. In another embodiment, the isolated cells may be used to generate cell lines, which may be used for one of the purposed described herein. A "cell line", in one embodiment, refers to a lineage of cells derived from a cell that has been immortalized. An "immortalized cell" refers, in one embodiment, to a cell that has enhanced ability to replicate, or to be propagated in cell culture. Each such use of the transgenic animals or cells derived from them represents an additional embodiment of the present invention.

In another embodiment, there is provided a method for identifying a therapeutic agent for the treatment of a disease or disorder associated with Nova-2 gene expression. In one embodiment, this method comprises the steps of (a) contacting a cell of a transgenic mouse described herein with a candidate therapeutic agent; (b) determining qualitative or quantitative changes in a parameter in the transgenic mouse associated with the disease or disorder in the presence of the candidate therapeutic agent; and (c) determining qualitative or quantitative changes in a parameter in the transgenic mouse associated with the disease or disorder in the absence of the candidate therapeutic agent. If amelioration or abrogation of the disease or disorder is observed in the transgenic mouse, this may indicate a therapeutic effect of the candidate therapeutic agent. In one embodiment, the parameter that is observed may be a symptom, indicator, or manifestation of the disease or disorder of interest.

In another embodiment, there is provided a method for studying a symptom, disease or disorder associated with Nova-2 gene expression, comprising ascertaining the presence or absence of the symptom, disease or disorder in the transgenic mouse described herein. In another embodiment, a quantitative, or qualitative change in the extent of the symptom, disease or disorder may be measured. In one embodiment, the symptom, disorder, or disease may be POMA, one of the diseases or disorders disclosed herein, or an associated symptom. In one embodiment, exhibition of the symptom, disease, or disorder in the transgenic mouse indicates involvement of Nova-2 gene expression in the symptom, disease, or disorder. In another embodiment, if the symptom, disease, or disorder is present in the transgenic mouse, the transgenic mouse may be used as a disease model. Methods for measuring or ascertaining a symptom, disorder, or disease are known in the art, and vary according to the particular symptom, disorder, or disease. In one embodiment, they may comprise direct observation, observation of a change in a behavior pattern, or observation of a physiological change, a histological change, or a manifestation of pain. In another embodiment, the method may comprise administering a test of the animal's fitness, activity level, immunological health, coordination, or mental ability. Each such method represents a separate embodiment of the present invention.

In another embodiment, there is provided a method for identifying a therapeutic agent for the treatment of a disease or disorder associated with Nova-2 gene expression, comprising (a) contacting a cell of transgenic mouse of the present invention with a candidate therapeutic agent; (b) assessing a parameter associated with the disease or disorder in the transgenic mouse in the presence of the candidate therapeutic agent; and (c) assessing a parameter associated with the disease or disorder in the transgenic mouse in the absence of the candidate therapeutic agent, wherein amelioration of the parameter in the transgenic mouse is an indication of a therapeutic effect of the candidate therapeutic agent.

Disease models may be used to test potential therapies or prophylactic measures, or to understand the etiology of a symptom, disease, or disorder. Methods for using mice as a disease model are known in the art, and vary according to the particular symptom, disorder, or disease. Each such method represents a separate embodiment of the present invention.

In one embodiment, the disease or disorder that is studied, or for which a therapeutic agent is identified, is a neurological disorder as described herein. In another embodiment, the disorder is POMA, Multiple Sclerosis, Alzheimer's Disease, Huntington's Disease or Parkinson's Disease. In one embodiment, the disorder is an autoimmune disorder as described herein.

In another embodiment, the method for studying a symptom, disease, or disorder may involve complementing the transgenic mouse with a wild-type Nova-2 gene. "Complementation", in one embodiment, refers to contacting a transgenic animal, or a cell derived from the animal, with a gene or nucleic acid molecule encoding a wild-type copy of a gene that has been mutated or deleted. Restoration of a phenotypic characteristic that is altered in the transgenic animal may indicate, in one embodiment, that the observed phenotypic characteristic is due to the altered gene. Techniques for complementation of mutated genes are known to those skilled in the art (see, for example, Ikenaka et al, Dev Neurosci. 17:127-36, and referenced cited herein for transgenic animals).

In another embodiment, complementation of the transgenic mouse with a wild-type Nova-2 gene may utilize a vector comprising a wild-type Nova-2 gene under the control of an inducible promoter. "Inducible promoters," in one embodiment, refer to promoters whose activity can be affected by the presence of one or more factors. Inducible promoters are familiar to those skilled in the art, and are discussed, for example, in Christen et al Transgenic Res. 11:587-95.

In another embodiment, the present invention provides a method of studying a Nova-2 protein function, comprising assessing a qualitative or quantitative change in a parameter in a transgenic mouse of the present invention, thereby studying a Nova-2 protein function.

In one embodiment, the parameter measured may be the pattern of splicing, localization, export from the nucleus, or export from the cell of an RNA molecule. In another embodiment, the parameter measured may be the pattern of expression, concentration, or activity of a protein molecule. Methods for measuring changes in splicing, localization, export, expression, concentration, or activity of an RNA or protein molecule have been described herein. In one embodiment, the changes detected may be a quantitative or qualitative change, increase, or decrease in the magnitude, frequency, duration, consistency, or reproducibility of the parameter.

In another embodiment, the method of determining downstream effects of altered Nova-2 gene expression may involve complementing the transgenic mouse with a wild-type Nova-2 gene as described herein. In this case, a parameter is measured in a wild-type mouse, an uncomplemented transgenic mouse, and a transgenic mouse that has been complemented with the wild-type Nova-2 gene. If a difference is observed between the wild-type and uncomplemented transgenic mice, partial or complete restoration of the wild-type phenotype in the complemented transgenic mouse provides corroborates the conclusion that altered Nova-2 gene expression affects the phenotype. In another embodiment, the complementation of the transgenic mouse with a wild-type Nova-2 gene may utilize a vector comprising a wild-type Nova-2 gene under the control of an inducible promoter, as described herein.

In another embodiment, the method of determining downstream effects of altered Nova-2 gene expression may involve isolating one or more nucleic acid molecules that interact with Nova-2 protein. In one embodiment, the isolation of the nucleic acid molecules may take place by any method known in the art, such as immunoprecipitation or any of the methods described herein. In one embodiment, the immunoprecipitation may be carried out with an antibody or antiserum that recognizes Nova protein as described herein. In another embodiment, the nucleic acid molecules may be purified. In another embodiment, the nucleic acid molecules may be identified. A change in a pattern of splicing, expression, localization, or export from the nucleus or from the cell of the nucleic acid molecules in the transgenic mouse may indicate that expression of Nova-2 protein affects the parameter measured.

In another embodiment, the method of isolating nucleic acid molecules that interact with Nova-2 protein may comprise the CLIP method disclosed herein. The CLIP fragments obtained from the wild-type and transgenic mouse may be compared to ascertain difference between them, the differences indicating an effect of altered Nova-2 gene expression.

In another embodiment, the method of isolating nucleic acid molecules that interact with Nova-2 protein may comprise the use of differential display. Mammals, such as human beings, have about 100,000 different genes in their genome, of which only a small fraction, perhaps 15%, are expressed in any individual cell. Differential display techniques permit the identification of genes specific for individual cell types. Briefly, in differential display, the 3' terminal portions of mRNAs are amplified and identified on the basis of size. Using a primer designed to bind to the 5' boundary of a poly(A) tail for reverse transcription, followed by amplification of the cDNA using upstream arbitrary sequence primers, mRNA sub-populations are obtained. Differential display techniques are described in more detail in U.S. Pat. No. 6,623,928 are references cited therein.

In another embodiment, the transgenic mouse may be used to determine whether a test compound exhibits Nova agonist or antagonist activity. This method comprises the steps of: (a) contacting a cell of the transgenic mouse of the present invention with a test compound; (b) contacting a cell of a Nova-2-expressing mouse with the test compound; and (c) determining changes in a parameter associated with Nova activity. In one embodiment, the parameter measured may be the splicing pattern of a gene affected by Nova (Example 4) such as, for example, one of the genes disclosed herein. In another embodiment, the parameter measured may be the pattern nucleic acid molecules isolated by the CLIP method with anti-Nova antisera, or isolated by another method known in the art for isolating nucleic acid molecules associated with a protein. Enhancement of Nova activity may be indicative of agonist activity, and diminution or abrogation of Nova activity may be indicative of antagonist activity.

EXAMPLES

Example 1

CLIP Specifically Isolates Covalently Bound RBP-RNA Complexes

Materials and Experimental Methods

Immunoblot Analysis.

The following antibodies were used: gephyrin (Transduction laboratories), rabbit Nova antiserum (Buckanovich, R. J. et al, Mol Cell Biol 17, 3194), Hsp90 (Transduction laboratories), rabbit brPTB antiserum (Polydorides, A. D. et al, Proc Natl Acad Sci USA 97, 6350), dimethyl-Histone H3 (Upstate Biotechnology). Antibody to neuronal Hu proteins and Human POMA serum were obtained from paraneoplastic neurologic disease patients. BrPTB antibody was used as previously described (Polydorides A D et al, Proc Natl Acad Sci USA 97: 6350-55).

Nova-1 Knockout Mice.

Nova-1 knockout mice were previously described (Jensen K B et al, Neuron 25:359-71).

UV Cross-Linking of Mouse Tissue.

Mouse hindbrain and spinal cord tissue was dissected from 60 postnatal day 4 P8 mice, and rapidly disaggregated in 50-milliliter (ml) polypropylene tubes using a rubber syringe plunger. This tissue suspension was filtered through a 200 micron (μm) nylon filter, the filter was washed with more PBS (total volume was about 100 ml), and flow-through was transferred to 50 ml falcon tubes and spun at 2500 rotations per minute (rpm), 10 minute (min) at 4° Celsius (C). Supernatant was removed and cells resuspended in 80 ml total volume of PBS. Washed tissue material was then resuspended with 1×PBS and placed in 150-millimeter (mm) culture plates (10 ml cell suspension per plate) for irradiation. Irradiation was carried out with a mercury light (maximum emission at 254 nm) to a final energy of 400 millijoule (mJ)/centimeter (cm)$^2$.

Suspension was collected, and then each irradiated plate washed with 15 ml fresh PBS. Wash and suspension were combined and pelleted at 2500 rpm, 10 min, 4° C.; then resuspended in 30 ml total volume of PBS. Suspension was distributed to Eppendorf tubes (1 ml per tube), pelleted, and supernatant removed. Pellets were frozen at −80° C. until use.

Immunoprecipitation

Solutions

PXL solution comprises 1×PBS (tissue culture grade; no Mg++, no Ca++) or 5×PBS (designated as 1×PXL and 5×PXL, respectively), 0.1% SDS, 0.5% sodium deoxycholate, and 0.5% Noniodet P-40 (NP-40).

1×PNK+ comprises 50 mM tris(hydroxymethyl)aminomethane (tris)-Cl pH 7.4, 10 mM MgCl2, and 0.5% NP-40.

Bead Preparation:

300 microliter (μl) of protein A-Dynabeads stock were used for each Eppendorf tube of cross-linked lysate. Beads were washed 3 times with 1×PXL and resuspended in 150 μl 1×PXL. 60 μl rabbit anti-Nova and protein A-Dynabeads were added to each 200 μl of bead stock. Tubes were rotated at room temperature for 30-45 min and washed 3 times with 1×PXL and 1 time with 5×PXL.

RBP-RNA Complex Isolation 350-400 μl per tube 1×PXL was added to cross-linked lysate, then lysate was incubated on ice for 10 minutes in a total volume of 900 μl 40 μl RNAsin and 40 μl of Promega RQ1 DNAse was added to each tube, and samples incubated at 37° for 15 min, rotating at 1000 rpm. 4-6 μl of Ambion biochemistry grade RNAse T1 diluted 1:500 in PXL was added, and tubes were incubated at 37° for 10 min. Lysates were centrifuged in pre-chilled micro-ultracentrifuge; 90,000 rpm for 25 min at 4° (polycarbonate tubes in TLA 120.2 rotor). Supernatant was removed, added to a prepared tube of beads, and rotated for 1 hour at 4°. Beads were then washed with ice-cold buffer, using wash volumes of 800-1000 μl, with the following Number of iterations: 2 times with 1×PXL, 1 time with 5×PXL, and 3 times with 1×PNK+. Beads were resuspended in 80 μl of 1×PNK+, and 10 μl of $^{32}$P gamma-ATP and 10 μl of T4 polynucleotide kinase enzyme added. Tubes were incubated in themomixer at 37° and 1000 rpm for 30 min. 5 μl of 100 mM Adenosine Triphosphate (ATP) was added, and tubes incubated another 5 min. Beads were washed 4 times with 1×PNK+.

RBP-RNA Complex Purification

Washed beads were resuspended in 30 μl of 1×PNK+ and 30 μl of Novex loading buffer, and incubated at 70° C. for 10 min at 1000 rpm. Beads were isolated and the supernatant loaded on a Novex NuPAGE 10% Bis-Tris gel. Each tube was loaded onto 3 wells. After gel run, gel was transferred to BA-85 NC Schleicher & Schuell Bioscience, Inc. (Keene, N.H.) using a Novex wet transfer apparatus. Most of the radioactive signal in the gel was below a MW of about 20-15 kDa, and this portion of the gel was cut off prior to transfer. After transfer, NC filter was rinsed in 1×PBS and gently blotted on Kimwipes; membrane was wrapped in plastic wrap and exposed to film.

RNA Isolation and Purification

Solutions

1×PK buffer comprises 100 mM Tris-Cl pH 7.5, 50 mM NaCl, and 10 mM EDTA. 1×PK buffer/7 M urea comprises 100 mM Tris-Cl pH 7.5, 50 mM NaCl, 10 mM EDTA, and 7 molar (M) urea. This buffer should be made fresh.

The piece of NC corresponding to the radioactive band (FIG. 1B) was cut out using a scalpel blade, and cut into pieces as small as possible. This band was positioned 510 kDa higher than Nova protein alone, as assayed by Western blotting (data not shown). 4 milligram (mg)/ml proteinase K (prot K) was added to 1×PK buffer and pre-incubated at 37° C. for 20 min to inactivate RNAses. 200 μl of prot K solution was combined with each isolated NC piece in a microcentrifuge tube and incubated 20 min, 37° at 1200 rpm. 200 μl of prot K/7M urea solution was added, and the tubes were incubated 20 min, 37° at 1200 rpm. 400 μl "RNA phenol" and 130 μl of CHCl$_3$ was added to tubes, which were then incubated at 37° for 20 min at 1400 rpm. "RNA phenol" is pure phenol that has been equilibrated with 0.15 M Sodium acetate (NaOAc) pH 5.2; "CHCl$_3$" is chloroform at a ratio of 49:1 with isoamyl alcohol. Tubes were spun at 14,000 rpm in a microcentrifuge, and aqueous phase was transferred to empty tubes. 50 μl 3M NaOAc pH 5.2 and 1 ml of 1:1 ethanol:isopropanol (EtOH:isopropanol) was added. Samples were precipitated overnight at −20°

RNA Ligations

RNA was spun down, washed and dried, and counted in scintillation counter (Chrenkov). 20% of sample was set aside as an unligated control.

Directional RNA Ligations:

The RL5 oligonucleotide (SEQ ID No 477) contained a 5'-OH and a 3'-OH group, which allowed it to be coupled to the 5' phosphorylated end of the RNA fragment. The RL3 RNA oligonucleotide (SEQ ID No 492) contained a 5' phosphate and a 3' end blocked with puromycin, and could only link to the tag at the 3' end. RL5 and RL3 were both obtained from the company Dharmacon. The ligation mixture comprised 1 µl 10×T4 RNA ligase buffer (3 U, Fermentas), 0.3 T4 RNA ligase (Fermentas), 1 µl BSA (0.2 mg/ml), 1 µl of 10 mM ATP, and 1 µl RL5 linker at 20 picomole (pmol)/µl, and 5.7 µl H$_2$O, in which RNA was resuspended. Mixture was incubated at 16° for 60 min, and 1 µl RL3 linker at 40 pmol/µl, 0.5 µl 0.5 ATP, and 0.2 µl T4 RNA ligase was added. Mixture was incubated again at 37° for 30 minutes. The following mixture was then added to the reaction: 77 µl H$_2$0, 11 µl 10×DNAse I buffer, 5 µl RNAsin, and 5 µl RQ1 DNAse (Promega). Mixture was incubated at 37° for 20 min. The following was then added to the reaction: 300 µl H$_2$0, 300 µl "RNA phenol", and 100 µl CHCl$_3$. The tube was vortexed and centrifuged, and aqueous layer taken. RNA was then precipitated by adding the following: 50 µl 3M NaOAc pH 5.2, 2 µl glycoblue (glycogen) (Ambion), 1 ml 1:1 EtOH:isopropanol, and incubating overnight at −20° C.

Size Separation of RNA

RNA pellets were centrifuged, washed, and dried, and recovery checked by counting in scintillation counter. RNA was resuspended in water and run on 20% denaturing polyacrylamide gel (1:19 acrylamide, 7M urea) along with pre-ligation RNA. Gel was visualized by autoradiography, and 2 fractions of 60-100 nucleotides (nt) and 100-200 nt were removed, placed into Eppendorf tubes with 350 µl of nucleic acid elution buffer, and crushed with a 1 ml syringe plunger. Tubes were incubated at 37° for 30 min at 1200 rpm, then gel slurry was added to a Costar SpinX column containing a 1 cm glass pre-filter. Columns were spun at 14,000 rpm in a microcentrifuge, and supernatant was removed. Nucleic acid elution buffer comprised 1M NaOAc pH 5.2 and 1 mM EDTA. The following was then added, then samples were precipitated overnight at −80° C.: 2 µl glycoblue and 1 ml 1:1 EtOH:isopropanol.

cDNA Synthesis and PCR

RNA was centrifuged, washed, dried, and counted in scintillation counter. RNA was resuspended in 9 µl H2O, and 2 µl of DP3 primer (SEQ ID No 494) at 5 pmol/µl was added. Tubes were heated at 65° for 5 min, chilled, and centrifuged for 10 seconds (sec). The following ingredients were then added: 2 µl 10 mM deoxynucleoside triphosphates (dNTP), 2 µl 0.1 M 1,4-dithio-threitol (DTT), 4 µl 5× Superscript RT buffer, 0.5 µl RNAsin, 0.5 µl SuperScriptII (Invitrogen), and tubes were incubated at 55° C. for 30 min, then at 90° for 5 min, then chilled. PCR reaction was performed, using the following reaction components and parameters, (respectively): 4 µl 10×Pfu buffer, 4 µl DP3 primer and 4 µl DP5 primer (SEQ ID No 493), both at 5 pmol/µl, 4 µl 2.5 mM dNTPs, 4 µl radiolabeled DPS primer at 0.5 pmol/µl, 1 pi Pfu, 3 pi of the RT reaction, and 16 µl H$_2$O; at 94° C., 30 seconds; 61° C., 30 seconds; 72° C., 30 seconds, for 35 cycles. The DNA primers were provided by Operon.

10 µl of each PCR reaction was run on a 10% denaturing polyacrylamide gel and visualized by autoradiography. Bands of 60-100 nt and 100-200 nt were excised and eluted with SpinX columns as described, and resuspended in 10 µl of water.

Re-PCR and Cloning

DNA was centrifuged, washed, dried, resuspended in 20 µA H$_2$O. Each reaction was split into 2 samples, and subjected to PCR using the ingredients 5 µl 10×Pfu buffer, 1 µl 10 mM dNTPs, 1 µl Pfu, 2 µl purified DNA, 37 µl H$_2$0, and the primer pairs DP5/DP3Nhe1 (SEQ ID No 493 and 496) (reaction A), or DP5EcoR1/DP3Nhe1 (SEQ ID No 495 and 496) (reaction B) with the parameters described hereinabove for 20 cycles. Each reaction was electrophoresed on an 8% denaturing polyacrylamide gel. The major band for each PCR reaction was excised using a UV box, and purified as described hereinabove. RT-PCR was then performed again with the same primer pairs, and the products were electrophoresed on a 4% metaphor agarose gel, and the DNA was purified.

Both reactions A and B were digested using the enzyme Nhe1 incubate for 1 h at 37°, then incubated for 20 min at 70°. Reaction B was additionally digested by adding 1 µl EcoR1 and incubated for 1 h at 37°. The reaction was then incubated for 20 min at 70°. Digestion products were desalted using a G25 column.

Ligation

The following mixture was incubated 3 h at 16° C.: 7 µl 10× ligation buffer, 3 µl T4 DNA ligase, 30 µl of digested tags A, and 30 µl of digested tags B. The mixture was then incubated 20 minutes at 60° to inactivate the ligase, desalted using an S200 column, and dried in a speedvac to 20 µl final volume. The DNA was purified by electrophoresing 20 µl of ligation product on a 2% agarose gel. Ligation was confirmed by visualization of bands 1, 2, 4, 6, and 8 times the size of the initial PCR product. Visible bands of 400-800 nucleotides length were excised, purified from the gel, and the purified DNA resuspended in 30 µl of EB.

TOPO Cloning and Sequencing

A 3' A end was generated using the following protocol: The following mixture was incubated at 72° for 20': 3.5 µl DNA, 0.5 µl 10×Taq buffer, 0.5 µl 10 mM dATP, and 0.5 µl Taq polymerase (5 U). The mixture was then placed on ice and used immediately in the TOPO cloning reaction. The following reagents were combined, mixed gently and incubated 5 min at room temperature: 2-4 µl DNA, H$_2$0 to 4 µl, 1 µl salt solution, and 1 µl pCR4-TOPO vector 2 µl of reaction was then added to a vial of Top 10 competent cells, which were transformed by incubating 10 min on ice, then 30 sec at 42°, then 2 min on ice. 250 µl SOC medium was added, and the cells incubated for 1 hr, shaking, at 37°. 10-50 µl of the cell suspension was spread on ampicillin plates (containing 40 µl each of IPTG & X-gal stock solutions (x-gal stock consisted of 400 mg X-Gal in 10 ml dimethylformamide and was stored at −20° C.); IPTG stock consisted of 238 IPTG/10 ml distilled and purified H20, and was filter sterilized, and stored at 4° C.). Miniprep DNA was prepared from white colonies following overnight incubation.

Sequencing

Inserts were then sequenced, using M13F primer (SEQ ID No 509) (custom ordered from Operon). 16 µl of miniprep DNA and 2 µl primer (diluted to 5 µM; 10 pmolar final concentration) was mixed and submitted to the facility.

Linker and Primer Sequences

The following RNA linkers were used in the initial ligation step: RL5 (5'-OH AGG GAG GAC GAU GCG G 3'-OH) (SEQ ID No 477) and RL3 5'-P CGA GAU GGC GGC UUC CUG C 3'-puromycin (SEQ ID NO 492).

The following DNA primers were used in RT-PCR and PCR: DP5 DNA primer: AGG GAG GAC GAT GCG G (SEQ ID NO 493), DP3 DNA primer: GCA GGA AGC CGC CAT CTC G (SEQ ID NO 494), DP5EcoR1: GAA TTC AGG GAG GAC GAT GCG G (SEQ ID NO 495), DP3Nhe1: GCT AGC AGG AAG CCG CCA TCT CG (SEQ ID NO 496). The following DNA primer was used in sequencing: M13F: GTAAAACGACGGCCAG (SEQ ID No 509).

Primers were gel purified.

Results

The protocol for purification of RNA molecules binding to Nova-1 or Nova-2 protein was depicted in FIG. 1A. Cross-linked cells from mouse brain tissue were collected, lysed, digested with DNAseI (not depicted) and limiting amounts of RNAse T1 and immunoprecipitated with anti-Nova antiserum. Immunoprecipitated RBP-RNA complexes were washed, and remaining RNA labeled with y-$^{32}$P ATP. Immunoprecipitated material was resolved by SDS-PAGE, then transferred to NC. RBP-RNA complexes were extracted from the NC, and RNA was purified by digestion of the protein, then directionally ligated to two RNA oligonucleotides. Fragments were then subjected to RT-PCR, ligation into cloning vectors, and sequencing.

When CLIP was used to identify Nova-RNA complexes from mouse brain, RNA was co-purified with Nova only following UV-B irradiation; in the absence of cross-linking, or when pre-immune rabbit serum was used for immunoprecipitation, no RNA co-purified with Nova (FIGS. 1, B and C). As an additional control to assess the specificity of the interaction, CLIP was performed using WT versus Nova-2$^{-/-}$ brain, with an antibody that recognizes both Nova-1 and Nova-2 proteins. In WT brain, cross-linked bands migrating with both Nova-1 and Nova-2 proteins were evident, but in Nova-2$^{-/-}$ brain, RNA cross-linked specifically to protein corresponding to Nova-1, while the band migrating at the molecular weight of 70 kDa, corresponding to Nova-2 isoform, was lost (FIG. 1C). Thus the ability of CLIP to isolate RNA was dependent on cross-linking and on the presence of immunoprecipitated Nova protein. These controls demonstrated that only RNA molecules that were covalently bound to Nova were detected using the CLIP method with anti-Nova antiserum. The radioactive band on the gel was positioned 5-10 kDa higher than Nova-1 without cross-linked RNA, as assayed by Western blotting (data not shown).

Example 2

Monitoring of Linker Ligation and RT-PCR of RNA Molecules $^{32}$P-labeled RNA was size purified after cross-linking and purification from N2A cells using anti-Nova antiserum as described in Example 1. The size of the RNA fragments ranged from 24-150 bases; the modal size of the RNA was approximately 60 bases (FIG. 2A). Purified RNA fragments were ligated to 5' and 3' linker oligonucleotides ("linkers"), which added 16 bases to each end of the molecule. The majority of the labeled fragment RNA shifted in size by 32 bases, indicating successful ligation (FIG. 2B). RNA isolated from regions 1 and 2 in FIG. 2B was amplified by RT-PCR with specific primers complementary to the linker sequences (FIG. 2C). The prominent band at 32 bases was the product from the ligation of the two RNA oligonucleotides without insert. The products in (C) were further divided and further amplified by PCR (FIG. 2D).

Example 3

CLIP Method Using Nova-1 Antisera Enabled the Isolation and Identification of Sequence Fragments Containing Nova-1 Binding Sites Materials and Experimental Methods Computer Analysis of Nova CLIP Fragments.

3400 control fragments were randomly generated by a computer program from a 200,000 nucleotides long sequence consisting of 66% intronic, 14% exonic and 20% 3'UTR sequences (corresponding to the ratio in Nova CLIP fragments) from random genes on mouse chromosome 1, such that they corresponded in their size to Nova CLIP fragments (with the average size of 71 nucleotides). Another program was made to count the number of particular polynucleotide (up to 20 nucleotides in a row) in each fragment, and calculate the frequency of fragments carrying a certain number of that polynucleotide (for example, YCAY, where Y represents either U or C). An additional program was made to calculate the average frequencies of nucleotides at three positions flanking a particular dinucleotide (CA in our case) in all fragments.

Nova-2 Protein Purification.

6×His-Nova-2-T7 protein was expressed in E. coli and purified with successive Chelating Sepharose fast flow column (Amersham 17-0575-01) and T7-fragment antibody agarose (Novagen, 69026).

Transcription of Oligonucleotide Templates.

The PCR products for each of the four tested CLIP fragments and genomic controls were annealed to the oligonucleotide 5'-AGTAATACGACTCACTAFRAGMENT-3' (SEQ ID NO: 510) for transcription with T7 polymerase (Promega), and RNA synthesis carried out by using α-P-UTP in standard transcription buffer (Promega). Transcripts were size-purified by using 20% denaturing PAGE.

Measurement of RNA-Protein Binding.

Binding dissociation constants were measured by a nitrocellulose filter binding assay (Carey, J et al, Biochem 22, 2601). 50-µl reactions containing 50-100 femtomole (fmol) of RNA internally labeled with $^{32}$P and concentrations of Nova-2 in 3-fold dilutions typically ranging from 0.2 nM to 493 nM were mixed in 1×BB (a buffer containing 50 mM TrisOAc pH 7.7, 200 mM KOAc, 1 mM MgOAc, 1 mM DTT, 0.2 mg/ml heparin) and were incubated at 10 min for 25° C., followed by filtering and washing. Dissociation constants were determined graphically by plotting the fraction of bound RNA versus the log of the protein concentration (Irvine, D. et al, J Mol Biol 222: 739).

Results

Figure 3G:
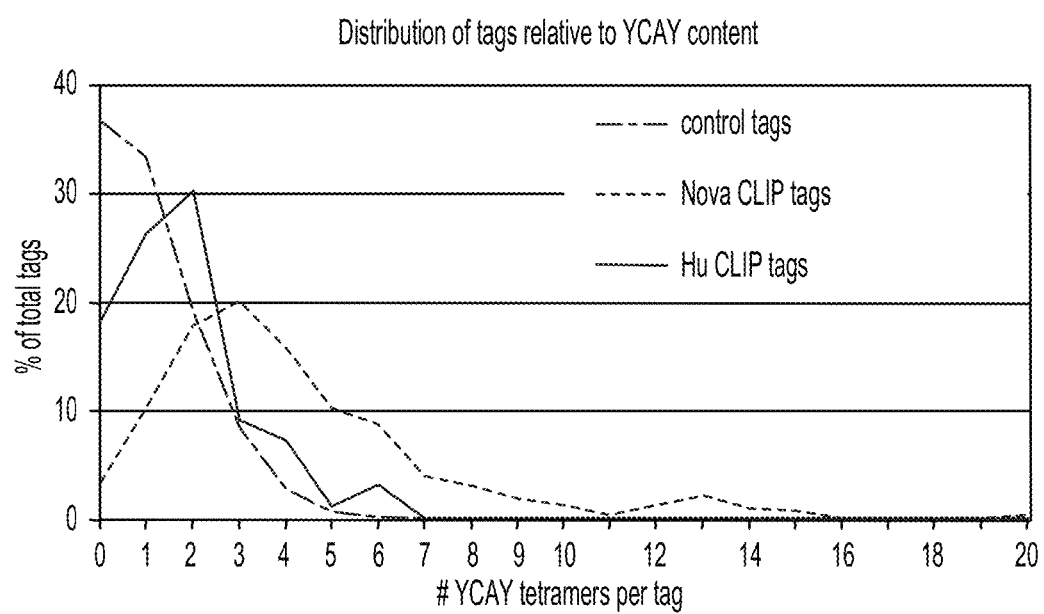

An unbiased screen was performed to identify Nova RNA targets in vivo. 340 Nova CLIP fragments were sequenced (FIG. 3A), which had an average length of 71 nucleotides. An annotated list of the CLIP fragments is shown in FIG. 3H, which have been assigned SEQ ID No. 1-335. The largest set of CLIP fragments (121) were within long introns; 99 (82%) of these were within the first 3 introns. 68 were found within introns shorter than 10 kb, and 18 (26%) of these flanked alternative exons. 58 were within 3' UTRs and 38 within exons, 2 of which were previously reported to be alternatively spliced. The sequences of the Nova CLIP fragments were compared with the known Nova binding element, multimers of the YCAY tetramer. Tetramer frequency analysis revealed that on average, each tag harbored 4.2 YCAY tetramers, compared to an expected frequency of 1.1 YCAY tetramers in random sequences, and the observed frequency of 1.1 and 1.7 in random genomic sequences and CLIP fragments obtained with an unrelated RBP (FIGS. 3B and 3G). Moreover, analysis of nucleotide frequencies flanking all CA dimers present in Nova CLIP fragments showed an overrepresentation of YCAY tetramers flanked by pyrimidines (FIG. 3C), which was also evident in the 5 most frequent hexamers, which were overrepresented 15-30 times; no such increase was evident in analysis of control tags (FIG. 3D). Filter binding assays were performed using purified Nova-2 protein and RNA transcribed from 4 different Nova CLIP fragments (FIG. 3E, F). All four RNAs bound Nova-2 with high affinity (FIG. 2E; 23 to 400 nanomolar [nM] affinity). Control tags of genomic sequence immediately 5' to the CLIP fragments did not bind, nor did CLIP fragments in which CA dinucleotides were mutated to AA (not shown). Thus, Nova protein was selectively crosslinked to high affinity RNA targets harboring Nova binding sites. The CLIP fragments identified reflected the UCAUY motif (SEQ ID NO. 469, in which "Y" may refer to Cytosine, Uridine, Thymidine, or derivatives thereof) repeated three times and YCAYC motifs observed in RNA selection experiments performed with Nova, and with functional studies demonstrating that Nova regulates alternative splicing by binding clusters of at least three intronic UCAU tetramers in target RNAs. Thus, CLIP fragments have been verified using several stringent tests: sequence comparisons with known Nova binding sites and demonstration of direct RNA-protein interactions. Taken together, this data further validates CLIP as a method of specifically purifying RNA sequence fragments directly binding to a protein of interest. Additionally, it delineates more than prior art the role of sequence surrounding YCAY tetramers in affecting Nova binding.

Example 4

Nova Regulates Alternative Splicing and Protein Expression of Jnk2, Neogenin, and Gephyrin Materials and Experimental Methods RT-PCR Analysis.

PCR of mouse JNK2 was performed at annealing temperature of 60° C. and 26 cycles, with primers F, 5'-TGATGACTCCCTATGTGGTAACTCG (SEQ ID No 497) and R, 5'-TCTCTGGCTTGACTTTTTT1ATTTTG (SEQ ID No 498), and PCR products were digested with AluI, which has sites in exons 6b and 7, PCR of mouse neogenin was performed at annealing temperature of 61° C. and 23 cycles, with primers F, 5'-ACACTGGCTGGAAGGAGGGG (SEQ ID No 499) and R, 5'-TGGGCTGTGGGAAGACTCTGG (SEQ ID No 500). PCR of mouse gephyrin was performed at annealing temperature of 61° C. and 23 cycles, with primers F, 5'-TGTGGAATAAGGGGGAAAACTCTG (SEQ ID No 501) and R, 5'-TCGTGGGAGCACCTGAACAC (SEQ ID No 502). Clontech first strand cDNAs were used for analysis of splicing in mouse tissues.

Results

Nova-2$^{-/-}$ mouse brain was used to validate candidate RNAs by assessing utilization of alternatively spliced exons present near Nova CLIP fragments. Of 18 RNAs assayed, seven showed changes in alternative splicing in Nova-2-null mouse brain ranging from 1.6-fold to 60-fold (FIG. 4A).

JNK2 is a cytoplasmic signaling protein that translocates to the nucleus to phosphorylate and activate several transcription factors including ATF2 and c-Jun. The alternatively spliced exons 6a and exon 6b encode isoforms that preferentially bind ATF2 or c-Jun, respectively, and are preferentially included in brain and non-neuronal tissues, respectively. A Nova CLIP fragment was identified in JNK2 pre-mRNA, near exon 6b (FIG. 4A). RT-PCR analysis revealed a net 6-fold change in exon utilization in Nova-2$^{-/-}$ relative to Nova-2$^{+/+}$ cortex: a 3-fold decrease in utilization of the exon 6a isoform, and a 2-fold increase in exon 6b in JNK2 RNA (FIG. 4A).

Neogenin, a homologue of DCC (Deleted in Colorectal Cancer), has been reported to bind netrin-1, although its role in axon guidance has not yet been fully elucidated. Neogenin is expressed in all adult mouse tissues, and has four alternative exons, one of which, exon 27, contains a Nova CLIP fragment. Splicing of all four alternative exons was assayed in RNA obtained from the cortex of Nova-2 null mice. Alternative splicing of exon 27 was drastically altered relative to wild-type brain, such that there was ~36 fold increase in utilization of the exon 27 in RNA from Nova-2$^{-/-}$ relative to Nova-2$^{+/+}$ cortex (FIG. 4B). In contrast, there was no change in utilization of the other three alternatively spliced neogenin exons in Nova2$^{-/-}$ relative to Nova-2$^{+/+}$ cortex, consistent with previous observations that Nova regulates splicing in only a subset of regulated exons.

Two Nova CLIP fragments were identified in gephyrin, one in intron 7, near the alternatively spliced exon 9, and a second in intron 14 (FIGS. 4C, 3H). In wild-type mouse brain, gephyrin transcripts preferentially excluded exon 9 (96%). In Nova-2$^{-/-}$ mouse brain, only 27% of gephyrin transcripts excluded exon 9, and there was a compensatory increase in exon 9 inclusion (73% vs. 4% in wild-type cortex; FIG. 4C). Each of the seven gephyrin exons reported to be alternatively spliced were examined and it was found that only exon 9 was regulated by Nova (FIG. 4C). Thus, the presence of Nova in neurons correlated with alternative exon skipping in gephyrin and neogenin transcripts.

Figure 4D:
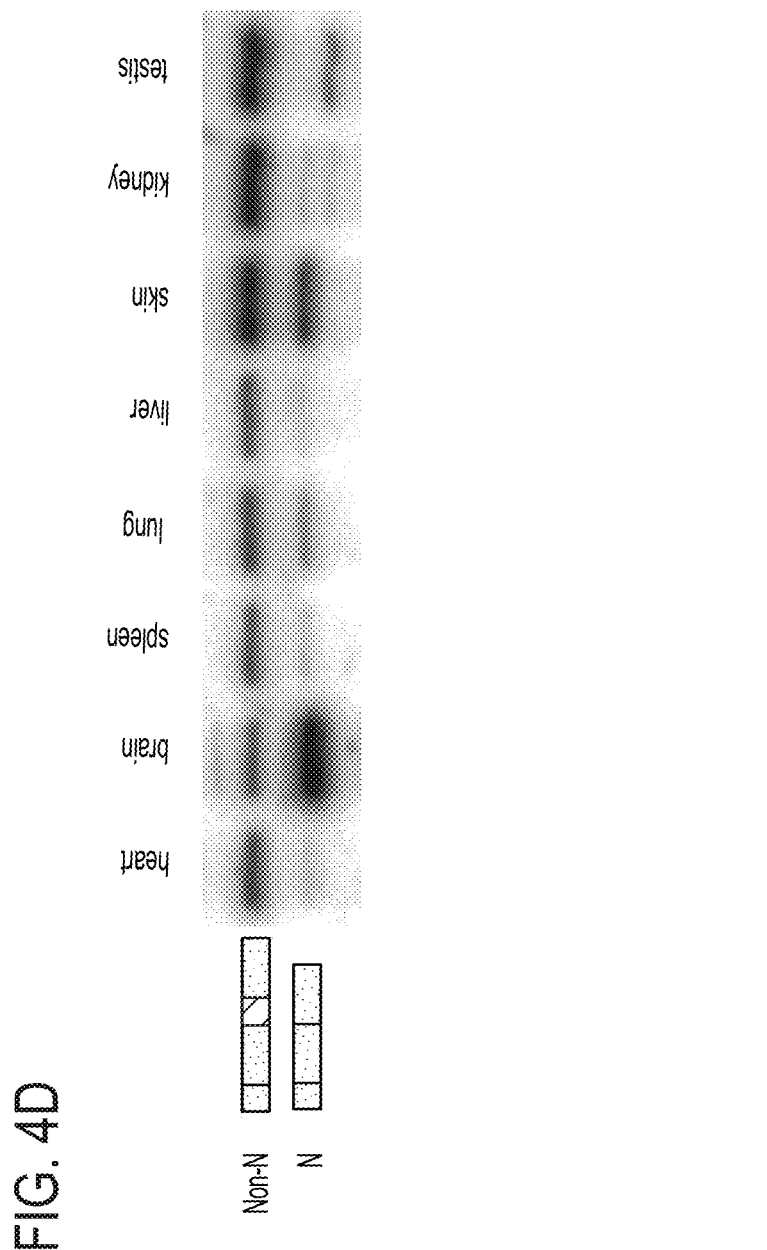

Changes in gephyrin protein isoform expression in Nova-2$^{-/-}$ cortex were also detected by Western blot (FIG. 4C), and these were consistent in magnitude with the changes seen gephyrin transcripts. Gephyrin exon 9 utilization in different tissues was surveyed by RT-PCR analysis, which revealed that gephyrin transcripts in non-neuronal tissues include 22-fold (testis) to 115-fold (heart) more exon 9 than brain (FIG. 4D), which is similar in scale to the 60-fold change seen in Nova-2$^{-/-}$ versus wild-type cortex (FIG. 4C).

Gephyrin RNA is a particularly interesting target for Nova action. Gephyrin is essential for the correct localization of GABA$_A$ γ2 and GlyRa2 subunits to the inhibitory synapse, and Nova regulates alternative splicing of transcripts encoding both of those receptors. Like Nova, gephyrin has been reported to be the target of a cancer-associated neurologic disorder manifest by excess motor activity. Finally, Nova-dependent regulation of a network of RNAs encoding proteins that mediate neuronal inhibition correlates with the defective motor inhibition in Nova$^{-/-}$ mice and in POMA patients.

(These observations indicate that Nova acts as a critical factor determining specificity of gephyrin alternative splicing in neurons, an observation not previously made in vivo with vertebrate splicing factors.

To summarize, the data in FIG. 4 demonstrate that Nova regulates alternative splicing (6-60 fold effects) of several RNAs identified by the CLIP method. Our results indicate that Nova may the primary, if not sole, determinant of brain-specific alternative splicing of these, and perhaps other, transcripts. These findings provide further evidence that the locations of Nova CLIP fragments are able to predict functional binding sites. In addition, these findings demonstrate the ability of CLIP to identify previous unknown RNA targets that are regulated by an RBP in vivo. In addition, the data in FIG. 4A demonstrate a unique role specifically for Nova regulation of JNK2 expression.

Example 5

Nova CLIP Fragments Fall within Several Known Genes Involved in Synaptic Function, Signaling, and Protein Synthesis In addition to gephyrin RNA, a number of RNAs were identified multiple times within the set of 340 Nova CLIP tags, suggesting that these might be a particularly robust subset of RNA targets. 77 CLIP tags (23%) mapped to only 34 transcripts, each of which contained 2 or more tags. 21 of these 34 transcripts correspond to characterized genes (FIG. 5A); 15 (71%) of these encode proteins that function in the synapse, which indicates that Nova may coordinately regulate a biologically coherent set of RNAs.

An intriguing subset of Nova target RNAs involved in synaptic biology are those involved in neuronal inhibition (FIG. 5B). These include the microtubule-associated protein MAP1b, which anchors $GABA_c$ receptors to the cytoskeleton and modulates their sensitivity; $GABA_b$ 2 receptor and GIRK2, which mediate slow inhibitory postsynaptic potentials; the K+ voltage-gated channel KCNQ3, which mediates inhibition of repetitive action potentials; the nicotinic acetylcholine receptors β2 and α2, which contain CLIP tags at homologous positions in exon 5 and are together as α4β2 heteropentamers highly expressed on GABAergic interneurons, thus influencing inhibitory activity; and the JNK proteins (FIG. 4A), which are essential for neuronal microtubule integrity by controlling phosphorylation of MAP1b and MAP2, and for the regulation of GABA action in *C. elegans* inhibitory motor neurons.

Example 6

Somatodendritic Nova

Simultaneous Detection with Gephyrin in the Postsynaptic Cytoplasm

Materials and Experimental Methods

Nuclear/Cytoplasmic Fractionation Method.

Brain tissue was Dounce homogenized in cold 10 mM 2-[4-(2-hydroxyethyl)-1-piperazinyl]ethanesulfonic acid (HEPES) (pH 7.9), 10 mM NaCl, 1.5 mM MgCl2, 0.2% Triton, 10 mM NaF, protease inhibitors (Roche), spun at 3000 times gravitational force (×G) for 3 min. Supernatant was collected as cytoplasmic fraction, and pellet was resuspended in 20 mM HEPES (pH 7.9), 25% glycerol, 1.5 mM MgCl2, 1.4 M KCl, 0.2 mM EDTA, 0.5% NP-40, 10 mM NaF, protease inhibitors (Roche), 5% DNAse, incubated 5 min at 37° C., dialyzed against 1×PBS, pH 7.4, 1.5 mM $MgCl_2$, 0.5% NP-40, 10 mM NaF, and collected as nuclear fraction. Both fractions were ultracentrifuged at 100000×G for 30'.

Tissue Preparation.

Adult Sprague-Dawley rats (Janvier, France) were deeply anaesthetized with pentobarbital (60 mg/kg body weight, i.p.), and intracardially perfused. For fluorescent immunocytochemistry and in situ hybridization (ISH), animals were perfused with 4% paraformaldehyde (PFA) in phosphate buffer saline (PBS) (0.1M, pH 7.2). For electron microscopy (EM), immunocytochemistry, and ISH, animals were perfused with 4% PFA and 0.1% glutaraldehyde in PBS. Spinal cords were removed and postfixed in 4% PFA in PBS overnight at 4° C. Spinal cord sections were cut on a vibratome and collected in PBS.

Fluorescent Immunocytochemistry on Spinal Cord Sections.

Spinal cord 30 μm sections were rinsed in 50 mM $NH_4Cl$ in PBS for 15 minutes (min) and permeabilized with 0.1% Triton X-100, 0.1% bovine gelatin in PBS for 10 min. Free-floating sections were incubated with primary antibodies, in 0.1% Triton X-100, 0.1% bovine gelatin in PBS, overnight, at 4° C.). The following day, sections were rinsed three times in PBS (10 min each) and revealed by the corresponding secondary antibodies in PBS, 2 hours at room temperature (RT). After three washes in PBS (10 min each), sections were mounted on slides with Vectashield (Vector Lab.).

Fluorescent Non-Radioactive In Situ Hybridization and Immunocytochemistry on Spinal Cord Sections.

Fluorescent in situ hybridization (FISH) was as previously described. Digoxigenin labeled probes and Nova proteins were labeled at the same time (in 100 mM Tris-HCl pH 7.5, 150 mM NaCl, 2% Bovine Serum Albumin (BSA), 0.3% Triton X-100, overnight, 4° C.). The anti-digoxigenin and anti-Nova-1 primary antibodies were detected by incubating sections with the appropriate secondary antibodies (in PBS, 2 hs at room temperature). Each incubation was followed by three washes in PBS (10 min each). Finally, sections were mounted on slides with Vectashield (Vector Lab.)

Image Acquisition.

Sections processed for fluorescent immunocytochemistry and ISH were observed with an epifluorescent Zeiss microscope, or a Leica confocal laser scanning microscope. For confocal images, background noise was reduced by applying a Gaussian filter to the optical sections.

Electron Microscopic Immunocytochemistry.

100 μm thick vibratome sections were cryoprotected in 20% glycerol-20% sucrose in PBS, and permeabilized by freezing and thawing. Sections were collected in PBS, rinsed in 50 mM $NH_4Cl$ in PBS for 15 min, and 0.1% bovine gelatin in PBS for 10 min. The free-floating sections were incubated with the primary antibodies (in 0.1% bovine gelatin in PBS, overnight, at 4° C.). The following day, sections were rinsed three times in PBS (10 min each) and incubated with the secondary antibodies (in PBS-1% BSA for biotinylated antibodies, 2 hr at RT; or PBS-0.2% fish gelatin for gold antibodies, overnight at 4° C.). Biotinylated antibodies were revealed with the ABC Elite kit (Vector Lab) in PBS, for 1 hour at RT, and the peroxidase reaction was carried out in the presence of DAB and hydrogen peroxide (Sigma Fast, Sigma). Nanogold-coupled antibodies were amplified as described.

Electron Microscopic Pre-Embedding Non-Radioactive In Situ Hybridization and immunocytochemistry.

50 μm sections were cryoprotected and permeabilized as for EM immunocytochemistry. Prehybridization and hybridization were as described above for fluorescent ISH. After the stringency washes, sections were rinsed in PBS and incubated in the primary antibody (1% BSA in PBS, overnight, at 4° C.). After three PBS rinses (10 min each), digoxigenin molecules and the primary antibody were detected by gold- and HRP-coupled antibodies, respectively (in 0.8% BSA, 0.2% Fish Gelatin in PBS, overnight, 4° C.). After three PBS rinses (10 min each) sections were incubated in 4% PFA in PBS (10 min), rinsed three times in PBS (10 min each) and several times in cold distillated water. Gold-coupled sheep anti-digoxigenin secondary antibodies were detected by a silver enhancement-gold toning protocol as described before. After three PBS rinses (10 min each), biotinylated antibodies were detected by peroxidase-DAB reaction as in classical immunocytochemical methods.

The sections processed for immunocytochemistry and ISH were dehydrated, osmicated and flat embedded in araldite (Fluka) resin. Ultrathin sections were prepared, mounted in copper grids and contrasted with uranyl acetate and lead citrate before examination under a Jeol CXII transmission electron microscope at 80 kilovolts (Kv).

Results

Figure 6:
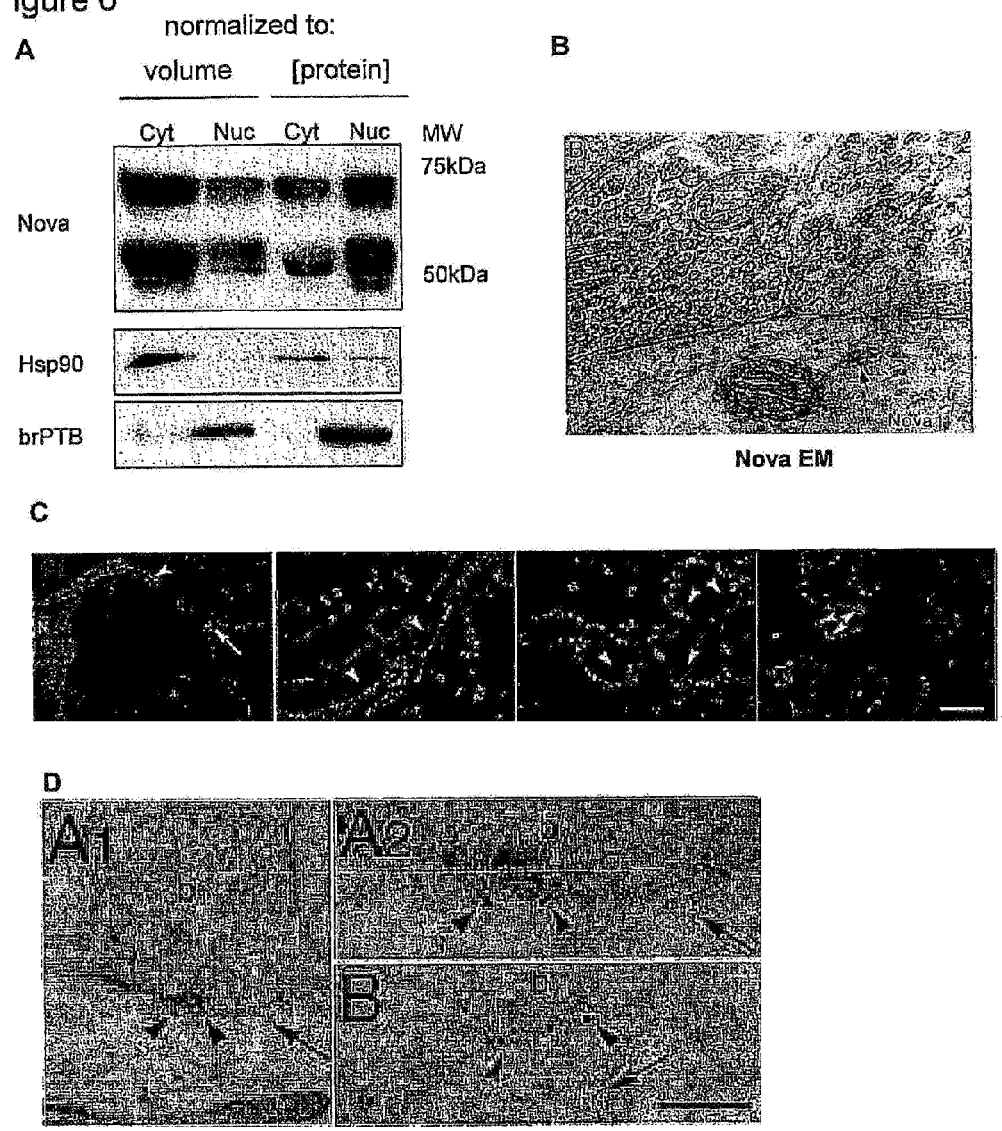
FIGS. 6A-6C depict Somatodendritic Nova: simultaneous detection with gephyrin in the postsynaptic cytoplasm.
FIG. 6D shows Electron microscopic co-detection of Nova and gephyrin immunoreactivity within the postsynaptic cytoplasm. A1, A2, B, Nova-1-IR (10 nm gold particles, arrows) beneath post-synaptic regions gephyrin IR (15 nm gold particles, arrowheads) A2, high magnification of the postsynaptic cytoplasm of A1. Synaptic boutons are indicated by the symbol "b". Antibodies: anti-Nova rabbit serum. Scale bar: 0.2 µm (A2, B); 0.4 µm (A1).

Seven of the 34 transcripts with multiple Nova CLIP fragments harbor one or more fragments within 3' the UTR (FIG. 3A), and two of these seven, MAP1B and KCNQ3, encode proteins that function in neuronal inhibition (FIG. 5B), indicating that part of Nova's role in regulating alternate splicing may be manifest in the dendrite or the inhibitory synapse. Fractionation of mouse brain into nuclear and cytoplasmic fractions revealed that two thirds of total Nova protein is present outside of the nucleus, although when normalized to protein mass, the highest concentration of Nova protein is in the nucleus (FIG. 6A). Immunofluorescence of rat spinal cord sections confirmed an abundance of Nova immunoreactivity outside of the nucleus in mouse motor neurons, including punctate reactivity in neuronal processes (FIG. 6C; see also FIG. 7A). To assess whether this reactivity corresponds to the localization of inhibitory synapses, we examined whether Nova and gephyrin reactivity co-localize, with gephyrin serving as a marker for localization to inhibitory synapses. Both immunofluorescence and electron microscopic evaluation demonstrate that Nova protein is present in the inhibitory synapse, in the vicinity of gephyrin protein (FIG. 6B-D). These data suggest a model in which Nova may regulate mRNAs within the dendrite, either by affecting their localization, translation, or half-life.

Example 7

Colocalization of Nova Protein and GlyRα2 mRNA in Motor Neurons

To examine the role of Nova in the regulation of RNA within the dendrite, Nova protein and GlyRα2 mRNA co-localization in mouse spinal cord motor neurons was determined by fluorescent and electron microscopy, and revealed that Nova protein co-localizes with GlyRα2 mRNA in the dendrite (FIG. 7A-F). Interestingly, both Nova protein and GlyRα2 mRNA were associated with membranous bodies suggestive of endoplasmic reticulum (FIG. 7C-F). Taken together, the data from Examples 6-7 show that at least a subset of Nova localizes to the inhibitory synapse. This suggests that Nova may coordinately regulate RNA information processed in the nucleus with RNA expression locally in the synapse. Since a hallmark feature of Nova antisera from POMA patients is that they abrogate RNA-protein interactions in vitro, these results suggest that disruption of such interactions, perhaps within the dendrite, may contribute to disease pathogenesis. Furthermore, the finding that Nova, gephyrin, and at least one regulated spliced mRNA, GlyRα2, localize to the inhibitory synapse further validates the CLIP method as a means of identifying RNA sequences that interact with a protein of interest.

Example 8

CLIP Method Using Antisera to Neuronal Hu Proteins Enabled the Isolation and Identification of Sequence Fragments Binding to Neuronal Hu Proteins Materials and Experimental Methods All experimental procedures were conducted as in Example 3, with the exception that antiserum against neuronal Hu proteins was utilized in place of anti-Nova serum. Sequences were aligned with the aid of the clustalw software package.

Results

Figure 8A:
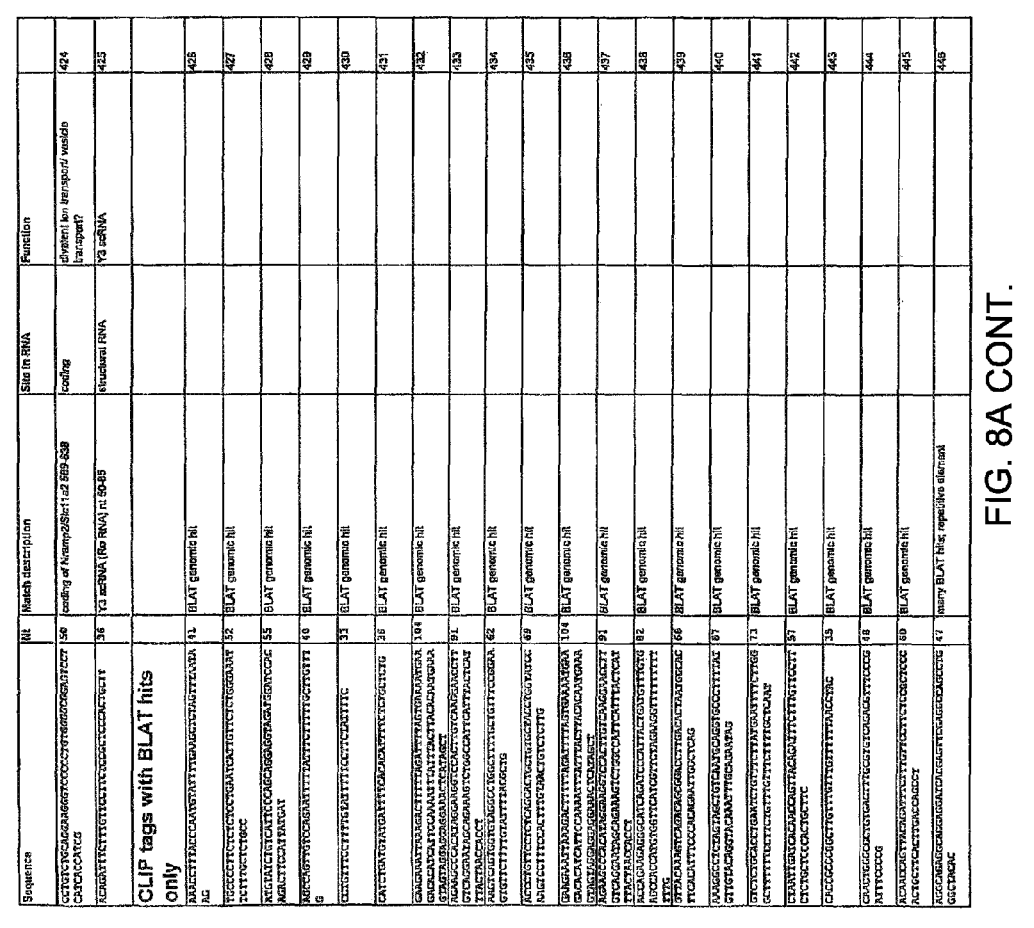
Figure 8B:
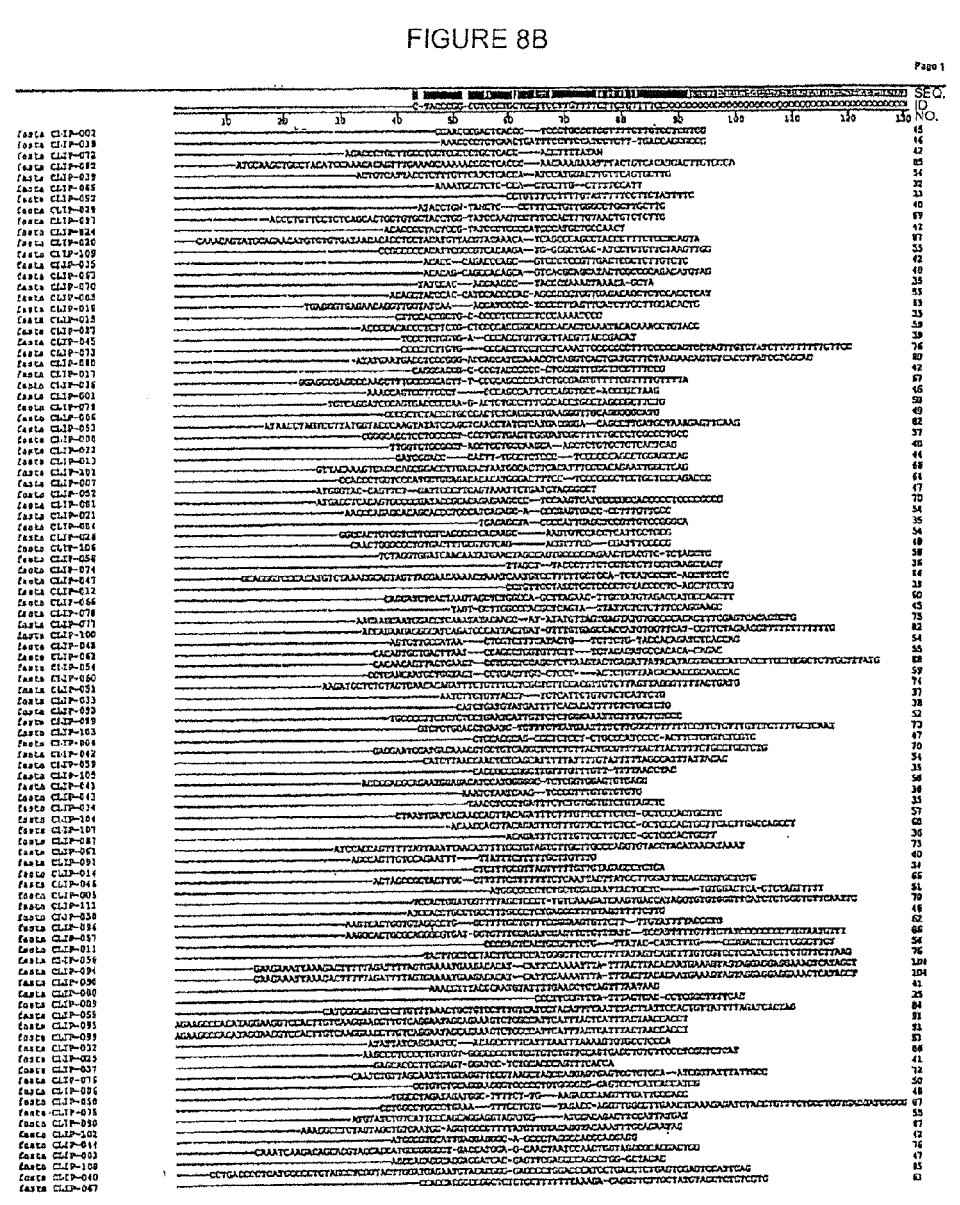
Figure 8B:
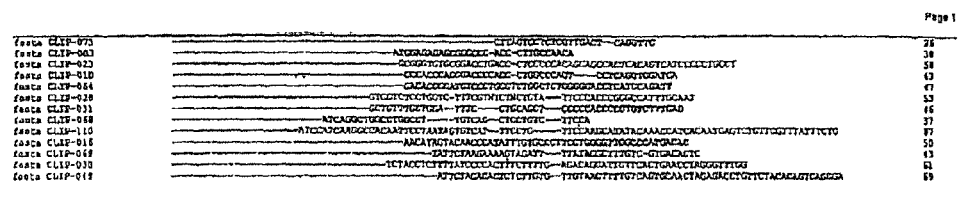

115 RNA fragments binding to Neuronal Hu proteins were sequenced and assigned SEQ ID No. 336-449 (FIG. 8A). As was the case with CLIP using anti-Nova-1 antisera, some of the RNA fragments corresponded to previously known proteins. Some of the fragments were located in introns of the genes (35%), others were in the 3' and 5' untranslated regions (45%), and in others (20%), the location could not be determined because the gene had not been identified. Obtained sequences were aligned using the clustalw website (FIG. 8B). A consensus sequence of the fragments was then determined, as depicted at the top.

Example 9

Generation and Characterization of Nova-2 Knockout Mice

Materials and Experimental Methods

Generation of Nova-2$^{-/-}$ Mice.

A Nova-2 lambda clone was isolated from an SV-129 mouse genomic library. To prepare a targeting construct, a left arm was generated by cloning a Xba1 and HindIII genomic fragment. This fragment was cut with Xho1 in the center and digested with ExoIII to remove the endogenous Methionine. This construct removed 45 nt of sequence upstream of the initiator methionine. This fragment was then digested with Xba1 to remove remaining 3' DNA, ends were blunt ended with Klenow fragment, and the fragment was ligated to create the short arm (pΔ1.1). pΔ1.1 was cut with BamHI and SacI (in the multiple cloning site) and ligated to SacI/BamHI adapters harboring a PacI site. The right arm was generated from a 6.0 kb SacI fragment, in which an internal PacI site was ablated by Klenow fragment treatment and re-ligation. This SacI (ΔPacI) fragment was inserted into the pΔ1.1 SacI adaptor. The PacI site was then used to insert an IRES-Cre-Flip-Neo-Flip cassette. This targeting vector was electroporated into ES cells, G418 resistant clones selected, and clones screened by Southern blot using a HindIII-BamHI 950 bp genomic fragment located immediately upstream of the left arm. Chimeric animals were bred to C57Bl/6 mice and agouti offspring genotyped and then bred to a transgenic mouse expressing Flip-recombinase to remove the Neo cassette. Heterozygous lines were outbred to C57Bl/6, CD1 and FVB strains.

Results

The function of Nova-2 protein was explored by generating Nova-2 null mice. While the neurologic disorder POMA is characterized by dysfunction of inhibition of motor systems, in up to 58% of patients progressive multifocal neurologic deficits develop, including encephalopathy and dementia with cerebral atrophy. Since POMA antisera are reactive against all CNS neurons, and Nova-2 is largely or exclusively expressed in neocortex and hippocampal neurons, it seems possible that immune targeting against Nova-2 may lead to disease in some POMA patients.

To generate Nova-2$^{-/-}$ mice, a targeting vector was constructed, consisting of genomic SV129 DNA fragments of 1.1 kB and 6 kB flanking a ~1.5 kB DNA fragment harboring the first known transcribed Nova-2 exon. An IRES-Cre FLIP-Neo-FLIP cassette was inserted into these arms such that it would be inserted into the first Nova-2 exon upstream of the ATG encoding the putative initiator methionine. (FIG. 9A). Following electroporation into ES cells and selection with G418, clones harboring homologous recombinants were screened by Southern blot (FIG. 9B) and injected into blastocysts. Following breeding of chimeric mice into the germ line, mice were bred with CMV-Flp recombinase transgenic mice to remove the neomycin cassette, generating mice heterozygous for a null Nova-2 allele.

Figure 9C:
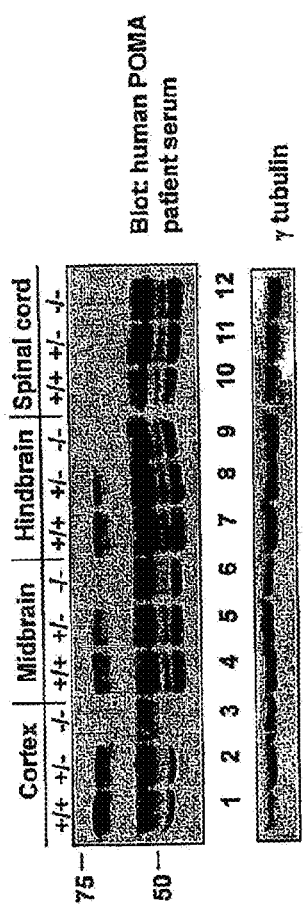

To confirm that these mice did not express Nova-2 protein, Western blots using extracts from several brain areas of Nova-2$^{-/-}$, Nova-2$^{+/-}$, or WT littermates were probed with POMA antisera. In each, case, Nova-2$^{+/-}$ or Nova-2$^{-/-}$ brain showed reduced or absent expression, respectively, of Nova-2 protein isoforms. Interestingly, these included both the single 55 kD Nova-2 protein species previously described, and a series of previously described but poorly understood protein isoforms of higher apparent molecular weight (approximately 70 kD) recognized by POMA antisera (FIG. 9C). These observations confirm that the Nova-2 targeting allele eliminated expression of any intact Nova-2 protein isoforms recognized by POMA antisera, and further implicate the higher MW POMA reactive proteins as products of the Nova-2 locus.

Figure 9E:
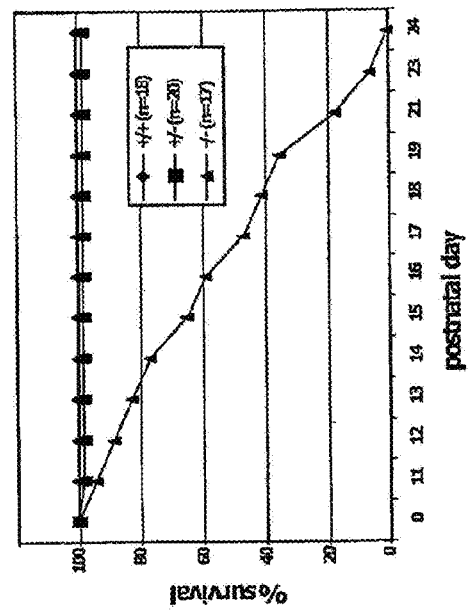
Figure 9D:
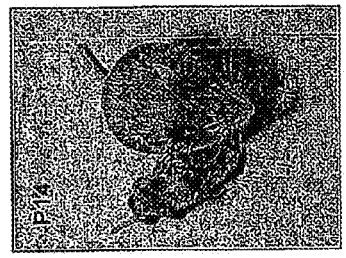

Nova-2$^{-/-}$ mice were phenotypically indistinguishable from their WT littermates at birth. Within the first postnatal week, however, these mice typically grew less than their WT littermates (FIG. 9D), a finding also seen in Nova-1$^{-/-}$ mice. By 1-2 weeks postnatal, the mice were less active, and by 2-3 weeks half of the Nova-2$^{-/-}$ mice died (FIG. 9E). The knockout mice also had abnormally high circulating levels of IGF-1 and abnormally low levels of serum glucose (data not shown).

Example 10

Alternate Splicing Defects in Nova-2 Knockout Mice

Nova-1$^{-/-}$ mice show specific defect in inclusion of GABA$_A$ γ2L and GlyRα2E3A exons in the spinal cord and hindbrain. To evaluate whether Nova-2 may mediate similar functions in mouse brain, alternative splicing of these exons in Nova-2$^{-/-}$ neocortex was analyzed. Inclusion of γ2L exon of GABA$_A$ Nova-2$^{-/-}$ was significantly reduced in neocortex of the knockout mice, and this effect was dose-dependent in the GABA$_A$ pre-mRNA, as seen in Nova-1$^{-/-}$ mice (FIG. 10A). This effect was specific, as shown by the finding that no changes in splicing of alternatively spliced neuronal exons in the proteins src, ced-3 homologue (ICH-1), or Nova-1 were evident in Nova-2$^{-/-}$ neocortex (FIG. 10B). In addition, while all regions of the brain showed differences in alternative splicing, the differences were most prominent in the neocortex, an area known to express high levels of Nova-2 protein and little or no Nova-1 protein (data not shown).

Since a defect in GlyRα2E3A exon inclusion is present in Nova-1$^{-/-}$ mouse hindbrain, but not neocortex, splicing of this transcript was assayed in Nova-2$^{-/-}$ mice. A significant deficiency in inclusion of exon E3A in neocortex of the Nova-2$^{-/-}$ mice was observed, of a similar magnitude to that seen in Nova-1$^{-/-}$ hindbrain (FIG. 10B). This effect was not evident in spinal cord, and there was not a significant effect in cerebellum; this relative specificity for neocortex was thus the reciprocal of the splicing defect seen in Nova-1$^{-/-}$ mice, which was specific to the spinal cord, and absent in cortex (data not shown). Taken together, these results are consistent with the pattern of Nova-1 and Nova-2 expression, and suggest that either protein is able to regulate alternative splicing in a similar manner, but in a different range of neuronal cell types.

What is claimed is:

1. A method for isolating one or more test RNA molecules having one or more binding sites interacting with an RNA binding protein (RBP) of interest from a biological sample, said method comprising the steps of:
   (a) irradiating a test biological sample to create an irreversible covalent crosslinking between the test RNA molecules and RBPs of interest in said test biological sample, thereby generating a sample of covalently-linked RBP-test RNA complexes which is substantially absent from a control biological sample which was not subjected to irradiation, wherein the one or more test RNA molecules are not modified with a chemical group to facilitate crosslinking with the RBP prior to irradiating the test biological sample;
   (b) cleaving the test RNA molecules of said covalently-linked RBP-test RNA complexes by contacting said sample of covalently-linked RBP-test RNA complexes with a nuclease, thereby generating a first population of covalently-linked RBP-test RNA fragment complexes;
   (c) generating a second population of covalently-linked RBP-test RNA fragment complexes by selecting covalently-linked RBP-test RNA fragment complexes in said first population by utilizing a molecule that specifically interacts with a component of said covalently-linked RBP-test RNA fragment complexes in said first population;
   (d) purifying said second population of covalently-linked RBP-test RNA fragment complexes obtained in step (c) under stringent conditions comprising the consecutive steps of:
      (i) washing the complexes with buffer;
      (ii) boiling the complexes in a denaturing ionic detergent;
      (iii) separating the complexes by SDS-PAGE; and
      (iv) transferring said complexes to a substrate that preferentially binds test RNA covalently crosslinked to protein over test RNA not covalently crosslinked to protein;
   (e) digesting said RBP with a protease to liberate said fragments of test RNA from said purified second population of covalently-linked RBP-test RNA fragment complexes; and
   (f) amplifying said fragments of test RNA obtained in step (e),
   thereby isolating the one or more test RNA molecules having the one or more binding sites interacting with the RNA binding protein of interest.

2. The method of claim 1, wherein said nuclease is RNAse T1.

3. The method of claim 1, further comprising labeling said test RNA molecule.

4. The method of claim 1, wherein said substrate is a nitrocellulose membrane.

5. The method of claim 1, wherein the irradiating of the biological sample comprises the input of sufficient energy to produce at least about a 4-fold enrichment in the frequency of occurrence of the one or more RBP binding sites in the second population of covalently-linked RBP-test RNA fragment complexes as compared with the expected random occurrence of the one or more RBP binding sites.

6. The method of claim 1, wherein the irradiating of the biological sample comprises the input of sufficient energy to produce at least about a 10-fold enrichment in the frequency of occurrence of the one or more RBP binding sites in the second population of covalently-linked RBP-test RNA fragment complexes as compared with the expected random occurrence of the one or more RBP binding sites.

7. The method of claim 1, wherein the irradiating of the biological sample comprises the input of sufficient energy to produce at least about a 4-fold to an at least about a 10-fold enrichment in the frequency of occurrence of the one or more RBP binding sites in the second population of covalently-linked RBP-test RNA fragment complexes as compared with the expected random occurrence of the one or more RBP binding sites.

8. The method of claim 1, wherein the irradiating of the biological sample comprises the input of about 400 milli-Joules per square centimeter of the biological sample.

9. The method of claim 1, wherein the fragments of the one or more test RNA molecules obtained in step (e) are amplified by ligating nucleotide linkers to said fragments of one or more test RNA molecules and subjecting the fragments of the one or more test RNA molecules to reverse transcriptase-polymerase chain reaction (RT-PCR).

10. The method of claim 9, wherein said nucleotide linkers are directionally oriented.

11. The method of claim 1, wherein the molecule that specifically interacts with the component of said RBP-test RNA fragment complexes is an antibody.

12. The method of claim 1, wherein the one or more binding sites on the one or more test RNA molecules interacting with an RNA binding protein of interest comprise an RNA motif which exhibits a particular structure.

13. The method of claim 12, wherein the RNA motif comprises a recurring RNA element, structure or sequence.

14. The method of claim 1, wherein the sequence of the one or more test RNA molecules interacting with an RNA binding protein of interest is determined.

15. The method of claim 1, wherein the one or more test RNA molecules interacting with an RNA binding protein of interest is subjected to RNA footprinting.

16. The method of claim 1, wherein the method is an unbiased screen.

17. The method of claim 16, wherein the one or more test RNA molecules interacting with an RNA binding protein of interest was not predetermined.

18. The method of claim 17, wherein the sequence of the one or more test RNA molecules interacting with an RNA binding protein of interest is determined.

19. The method of claim 18, wherein the fragments of the one or more test RNA molecules obtained in step (e) are amplified by ligating nucleotide linkers to said fragments of RNA and subjecting the test RNA fragments to reverse transcriptase-polymerase chain reaction (RT-PCR).

20. The method of claim 19, wherein said nucleotide linkers are directionally oriented.

21. The method of claim 1, wherein the test biological sample is selected from the group consisting of whole tissue biopsy, tissue sample biopsy and whole organ.

22. The method of claim 1, wherein the test RNA fragment is derived from a transfer RNA, a small nuclear RNA, a ribosomal RNA, a messenger RNA, an antisense RNA, a small inhibitory RNA, a micro RNA or a ribozyme.

* * * * *